US010611806B2

(12) United States Patent
Baum et al.

(10) Patent No.: US 10,611,806 B2
(45) Date of Patent: Apr. 7, 2020

(54) CHIMERIC INSECTICIDAL PROTEINS TOXIC OR INHIBITORY TO LEPIDOPTERAN PESTS

(71) Applicant: Monsanto Technology LLC, St. Louis, MO (US)

(72) Inventors: James A. Baum, Webster Groves, MO (US); Thomas A. Cerruti, Newton, MA (US); Crystal L. Dart, Norton, MA (US); Leigh H. English, Chesterfield, MO (US); Stanislaw Flasinski, Chesterfield, MO (US); Xiaoran Fu, Belmont, MA (US); Victor M. Guzov, Cambridge, MA (US); Arlene R. Howe, Chesterfield, MO (US); Jay P. Morgenstern, Boston, MA (US); James K. Roberts, Chesterfield, MO (US); Sara A. Salvador, Wildwood, MO (US); Jinling Wang, Belmont, MA (US)

(73) Assignee: Monsanto Technology LLC, St. Louis, MO (US)

( * ) Notice: Subject to any disclaimer, the term of this patent is extended or adjusted under 35 U.S.C. 154(b) by 182 days.

(21) Appl. No.: 15/849,218

(22) Filed: Dec. 20, 2017

(65) Prior Publication Data

US 2018/0127775 A1 May 10, 2018

Related U.S. Application Data

(63) Continuation of application No. 14/884,469, filed on Oct. 15, 2015, now Pat. No. 10,233,217.

(60) Provisional application No. 62/064,989, filed on Oct. 16, 2014.

(51) Int. Cl.
*C07K 14/325* (2006.01)
*C12N 15/82* (2006.01)
*A01N 63/02* (2006.01)
*C12N 15/62* (2006.01)

(52) U.S. Cl.
CPC .......... *C07K 14/325* (2013.01); *A01N 63/02* (2013.01); *C12N 15/8286* (2013.01); *C07K 2319/00* (2013.01); *C12N 15/62* (2013.01); *Y02A 40/162* (2018.01)

(58) Field of Classification Search
None
See application file for complete search history.

(56) References Cited

U.S. PATENT DOCUMENTS

| | | | |
|---|---|---|---|
| 5,188,642 A | 2/1993 | Shah et al. | |
| 5,312,910 A | 5/1994 | Kishore et al. | |
| 5,500,365 A | 3/1996 | Fischhoff et al. | |
| 5,510,471 A | 4/1996 | Lebrun et al. | |
| 5,627,061 A | 5/1997 | Barry et al. | |
| 5,633,435 A | 5/1997 | Barry et al. | |
| 5,633,448 A | 5/1997 | Lebrun et al. | |
| 5,723,758 A * | 3/1998 | Payne ................ | A01N 63/00 435/252.3 |
| 5,728,925 A | 3/1998 | Herrera-Estrella et al. | |
| 5,880,275 A | 3/1999 | Fischhoff et al. | |
| 6,017,534 A | 1/2000 | Malvar et al. | |
| 6,033,874 A | 3/2000 | Baum et al. | |
| 6,204,246 B1 | 3/2001 | Bosch et al. | |
| 6,218,188 B1 * | 4/2001 | Cardineau ........... | C07K 14/325 435/468 |
| 6,501,009 B1 | 12/2002 | Romano | |
| 6,713,063 B1 | 3/2004 | Malvar et al. | |
| 6,962,705 B2 | 11/2005 | Malvar et al. | |
| 7,064,249 B2 | 6/2006 | Corbin et al. | |
| 7,070,982 B2 | 7/2006 | Malvar et al. | |
| 7,193,133 B2 | 3/2007 | Lassner et al. | |
| 7,510,878 B2 | 3/2009 | Abad et al. | |
| 7,772,465 B2 | 8/2010 | Abad et al. | |
| 7,812,129 B1 | 10/2010 | Abad et al. | |
| 8,344,207 B2 | 1/2013 | Bogdanova et al. | |
| 8,609,936 B2 | 12/2013 | Baum et al. | |
| 8,772,577 B2 * | 7/2014 | Abad .................. | A01N 63/02 800/302 |
| 2003/0119158 A1 * | 6/2003 | Malvar ............... | C07K 14/325 435/184 |
| 2006/0021087 A1 | 1/2006 | Baum et al. | |
| 2006/0112447 A1 | 5/2006 | Bogdanova et al. | |
| 2008/0172762 A1 | 7/2008 | Cerf et al. | |
| 2008/0256667 A1 | 10/2008 | Dersch et al. | |
| 2008/0280361 A1 | 11/2008 | Calabotta et al. | |
| 2008/0282432 A1 | 11/2008 | Duncan et al. | |

(Continued)

FOREIGN PATENT DOCUMENTS

| | | |
|---|---|---|
| EP | 0189707 A2 | 8/1986 |
| EP | 0508909 A1 | 10/1992 |

(Continued)

OTHER PUBLICATIONS

Fourgoux-Nicol et al, Plant Mol. Biol. (1999) 40: 857-872.*

(Continued)

*Primary Examiner* — Mykola V. Kovalenko
(74) *Attorney, Agent, or Firm* — Carine M. Doyle; Arnold & Porter Kaye Scholer LLP

(57) ABSTRACT

Nucleotide sequences are disclosed that encode novel chimeric insecticidal proteins exhibiting Lepidopteran inhibitory activity. Particular embodiments provide compositions and transformed plants, plant parts, and seeds containing the recombinant nucleic acid molecules encoding one or more of the chimeric insecticidal proteins.

19 Claims, No Drawings

Specification includes a Sequence Listing.

(56) References Cited

U.S. PATENT DOCUMENTS

| | | | |
|---|---|---|---|
| 2009/0138985 | A1 | 5/2009 | Martinell et al. |
| 2009/0142837 | A1 | 6/2009 | Adams, Jr. et al. |
| 2009/0313721 | A1 | 12/2009 | Abad et al. |
| 2010/0004176 | A1 | 1/2010 | Sampson et al. |
| 2010/0017914 | A1 | 1/2010 | Hart et al. |
| 2010/0077507 | A1 | 3/2010 | Abad et al. |
| 2010/0077508 | A1 | 3/2010 | Abad et al. |
| 2010/0137216 | A1 | 6/2010 | Carozzi et al. |
| 2010/0160231 | A1 | 6/2010 | Sampson et al. |
| 2010/0192256 | A1 | 6/2010 | Abad et al. |
| 2010/0197592 | A1 | 8/2010 | Heinrichs |
| 2010/0269221 | A1 | 10/2010 | Abad et al. |
| 2010/0317569 | A1 | 12/2010 | Lira et al. |
| 2010/0319092 | A1 | 12/2010 | Lira et al. |
| 2010/0319093 | A1 | 12/2010 | Lira et al. |
| 2011/0030096 | A1 | 2/2011 | Lira et al. |
| 2011/0055968 | A1 | 3/2011 | Cerf et al. |
| 2011/0112013 | A1 | 5/2011 | Abad et al. |
| 2011/0154536 | A1 | 6/2011 | Abad et al. |
| 2012/0047606 | A1 | 2/2012 | Abad et al. |
| 2012/0117690 | A1 | 5/2012 | Cerf et al. |
| 2012/0167259 | A1 | 6/2012 | Liu et al. |
| 2012/0192310 | A1 | 7/2012 | Abad et al. |
| 2012/0210462 | A1 | 8/2012 | Bermudez et al. |
| 2012/0233726 | A1 | 9/2012 | Abad et al. |
| 2012/0317681 | A1 | 12/2012 | Meade et al. |
| 2013/0055469 | A1 | 2/2013 | Sampson et al. |
| 2013/0097735 | A1 | 4/2013 | Bowen et al. |
| 2013/0104259 | A1 | 4/2013 | Sampson et al. |
| 2013/0117884 | A1 | 5/2013 | Hargiss et al. |
| 2013/0167264 | A1 | 6/2013 | Sampson et al. |
| 2013/0219570 | A1 | 8/2013 | Lira et al. |
| 2013/0269060 | A1 | 10/2013 | Baum et al. |
| 2013/0303440 | A1 | 11/2013 | Sampson et al. |
| 2013/0310543 | A1 | 11/2013 | Sampson et al. |
| 2014/0007292 | A1 | 1/2014 | Cerf et al. |
| 2014/0033361 | A1 | 1/2014 | Altier et al. |
| 2014/0033363 | A1 | 1/2014 | Sampson |
| 2014/0196175 | A1 | 7/2014 | Sampson et al. |
| 2014/0223599 | A1 | 8/2014 | Sampson et al. |
| 2014/0245491 | A1 | 8/2014 | Sampson et al. |
| 2014/0298538 | A1 | 10/2014 | Heinrichs et al. |
| 2014/0366227 | A1 | 12/2014 | Gatehouse et al. |
| 2014/0373195 | A1 | 12/2014 | Sampson et al. |

FOREIGN PATENT DOCUMENTS

| | | |
|---|---|---|
| EP | 0218571 B1 | 2/1993 |
| EP | 0924299 A1 | 6/1999 |
| JP | 2009-505679 A | 2/2009 |
| JP | 2013-514769 A | 5/2013 |
| WO | WO 90/10076 | 9/1990 |
| WO | WO 99/24581 A2 | 5/1999 |
| WO | WO 01/14562 A1 | 3/2001 |
| WO | WO 01/19859 A2 | 3/2001 |
| WO | WO 02/14517 A1 | 2/2002 |
| WO | WO 2004/020636 A1 | 3/2004 |
| WO | WO2007027777 A1 | 3/2007 |
| WO | WO 2011/075588 A1 | 6/2011 |
| WO | WO2011075588 A1 | 6/2011 |
| WO | WO 2014/008054 A2 | 1/2014 |
| WO | WO 2014/055881 A1 | 4/2014 |

OTHER PUBLICATIONS

Pardo Lopez et al, Peptides (2009) 30:589-595.*
Aronson et al, FEMS Microbiol. Lett. (2001) 195:1-8.*
Herrero et al., Biochem. J. (2004) 384, 507-513.*
Abdul-Rauf et al, Curr. Microbiol. (1999) 39, 94-98.*
Bravo et al., "Evolution of *Bacillus thuringiencis* Cry toxins insecticidal activity," *Microbial Biotechnology*, 6:17-26 (2012).
Gen Bank Database, Apr. 25, 1994, Accession No. AAA 22344.1.
GenBank Database, Aug. 24, 1998, Accession No. AAC 32850.1.
GenBank Database, Apr. 18, 2005, Accession No. CAA 31951.1.
GenBank Database, Dec. 31, 2013, Accession No. AEH 31431.1.
GenBank Database, Apr. 26, 1993, Accession No. AAA 22561.1.
Gen Bank Database, Apr. 26, 1993, Accession No. AAA 22331.1.
GenBank Database, Nov. 18, 2005, Accession No. ABB 766664.1.
Maagd R. A. et al., "*Bacillus thuringiencis* Delta-Endotoxin Cry1C Domain III Can Function as a Specificity Determinant for *Spodoptera exigua* in Different, but Not All, Cry1-Cry1C Hybrids," *Applied and Environmental Microbiology*, 66(4):1559-1563 (2000).
Office Action in corresponding Application No. JP 2017-0520352, dated Feb. 5, 2019.
Abdul-Rauf et al., "Mutations of Loop 2 and Loop 3 Residues in Domain II of *Bacillus thuringiensis* Cry1C δ-Endotoxin Affect Insecticidal Specificity and Initial Binding to *Spodoptera littoralis* and *Aedes aegypti* Midgut Membranes," *Current Microbiology*, 39:94-98 (1999).
Aronson et al., "Why *Bacillus thuringiensis* insecticidal toxins are so effective: unique features of their mode of action," *FEMS Microbiology Letters*, 195:1-8 (2001).
Baig et al., "cry Genes profiling and the toxicity of isolates of *Bacillus thuringiensis* from soil samples against American bollworm, *Helicoverpa armigera*," *Journal of Applied Microbiology*, 109:1967-1978 (2010).
Bravo et al., "Mode of action of *Bacillus thuringiensis* Cry and Cyt toxins and their potential for insect control," *Toxins*, 49:423-435 (2007).
Database UniProt, Database accession No. D9U3MO (2010).
De Maagd et al., "*Bacillus thuringiensis* delta-endotoxin Cry1C domain III Can Function as a Specificity Determinant for *Spodoptera exigua* in Different, but Not All, Cryl-Cry1C Hybrids," *Applied and Environmental Microbiology*, 66(4):1559-1563 (2000).
Della-Cioppa et al., "Translocation of the precursor of 5-enolpyruvylshikimate-3-phosphate synthase into chloroplasts of higher plants in vitro," *Proc. Natl. Acad. Sci. USA*, 83:6873-6877, (1986).
Forgoux-Nicol et al., "Isolation of repeseed genes expressed early and specifically during development of the male gametophyte," *Plant Molecular Biology*, 40:857-872 (1999).
Herrero et al., "Mutations in the *Bacillus thuringiensis* Cry1 Ca toxin demonstrate the role of domains II and III in specificity towards *Spodoptera exigua* larvae," *Biochem J.*, 384:507-513 (2004).
International Search Report dated Jun. 6, 2016, in International Patent Application No. PCT US2015/055800.
IUPAC-IUB Joint Commission on Biochemical Nomenclature, "Nomenclature and Symbolism for Amino Acids and Peptides," *Eur. J. Biochem.* 138:9-37(1984).
Klee et al., "Cloning of an *Arabidopsis thaliana* gene encoding 5-enolpyruvylshikimate-3-phosphate synthase: sequence analysis and manipulation to obtain glyphosate-tolerant plants," *Mol Gen Genet*, 210:437-442 (1987).
Knight et al., "A Strategy for Shuffling Numerous *Bacillus thuringiensis* Crystal Protein Domains," *Journal of Economic Entomology*, 97:1805-1813 (2004).
James, "Global Status of Commercialized Biotech/GM Crops: 2012," *ISAAA*, Brief No. 44 (2012).
Lucena et al., "Molecular Approaches to Improve the Insecticidal Activity of Bacillus thuringiensis Cry toxins," *Toxins*, 6(8):2393-2423 (2014).
Pardo-Lopez et al., "Strategies to improve the insecticidal activity of Cry toxins from *Bacillus thuringiensis*," *Peptides*, 30:589-595 (2009).
Pardo-Lopez et al., "*Bacillus thuringiensis* insecticidal three-domain Cry toxins: mode of action, insect resistance and consequences for crop protection," *FEMS Microbiology Reviews*, 37:3-22 (2013).
Thompson et al., "CLUSTAL W: improving the sensitivity of progressive multiple sequence alignment through sequence weighting, position-specific gap penalties and weight matrix choice," *Nucleic Acids Research*, 22:4673-4680 (1994).
Perlak et al., Insect Resistant Cotton Plants. *FEMS Microbiology Reviews*, 37:3-22 (2013).

\* cited by examiner

SEQUENCE LISTING

```
<160> NUMBER OF SEQ ID NOS: 53

<210> SEQ ID NO 1
<211> LENGTH: 3570
<212> TYPE: DNA
<213> ORGANISM: Artificial
<220> FEATURE:
<223> OTHER INFORMATION: Recombinant nucleotide sequence used for
      expression in a bacterial cell encoding TIC1100.

<400> SEQUENCE: 1
atggagatag tgaataatca gaatcaatgc gtgccttata attgtttgaa taatcccgaa        60
atcgaaatat tagaaggcgg aagaatatca gttggtaata ccccaattga tatttctctt       120
tcgcttactc agtttctttt gagtgaattt gtcccaggtg cggggtttgt attaggatta       180
attgatttaa tatggggatt tgtaggtcct tcccaatggg acgcatttct tgctcaagtg       240
gaacagttaa ttaaccaaag aatagcagaa gctgtaagaa atacagcaat tcaggaatta       300
gagggaatgg cacgggttta tagaacctat gctactgctt ttgctgagtg ggaaaaagct       360
cctgatgacc cagagctaag agaagcacta cgtacacaat ttacagcaac tgagacttat       420
ataagtggaa gaatatccgt tttaaaaatt caaacttttg aagtacagct gttatcagtg       480
tttgcccaag ctgcaaattt acatttatct ttattaagag acgttgtgtt ttttgggcaa       540 agatgggggtt tttcaacgac aaccgtaaat aattactaca atgatttaac agaagggatt       600
agtacctata cagattatgc tgtacgctgg tacaatacgg gattagaacg tgtatgggga       660
ccggattcta gagattgggt aaggtataat caatttagaa gagaattaac actaactgta       720
ttagatatcg ttgctctgtt cccgaattat gatagtagaa gatatccaat tcgaacagtt       780
tcccaattaa caagagaaat ttatacaaac ccagtattag aaaattttga tggtagtttt       840
cgaggctcgg ctcagggcat agaaagaagt attaggagtc cacatttgat ggatatactt       900
aacagtataa ccatctatac ggatgctcat aggggttatt attattggtc agggcatcaa       960
ataatggctt ctcctgtcgg ttttttcgggg ccagaattca cgtttccgct atatggaacc      1020
atgggaaatg cagctccaca acaacgtatt gttgctcaac taggtcaggg cgtgtataga      1080
acattatcgt ccactttata tagaagacct tttaatatag ggataaataa tcaacaacta      1140
tctgttcttg acgggacaga atttgcttat ggaacctcct caaatttgcc atccgctgta      1200
tacagaaaaa gcggaacggt agattcgctg gatgaaatac cgccacagaa taacaacgtg      1260
ccacctaggc aaggatttag tcatcgatta agccatgttt caatgtttcg ttcaggcttt      1320
agtaatagta gtgtaagtat aataagagct cctatgttct cttggataca tcgtagtgct      1380
```

```
gaatttaata atataattgc atcggatagt attaatcaaa tacctttagt gaaaggattt      1440
agagtttggg ggggcacctc tgtcattaca ggaccaggat ttacaggagg ggatatcctt      1500
cgaagaaata cctttggtga ttttgtatct ctacaagtca atattaattc accaattacc      1560
caaagatacc gtttaagatt tcgttacgct tccagtaggg atgcacgagt tatagtatta      1620
acaggagcgg catccacagg agtgggaggc caagttagtg taaatatgcc tcttcagaaa      1680
actatgaaaa taggggagaa cttaacatct agaacattta gatataccga ttttagtaat      1740
ccttttcat ttagagctaa tccagatata attgggataa gtgaacaacc tctatttggt       1800
gcaggttcta ttagtagcgg tgaactttat atagataaaa ttgaaattat tctagcagat      1860
gcaacatttg aagcagaatc tgatttagaa agagcgcaga aggcggtgaa tgcgctgttt      1920
acgtctacaa accaactagg gctaaaaaca aatgtaacgg attatcatat tgatcaagtg      1980
tccaatttag ttacgtattt atcggatgaa ttttgtctgg atgaaaagcg agaattgtcc      2040
gagaaagtca acatgcgaa gcgactcagt gatgaacgca atttactcca agattcaaat       2100
ttcaaagaca ttaataggca accagaacgt gggtggggcg gaagtacagg gattaccatc      2160
caaggagggg atgacgtatt taagaaaat tacgtcacac tatcaggtac ctttgatgag       2220
tgctatccaa catatttgta tcaaaaaatc gatgaatcaa aattaaaagc ctttacccgt      2280
tatcaattaa gagggtatat cgaagatagt caagacttag aaatctattt aattcgctac      2340
aatgcaaaac atgaaacagt aaatgtgcca ggtacgggtt ccttatggcc gctttcagcc      2400
caaagtccaa tcggaaagtg tggagagccg aatcgatgcg cgccacacct tgaatggaat      2460
cctgacttag attgttcgtg tagggatgga gaaaagtgtg cccatcattc gcatcatttc      2520
tccttagaca ttgatgtagg atgtacagac ttaaatgagg acctaggtgt atgggtgatc      2580
tttaagatta agacgcaaga tgggcacgca agactaggga atctagagtt ctctcgaagag     2640
aaaccattag taggagaagc gctagctcgt gtgaaaagag cggagaaaaa atggagagac      2700
aaacgtgaaa aattggaatg ggaaacaaat atcgtttata agaggcaaa agaatctgta       2760
gatgctttat ttgtaaactc tcaatatgat caattacaag cggatacgaa tattgccatg      2820
attcatgcgg cagataaacg tgttcatagc attcgagaag cttatctgcc tgagctgtct      2880
gtgattccgg gtgtcaatgc ggctattttt gaagaattag aagggcgtat tttcactgca      2940
ttctccctat atgatgcgag aaatgtcatt aaaaatggtg attttaataa tggcttatcc      3000
tgctggaacg tgaaagggca tgtagatgta gaagaacaaa acaaccaacg ttcggtcctt      3060
gttgttccga atgggaagc agaagtgtca caagaagttc gtgtctgtcc gggtcgtggc       3120
tatatccttc gtgtcacagc gtacaaggag ggatatggag aaggttgcgt aaccattcat      3180
gagatcgaga acaatacaga cgaactgaag tttagcaact gcgtagaaga ggaaatctat      3240
ccaaataaca cggtaacgtg taatgattat actgtaaatc aagaagaata cggaggtgcg      3300
tacacttctc gtaatcgagg atataacgaa gctccttccg taccagctga ttatgcgtca      3360
gtctatgaag aaaaatcgta tacagatgga cgaagagaga atccttgtga atttaacaga      3420
gggtataggg attacacgcc actaccagtt ggttatgtga caaaagaatt agaatacttc      3480
ccagaaaccg ataaggtatg gattgagatt ggagaaacgg aaggaacatt tatcgtggac      3540
agcgtggaat tactccttat ggaggaatga                                        3570
```

<210> SEQ ID NO 2
<211> LENGTH: 3570
<212> TYPE: DNA

<213> ORGANISM: Artificial
<220> FEATURE:
<223> OTHER INFORMATION: Synthetic nucleotide sequence designed for expression in a plant cell encoding TIC1100.

<400> SEQUENCE: 2

```
atggagattg tgaacaacca gaaccagtgc gttccttaca actgcttgaa caaccctgag    60
attgagattc ttgagggtgg tagaatttct gttggcaaca ctcctattga catctctttg   120
agtttgactc aattcttgtt gagtgagttc gttcctggtg ctggtttcgt cttgggtttg   180
attgatttga tttggggttt cgttggtcct agtcaatggg atgctttctt ggctcaagtt   240
gagcaattga ttaaccagag gatcgctgag gctgtgagga cactgctat tcaagagttg    300
gagggtatgg ctagagttta cagaacttac gctactgctt tcgctgagtg ggagaaggct   360
cctgatgacc tgagttgag ggaggctttg agaactcaat tcactgctac tgagacttac    420
atcagtggta gaatcagtgt cttgaagatt caaactttcg aggttcaatt gctttctgtg   480
ttcgctcaag ctgcaaactt gcacttgtct tgcttagag atgttgtgtt ctttggtcaa    540
agatggggtt tctccactac taccgtgaac aattactaca acgatttgac tgagggtatt   600
tctacttaca ctgattacgc tgttagatgg tacaacactg gtttggagag agtttggggt   660
ccagattcca gagattgggt cagatacaac cagttcagaa gggagttgac tttgactgtc   720
ttggacattg ttgctctctt ccctaactac gatagtcgtc gttaccctat tagaactgtt   780
tctcaactta ctagggaaat ctacactaac cctgttcttg agaacttcga tggtagtttc   840
cgtggtagtg ctcaagggat tgagcgttct attcgttctc ctcatcttat ggacattctt   900
aactctatta ctatctacac tgatgctcat cgtggttact attactggtc tggtcatcaa   960
attatggcta gtcctgttgg tttcagtggt cctgagttca ctttccctct ttacggtact  1020
atgggcaacg ctgcacctca acagaggatc gttgctcaac ttggtcaagg tgtttacagg  1080
actctttctt caacccttta caggcgtcct ttcaacattg ggatcaacaa ccagcagctt  1140
tctgttcttg atggaaccga gttcgcttac ggaacctctt caaaccttcc tagtgctgtt  1200
tacaggaagt ctggaaccgt tgacagtctt gatgagattc caccgcagaa caataacgtt  1260
ccacccaggc aaggcttcag tcataggctt tctcatgttt ctatgttccg ctctggattc  1320
agcaactctt cagtttctat tatcagggct ccaatgttct cgtggattca taggtctgcc  1380
gagttcaaca acattatcgc ttccgatagc attaaccaga ttccacttgt taagggattc  1440
cgtgtttggg gaggcacctc tgttattacc ggaccaggct tcaccggagg cgacattctt  1500
cgtcgtaaca ccttcggaga tttcgtttca cttcaagtga acattaactc accaatcacc  1560
cagcgctaca ggcttcgctt ccgctacgca tcatccaggg atgcaagggt gatcgtgctt  1620
accggagcag cctcaaccgg agtgggaggc caagtgagcg tgaacatgcc acttcagaag  1680
acgatggaga tcggcgagaa ccttacctca gaacctttc gttacaccga tttcagcaac  1740
ccattcagct ttcgtgcaaa cccagacatc atagggatct cagagcagcc actgtttgga  1800
gctggatcaa tctcatccgg agagctttac atcgacaaga tcgagatcat actcgcagat  1860
gcaaccttcg aggctgagag cgatctggag cgtgcacaga aggcagtgaa cgcactcttt  1920
acctctacca accagctcgg actcaagacc aacgtgaccg attaccacat cgaccaagtg  1980
agcaacctcg tgacctacct ctcagatgag ttctgcttgg atgagaaacg cgaactcagc  2040
gagaaggtga agcacgcaaa gcgtctctca gatgagcgta acctcctcca ggatagcaat  2100
ttcaaggaca tcaatcgtca gccagagcgt ggatgggag gctcaaccgg aatcaccatc  2160
```

```
caggggaggcg atgatgtgtt taaggagaat tacgtgacac tctccggaac attcgatgag      2220
tgctacccaa catacctcta tcagaagatc gacgagtcca agctcaaggc gttcacccgt      2280
tatcagctcc gtggctacat cgaggatagt caagacctgg aaatctacct catccgctac      2340
aatgcaaagc acgagacagt gaatgtgcca ggaacaggct ccctctggcc actctccgca      2400
cagtctccaa tcggcaagtg cggcgagcca atcgctgcg cgccacacct ggagtggaat       2460
cccgacctgg actgctcctg ccgcgacggc gagaagtgcg cccaccactc ccaccacttt      2520
agcctggaca tcgacgtggg ctgtacagac ctgaatgagg atctgggcgt gtgggtgatc      2580
tttaagatca agacacagga cggccacgcc cgcctgggca atctggagtt tctggaggag      2640
aagcctctgg tgggcgaagc cctggcccgc gtgaagcgcg ccgagaagaa atggcgcgac      2700
aaacgcgaga aactggaatg ggaaacaaac atcgtgtaca agaagccaa agaatccgtg       2760 gacgccctat ttgtgaactc ccagtatgac cagctacagg ccgacacaaa catcgcgatg      2820
atccacgctg cggacaagcg cgtgcactcc atacgcgaag cctatctacc cgaactatcc      2880
gtgatacccg gcgtcaatgc cgcgatcttt gaagaattgg aaggccgcat cttcacagcc      2940
tttagcctct atgacgcccg aaatgtcatc aagaatggcg actttaacaa tgggctatcc      3000
tgttggaatg tcaaagggca cgtggacgtc gaagagcaga acaatcagcg atccgtctta      3060
gtcgtacccg aatgggaagc cgaagtctcc caggaagtcc gagtctgtcc tggtagaggt      3120
tacatcttga gagtgactgc ttacaaggag ggttacggtg agggatgcgt gactattcac      3180
gagattgaga caacactga tgagttgaag ttcagtaact gcgtggagga ggaaatctac       3240
cccaacaaca ctgtgacttg taacgattac accgtgaacc aggaggaata cggaggcgct      3300
tacacctcca gaaaccgtgg atacaatgag gctccctcgg tccccgctga ttatgcctcc      3360
gtctatgagg agaagtccta caccgatgga aggcgcgaga atccctgcga gttcaatcgc      3420
ggctatcgag actacactcc gctacccgtt ggctatgtca caaaggaact ggaatacttc      3480
ccggaaacag acaaagtctg gatcgaaatc ggcgaaacag aagggacgtt catagtcgat      3540
agcgtagaac ttctccttat ggaagaatga                                       3570
```

<210> SEQ ID NO 3
<211> LENGTH: 3570
<212> TYPE: DNA
<213> ORGANISM: Artificial
<220> FEATURE:
<223> OTHER INFORMATION: Synthetic nucleotide sequence designed for
      expression in a plant cell encoding TIC1100.

<400> SEQUENCE: 3

```
atggagattg tgaacaacca gaaccagtgc gttccttaca actgcttgaa caaccctgag        60
attgagattc ttgagggtgg tagaatttct gttggcaaca ctcctattga catctctttg       120
agtttgactc aattcttgtt gagtgagttc gttcctggtg ctggtttcgt cttgggtttg       180
attgatttga tttggggttt cgttggtcct agtcaatggg atgctttctt ggctcaagtt       240
gagcaattga ttaaccagag gatcgctgag gctgtgagga cactgctat tcaagagttg        300 gagggtatgg ctagagttta cagaacttac gctactgctt tcgctgagtg ggagaaggct       360
cctgatgacc ctgagttgag ggaggctttg agaactcaat tcactgctac tgagacttac       420
atcagtggta gaatcagtgt cttgaagatt caaactttcg aggttcaatt gctttctgtg       480
ttcgctcaag ctgcaaactt gcacttgtct ttgcttagag atgttgtgtt ctttggtcaa       540
agatggggtt tctccactac taccgtgaac aattactaca acgatttgac tgagggtatt       600
```

```
tctacttaca ctgattacgc tgttagatgg tacaacactg gtttggagag agtttggggt    660
ccagattcca gagattgggt cagatacaac cagttcagaa gggagttgac tttgactgtc    720
ttggacattg ttgctctctt ccctaactac gatagtcgtc gttaccctat tagaactgtt    780
tctcaactta ctagggaaat ctacactaac cctgttcttg agaacttcga tggtagtttc    840
cgtggtagtg ctcaagggat tgagcgttct attcgttctc ctcatcttat ggacattctt    900
aactctatta ctatctacac tgatgctcat cgtggttact attactggtc tggtcatcaa    960
attatggcta gtcctgttgg tttcagtggt cctgagttca cttttccctct ttacggtact    1020
atgggcaacg ctgcacctca acagaggatc gttgctcaac ttggtcaagg tgtttacagg    1080
actctttctt caacccttta caggcgtcct ttcaacattg ggatcaacaa ccagcagctt    1140
tctgttcttg atggaaccga gttcgcttac ggaacctctt caaaccttcc tagtgctgtt    1200
tacaggaagt ctggaaccgt tgacagtctt gatgagattc caccgcagaa caataacgtt    1260
ccacccaggc aaggcttcag tcataggctt tctcatgttt ctatgttccg ctctggattc    1320
agcaactctt cagtttctat tatcagggct ccaatgttct cgtggattca taggtctgcc    1380
gagttcaaca acattatcgc ttccgatagc attaaccaga ttccacttgt taagggattc    1440
cgtgtttggg gaggcacctc tgttattacc ggaccaggct tcaccggagg cgacattctt    1500
cgtcgtaaca ccttcggaga tttcgtttca cttcaagtga acattaactc accaatcacc    1560
cagcgctaca ggcttcgctt ccgctacgca tcatccaggg atgcaagggt gatcgtgctt    1620
accggagcag cctcaaccgg agtgggaggc caagtgagcg tgaacatgcc acttcagaag    1680
acgatggaga tcggcgagaa ccttacctca agaacctttc gttacaccga tttcagcaac    1740
ccattcagct ttcgtgcaaa cccagacatc atagggatct cagagcagcc actgtttgga    1800
gctggatcaa tctcatccgg agagctttac atcgacaaga tcgagatcat actcgcagat    1860
gcaaccttcg aggctgagag cgatctggag cgtgcacaga aggcagtgaa cgcactcttt    1920
acctctacca accagctcgg actcaagacc aacgtgaccg attaccacat cgaccaagtg    1980
agcaacctcg tgacctacct ctcagatgag ttctgcttgg atgagaaacg cgaactcagc    2040
gagaaggtga agcacgcaaa gcgtctctca gatgagcgta acctcctcca ggatagcaat    2100
ttcaaggaca tcaatcgtca gccagagcgt ggatgggag gctcaaccgg aatcaccatc    2160
cagggaggcg atgatgtgtt taaggagaat tacgtgacac tctccggaac attcgatgag    2220
tgctacccaa catacctcta tcagaagatc gacgagtcca agctcaaggc gttcacccgt    2280
tatcagctcc gtggctacat cgaggatagt caagacctgg aaatctacct catccgctac    2340
aatgcaaagc acgagacagt gaatgtacca ggaacaggct ccctctggcc actctccgca    2400
cagtctccaa tcggcaagtg cggcgagcca aatcgctgcg cgccacacct ggagtggaat    2460
cccgacctgg actgctcctg ccgcgacggc gagaagtgcg cccaccactc ccaccacttt    2520
agcctggaca tcgacgtggg ctgtacagac ctgaatgagg atctgggcgt gtgggtgatc    2580
tttaagatca agacacagga cggccacgcc cgcctgggca atctggagtt tctggaggag    2640
aagcctctgg tgggcgaagc cctggcccgc gtgaagcgcg ccgagaagaa atggcgcgac    2700
aaacgcgaga aactggaatg ggaaacaaac atcgtgtaca agaagccaa agaatccgtg    2760
gacgccctat ttgtgaactc ccagtatgac cagctacagg ccgacacaaa catcgcgatg    2820
atccacgctg cggacaagcg cgtgcactcc atacgcgaag cctatctacc cgaactatcc    2880
gtgatacccg cgtcaatgc cgcgatcttt gaagaattgg aaggccgcat cttcacagcc    2940
tttagcctct atgacgcccg aaatgtcatc aagaatggcg actttaacaa tgggctatcc    3000
```

```
tgttggaatg tcaaagggca cgtggacgtc gaagagcaga acaatcagcg atccgtctta    3060
gtcgtacccg aatgggaagc cgaagtctcc caggaagtcc gagtctgtcc tggtagaggt    3120
tacatcttga gagtgactgc ttacaaggag ggttacggtg agggatgcgt gactattcac    3180
gagattgaga acaacactga tgagttgaag ttcagtaact gcgtggagga ggaaatctac    3240
cccaacaaca ctgtgacttg taacgattac accgtgaacc aggaggaata cggaggcgct    3300
tacacctcca gaaaccgtgg atacaatgag gctccctcgg tccccgctga ttatgcctcc    3360
gtctatgagg agaagtccta caccgatgga aggcgcgaga atccctgcga gttcaatcgc    3420
ggctatcgag actacactcc gctacccgtt ggctatgtca caaggaact  ggaatacttc    3480 ccggaaacag acaaagtctg gatcgaaatc ggcgaaacag aagggacgtt catagtcgat    3540
agcgtagaac ttctccttat ggaagaatga                                    3570
```

<210> SEQ ID NO 4
<211> LENGTH: 1189
<212> TYPE: PRT
<213> ORGANISM: Artificial
<220> FEATURE:
<223> OTHER INFORMATION: Amino acid sequence of the chimeric protein
      TIC1100.

<400> SEQUENCE: 4

```
Met Glu Ile Val Asn Asn Gln Asn Gln Cys Val Pro Tyr Asn Cys Leu
1               5                   10                  15

Asn Asn Pro Glu Ile Glu Ile Leu Glu Gly Gly Arg Ile Ser Val Gly
            20                  25                  30

Asn Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Ile Asp Leu Ile
    50                  55                  60

Trp Gly Phe Val Gly Pro Ser Gln Trp Asp Ala Phe Leu Ala Gln Val
65                  70                  75                  80

Glu Gln Leu Ile Asn Gln Arg Ile Ala Glu Ala Val Arg Asn Thr Ala
                85                  90                  95

Ile Gln Glu Leu Glu Gly Met Ala Arg Val Tyr Arg Thr Tyr Ala Thr
            100                 105                 110

Ala Phe Ala Glu Trp Glu Lys Ala Pro Asp Asp Pro Glu Leu Arg Glu
        115                 120                 125

Ala Leu Arg Thr Gln Phe Thr Ala Thr Glu Thr Tyr Ile Ser Gly Arg
    130                 135                 140

Ile Ser Val Leu Lys Ile Gln Thr Phe Glu Val Gln Leu Leu Ser Val
145                 150                 155                 160

Phe Ala Gln Ala Ala Asn Leu His Leu Ser Leu Leu Arg Asp Val Val
                165                 170                 175

Phe Phe Gly Gln Arg Trp Gly Phe Ser Thr Thr Thr Val Asn Asn Tyr
            180                 185                 190

Tyr Asn Asp Leu Thr Glu Gly Ile Ser Thr Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255
```

```
Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
            275                 280                 285

Arg Ser Ile Arg Ser Pro His Leu Met Asp Ile Leu Asn Ser Ile Thr
            290                 295                 300

Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
450                 455                 460

Ile Ile Ala Ser Asp Ser Ile Asn Gln Ile Pro Leu Val Lys Gly Phe
465                 470                 475                 480

Arg Val Trp Gly Gly Thr Ser Val Ile Thr Gly Pro Gly Phe Thr Gly
                485                 490                 495

Gly Asp Ile Leu Arg Arg Asn Thr Phe Gly Asp Phe Val Ser Leu Gln
                500                 505                 510

Val Asn Ile Asn Ser Pro Ile Thr Gln Arg Tyr Arg Leu Arg Phe Arg
            515                 520                 525

Tyr Ala Ser Ser Arg Asp Ala Arg Val Ile Val Leu Thr Gly Ala Ala
530                 535                 540

Ser Thr Gly Val Gly Gly Gln Val Ser Val Asn Met Pro Leu Gln Lys
545                 550                 555                 560

Thr Met Glu Ile Gly Glu Asn Leu Thr Ser Arg Thr Phe Arg Tyr Thr
                565                 570                 575

Asp Phe Ser Asn Pro Phe Ser Phe Arg Ala Asn Pro Asp Ile Ile Gly
            580                 585                 590

Ile Ser Glu Gln Pro Leu Phe Gly Ala Gly Ser Ile Ser Ser Gly Glu
            595                 600                 605

Leu Tyr Ile Asp Lys Ile Glu Ile Ile Leu Ala Asp Ala Thr Phe Glu
            610                 615                 620

Ala Glu Ser Asp Leu Glu Arg Ala Gln Lys Ala Val Asn Ala Leu Phe
625                 630                 635                 640

Thr Ser Thr Asn Gln Leu Gly Leu Lys Thr Asn Val Thr Asp Tyr His
                645                 650                 655

Ile Asp Gln Val Ser Asn Leu Val Thr Tyr Leu Ser Asp Glu Phe Cys
            660                 665                 670
```

-continued

```
Leu Asp Glu Lys Arg Glu Leu Ser Glu Lys Val Lys His Ala Lys Arg
            675                 680                 685

Leu Ser Asp Glu Arg Asn Leu Leu Gln Asp Ser Asn Phe Lys Asp Ile
    690                 695                 700

Asn Arg Gln Pro Glu Arg Gly Trp Gly Gly Ser Thr Gly Ile Thr Ile
705                 710                 715                 720

Gln Gly Gly Asp Asp Val Phe Lys Glu Asn Tyr Val Thr Leu Ser Gly
                725                 730                 735

Thr Phe Asp Glu Cys Tyr Pro Thr Tyr Leu Tyr Gln Lys Ile Asp Glu
            740                 745                 750

Ser Lys Leu Lys Ala Phe Thr Arg Tyr Gln Leu Arg Gly Tyr Ile Glu
    755                 760                 765

Asp Ser Gln Asp Leu Glu Ile Tyr Leu Ile Arg Tyr Asn Ala Lys His
    770                 775                 780

Glu Thr Val Asn Val Pro Gly Thr Gly Ser Leu Trp Pro Leu Ser Ala
785                 790                 795                 800

Gln Ser Pro Ile Gly Lys Cys Gly Glu Pro Asn Arg Cys Ala Pro His
                805                 810                 815

Leu Glu Trp Asn Pro Asp Leu Asp Cys Ser Cys Arg Asp Gly Glu Lys
            820                 825                 830

Cys Ala His His Ser His His Phe Ser Leu Asp Ile Asp Val Gly Cys
    835                 840                 845

Thr Asp Leu Asn Glu Asp Leu Gly Val Trp Val Ile Phe Lys Ile Lys
850                 855                 860

Thr Gln Asp Gly His Ala Arg Leu Gly Asn Leu Glu Phe Leu Glu Glu
865                 870                 875                 880

Lys Pro Leu Val Gly Glu Ala Leu Ala Arg Val Lys Arg Ala Glu Lys
                885                 890                 895

Lys Trp Arg Asp Lys Arg Glu Lys Leu Glu Trp Glu Thr Asn Ile Val
            900                 905                 910

Tyr Lys Glu Ala Lys Glu Ser Val Asp Ala Leu Phe Val Asn Ser Gln
    915                 920                 925

Tyr Asp Gln Leu Gln Ala Asp Thr Asn Ile Ala Met Ile His Ala Ala
    930                 935                 940

Asp Lys Arg Val His Ser Ile Arg Glu Ala Tyr Leu Pro Glu Leu Ser
945                 950                 955                 960

Val Ile Pro Gly Val Asn Ala Ala Ile Phe Glu Glu Leu Glu Gly Arg
                965                 970                 975

Ile Phe Thr Ala Phe Ser Leu Tyr Asp Ala Arg Asn Val Ile Lys Asn
            980                 985                 990

Gly Asp Phe Asn Asn Gly Leu Ser Cys Trp Asn Val Lys Gly His Val
    995                 1000                1005

Asp Val Glu Glu Gln Asn Asn Gln Arg Ser Val Leu Val Val Pro
    1010                1015                1020

Glu Trp Glu Ala Glu Val Ser Gln Glu Val Arg Val Cys Pro Gly
    1025                1030                1035

Arg Gly Tyr Ile Leu Arg Val Thr Ala Tyr Lys Glu Gly Tyr Gly
    1040                1045                1050

Glu Gly Cys Val Thr Ile His Glu Ile Glu Asn Asn Thr Asp Glu
    1055                1060                1065

Leu Lys Phe Ser Asn Cys Val Glu Glu Glu Ile Tyr Pro Asn Asn
    1070                1075                1080

Thr Val Thr Cys Asn Asp Tyr Thr Val Asn Gln Glu Glu Tyr Gly
```

```
                    1085                  1090                     1095
Gly  Ala  Tyr  Thr  Ser  Arg  Asn  Arg  Gly  Tyr  Asn  Glu  Ala  Pro  Ser
        1100                    1105                   1110

Val  Pro  Ala  Asp  Tyr  Ala  Ser  Val  Tyr  Glu  Glu  Lys  Ser  Tyr  Thr
        1115                    1120                   1125

Asp  Gly  Arg  Arg  Glu  Asn  Pro  Cys  Glu  Phe  Asn  Arg  Gly  Tyr  Arg
        1130                    1135                   1140

Asp  Tyr  Thr  Pro  Leu  Pro  Val  Gly  Tyr  Val  Thr  Lys  Glu  Leu  Glu
        1145                    1150                   1155

Tyr  Phe  Pro  Glu  Thr  Asp  Lys  Val  Trp  Ile  Glu  Ile  Gly  Glu  Thr
        1160                    1165                   1170

Glu  Gly  Thr  Phe  Ile  Val  Asp  Ser  Val  Glu  Leu  Leu  Leu  Met  Glu
        1175                    1180                   1185

Glu

<210> SEQ ID NO 5
<211> LENGTH: 3672
<212> TYPE: DNA
<213> ORGANISM: Artificial
<220> FEATURE:
<223> OTHER INFORMATION: Recombinant nucleotide sequence used for
      expression in a bacterial cell encoding TIC860.

<400> SEQUENCE: 5
atgacttcaa ataggaaaaa tgagaatgaa attataaatg ctttatcgat tccaacggta      60
tcgaatcctt ccacgcaaat gaatctatca ccagatgctc gtattgaaga tagcttgtgt     120
gtagccgagg tgaacaatat tgatccattt gttagcgcat caacagtcca aacgggtata     180
aacatagctg gtagaatatt gggcgtatta ggtgtgccgt ttgctggaca actagctagt     240
ttttatagtt ttcttgttgg ggaattatgg cctagtggca gagatccatg ggaaattttc     300
ctggaacatg tagaacaact tataagacaa caagtaacag aaaatactag gaatacggct     360
attgctcgat tagaaggtct aggaagaggc tatagatctt accagcaggc tcttgaaact     420
tggttagata accgaaatga tgcaagatca agaagcatta ttcttgagcg ctatgttgct     480
ttagaacttg acattactac tgctataccg cttttcagaa tacgaaatga agaagttcca     540
ttattaatgg tatatgctca agctgcaaat ttacacctat tattattgag agacgcatcc     600 cttttttggta gtgaatgggg gatggcatct tccgatgtta accaatatta ccaagaacaa     660
atcagatata cagaggaata ttctaaccat tgcgtacaat ggtataatac agggctaaat     720
aacttaagag ggacaaatgc tgaaagttgg ttgcggtata tcaattccg tagagaccta     780 acgttagggg tattagattt agtagcccta ttcccaagct atgatactcg cacttatcca     840
atcaatacga gtgctcagtt aacaagagaa atttatacag atccaattgg agaacaaat      900 gcaccttcag gatttgcaag tacgaattgg tttaataata tgcaccatc gttttctgcc      960 atagaggctg ccattttcag gcctccgcat ctacttgatt ttccagaaca acttacaatt    1020
tacagtgcat caagccgttg gagtagcact caacatatga attattgggt gggacatagg    1080
cttaacttcc gcccaatagg agggacatta aatacctcaa cacaaggact tactaataat    1140
acttcaatta tcctgtaac attacagttt acgtctcgag acgtttatag aacagaatca    1200
aatgcaggga caaatatact atttactact cctgtgaatg gagtaccttg ggctagattt    1260
aattttatta accctcagaa tatttatgaa agaggcgcca ctacctacag tcaaccgtat    1320
cagggagttg ggattcaatt atttgattca gaaactgaat taccaccaga acaacagaa    1380
```

```
cgaccaaatt atgaatcata tagtcataga ttatctcata taggactaat cataggaaac    1440
actttgagag caccagtcta ttcttggacg catcgtagtg cagatcgtac gaatacgatt    1500
ggaccaaata gaattaatca aataccttta gtgaaaggat ttagagtttg gggggcacc     1560 tctgtcatta caggaccagg atttacagga ggggatatcc ttcgaagaaa tacctttggt    1620
gattttgtat ctctacaagt caatattaat tcaccaatta cccaaagata ccgtttaaga    1680
tttcgttacg cttccagtag ggatgcacga gttatagtat taacaggagc ggcatccaca    1740
ggagtgggag gccaagttag tgtaaatatg cctcttcaga aaactatgga aataggggag    1800
aacttaacat ctagaacatt tagatatacc gattttagta atccttttc atttagagct     1860 aatccagata taattgggat aagtgaacaa cctctatttg gtgcaggttc tattagtagc    1920
ggtgaacttt atatagataa aattgaaatt attctagcag atgcaacatt tgaagcagaa    1980
tctgatttag aaagagcgca aaggcggtg aatgcgctgt ttacgtctac aaaccaacta    2040
gggctaaaaa caaatgtaac ggattatcat attgatcaag tgtccaattt agttacgtat    2100
ttatcggatg aattttgtct ggatgaaaag cgagaattgt ccgagaaagt caaacatgcg    2160
aagcgactca gtgatgaacg caatttactc caagattcaa atttcaaaga cattaatagg    2220
caaccagaac gtgggtgggg cggaagtaca gggattacca tccaaggagg ggatgacgta    2280
tttaaagaaa attacgtcac actatcaggt acctttgatg agtgctatcc aacatatttg    2340
tatcaaaaaa tcgatgaatc aaaattaaaa gcctttaccc gttatcaatt aagagggtat    2400
atcgaagata gtcaagactt agaaatctat ttaattcgct acaatgcaaa acatgaaaca    2460
gtaaatgtgc caggtacggg ttccttatgg ccgctttcag cccaaagtcc aatcggaaag    2520
tgtggagagc cgaatcgatg cgcgccacac cttgaatgga atcctgactt agattgttcg    2580
tgtagggatg gagaaagtg tgcccatcat tcgcatcatt tctccttaga cattgatgta    2640
ggatgtacag acttaaatga ggacctaggt gtatgggtga tctttaagat taagacgcaa    2700
gatgggcacg caagactagg gaatctgag tttctcgaag agaaaccatt agtaggagaa    2760
gcgctagctc gtgtgaaaag agcggagaaa aaatggagag acaaacgtga aaaattggaa    2820
tgggaaacaa atatcgttta taagaggca aaagaatctg tagatgcttt atttgtaaac    2880
tctcaatatg atcaattaca agcggatacg aatattgcca tgattcatgc ggcagataaa    2940
cgtgttcata gcattcgaga agcttatctg cctgagctgt ctgtgattcc gggtgtcaat    3000
gcggctattt ttgaagaatt agaagggcgt attttcactg cattctccct atatgatgcg    3060
agaaatgtca ttaaaaatgg tgattttaat aatggcttat cctgctggaa cgtgaaaggg    3120
catgtagatg tagaagaaca aaacaaccaa cgttcggtcc ttgttgttcc ggaatgggaa    3180
gcagaagtgt cacaagaagt tcgtgtctgt ccgggtcgtg gctatatcct tcgtgtcaca    3240
gcgtacaagg agggatatgg agaaggttgc gtaaccattc atgagatcga gaacaataca    3300
gacgaactga gtttagcaa ctgcgtagaa gaggaaatct atccaaataa cacggtaacg    3360
tgtaatgatt atactgtaaa tcaagaagaa tacggaggtg cgtacacttc tcgtaatcga    3420
ggatataacg aagctccttc cgtaccagct gattatgcgt cagtctatga gaaaaatcg     3480 tatacagatg gacgaagaga gaatccttgt gaatttaaca gagggtatag ggattacacg    3540
ccactaccag ttggttatgt gacaaaagaa ttagaatact tcccagaaac cgataaggta    3600
tggattgaga ttggagaaac ggaaggaaca tttatcgtgg acagcgtgga attactcctt    3660
atggaggaat ag                                                        3672
```

```
<210> SEQ ID NO 6
<211> LENGTH: 3672
<212> TYPE: DNA
<213> ORGANISM: Artificial
<220> FEATURE:
<223> OTHER INFORMATION: Synthetic nucleotide sequence designed for
      expression in a plant cell encoding TIC860.

<400> SEQUENCE: 6
atgaccagca accggaagaa cgagaacgag atcatcaacg ccctgagcat cccgaccgtg      60 agcaaccta gcacccagat gaacctgagc cctgacgctc gcatcgagga ctccctctgc     120
gtggctgagg tgaacaacat cgacccgttc gtgtccgcct ccaccgtgca gaccggcatc     180
aacatcgcgg gccgcatcct cggcgtgctc ggcgtgccct tgcgggccca gctcgcctcc     240
ttctactcct cctcgtggg agagctgtgg ccctccggcc gcgacccgtg ggagatcttc     300
ctggagcacg tggagcagct catccgccag caagtcaccg agaacaccg caacaccgcc      360 atcgcccgcc tggagggcct gggccgtggc taccgctcct accagcaagc cctggagacc     420
tggctcgaca accgcaacga cgcccgctcc cgctccatca tcctggagcg ctacgtcgcc     480
ctggaactgg acatcaccac tgccatccca ctcttccgca tcaggaacga ggaggtgcct     540
ctgctgatgg tgtacgccca ggctgcgaac ctgcacctgc tgctgctgcg cgacgcaagc     600
ctgtttggct ccgagtgggg tatggcaagc tccgacgtca accagtacta ccaggagcag     660
atccgctaca ccgaggagta cagcaaccac tgcgtccagt ggtacaacac cggtctgaac     720
aatctcagag ggaccaacgc tgagagctgg ctgcgctaca accagttccg gcgggatctg     780
accctaggtg tcctggatct ggtcgctctg ttccccgagct acgataccag gacgtaccct     840
atcaacacct tgctcagct taccagggag atctacactg atcctatcgg taggactaac     900
gctcctagtg gtttcgccag cactaactgg ttcaacaaca acgcgcctag tttctctgcc     960
atcgaggcgg cgatcttccg gcctcctcac ctcctcgact tcccggagca gcttactatc    1020
tactctgcgt cttcgcggtg gtcttcgact cagcacatga actactgggt tggtcaccgg    1080
cttaacttcc gcccgattgg aggaactctt aacaccagta cgcaaggtct tacgaacaac    1140
acttccatca acccggttac gttgcagttc acgtctcggg acgtttaccg gacggagtcg    1200
aatgctggga cgaacatcct gttcacgaca ccggtgaatg tgttccgtg gcacgtttc     1260 aacttcatca acccgcagaa catctacgag cgtggagcaa cgacatactc gcaaccatac    1320
caaggcgttg gcatccaact gtttgactcg gagacggaac tgccaccaga gacgacagaa    1380
cgtccgaatt acgagtcata ctcacacaga ctatcacaca ttggactcat tatcggaaac    1440
acactgagag caccagtgta ctcatggaca catcggtcag cagatcgtac gaacaccatc    1500
ggacccaatc ggatcaacca gatcccgctc gtgaagggct tccgcgtgtg ggcggcacc     1560 tccgtcatca ccggtccggg cttcaccggc ggcgacatcc tccgccgcaa caccttcggc    1620
gacttcgtgt cactccaagt gaacatcaac agcccgatca cccagcgcta tcgcctccgc    1680
ttccgctacg cctcctcccg cgacgctaga gtgatcgtgc tcaccggagc ggcgtccaca    1740
ggcgtaggcg gccaagtgtc tgtgaacatg ccgctccaga agactatgga gattggtgag    1800
aacctcacct ctcgcacctt ccgctacacc gacttctcca atccgttctc cttcagagcc    1860
aacccagaca tcatcggcat ctccgagcag cctctctttg gcgctggctc catctcctcc    1920
ggcgagctgt acatcgacaa gattgagatc atccttgccg acgccacctt cgaagctgag    1980
tccgatctcg agcgcgccca gaaggccgtg aacgcccctct tcactagcac taaccagctc    2040
ggcctcaaga ctaacgtgac cgactaccac attgaccaag tgagcaacct agtgacctac    2100
```

```
cttagcgacg agttctgcct tgacgagaag cgtgagctga gcgagaaggt gaagcacgcc    2160
aagcgcctct ccgacgagcg caacctcctc caggactcca acttcaagga catcaaccgc    2220
cagcccgagc gcggctgggg cggtagcacc ggcatcacca tccagggcgg tgacgatgtg    2280
ttcaaggaga actacgtgac cctctccggc accttcgacg agtgctaccc gacctacctc    2340
taccagaaga tcgacgagtc caagctcaag gcgttcaccc gctaccagct tcgcggctac    2400
atcgaggact cccaggatct ggagatctac ctcatccgct acaacgccaa gcacgagacc    2460
gtgaacgtgc ccggcaccgg ctccctctgg ccgctctccg cccagagccc tatcggcaag    2520
tgcggcgagc ccaaccgctg cgcgcctcac ctggagtgga accctgacct cgactgctcc    2580
tgccgcgacg gcgagaagtg cgcccaccat agccaccact tctctctcga catcgacgtg    2640
ggctgcaccg acctcaacga ggatctgggc gtgtgggtga tcttcaagat caagacccag    2700
gacggccacg ccaggctggg caacctggag ttcctggagg agaagcctct ggtgggtgag    2760
gccctggcca gggtcaagag ggctgagaag aaatggaggg acaagaggga gaagctggag    2820
tgggagacca acatcgtgta caaggaggct aaggagtccg tggacgctct gttcgtcaac    2880
tctcagtacg atcagctcca ggctgacacc aacatcgcta tgatccacgc tgcggataag    2940
agggtccact ctatcaggga ggcttacctg cctgagcttt ctgtcatccc tggtgtcaac    3000
gcggcaatct tcgaggaact tgagggccgc atcttcactg cgttctcgct ttacgatgcg    3060
cggaacgtca ttaagaacgg tgacttcaac aatggtcttt cgtgctggaa cgtcaagggt    3120
catgtcgatg tcgaggaaca gaacaaccag cggtcggtcc ttgtcgttcc cgagtgggag    3180
gccgaggtct cgcaagaggt ccgggtctgc cctgggcgcg gtacattct tcgtgtcact    3240
gcgtacaagg agggctacgg cgagggctgc gttactattc atgagattga gaacaatacg    3300
gatgagctta agtttagtaa ctgtgttgag gaggagatct acccgaacaa tacggttacg    3360
tgcaatgatt acacggtgaa ccaggaggaa tacggcggag catacacctc acgtaataga    3420
gggtacaatg aggcaccgtc agttccggca gattatgcct cagtttatga ggagaagtcc    3480
tacacggatg gaagacgcga gaatccatgt gagtttaata gaggataccg agactacaca    3540
ccactcccag ttggatacgt tacaaaggag ttggaatact ccccagaaac agataaagtt    3600
tggatagaga tcggagaaac agaaggaacc ttcatcgtgg acagtgtaga actgctgctg    3660
atggaagaat ga                                                         3672
```

<210> SEQ ID NO 7
<211> LENGTH: 1223
<212> TYPE: PRT
<213> ORGANISM: Artificial
<220> FEATURE:
<223> OTHER INFORMATION: Amino acid sequence of the chimeric protein TIC860.

<400> SEQUENCE: 7

Met Thr Ser Asn Arg Lys Asn Glu Asn Glu Ile Ile Asn Ala Leu Ser
1               5                   10                  15

Ile Pro Thr Val Ser Asn Pro Ser Thr Gln Met Asn Leu Ser Pro Asp
            20                  25                  30

Ala Arg Ile Glu Asp Ser Leu Cys Val Ala Glu Val Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser

```
            65                  70                  75                  80
    Phe Tyr Ser Phe Leu Val Gly Glu Leu Trp Pro Ser Gly Arg Asp Pro
                    85                  90                  95

Trp Glu Ile Phe Leu Glu His Val Glu Gln Leu Ile Arg Gln Gln Val
                    100                 105                 110

Thr Glu Asn Thr Arg Asn Thr Ala Ile Ala Arg Leu Glu Gly Leu Gly
                    115                 120                 125

Arg Gly Tyr Arg Ser Tyr Gln Gln Ala Leu Glu Thr Trp Leu Asp Asn
        130                 135                 140

Arg Asn Asp Ala Arg Ser Arg Ser Ile Ile Leu Glu Arg Tyr Val Ala
    145                 150                 155                 160

Leu Glu Leu Asp Ile Thr Thr Ala Ile Pro Leu Phe Arg Ile Arg Asn
                    165                 170                 175

Glu Glu Val Pro Leu Leu Met Val Tyr Ala Gln Ala Ala Asn Leu His
                    180                 185                 190

Leu Leu Leu Leu Arg Asp Ala Ser Leu Phe Gly Ser Glu Trp Gly Met
                    195                 200                 205

Ala Ser Ser Asp Val Asn Gln Tyr Tyr Gln Glu Gln Ile Arg Tyr Thr
        210                 215                 220

Glu Glu Tyr Ser Asn His Cys Val Gln Trp Tyr Asn Thr Gly Leu Asn
    225                 230                 235                 240

Asn Leu Arg Gly Thr Asn Ala Glu Ser Trp Leu Arg Tyr Asn Gln Phe
                    245                 250                 255

Arg Arg Asp Leu Thr Leu Gly Val Leu Asp Leu Val Ala Leu Phe Pro
                    260                 265                 270

Ser Tyr Asp Thr Arg Thr Tyr Pro Ile Asn Thr Ser Ala Gln Leu Thr
                    275                 280                 285

Arg Glu Ile Tyr Thr Asp Pro Ile Gly Arg Thr Asn Ala Pro Ser Gly
                    290                 295                 300

Phe Ala Ser Thr Asn Trp Phe Asn Asn Asn Ala Pro Ser Phe Ser Ala
    305                 310                 315                 320

Ile Glu Ala Ala Ile Phe Arg Pro Pro His Leu Leu Asp Phe Pro Glu
                    325                 330                 335

Gln Leu Thr Ile Tyr Ser Ala Ser Ser Arg Trp Ser Ser Thr Gln His
                    340                 345                 350

Met Asn Tyr Trp Val Gly His Arg Leu Asn Phe Arg Pro Ile Gly Gly
                    355                 360                 365

Thr Leu Asn Thr Ser Thr Gln Gly Leu Thr Asn Asn Thr Ser Ile Asn
        370                 375                 380

Pro Val Thr Leu Gln Phe Thr Ser Arg Asp Val Tyr Arg Thr Glu Ser
    385                 390                 395                 400

Asn Ala Gly Thr Asn Ile Leu Phe Thr Thr Pro Val Asn Gly Val Pro
                    405                 410                 415

Trp Ala Arg Phe Asn Phe Ile Asn Pro Gln Asn Ile Tyr Glu Arg Gly
                    420                 425                 430

Ala Thr Thr Tyr Ser Gln Pro Tyr Gln Gly Val Gly Ile Gln Leu Phe
                    435                 440                 445

Asp Ser Glu Thr Glu Leu Pro Pro Glu Thr Thr Glu Arg Pro Asn Tyr
                    450                 455                 460

Glu Ser Tyr Ser His Arg Leu Ser His Ile Gly Leu Ile Ile Gly Asn
    465                 470                 475                 480

Thr Leu Arg Ala Pro Val Tyr Ser Trp Thr His Arg Ser Ala Asp Arg
                    485                 490                 495
```

```
Thr Asn Thr Ile Gly Pro Asn Arg Ile Asn Gln Ile Pro Leu Val Lys
            500                 505                 510

Gly Phe Arg Val Trp Gly Gly Thr Ser Val Ile Thr Gly Pro Gly Phe
            515                 520                 525

Thr Gly Gly Asp Ile Leu Arg Arg Asn Thr Phe Gly Asp Phe Val Ser
            530                 535                 540

Leu Gln Val Asn Ile Asn Ser Pro Ile Thr Gln Arg Tyr Arg Leu Arg
545                 550                 555                 560

Phe Arg Tyr Ala Ser Ser Arg Asp Ala Arg Val Ile Val Leu Thr Gly
                565                 570                 575

Ala Ala Ser Thr Gly Val Gly Gly Gln Val Ser Val Asn Met Pro Leu
            580                 585                 590

Gln Lys Thr Met Glu Ile Gly Glu Asn Leu Thr Ser Arg Thr Phe Arg
            595                 600                 605

Tyr Thr Asp Phe Ser Asn Pro Phe Ser Phe Arg Ala Asn Pro Asp Ile
            610                 615                 620

Ile Gly Ile Ser Glu Gln Pro Leu Phe Gly Ala Gly Ser Ile Ser Ser
625                 630                 635                 640

Gly Glu Leu Tyr Ile Asp Lys Ile Glu Ile Ile Leu Ala Asp Ala Thr
                645                 650                 655

Phe Glu Ala Glu Ser Asp Leu Glu Arg Ala Gln Lys Ala Val Asn Ala
            660                 665                 670

Leu Phe Thr Ser Thr Asn Gln Leu Gly Leu Lys Thr Asn Val Thr Asp
            675                 680                 685

Tyr His Ile Asp Gln Val Ser Asn Leu Val Thr Tyr Leu Ser Asp Glu
            690                 695                 700

Phe Cys Leu Asp Glu Lys Arg Glu Leu Ser Glu Lys Val Lys His Ala
705                 710                 715                 720

Lys Arg Leu Ser Asp Glu Arg Asn Leu Leu Gln Asp Ser Asn Phe Lys
                725                 730                 735

Asp Ile Asn Arg Gln Pro Glu Arg Gly Trp Gly Gly Ser Thr Gly Ile
            740                 745                 750

Thr Ile Gln Gly Gly Asp Asp Val Phe Lys Glu Asn Tyr Val Thr Leu
            755                 760                 765

Ser Gly Thr Phe Asp Glu Cys Tyr Pro Thr Tyr Leu Tyr Gln Lys Ile
            770                 775                 780

Asp Glu Ser Lys Leu Lys Ala Phe Thr Arg Tyr Gln Leu Arg Gly Tyr
785                 790                 795                 800

Ile Glu Asp Ser Gln Asp Leu Glu Ile Tyr Leu Ile Arg Tyr Asn Ala
                805                 810                 815

Lys His Glu Thr Val Asn Val Pro Gly Thr Gly Ser Leu Trp Pro Leu
            820                 825                 830

Ser Ala Gln Ser Pro Ile Gly Lys Cys Gly Glu Pro Asn Arg Cys Ala
            835                 840                 845

Pro His Leu Glu Trp Asn Pro Asp Leu Asp Cys Ser Cys Arg Asp Gly
            850                 855                 860

Glu Lys Cys Ala His His Ser His His Phe Ser Leu Asp Ile Asp Val
865                 870                 875                 880

Gly Cys Thr Asp Leu Asn Glu Asp Leu Gly Val Trp Val Ile Phe Lys
                885                 890                 895

Ile Lys Thr Gln Asp Gly His Ala Arg Leu Gly Asn Leu Glu Phe Leu
            900                 905                 910
```

Glu Glu Lys Pro Leu Val Gly Glu Ala Leu Ala Arg Val Lys Arg Ala
            915                 920                 925

Glu Lys Lys Trp Arg Asp Lys Arg Glu Lys Leu Glu Trp Glu Thr Asn
        930                 935                 940

Ile Val Tyr Lys Glu Ala Lys Glu Ser Val Asp Ala Leu Phe Val Asn
945                 950                 955                 960

Ser Gln Tyr Asp Gln Leu Gln Ala Asp Thr Asn Ile Ala Met Ile His
            965                 970                 975

Ala Ala Asp Lys Arg Val His Ser Ile Arg Glu Ala Tyr Leu Pro Glu
            980                 985                 990

Leu Ser Val Ile Pro Gly Val Asn  Ala Ala Ile Phe Glu  Glu Leu Glu
            995                 1000                1005

Gly Arg  Ile Phe Thr Ala Phe  Ser Leu Tyr Asp Ala  Arg Asn Val
    1010                1015                1020

Ile Lys  Asn Gly Asp Phe Asn  Asn Gly Leu Ser Cys  Trp Asn Val
    1025                1030                1035

Lys Gly  His Val Asp Val Glu  Glu Gln Asn Asn Gln  Arg Ser Val
    1040                1045                1050

Leu Val  Val Pro Glu Trp Glu  Ala Glu Val Ser Gln  Glu Val Arg
    1055                1060                1065

Val Cys  Pro Gly Arg Gly Tyr  Ile Leu Arg Val Thr  Ala Tyr Lys
    1070                1075                1080

Glu Gly  Tyr Gly Glu Gly Cys  Val Thr Ile His Glu  Ile Glu Asn
    1085                1090                1095

Asn Thr  Asp Glu Leu Lys Phe  Ser Asn Cys Val Glu  Glu Glu Ile
    1100                1105                1110

Tyr Pro  Asn Asn Thr Val Thr  Cys Asn Asp Tyr Thr  Val Asn Gln
    1115                1120                1125

Glu Glu  Tyr Gly Gly Ala Tyr  Thr Ser Arg Asn Arg  Gly Tyr Asn
    1130                1135                1140

Glu Ala  Pro Ser Val Pro Ala  Asp Tyr Ala Ser Val  Tyr Glu Glu
    1145                1150                1155

Lys Ser  Tyr Thr Asp Gly Arg  Arg Glu Asn Pro Cys  Glu Phe Asn
    1160                1165                1170

Arg Gly  Tyr Arg Asp Tyr Thr  Pro Leu Pro Val Gly  Tyr Val Thr
    1175                1180                1185

Lys Glu  Leu Glu Tyr Phe Pro  Glu Thr Asp Lys Val  Trp Ile Glu
    1190                1195                1200

Ile Gly  Glu Thr Glu Gly Thr  Phe Ile Val Asp Ser  Val Glu Leu
    1205                1210                1215

Leu Leu  Met Glu Glu
    1220

<210> SEQ ID NO 8
<211> LENGTH: 3564
<212> TYPE: DNA
<213> ORGANISM: Artificial
<220> FEATURE:
<223> OTHER INFORMATION: Recombinant nucleotide sequence used for
      expression in a bacterial cell encoding TIC867.

<400> SEQUENCE: 8
atgacttcaa ataggaaaaa tgagaatgaa attataaatg ctttatcgat tccagctgta      60
tcgaatcatt ccgcacaaat gaatctatca accgatgctc gtattgagga tagcttgtgt     120
atagccgagg ggaacaatat cgatccattt gttagcgcat caacagtcca aacgggtatt     180

```
aacatagctg gtagaatact aggtgtatta ggcgtaccgt ttgctggaca aatagctagt    240
ttttatagtt ttcttgttgg tgaattatgg ccccgcggca gagatccttg ggaaattttc    300
ctagaacatg tcgaacaact tataagacaa caagtaacag aaaatactag ggatacggct    360
cttgctcgat tacaaggttt aggaaattcc tttagagcct atcaacagtc acttgaagat    420
tggctagaaa accgtgatga tgcaagaacg agaagtgttc tttatacccca atatatagcc    480 ttagaacttg attttcttaa tgcgatgccg cttttcgcaa ttagaaacca agaagttcca    540
ttattaatgg tatatgctca agctgcaaat ttacacctat tattattgag agatgcctct    600 cttttttggta gtgaatttgg gcttacatcc caagaaattc aacgttatta tgagcgccaa    660
gtggaaaaaa cgagagaata ttctgattat tgcgcaagat ggtataatac gggtttaaat    720
aatttgagag gacaaatgc tgaaagttgg ttgcgatata atcaattccg tagagactta    780
acgctaggag tattagatct agtggcacta ttcccaagct atgacacgcg tgtttatcca    840
atgaatacca gtgctcaatt aacaagagaa atttatacag atccaattgg gagaacaaat    900
gcaccttcag gatttgcaag tacgaattgg tttaataata tgcaccatc gttttctgcc    960 atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacggaaa taccaatact   1140
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta cacaaatacc attggtaaag gcgcataccc tccaatcggg taccactgta   1560
gtaaaagggc cagggtttac aggaggggat atcctccgtc gaacaagtgg aggaccattt   1620
gcttttagta atgttaatct agattttaac ttgtcacaaa ggtatcgtgc tagaattcgt   1680
tatgcctcta ctactaacct aagaatttac gtaacggttg caggtgaacg aattttttgct   1740 ggtcaatttg acaaaactat ggatgctggt gccccattaa cattccaatc ttttagttac   1800
gcaactatta atacagcttt tacattccca gaaagatcga gcagcttgac tgtaggtgcc   1860
gatacgttta gttcaggtaa tgaagtttat gtagatagat ttgaattaat cccagttact   1920
gcaaccttcg aggcagaatc tgatttagaa agagcacaaa aggcggtgaa tgagctgttt   1980
acttcttcca atcaaatcgg gttaaaaaca gatgtgacgg attatcatat tgatcaagta   2040
tccaatttag ttgagtgttt atctgatgaa ttttgtctgg atgaaaaaaa agaattgtcc   2100
gagaaagtca acatgcgaa gcgacttagt gatgagcgga atttacttca agatccaaac   2160
tttagaggga tcaatagaca actagaccgt ggctggagag aagtacgga tattaccatc   2220 caaggaggcg atgacgtatt caaagagaat tacgttacgc tatttgggtac ctttgatgag   2280 tgctatccaa cgtatttata tcaaaaaata gatgagtcga aattaaaagc ctatacccgt   2340
taccaattaa gagggtatat cgaagatagt caagacttag aaatctatttt aattcgctac   2400 aatgccaaac acgaaacagt aaatgtgcca ggtacgggtt ccttatggcc gctttcagcc   2460
ccaagtccaa tcggaaaatg tgcccatcat tcccatcatt tctccttgga cattgatgtt   2520
```

```
ggatgtacag acttaaatga ggacttaggt gtatgggtga tattcaagat taagacgcaa    2580
gatggccatg caagactagg aaatctagaa tttctcgaag agaaaccatt agtaggagaa    2640
gcactagctc gtgtgaaaag agcggagaaa aaatggagag acaaacgtga aaaattggaa    2700
tgggaaacaa atattgttta taagaggca aaagaatctg tagatgcttt atttgtaaac    2760
tctcaatatg atagattaca agcggatacc aacatcgcga tgattcatgc ggcagataaa    2820
cgcgttcata gcattcgaga agcttatctg cctgagctgt ctgtgattcc gggtgtcaat    2880
gcggctattt ttgaagaatt agaagggcgt attttcactg cattctccct atatgatgcg    2940
agaaatgtca ttaaaaatgg tgattttaat aatggcttat cctgctggaa cgtgaaaggg    3000
catgtagatg tagaagaaca aaacaaccac cgttcggtcc ttgttgttcc ggaatgggaa    3060
gcagaagtgt cacaagaagt tcgtgtctgt ccgggtcgtg gctatatcct tcgtgtcaca    3120
gcgtacaagg agggatatgg agaaggttgc gtaaccattc atgagatcga gaacaataca    3180
gacgaactga gtttagcaa ctgtgtagaa gaggaagtat atccaaacaa cacggtaacg    3240
tgtaatgatt atactgcgac tcaagaagaa tatgagggta cgtacacttc tcgtaatcga    3300
ggatatgacg gagcctatga aagcaattct tctgtaccag ctgattatgc atcagcctat    3360
gaagaaaaag catatacaga tggacgaaga gacaatcctt gtgaatctaa cagaggatat    3420
ggggattaca caccactacc agctggctat gtgacaaaag aattagagta cttcccagaa    3480
accgataagg tatggattga gatcggagaa acggaaggaa cattcatcgt ggacagcgtg    3540
gaattacttc ttatggagga atag                                            3564
```

```
<210> SEQ ID NO 9
<211> LENGTH: 3564
<212> TYPE: DNA
<213> ORGANISM: Artificial
<220> FEATURE:
<223> OTHER INFORMATION: Synthetic nucleotide sequence designed for
      expression in a plant cell encoding TIC867.

<400> SEQUENCE: 9
```

```
atgaccagca accgaaagaa cgagaacgag atcatcaacg ccctgtccat accggccgtg     60
tcaaaccact ccgcccagat gaacctctcc accgacgcga ggatcgagga ctccctctgc    120
atcgccgagg gcaacaacat cgacccgttc gtgtctgcaa gcacggtcca gaccggcatc    180
aacatcgcgg gccgcatcct gggcgtgctc ggcgtgccct tcgcgggtca aatcgcctct    240
ttctactcat tcctcgtggg cgagctgtgg ccgcgcggac gtgaccgtg ggaaatcttc    300 ctggagcacg ttgagcagct catccggcag caagtgaccg agaacaccag ggacaccgca    360
ctggcacggc tccagggcct tggcaacagc ttccgcgcct accagcagtc gctggaggac    420
tggctggaga accgagacga cgccagaacc cgctcagttc tgtacacaca gtacatcgcc    480
ctagagctgg acttcctcaa cgctatgccg ctcttcgcca tccgtaacca ggaagtaccg    540
cttctgatgt tgtacgcaca agcagcgaac ctccatctgc tcctgctgcg agacgcatct    600
ctgttcggca gtgagttcgg gctgacgagc caggagatcc agcgctacta cgagcgccaa    660
gtggagaaga ctcgtgagta cagcgactac tgcgcgcgct ggtacaacac gggcttgaac    720
aaccttcgcg ggacaaacgc cgaatcctgg cttcgctaca accagttccg ccgcgacctc    780
acgctgggtg tgctggacct ggtcgcgctc tttcccgtcct acgacacacg ggtgtaccca    840
atgaacacga gcgcacagct cacccgtgag atctacacag atcccatcgg ccgcaccaac    900
gctcccagtg gcttcgcaag cacgaattgg ttcaacaata acgctccttc tttctctgcc    960
```

```
atcgaggccg ctgtcatcag accgccgcac ttactcgatt tcccggagca gctcactatc    1020
ttctctgtgt tgtcccggtg gtcgaacacg cagtacatga actactgggt gggccacagg    1080
ctagagagcc ggaccatccg tggcagtctc tcaacctcga cccacggcaa cacgaacacg    1140
agcatcaacc ctgtcactct ccagtttaca tctagggacg tttacaggac agagtcgttc    1200
gctggcatta acattctgtt gaccactccg gtgaacggcg tcccttgggc ccgcttcaac    1260
tggaggaatc tctgaactc actgcgcggc agccttctct acactatcgg ctacaccggc     1320
gttgggacgc aactcttcga ctcggagacc gagctgccgc ccgagaccac cgagcggcct    1380
aactacgaga gttattcaca caggctctcc aacatccgct tgatttctgg gaacaccttg    1440
cgggctccgg tgtactcctg gacgcaccgc agcgccgaca gaactaatac catcagctcc    1500
gactcgatca cccagatccc gctggtgaag gctcacacgc ttcagtcggg caccacagtc    1560
gtcaagggcc ctggcttcac cggcggcgac atcctgcgtc gcacatctgg cggaccyrryc  1620 gccttcagca acgtgaactt ggacttcaat ttgtcacagc ggtatcgtgc cagaatccgg    1680
tacgccagca ctacgaacct gcgaatctat gttactgtgg cgggcgagcg gatcttcgcc    1740
gggcaattcg acaagacgat ggacgcggga gcacctctga cattccagtc attctcttac    1800
gccacgatca acacggcatt cacgtttccg gagcgttcca gtagcctgac cgtgggcgct    1860
gataccttca gtagcgggaa cgaggtgtac gttgaccgtt tcgagctgat cccggtcacc    1920
gccaccttcg aagctgagtc ggacctggag cgtgcacaga aggcagtcaa cgagctgttc    1980
acctctagca accagatcgg cctcaagacc gacgtcacag actaccacat cgaccaagtg    2040
tccaacctgg tcgagtgcct tagcgacgag ttctgcctag acgagaagaa ggagctgtcg    2100
gagaaggtca acacgccaa gcgtctgagc gatgagcgca acctgctcca agaccctaac     2160
ttccgtggca tcaacaggca gcttgaccgt ggctggcgcg gtcgacgga catcacgatc      2220 cagggtggcg acgacgtatt caaggagaat tacgtgacct tgcttgggac gtttgacgag    2280
tgctatccca cctacctcta ccagaagatt gatgaatcga aattgaaggc gtacacgaga    2340
taccagctcc gtggctacat cgaggacagc caggacttgg agatctacct catacgctac    2400
aacgctaaac atgagaccgt gaacgtccct gggacgggca gtctgtggcc actctctgct    2460
cctagcccta tcggcaagtg cgctcaccac tcgcaccact tcagccttga catcgacgtg    2520
ggatgtactg acctcaacga agaccctggg cgtctgggtta tcttcaagat caagacccag   2580
gacggccacg cccgactcgg caacctggag ttcctggagg agaaaccact ggtgggcgag    2640
gcgctcgccc gcgtgaagcg tgccgagaag aagtggcggg acaagaggga gaagctagaa    2700
tgggagacga acatcgtgta caaggaggcc aaggaaagcg tcgatgccct gttcgtgaac    2760
tcacagtacg accgtctcca ggcggacacg aacatcgcca tgatccacgc ggctgacaag    2820
cgcgtccact ccatccgcga ggcgtactta ccggagctgt cggtgatccc aggcgtaaac    2880
gcggcgatct tcgaggagct agagggacgc atcttcacag cgttcagcct gtacgacgca    2940
cgcaacgtca tcaagaacgg cgatttcaac aacggactgt cctgctggaa cgtgaagggc    3000
cacgtcgatg tcgaggaaca gaacaaccac cgctctgtcc tggtggtccc agagtgggag    3060
gccgaggtct cccaggaggt ccgcgtgtgc cctgggcgtg gctacatcct ccgtgtgaca    3120
gcctacaagg agggctacgg tgagggctgc gtcaccattc acgagatcga gaacaacact    3180
gacgaactca gttctcgaa ttgcgtggag gaggaggtgt acccgaacaa tacggtgacg     3240
tgcaacgact acacggcaac ccaagaggag tacgagggca cctacaccag taggaaccgt    3300
ggctacgacg gtgcctacga gtcgaactcc agcgtccctg cggactacgc cagcgcgtac    3360
```

```
gaggagaagg cttacaccga cggacgccgg gacaacccat gcgagagcaa ccgtggctac    3420
ggcgactaca ctcctctccc ggccggatac gtcacaaagg agctggagta tttcccagag    3480
acggacaagg tgtggatcga aatcggagag acagagggaa ccttcatcgt ggacagcgtg    3540
gagctgctcc tcatggagga gtga                                          3564
```

```
<210> SEQ ID NO 10
<211> LENGTH: 1187
<212> TYPE: PRT
<213> ORGANISM: Artificial
<220> FEATURE:
<223> OTHER INFORMATION: Amino acid sequence of the chimeric protein
      TIC867.

<400> SEQUENCE: 10
```

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320
```

```
Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
            370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
            485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
            515                 520                 525

Gly Asp Ile Leu Arg Arg Thr Ser Gly Gly Pro Phe Ala Phe Ser Asn
            530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
            565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
            595                 600                 605

Phe Pro Glu Arg Ser Ser Ser Leu Thr Val Gly Ala Asp Thr Phe Ser
            610                 615                 620

Ser Gly Asn Glu Val Tyr Val Asp Arg Phe Glu Leu Ile Pro Val Thr
625                 630                 635                 640

Ala Thr Phe Glu Ala Glu Ser Asp Leu Glu Arg Ala Gln Lys Ala Val
            645                 650                 655

Asn Glu Leu Phe Thr Ser Ser Asn Gln Ile Gly Leu Lys Thr Asp Val
            660                 665                 670

Thr Asp Tyr His Ile Asp Gln Val Ser Asn Leu Val Glu Cys Leu Ser
            675                 680                 685

Asp Glu Phe Cys Leu Asp Glu Lys Lys Glu Leu Ser Glu Lys Val Lys
            690                 695                 700

His Ala Lys Arg Leu Ser Asp Glu Arg Asn Leu Leu Gln Asp Pro Asn
705                 710                 715                 720

Phe Arg Gly Ile Asn Arg Gln Leu Asp Arg Gly Trp Arg Gly Ser Thr
            725                 730                 735
```

-continued

Asp Ile Thr Ile Gln Gly Gly Asp Val Phe Lys Glu Asn Tyr Val
            740                 745                 750
Thr Leu Leu Gly Thr Phe Asp Glu Cys Tyr Pro Thr Tyr Leu Tyr Gln
            755                 760                 765
Lys Ile Asp Glu Ser Lys Leu Lys Ala Tyr Thr Arg Tyr Gln Leu Arg
    770                 775                 780
Gly Tyr Ile Glu Asp Ser Gln Asp Leu Glu Ile Tyr Leu Ile Arg Tyr
785                 790                 795                 800
Asn Ala Lys His Glu Thr Val Asn Val Pro Gly Thr Gly Ser Leu Trp
                805                 810                 815
Pro Leu Ser Ala Pro Ser Pro Ile Gly Lys Cys Ala His His Ser His
            820                 825                 830
His Phe Ser Leu Asp Ile Asp Val Gly Cys Thr Asp Leu Asn Glu Asp
            835                 840                 845
Leu Gly Val Trp Val Ile Phe Lys Ile Lys Thr Gln Asp Gly His Ala
    850                 855                 860
Arg Leu Gly Asn Leu Glu Phe Leu Glu Glu Lys Pro Leu Val Gly Glu
865                 870                 875                 880
Ala Leu Ala Arg Val Lys Arg Ala Glu Lys Lys Trp Arg Asp Lys Arg
                885                 890                 895
Glu Lys Leu Glu Trp Glu Thr Asn Ile Val Tyr Lys Glu Ala Lys Glu
            900                 905                 910
Ser Val Asp Ala Leu Phe Val Asn Ser Gln Tyr Asp Arg Leu Gln Ala
            915                 920                 925
Asp Thr Asn Ile Ala Met Ile His Ala Ala Asp Lys Arg Val His Ser
    930                 935                 940
Ile Arg Glu Ala Tyr Leu Pro Glu Leu Ser Val Ile Pro Gly Val Asn
945                 950                 955                 960
Ala Ala Ile Phe Glu Glu Leu Glu Gly Arg Ile Phe Thr Ala Phe Ser
                965                 970                 975
Leu Tyr Asp Ala Arg Asn Val Ile Lys Asn Gly Asp Phe Asn Asn Gly
            980                 985                 990
Leu Ser Cys Trp Asn Val Lys Gly His Val Asp Val Glu Glu Gln Asn
            995                 1000                1005
Asn His Arg Ser Val Leu Val Val Pro Glu Trp Glu Ala Glu Val
    1010                1015                1020
Ser Gln Glu Val Arg Val Cys Pro Gly Arg Gly Tyr Ile Leu Arg
    1025                1030                1035
Val Thr Ala Tyr Lys Glu Gly Tyr Gly Glu Gly Cys Val Thr Ile
    1040                1045                1050
His Glu Ile Glu Asn Asn Thr Asp Glu Leu Lys Phe Ser Asn Cys
    1055                1060                1065
Val Glu Glu Glu Val Tyr Pro Asn Asn Thr Val Thr Cys Asn Asp
    1070                1075                1080
Tyr Thr Ala Thr Gln Glu Glu Tyr Glu Gly Thr Tyr Thr Ser Arg
    1085                1090                1095
Asn Arg Gly Tyr Asp Gly Ala Tyr Glu Ser Asn Ser Ser Val Pro
    1100                1105                1110
Ala Asp Tyr Ala Ser Ala Tyr Glu Glu Lys Ala Tyr Thr Asp Gly
    1115                1120                1125
Arg Arg Asp Asn Pro Cys Glu Ser Asn Arg Gly Tyr Gly Asp Tyr
    1130                1135                1140
Thr Pro Leu Pro Ala Gly Tyr Val Thr Lys Glu Leu Glu Tyr Phe

```
                1145                 1150                 1155
Pro Glu Thr Asp Lys Val Trp Ile Glu Ile Gly Glu Thr Glu Gly
            1160                 1165                 1170

Thr Phe Ile Val Asp Ser Val Glu Leu Leu Leu Met Glu Glu
        1175                 1180                 1185

<210> SEQ ID NO 11
<211> LENGTH: 3642
<212> TYPE: DNA
<213> ORGANISM: Artificial
<220> FEATURE:
<223> OTHER INFORMATION: Recombinant nucleotide sequence used for
      expression in a bacterial cell encoding TIC867_20.

<400> SEQUENCE: 11
atgacttcaa ataggaaaaa tgagaatgaa attataaatg ctttatcgat tccagctgta     60
tcgaatcatt ccgcacaaat gaatctatca accgatgctc gtattgagga tagcttgtgt    120
atagccgagg ggaacaatat cgatccattt gttagcgcat caacagtcca acgggtatt    180 aacatagctg gtagaatact aggtgtatta ggcgtaccgt tgctggaca aatagctagt    240 tttatagtt tccttgttgg tgaattatgg ccccgcggca gagatccttg ggaaattttc    300
ctagaacatg tcgaacaact tataagacaa caagtaacag aaaatactag ggatacggct    360
cttgctcgat tacaaggttt aggaaattcc tttagagcct atcaacagtc acttgaagat    420
tggctagaaa accgtgatga tgcaagaacg agaagtgttc tttataccca atatatagcc    480
ttagaacttg attttcttaa tgcgatgccg cttttcgcaa ttagaaacca agaagttcca    540
ttattaatgg tatatgctca agctgcaaat ttacacctat tattattgag agatgcctct    600 cttttttggta gtgaatttgg gcttacatcc caagaaattc aacgttatta tgagcgccaa    660
gtggaaaaaa cgagagaata ttctgattat tgcgcaagat ggtataatac gggtttaaat    720
aatttgagag gacaaatgc tgaaagttgg ttgcgatata tcaattccg tagagactta    780 acgctaggag tattagatct agtggcacta ttcccaagct atgacacgcg tgtttatcca    840
atgaatacca gtgctcaatt aacaagagaa atttatacag atccaattgg agaacaaat    900 gcaccttcag gatttgcaag tacgaattgg tttaataata tgcaccatc gttttctgcc    960 atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacggaaa taccaatact   1140
tctattaatc ctgtaacatt acagttcaca tctcgagacg tttatagaac agaatcatttt  1200 gcagggataa atatacttct aactactcct gtgaatggag taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta cacaaatacc attggtaaag gcgcatacccc tccaatcggg taccactgta  1560
gtaaaagggc cagggtttac aggaggggat atcctccgtc gaacaagtgg aggaccattt   1620
gcttttagta atgttaatct agattttaac ttgtcacaaa ggtatcgtgc tagaattcgt   1680
tatgcctcta ctactaacct aagaatttac gtaacggttg caggtgaacg aattttttgct   1740 ggtcaatttg acaaaactat ggatgctggt gccccattaa cattccaatc ttttagttac   1800
```

-continued

```
gcaactatta atacagcttt tacattccca gaaagatcga gcagcttgac tgtaggtgcc    1860
gatacgttta gttcaggtaa tgaagtttat gtagatagat ttgaattaat cccagttact    1920
gcaacctttg aggcagaata tgatttagaa agagcgcaaa aggtggtgaa tgccctgttt    1980
acgtctacaa accaactagg gctaaaaaca gatgtgacgg attatcatat tgatcaggta    2040
tccaatctag ttgcgtgttt atcggatgaa ttttgtctgg atgaaaagag agaattgtcc    2100
gagaaagtta acatgcaaa gcgactcagt gatgagcgga atttacttca agatccaaac    2160
ttcagaggga tcaataggca accagaccgt ggctggagag aagtacgga tattactatc    2220 caaggaggag atgacgtatt caaagagaat tacgttacgc taccgggtac ctttgatgag    2280
tgctatccaa cgtatttata tcaaaaaata gatgagtcga aattaaaagc ctatacccgt    2340
tatcaattaa gagggtatat cgaagatagt caagacttag aaatctattt aattcgttac    2400
aatgcaaaac acgaaatagt aaatgtacca ggtacaggaa gtttatggcc tctttctgta    2460
gaaaatcaaa ttggaccttg tggagaaccg aatcgatgcg cgccacacct tgaatggaat    2520
cctgatttac actgttcctg cagagacggg gaaaaatgtg cacatcattc tcatcatttc    2580
tctttggaca ttgatgttgg atgtacagac ttaaatgagg acttaggtgt atgggtgata    2640
ttcaagatta agacgcaaga tggccacgca cgactaggga tctagagtt tctcgaagag    2700 aaaccattat taggagaagc actagctcgt gtgaaaagag cggagaaaaa atggagagac    2760
aaacgcgaaa cattacaatt ggaaacaact atcgtttata agaggcaaa gaatctgta     2820 gatgctttat ttgtaaactc tcaatatgat agattacaag cggatacgaa catcgcgatg    2880
attcatgcgg cagataaacg cgttcataga attcgagaag cgtatctgcc ggagctgtct    2940
gtgattccgg gtgtcaatgc ggctattttt gaagaattag aagagcgtat tttcactgca    3000
tttttcccta tatgatgcgag aaatattatt aaaaatggcg atttcaataa tggcttatta   3060
tgctggaacg tgaaagggca tgtagaggta gaagaacaaa acaatcaccg ttcagtcctg    3120
gttatcccag aatgggaggc agaagtgtca caagaggttc gtgtctgtcc aggtcgtggc    3180
tatatccttc gtgttacagc gtacaaagag ggatatggag aaggttgcgt aacgatccat    3240
gagatcgaga acaatacaga cgaactgaaa ttcaacaact gtgtagaaga ggaagtatat    3300
ccaaacaaca cggtaacgtg tattaattat actgcgactc aagaagaata tgagggtacg    3360
tacacttctc gtaatcgagg atatgacgaa gcctatggta taaccccttc cgtaccagct    3420
gattatgcgt cagtctatga agaaaaatcg tatacagata gacgaagaga gaatccttgt    3480
gaatctaaca gaggatatgg agattacaca ccactaccag ctggttatgt aacaaaggaa    3540
ttagagtact tcccagagac cgataaggta tggattgaga ttggagaaac agaaggaaca    3600
ttcatcgtgg acagcgtgga attactcctt atggaggaat ag                      3642
```

<210> SEQ ID NO 12
<211> LENGTH: 3642
<212> TYPE: DNA
<213> ORGANISM: Artificial
<220> FEATURE:
<223> OTHER INFORMATION: Synthetic nucleotide sequence designed for
     expression in a plant cell encoding TIC867_20.

<400> SEQUENCE: 12

```
atgaccagca accgaaagaa cgagaacgag atcatcaacg ccctgtccat accggccgtg      60
tcaaaccact ccgcccagat gaacctctcc accgacgcga ggatcgagga ctccctctgc     120
atcgccgagg gcaacaacat cgacccgttc gtgtctgcaa gcacggtcca gaccggcatc     180
```

```
aacatcgcgg gccgcatcct gggcgtgctc ggcgtgccct tcgcgggtca aatcgcctct    240
ttctactcat tcctcgtggg cgagctgtgg ccgcgcggac gtgacccgtg ggaaatcttc    300
ctggagcacg ttgagcagct catccggcag caagtgaccg agaacaccag ggacaccgca    360
ctggcacggc tccagggcct tggcaacagc ttccgcgcct accagcagtc gctggaggac    420
tggctggaga accgagacga cgccagaacc cgctcagttc tgtacacaca gtacatcgcc    480
ctagagctgg acttcctcaa cgctatgccg ctcttcgcca tccgtaacca ggaagtaccg    540
cttctgatgg tgtacgcaca agcagcgaac ctccatctgc tcctgctgcg agacgcatct    600
ctgttcggca gtgagttcgg gctgacgagc caggagatcc agcgctacta cgagcgccaa    660
gtggagaaga ctcgtgagta cagcgactac tgcgcgcgct ggtacaacac gggcttgaac    720
aaccttcgcg ggacaaacgc cgaatcctgg cttcgctaca accagttccg ccgcgacctc    780
acgctgggtg tgctggacct ggtcgcgctc ttcccgtcct acgacacacg ggtgtaccca    840
atgaacacga gcgcacagct cacccgtgag atctacacag atcccatcgg ccgcaccaac    900
gctcccagtg gcttcgcaag cacgaattgg ttcaacaata cgctccttc tttctctgcc     960 atcgaggccg ctgtcatcag accgccgcac ttactcgatt tcccggagca gctcactatc   1020
ttctctgtgt tgtcccggtg gtcgaacacg cagtacatga actactgggt gggccacagg   1080
ctagagagcc ggaccatccg tggcagtctc tcaacctcga cccacggcaa cacgaacacg   1140
agcatcaacc ctgtcactct ccagtttaca tctaggacg tttacaggac agagtcgttc    1200
gctggcatta acattctgtt gaccactccg gtgaacggcg tcccttgggc ccgcttcaac   1260
tggaggaatc ctctgaactc actgcgcggc agccttctct acactatcgg ctacaccggc   1320
gttgggacgc aactcttcga ctcggagacc gagctgccgc ccgagaccac cgagcggcct   1380
aactacgaga gttattcaca caggctctcc aacatccgct tgatttctgg gaacaccttg   1440
cgggctccgg tgtactcctg gacgcaccgc agcgccgaca gaactaatac catcagctcc   1500
gactcgatca cccagatccc gctggtgaag gctcacacgc ttcagtcggg caccacagtc   1560
gtcaagggcc ctggcttcac cggcggcgac atcctgcgtc gcacatctgg cggacccttc   1620
gccttcagca acgtgaactt ggacttcaat ttgtcacagc ggtatcgtgc cagaatccgg   1680
tacgccagca ctacgaacct gcgaatctat gttactgtgg cgggcgagcg gatcttcgcc   1740
gggcaattcg acaagacgat ggacgcggga gcacctctga cattccagtc attctcttac   1800
gccacgatca acacggcatt cacgtttccg gagcgttcca gtagcctgac cgtgggcgct   1860
gataccttca gtagcgggaa cgaggtgtac gttgaccgtt tcgagctgat cccggtcacc   1920
gccaccttcg aggccgagta cgaccttgag cgcgcccaga aggtggtgaa cgccctcttc   1980
actagcacta accagctagg cctgaagact gacgtgaccg actaccacat cgaccaagtg   2040
agcaacctag tggcctgcct ctccgacgag ttctgcctcg acgagaagcg cgagctgtcc   2100
gagaaggtga agcacgccaa cgcgcctctcc gacgagcgca acctgctcca ggaccccaac   2160 ttcagggca tcaacaggca gcccgaccgc ggctggcgcg ctccaccga catcaccatc     2220 cagggcggtg acgacgtatt caaggagaac tacgttaccc tccccggcac cttcgacgag   2280
tgttacccca cctacctcta ccagaagatc gacgagtcca agctgaaggc ctacacccgc   2340
taccagctcc gcggctacat cgaggactcc caggacctgg aaatctacct catccgctac   2400
aacgccaagc acgagatcgt gaacgtgcct ggcaccggca gcctctggcc tctcagcgtg   2460
gagaaccaga tcgcccttg cggcgagcct aaccgctgcg cccctcacct cgagtggaac   2520
cctgacctcc actgctcgtg cagggacggc gagaagtgcg cccaccatag ccaccacttc   2580
```

-continued

```
tctctggaca tcgacgtggg ctgcaccgac ctgaacgagg acctgggcgt gtgggttatc    2640
ttcaagatca agacccagga cggtcacgcc aggctgggta acctggagtt ccttgaggaa    2700
aagcctctgc tgggtgaggc cctggccagg gtcaagaggg ctgagaagaa atggagggat    2760
aagagggaga ccctgcagct ggagaccact atcgtctaca aggaggctaa ggagtctgtc    2820
gatgctctgt tcgtcaactc tcagtacgat agactgcaag ctgataccaa catcgctatg    2880
atccacgctg cggataagcg ggtccaccgg atccgggagg cttaccttcc ggagctttct    2940
gtcatcccgg gtgtcaacgc tgcgatcttc gaggaacttg aggaacggat cttcactgcg    3000
tttagtcttt acgatgcgcg gaacatcatc aagaacgggg acttcaacaa tggtctgctg    3060
tgctggaacg tcaagggtca tgtcgaggtc gaggaacaaa acaatcatcg tagtgtcctt    3120
gtcattcctg agtgggaggc ggaggtctct caagaggtcc gtgtttgccc ggggcgtggg    3180
tacattcttc gtgttactgc gtacaaggag gggtacgggg aggggtgcgt tactattcat    3240
gagattgaga acaatactga tgagcttaag ttcaacaatt gtgttgagga ggaggtttac    3300
ccgaacaata ctgttacgtg catcaactac acggcaacgc aagaggaata cgagggacg     3360 tacacctcgc gtaatagagg gtatgatgag gcgtacggaa acaacccgtc ggttccagca    3420
gattatgcct cggtttatga ggagaagtcg tacacggata gacgacgcga gaatccatgt    3480
gagtcaaatc gaggatacgg agattacaca ccattaccag caggatacgt tacaaaggag    3540
ttggaatact ccccggaaac agataaagtt tggattgaaa tcggagaaac agaaggaaca    3600
ttcatcgtcg actcagtaga attgttgttg atggaagaat ga                      3642
```

<210> SEQ ID NO 13
<211> LENGTH: 1213
<212> TYPE: PRT
<213> ORGANISM: Artificial
<220> FEATURE:
<223> OTHER INFORMATION: Amino acid sequence of the chimeric protein variant TIC867_20.

<400> SEQUENCE: 13

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
                20                  25                  30

Ala Arg Ile Glu Asp Ser Leu Cys Ile Ala Glu Gly Asn Asn Ile Asp
            35                  40                  45

Pro Phe Val Ser Ala Ser Thr Val Gln Thr Gly Ile Asn Ile Ala Gly
        50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
                100                 105                 110

Thr Glu Asn Thr Arg Asp Thr Ala Leu Ala Arg Leu Gln Gly Leu Gly
            115                 120                 125

Asn Ser Phe Arg Ala Tyr Gln Gln Ser Leu Glu Asp Trp Leu Glu Asn
        130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
```

```
                165                 170                 175
Gln Glu Val Pro Leu Leu Met Val Tyr Ala Gln Ala Ala Asn Leu His
            180                 185                 190
Leu Leu Leu Leu Arg Asp Ala Ser Leu Phe Gly Ser Glu Phe Gly Leu
        195                 200                 205
Thr Ser Gln Glu Ile Gln Arg Tyr Tyr Glu Arg Gln Val Glu Lys Thr
    210                 215                 220
Arg Glu Tyr Ser Asp Tyr Cys Ala Arg Trp Tyr Asn Thr Gly Leu Asn
225                 230                 235                 240
Asn Leu Arg Gly Thr Asn Ala Glu Ser Trp Leu Arg Tyr Asn Gln Phe
            245                 250                 255
Arg Arg Asp Leu Thr Leu Gly Val Leu Asp Leu Val Ala Leu Phe Pro
        260                 265                 270
Ser Tyr Asp Thr Arg Val Tyr Pro Met Asn Thr Ser Ala Gln Leu Thr
    275                 280                 285
Arg Glu Ile Tyr Thr Asp Pro Ile Gly Arg Thr Asn Ala Pro Ser Gly
290                 295                 300
Phe Ala Ser Thr Asn Trp Phe Asn Asn Asn Ala Pro Ser Phe Ser Ala
305                 310                 315                 320
Ile Glu Ala Ala Val Ile Arg Pro Pro His Leu Leu Asp Phe Pro Glu
                325                 330                 335
Gln Leu Thr Ile Phe Ser Val Leu Ser Arg Trp Ser Asn Thr Gln Tyr
            340                 345                 350
Met Asn Tyr Trp Val Gly His Arg Leu Glu Ser Arg Thr Ile Arg Gly
            355                 360                 365
Ser Leu Ser Thr Ser Thr His Gly Asn Thr Asn Thr Ser Ile Asn Pro
        370                 375                 380
Val Thr Leu Gln Phe Thr Ser Arg Asp Val Tyr Arg Thr Glu Ser Phe
385                 390                 395                 400
Ala Gly Ile Asn Ile Leu Leu Thr Thr Pro Val Asn Gly Val Pro Trp
                405                 410                 415
Ala Arg Phe Asn Trp Arg Asn Pro Leu Asn Ser Leu Arg Gly Ser Leu
            420                 425                 430
Leu Tyr Thr Ile Gly Tyr Thr Gly Val Gly Thr Gln Leu Phe Asp Ser
        435                 440                 445
Glu Thr Glu Leu Pro Pro Glu Thr Thr Glu Arg Pro Asn Tyr Glu Ser
    450                 455                 460
Tyr Ser His Arg Leu Ser Asn Ile Arg Leu Ile Ser Gly Asn Thr Leu
465                 470                 475                 480
Arg Ala Pro Val Tyr Ser Trp Thr His Arg Ser Ala Asp Arg Thr Asn
                485                 490                 495
Thr Ile Ser Ser Asp Ser Ile Thr Gln Ile Pro Leu Val Lys Ala His
            500                 505                 510
Thr Leu Gln Ser Gly Thr Thr Val Val Lys Gly Pro Gly Phe Thr Gly
        515                 520                 525
Gly Asp Ile Leu Arg Arg Thr Ser Gly Gly Pro Phe Ala Phe Ser Asn
    530                 535                 540
Val Asn Leu Asp Phe Asn Leu Ser Gln Arg Tyr Arg Ala Arg Ile Arg
545                 550                 555                 560
Tyr Ala Ser Thr Thr Asn Leu Arg Ile Tyr Val Thr Val Ala Gly Glu
                565                 570                 575
Arg Ile Phe Ala Gly Gln Phe Asp Lys Thr Met Asp Ala Gly Ala Pro
            580                 585                 590
```

-continued

```
Leu Thr Phe Gln Ser Phe Ser Tyr Ala Thr Ile Asn Thr Ala Phe Thr
        595                 600                 605

Phe Pro Glu Arg Ser Ser Ser Leu Thr Val Gly Ala Asp Thr Phe Ser
        610                 615                 620

Ser Gly Asn Glu Val Tyr Val Asp Arg Phe Glu Leu Ile Pro Val Thr
625                 630                 635                 640

Ala Thr Phe Glu Ala Glu Tyr Asp Leu Glu Arg Ala Gln Lys Val Val
            645                 650                 655

Asn Ala Leu Phe Thr Ser Thr Asn Gln Leu Gly Leu Lys Thr Asp Val
                660                 665                 670

Thr Asp Tyr His Ile Asp Gln Val Ser Asn Leu Val Ala Cys Leu Ser
            675                 680                 685

Asp Glu Phe Cys Leu Asp Glu Lys Arg Glu Leu Ser Glu Lys Val Lys
        690                 695                 700

His Ala Lys Arg Leu Ser Asp Glu Arg Asn Leu Leu Gln Asp Pro Asn
705                 710                 715                 720

Phe Arg Gly Ile Asn Arg Gln Pro Asp Arg Gly Trp Arg Gly Ser Thr
                725                 730                 735

Asp Ile Thr Ile Gln Gly Gly Asp Asp Val Phe Lys Glu Asn Tyr Val
            740                 745                 750

Thr Leu Pro Gly Thr Phe Asp Glu Cys Tyr Pro Thr Tyr Leu Tyr Gln
        755                 760                 765

Lys Ile Asp Glu Ser Lys Leu Lys Ala Tyr Thr Arg Tyr Gln Leu Arg
    770                 775                 780

Gly Tyr Ile Glu Asp Ser Gln Asp Leu Glu Ile Tyr Leu Ile Arg Tyr
785                 790                 795                 800

Asn Ala Lys His Glu Ile Val Asn Val Pro Gly Thr Gly Ser Leu Trp
                805                 810                 815

Pro Leu Ser Val Glu Asn Gln Ile Gly Pro Cys Gly Glu Pro Asn Arg
            820                 825                 830

Cys Ala Pro His Leu Glu Trp Asn Pro Asp Leu His Cys Ser Cys Arg
        835                 840                 845

Asp Gly Glu Lys Cys Ala His His Ser His His Phe Ser Leu Asp Ile
    850                 855                 860

Asp Val Gly Cys Thr Asp Leu Asn Glu Asp Leu Gly Val Trp Val Ile
865                 870                 875                 880

Phe Lys Ile Lys Thr Gln Asp Gly His Ala Arg Leu Gly Asn Leu Glu
                885                 890                 895

Phe Leu Glu Glu Lys Pro Leu Leu Gly Glu Ala Leu Ala Arg Val Lys
            900                 905                 910

Arg Ala Glu Lys Lys Trp Arg Asp Lys Arg Glu Thr Leu Gln Leu Glu
        915                 920                 925

Thr Thr Ile Val Tyr Lys Glu Ala Lys Glu Ser Val Asp Ala Leu Phe
    930                 935                 940

Val Asn Ser Gln Tyr Asp Arg Leu Gln Ala Asp Thr Asn Ile Ala Met
945                 950                 955                 960

Ile His Ala Ala Asp Lys Arg Val His Arg Ile Arg Glu Ala Tyr Leu
                965                 970                 975

Pro Glu Leu Ser Val Ile Pro Gly Val Asn Ala Ala Ile Phe Glu Glu
            980                 985                 990

Leu Glu Gly Arg Ile Phe Thr Ala  Phe Ser Leu Tyr Asp  Ala Arg Asn
        995                 1000                1005
```

| | | | | | | | | | | |
|---|---|---|---|---|---|---|---|---|---|---|
| Ile | Ile | Lys | Asn | Gly | Asp | Phe | Asn | Asn | Gly | Leu | Leu | Cys | Trp | Asn |
| 1010 | | | | | 1015 | | | | | 1020 |

Ile Ile Lys Asn Gly Asp Phe Asn Asn Gly Leu Leu Cys Trp Asn
1010              1015              1020

Val Lys Gly His Val Glu Val Glu Glu Gln Asn Asn His Arg Ser
    1025              1030              1035

Val Leu Val Ile Pro Glu Trp Glu Ala Glu Val Ser Gln Glu Val
    1040              1045              1050

Arg Val Cys Pro Gly Arg Gly Tyr Ile Leu Arg Val Thr Ala Tyr
    1055              1060              1065

Lys Glu Gly Tyr Gly Glu Gly Cys Val Thr Ile His Glu Ile Glu
    1070              1075              1080

Asn Asn Thr Asp Glu Leu Lys Phe Asn Asn Cys Val Glu Glu Glu
    1085              1090              1095

Val Tyr Pro Asn Asn Thr Val Thr Cys Ile Asn Tyr Thr Ala Thr
    1100              1105              1110

Gln Glu Glu Tyr Glu Gly Thr Tyr Thr Ser Arg Asn Arg Gly Tyr
    1115              1120              1125

Asp Glu Ala Tyr Gly Asn Asn Pro Ser Val Pro Ala Asp Tyr Ala
    1130              1135              1140

Ser Val Tyr Glu Glu Lys Ser Tyr Thr Asp Arg Arg Arg Glu Asn
    1145              1150              1155

Pro Cys Glu Ser Asn Arg Gly Tyr Gly Asp Tyr Thr Pro Leu Pro
    1160              1165              1170

Ala Gly Tyr Val Thr Lys Glu Leu Glu Tyr Phe Pro Glu Thr Asp
    1175              1180              1185

Lys Val Trp Ile Glu Ile Gly Glu Thr Glu Gly Thr Phe Ile Val
    1190              1195              1200

Asp Ser Val Glu Leu Leu Leu Met Glu Glu
    1205              1210

<210> SEQ ID NO 14
<211> LENGTH: 3690
<212> TYPE: DNA
<213> ORGANISM: Artificial
<220> FEATURE:
<223> OTHER INFORMATION: Recombinant nucleotide sequence used for
      expression in a bacterial cell encoding TIC867_21.

<400> SEQUENCE: 14

```
atgacttcaa ataggaaaaa tgagaatgaa attataaatg ctttatcgat tccagctgta      60
tcgaatcatt ccgcacaaat gaatctatca accgatgctc gtattgagga tagcttgtgt     120
atagccgagg gaacaatat cgatccattt gttagcgcat caacagtcca acgggtatt      180 aacatagctg gtagaatact aggtgtatta ggcgtaccgt ttgctggaca aatagctagt     240
ttttatagtt ttcttgttgg tgaattatgg ccccgcggca gagatccttg ggaattttc     300 ctagaacatg tcgaacaact tataagacaa caagtaacag aaaatactag ggatacggct     360
cttgctcgat tacaaggttt aggaaattcc tttagagcct atcaacagtc acttgaagat     420
tggctagaaa accgtgatga tgcaagaacg agaagtgttc tttataccca atatatagcc     480
ttagaacttg attttcttaa tcgatgccg cttttcgcaa ttagaaacca agaagttcca     540
ttattaatgg tatatgctca agctgcaaat ttacacctat tattattgag agatgcctct     600
ctttttggta gtgaatttgg gcttacatcc caagaaattc aacgttatta tgagcgccaa     660 gtggaaaaa cgagagaata ttctgattat tgcgcaagat ggtataatac gggtttaaat     720
aatttgagag ggacaaatgc tgaaagttgg ttgcgatata atcaattccg tagagactta     780
```

```
acgctaggag tattagatct agtggcacta ttcccaagct atgacacgcg tgtttatcca    840
atgaatacca gtgctcaatt aacaagagaa atttatacag atccaattgg gagaacaaat    900
gcaccttcag gatttgcaag tacgaattgg tttaataata atgcaccatc gttttctgcc    960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacggaaa taccaatact   1140
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta cacaaatacc attggtaaag gcgcataccc tccaatcggg taccactgta   1560
gtaaaagggc cagggtttac aggaggggat atcctccgtc gaacaagtgg aggaccattt   1620
gcttttagta atgttaatct agattttaac ttgtcacaaa ggtatcgtgc tagaattcgt   1680
tatgcctcta ctactaacct aagaatttac gtaacggttg caggtgaacg aatttttgct   1740
ggtcaatttg acaaaactat ggatgctggt gccccattaa cattccaatc ttttagttac   1800
gcaactatta atacagcttt tacattccca gaaagatcga gcagcttgac tgtaggtgcc   1860
gatacgttta gttcaggtaa tgaagtttat gtagatagat ttgaattaat cccagttact   1920
gcaaccggaa cgacaaccta tgagtatgaa gagaagcaga atctagaaaa agcgcagaaa   1980
gcgttgaacg ctttgtttac ggatggcacg aatggctatc tacaaatgga tgccactgat   2040
tatgatatca atcaaactgc aaacttaata gaatgtgtat cagatgaatt gtatgcaaaa   2100
gaaaagatag ttttattaga tgaagtcaaa tatgcgaagc ggcttagcat atcacgtaac   2160
ctactttttga acgatgattt agaattttca gatggatttg gagaaaacgg atggacgaca   2220
agtgataata tttcaatcca ggcggataat ccccttttta aggggaatta tttaaaaatg   2280
tttgggcaa gagatattga tggaacccta tttccaactt atctctatca aaaaatagat   2340
gagtccaggt taaaaccata tacacgttat cgagtaagag ggtttgtggg aagtagtaaa   2400
aatctaaaat tagtggtaac acgctatgag aaagaaattg atgccattat gaatgttcca   2460
aatgatttgg cacatatgca gcttaaccct tcatgtggag attatcgctg tgaatcatcg   2520
tcccagtttt tggtgaacca agtgcatcct acaccaacag ctggatatgc tcttgatatg   2580
tatgcatgcc cgtcaagttc agataaaaaa catattatgt gtcacgatcg tcatccattt   2640
gattttcata ttgacaccgg agaattaaat ccaaacacaa acctgggtat tgatgtcttg   2700
tttaaaattt ctaatccaaa tggatacgct acattaggga atctagaagt cattgaagaa   2760
ggaccactaa cagatgaagc attggtacat gtaaaacaaa aggaaaagaa atggcgtcag   2820
cacatggaga aaaacgaat ggaaacacaa caagcctatg atccagcaaa acaagctgta   2880
gatgcattat ttacaaatga acaagagtta gactatcata ctactttaga tcatattcag   2940
aacgccgatc agctggtaca ggcgattccc tatgtacacc atgcttggtt accggatgct   3000
ccaggtatga actatgatgt atatcaaggg ttaaacgcac gtatcatgca ggcgtacaat   3060
ttatatgatg cacgaaatgt cataataaat ggtgacttta caaggact acaaggatgg   3120
cacgcaacag gaaaagcagc ggtacaacaa atagatggag cttcagtatt agttctatca   3180
```

| | |
|---|---:|
| aactggagtg ccgaggtatc tcagaatctg catgcccaag atcatcatgg atatatgtta | 3240 |
| cgtgtgattg ccaaaaaaga aggtcctgga aagggtatg taatgatgat ggattttaat | 3300 |
| ggaaagcagg aaacacttac gttcacttct tgtgaagaag gatatataac aaaaacaata | 3360 |
| gaggtattcc cggaaagtga tcgaatacga attgaaatgg gagaaacaga gggtacgttt | 3420 |
| tatgtagata gcatcgagtt gctttgtatg caaggatatg ctagcgataa taacccgcac | 3480 |
| acgggtaata tgtatgagca aagttataat ggaaattata atcaaaatac tagcgatgtg | 3540 |
| tatcaccaag gatatataaa caactataac caaaattcta gtagtatgta taatcaaaat | 3600 |
| tatattaaca atgatgacct gcattccggt tgcacatgta accaagggca taactctggc | 3660 |
| tgtacatgta atcaaggata taaccgttag | 3690 |

<210> SEQ ID NO 15
<211> LENGTH: 3690
<212> TYPE: DNA
<213> ORGANISM: Artificial
<220> FEATURE:
<223> OTHER INFORMATION: Synthetic nucleotide sequence designed for
      expression in a plant cell encoding TIC867_21.

<400> SEQUENCE: 15

| | |
|---|---:|
| atgaccagca accgaaagaa cgagaacgag atcatcaacg ccctgtccat accggccgtg | 60 |
| tcaaaccact ccgcccagat gaacctctcc accgacgcga ggatcgagga ctccctctgc | 120 |
| atcgccgagg caacaacat cgacccgttc gtgtctgcaa gcacggtcca gaccggcatc | 180 |
| aacatcgcgg gccgcatcct gggcgtgctc ggcgtgccct cgcgggtca aatcgcctct | 240 |
| ttctactcat tcctcgtggg cgagctgtgg ccgcgcggac gtgacccgtg ggaaatcttc | 300 |
| ctggagcacg ttgagcagct catccggcag caagtgaccg agaacaccag ggacaccgca | 360 |
| ctggcacggc tccagggcct tggcaacagc ttccgcgcct accagcagtc gctggaggac | 420 |
| tggctggaga accgagacga cgccagaacc cgctcagttc tgtacacaca gtacatcgcc | 480 |
| ctagagctgg acttcctcaa cgctatgccg ctcttcgcca tccgtaacca ggaagtaccg | 540 |
| cttctgatgg tgtacgcaca agcagcgaac ctccatctgc tcctgctgcg agacgcatct | 600 |
| ctgttcggca gtgagttcgg gctgacgagc caggagatcc agcgctacta cgagcgccaa | 660 |
| gtggagaaga ctcgtgagta cagcgactac tgcgcgcgct ggtacaacac gggcttgaac | 720 |
| aaccttcgcg ggacaaacgc cgaatcctgg cttcgctaca accagttccg ccgcgacctc | 780 |
| acgctgggtg tgctggacct ggtcgcgctc ttcccgtcct acgacacacg ggtgtaccca | 840 |
| atgaacacga gcgcacagct cacccgtgag atctacacag atcccatcgg ccgcaccaac | 900 |
| gctcccagtg gcttcgcaag cacgaattgg ttcaacaata cgctccttc tttctctgcc | 960 |
| atcgaggccg ctgtcatcag accgccgcac ttactcgatt tcccggagca gctcactatc | 1020 |
| ttctctgtgt tgtcccggtg gtcgaacacg cagtacatga actactgggt gggccacagg | 1080 |
| ctagagagcc ggaccatccg tggcagtctc tcaacctcga cccacggcaa cacgaacacg | 1140 |
| agcatcaacc ctgtcactct ccagtttaca tctagggacg tttacaggac agagtcgttc | 1200 |
| gctggcatta acattctgtt gaccactccg gtgaacggcg tcccttgggc ccgcttcaac | 1260 |
| tggaggaatc ctctgaactc actgcgcggc agccttctct acactatcgg ctacaccggc | 1320 |
| gttgggacgc aactcttcga ctcggagacc gagctgccgc ccgagaccac cgagcggcct | 1380 |
| aactacgaga gttattcaca caggctcctc aacatccgct tgatttctgg gaacaccttg | 1440 |
| cgggctccgg tgtactcctg gacgcaccgc agcgccgaca gaactaatac catcagctcc | 1500 |

```
gactcgatca cccagatccc gctggtgaag gctcacacgc ttcagtcggg caccacagtc    1560
gtcaagggcc ctggcttcac cggcggcgac atcctgcgtc gcacatctgg cggacccttc    1620
gccttcagca acgtgaactt ggacttcaat ttgtcacagc ggtatcgtgc cagaatccgg    1680
tacgccagca ctacgaacct gcgaatctat gttactgtgg cgggcgagcg gatcttcgcc    1740
gggcaattcg acaagacgat ggacgcggga gcacctctga cattccagtc attctcttac    1800
gccacgatca acacggcatt cacgtttccg gagcgttcca gtagcctgac cgtgggcgct    1860
gataccttca gtagcgggaa cgaggtgtac gttgaccgtt tcgagctgat cccggtcacc    1920
gccaccggga ctaccaccta cgagtacgag gagaagcaga atctcgagaa ggctcagaag    1980
gctctgaacg ctctgttcac tgacgggacc aacggctacc tccagatgga cgccactgac    2040
tacgacatca accagacagc taacctgatt gagtgtgtga gtgacgaact gtacgctaag    2100
gagaagatcg tactcctgga cgaggtgaag tacgctaagc gcctgagcat tagccgtaac    2160
ctgctgctga cgacgatct ggagttcagc gacggctttg cgagaacgg ctggaccacc     2220 agcgacaaca tctccatcca ggccgacaat ccactcttca aaggcaacta cctcaagatg    2280
ttcggagcca gggacatcga cggcaccctc tttccgacct acctctacca gaagatcgac    2340
gagtcccgcc tcaaacccta cacccgctac agggtgcgcg gcttcgtggg cagcagcaag    2400
aacctcaagc tcgtggtcac acggtatgag aaggagatcg acgccatcat gaacgtgccc    2460
aacgatctcg cccacatgca gctcaatcca tcctgcggcg actaccggtg cgagtccagc    2520
tcccagttcc tcgtgaacca ggtgcaccct actccgaccg ctggctatgc cctggacatg    2580
tacgcctgcc ctagttcctc cgacaagaag cacatcatgt gccacgaccg tcatccgttc    2640
gacttccaca tcgacaccgg cgaactgaac ccgaacacca acctgggcat cgacgtactg    2700
ttcaagattt ccaacccgaa cgggtacgcc accttgggca acctggaggt catcgaagaa    2760
ggcccgctga ccgacgaggc cctggtccac gtcaaacaga aggagaagaa gtggcggcag    2820
cacatggaga agaagcggat ggagactcaa caagcctacg acccggccaa gcaagctgtg    2880
gacgctctgt tcaccaacga gcaagagctt gactaccaca ctactcttga ccacatccag    2940
aatgctgacc agcttgtcca ggctattccg tacgtccacc acgcttggct accggacgct    3000
ccagggatga actacgatgt gtaccagggt ctgaacgcgc ggatcatgca agcgtacaac    3060
ctgtacgacg cgcgtaacgt catcatcaac ggtgacttca ctcagggtct tcaaggttgg    3120
cacgcgactg gcaaagcggc agtccagcag attgatggtg cgtctgttct tgtgttgagc    3180
aactggtctg cggaggtttc tcagaacctg cacgcacagg atcaccacgg ctacatgctg    3240
agggtgattg ctaagaagga gggccctggc aaaggctacg tcatgatgat ggacttcaac    3300
ggaaagcaag aaaccctgac cttcactagc tgtgaggagg gctacatcac taagaccatt    3360
gaggtctttc cggagtctga ccgcatccgg atcgagatgg gcgagaccga aggcacgttc    3420
tacgtggact ccatcgaact cctctgcatg caaggctacg cctccgacaa caacccacac    3480
acgggcaaca tgtacgagca gtcctacaac gggaactaca ccagaacacc ctccgatgtg    3540
taccatcagg gctacatcaa caactacaac cagaacagca gcagcatgta caaccagaac    3600
tacatcaaca cgatgacttt gcactcgggt tgcacctgca accagggtca aacagtgggg    3660
tgcacgtgca accagggata caaccgttga                                    3690
```

<210> SEQ ID NO 16
<211> LENGTH: 1229
<212> TYPE: PRT

<213> ORGANISM: Artificial
<220> FEATURE:
<223> OTHER INFORMATION: Amino acid sequence of the chimeric protein variant TIC867_21.

<400> SEQUENCE: 16

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
                20                  25                  30

Ala Arg Ile Glu Asp Ser Leu Cys Ile Ala Glu Gly Asn Asn Ile Asp
            35                  40                  45

Pro Phe Val Ser Ala Ser Thr Val Gln Thr Gly Ile Asn Ile Ala Gly
        50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
                100                 105                 110

Thr Glu Asn Thr Arg Asp Thr Ala Leu Ala Arg Leu Gln Gly Leu Gly
                115                 120                 125

Asn Ser Phe Arg Ala Tyr Gln Gln Ser Leu Glu Asp Trp Leu Glu Asn
130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
                195                 200                 205

Thr Ser Gln Glu Ile Gln Arg Tyr Tyr Glu Arg Gln Val Glu Lys Thr
210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Val Tyr Pro Met Asn Thr Ser Ala Gln Leu Thr
                275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
                340                 345                 350

Met Asn Tyr Trp Val Gly His Arg Leu Glu Ser Arg Thr Ile Arg Gly
                355                 360                 365

Ser Leu Ser Thr Ser Thr His Gly Asn Thr Asn Thr Ser Ile Asn Pro
                370                 375                 380
```

```
Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
            405                 410                 415

Ala Arg Phe Asn Trp Arg Asn Pro Leu Asn Ser Leu Arg Gly Ser Leu
        420                 425                 430

Leu Tyr Thr Ile Gly Tyr Thr Gly Val Gly Thr Gln Leu Phe Asp Ser
    435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
        515                 520                 525

Gly Asp Ile Leu Arg Arg Thr Ser Gly Gly Pro Phe Ala Phe Ser Asn
530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
        595                 600                 605

Phe Pro Glu Arg Ser Ser Leu Thr Val Gly Ala Asp Thr Phe Ser
610                 615                 620

Ser Gly Asn Glu Val Tyr Val Asp Arg Phe Glu Leu Ile Pro Val Thr
625                 630                 635                 640

Ala Thr Gly Thr Thr Tyr Glu Tyr Glu Glu Lys Gln Asn Leu Glu
                645                 650                 655

Lys Ala Gln Lys Ala Leu Asn Ala Leu Phe Thr Asp Gly Thr Asn Gly
            660                 665                 670

Tyr Leu Gln Met Asp Ala Thr Asp Tyr Asp Ile Asn Gln Thr Ala Asn
        675                 680                 685

Leu Ile Glu Cys Val Ser Asp Glu Leu Tyr Ala Lys Glu Lys Ile Val
690                 695                 700

Leu Leu Asp Glu Val Lys Tyr Ala Lys Arg Leu Ser Ile Ser Arg Asn
705                 710                 715                 720

Leu Leu Leu Asn Asp Asp Leu Glu Phe Ser Asp Gly Phe Gly Glu Asn
                725                 730                 735

Gly Trp Thr Thr Ser Asp Asn Ile Ser Ile Gln Ala Asp Asn Pro Leu
            740                 745                 750

Phe Lys Gly Asn Tyr Leu Lys Met Phe Gly Ala Arg Asp Ile Asp Gly
        755                 760                 765

Thr Leu Phe Pro Thr Tyr Leu Tyr Gln Lys Ile Asp Glu Ser Arg Leu
        770                 775                 780

Lys Pro Tyr Thr Arg Tyr Arg Val Arg Gly Phe Val Gly Ser Ser Lys
785                 790                 795                 800

Asn Leu Lys Leu Val Val Thr Arg Tyr Glu Lys Glu Ile Asp Ala Ile
```

```
                805                 810                 815
Met Asn Val Pro Asn Asp Leu Ala His Met Gln Leu Asn Pro Ser Cys
                820                 825                 830

Gly Asp Tyr Arg Cys Glu Ser Ser Gln Phe Leu Val Asn Gln Val
            835                 840                 845

His Pro Thr Pro Thr Ala Gly Tyr Ala Leu Asp Met Tyr Ala Cys Pro
    850                 855                 860

Ser Ser Ser Asp Lys Lys His Ile Met Cys His Asp Arg His Pro Phe
865                 870                 875                 880

Asp Phe His Ile Asp Thr Gly Glu Leu Asn Pro Asn Thr Asn Leu Gly
                885                 890                 895

Ile Asp Val Leu Phe Lys Ile Ser Asn Pro Asn Gly Tyr Ala Thr Leu
            900                 905                 910

Gly Asn Leu Glu Val Ile Glu Glu Gly Pro Leu Thr Asp Glu Ala Leu
            915                 920                 925

Val His Val Lys Gln Lys Glu Lys Lys Trp Arg Gln His Met Glu Lys
        930                 935                 940

Lys Arg Met Glu Thr Gln Gln Ala Tyr Asp Pro Ala Lys Gln Ala Val
945                 950                 955                 960

Asp Ala Leu Phe Thr Asn Glu Gln Glu Leu Asp Tyr His Thr Thr Leu
                965                 970                 975

Asp His Ile Gln Asn Ala Asp Gln Leu Val Gln Ala Ile Pro Tyr Val
            980                 985                 990

His His Ala Trp Leu Pro Asp Ala Pro Gly Met Asn Tyr Asp Val Tyr
            995                 1000                1005

Gln Gly Leu Asn Ala Arg Ile Met Gln Ala Tyr Asn Leu Tyr Asp
        1010                1015                1020

Ala Arg Asn Val Ile Ile Asn Gly Asp Phe Thr Gln Gly Leu Gln
        1025                1030                1035

Gly Trp His Ala Thr Gly Lys Ala Ala Val Gln Gln Ile Asp Gly
        1040                1045                1050

Ala Ser Val Leu Val Leu Ser Asn Trp Ser Ala Glu Val Ser Gln
        1055                1060                1065

Asn Leu His Ala Gln Asp His His Gly Tyr Met Leu Arg Val Ile
        1070                1075                1080

Ala Lys Lys Glu Gly Pro Gly Lys Gly Tyr Val Met Met Met Asp
        1085                1090                1095

Phe Asn Gly Lys Gln Glu Thr Leu Thr Phe Thr Ser Cys Glu Glu
        1100                1105                1110

Gly Tyr Ile Thr Lys Thr Ile Glu Val Phe Pro Glu Ser Asp Arg
        1115                1120                1125

Ile Arg Ile Glu Met Gly Glu Thr Glu Gly Thr Phe Tyr Val Asp
        1130                1135                1140

Ser Ile Glu Leu Leu Cys Met Gln Gly Tyr Ala Ser Asp Asn Asn
        1145                1150                1155

Pro His Thr Gly Asn Met Tyr Glu Gln Ser Tyr Asn Gly Asn Tyr
        1160                1165                1170

Asn Gln Asn Thr Ser Asp Val Tyr His Gln Gly Tyr Ile Asn Asn
        1175                1180                1185

Tyr Asn Gln Asn Ser Ser Ser Met Tyr Asn Gln Asn Tyr Ile Asn
        1190                1195                1200

Asn Asp Asp Leu His Ser Gly Cys Thr Cys Asn Gln Gly His Asn
        1205                1210                1215
```

Ser Gly Cys Thr Cys Asn Gln Gly Tyr Asn Arg
    1220              1225

<210> SEQ ID NO 17
<211> LENGTH: 3432
<212> TYPE: DNA
<213> ORGANISM: Artificial
<220> FEATURE:
<223> OTHER INFORMATION: Recombinant nucleotide sequence used for
      expression in a bacterial cell encoding TIC867_22.

<400> SEQUENCE: 17

| | | | | | |
|---|---|---|---|---|---|
| atgacttcaa | ataggaaaaa | tgagaatgaa | attataaatg | ctttatcgat | tccagctgta | 60 |
| tcgaatcatt | ccgcacaaat | gaatctatca | accgatgctc | gtattgagga | tagcttgtgt | 120 |
| atagccgagg | ggaacaatat | cgatccattt | gttagcgcat | caacagtcca | aacgggtatt | 180 |
| aacatagctg | gtagaatact | aggtgtatta | ggcgtaccgt | ttgctggaca | aatagctagt | 240 |
| tttatagtt | ttcttgttgg | tgaattatgg | ccccgcggca | gagatccttg | ggaaattttc | 300 |
| ctagaacatg | tcgaacaact | tataagacaa | caagtaacag | aaaatactag | ggatacggct | 360 |
| cttgctcgat | tacaaggttt | aggaaaattcc | tttagagcct | atcaacagtc | acttgaagat | 420 |
| tggctagaaa | accgtgatga | tgcaagaacg | agaagtgttc | tttataccca | atatatagcc | 480 |
| ttagaacttg | attttcttaa | tgcgatgccg | cttttcgcaa | ttagaaacca | agaagttcca | 540 |
| ttattaatgg | tatatgctca | agctgcaaat | ttacacctat | tattattgag | agatgcctct | 600 |
| ctttttggta | gtgaatttgg | gcttacatcc | caagaaaattc | aacgttatta | tgagcgccaa | 660 |
| gtggaaaaaa | cgagagaata | ttctgattat | tgcgcaagat | ggtataatac | gggtttaaat | 720 |
| aatttgagag | ggacaaatgc | tgaaagttgg | ttgcgatata | atcaattccg | tagagactta | 780 |
| acgctaggag | tattagatct | agtggcacta | ttcccaagct | atgacacgcg | tgtttatcca | 840 |
| atgaatacca | gtgctcaatt | aacaagagaa | atttatacag | atccaattgg | agaacaaat | 900 |
| gcaccttcag | gatttgcaag | tacgaattgg | tttaataata | atgcaccatc | gttttctgcc | 960 |
| atagaggctg | ccgttattag | gcctccgcat | ctacttgatt | ttccagaaca | gcttacaatt | 1020 |
| ttcagcgtat | taagtcgatg | gagtaatact | caatatatga | attactgggt | gggacataga | 1080 |
| cttgaatcgc | gaacaataag | ggggtcatta | agtacctcga | cacacggaaa | taccaatact | 1140 |
| tctattaatc | ctgtaacatt | acagttcaca | tctcgagacg | tttatagaac | agaatcattt | 1200 |
| gcagggataa | atatacttct | aactactcct | gtgaatggag | taccttgggc | tagatttaat | 1260 |
| tggagaaatc | ccctgaattc | tcttagaggt | agccttctct | atactatagg | gtatactgga | 1320 |
| gtggggacac | aactatttga | ttcagaaact | gaattaccac | cagaaacaac | agaacgacca | 1380 |
| aattatgaat | cttacagtca | tagattatct | aatataagac | taatatcagg | aaacactttg | 1440 |
| agagcaccag | tatattcttg | gacgcaccgt | agtgcagatc | gtacaaatac | cattagttca | 1500 |
| gatagcatta | cacaaatacc | attggtaaag | gcgcataccc | tccaatcggg | taccactgta | 1560 |
| gtaaaagggc | agggtttac | aggaggggat | atcctccgtc | gaacaagtgg | aggaccattt | 1620 |
| gcttttagta | atgttaatct | agattttaac | ttgtcacaaa | ggtatcgtgc | tagaattcgt | 1680 |
| tatgcctcta | ctactaacct | aagaatttac | gtaacggttg | caggtgaacg | aatttttgct | 1740 |
| ggtcaatttg | acaaaactat | ggatgctggt | gccccattaa | cattccaatc | ttttagttac | 1800 |
| gcaactatta | atacagcttt | tacattccca | gaaagatcga | gcagcttgac | tgtaggtgcc | 1860 |
| gatacgttta | gttcaggtaa | tgaagtttat | gtagatagat | ttgaattaat | cccagttact | 1920 |

```
gcaaccaatc cgacgcgaga ggcggaagag gatctagaag cagcgaagaa agcggtggcg    1980
agcttgttta cacgtacaag ggacggatta caagtaaatg tgacagatta tcaagtcgat    2040
caagcggcaa atttagtgtc atgcttatca gatgaacaat atgggcatga caaaaagatg    2100
ttattggaag cggtaagagc ggcaaaacgc ctcagccgag aacgcaactt acttcaggat    2160
ccagatttta atacaatcaa tagtacagaa gaaaatggat ggaaagcaag taacggcgtt    2220
actattagcg agggcggtcc attctataaa ggccgtgcgc ttcagctagc aagcgcaaga    2280
gaaaattacc caacatacat ttatcaaaaa gtaaatgcat cagagttaaa gccgtataca    2340
cgttatagac tggatgggtt cgtgaagagt agtcaagatt tagaaattga tctcattcac    2400
catcataaag tccatctcgt gaaaaatgta ccagataatt tagtatccga tacttactcg    2460
gatggttctt gcagtggaat gaatcgatgt gaggaacaac agatggtaaa tgcgcaactg    2520
gaaacagaac atcatcatcc gatggattgc tgtgaagcgg ctcaaacaca tgagttttct    2580
tcctatatta atacaggcga tctaaattca agtgtagatc aaggcatttg ggttgtattg    2640
aaagttcgaa caaccgatgg ttatgcgacg ctaggaaatc ttgaattggt agaggtcgga    2700
ccgttatcgg gtgaatctct agaacgtgaa caaagggata tgcgaaatg gagtgcagag    2760 ctaggaagaa agcgtgcaga aacagatcgc gtgtatcaag atgccaaaca atccatcaat    2820
catttatttg tggattatca agatcaacaa ttaaatccag aaatagggat ggcagatatt    2880
attgacgctc aaaatcttgt cgcatcaatt tcagatgtgt atagcgatgc agtactgcaa    2940
atccctggaa ttaactatga gatttacaca gagctatcca atcgcttaca acaagcatcg    3000
tatctgtata cgtctcgaaa tgcggtgcaa aatgggact ttaacagcgg tctagatagt    3060
tggaatgcaa caggggggggc tacggtacaa caggatggca atacgcattt cttagttctt    3120
tctcattggg atgcacaagt ttctcaacaa tttagagtgc agccgaattg taaatatgta    3180
ttacgtgtaa cagcagagaa agtaggcggc ggagacggat acgtgacaat ccgggatggt    3240
gctcatcata cagaaaagct tacatttaat gcatgtgatt atgatataaa tggcacgtac    3300
gtgactgata atacgtatct aacaaaagaa gtggtattct attcacatac agaacacatg    3360
tgggtagagg taagtgaaac agaaggtgca tttcatatag atagtattga attcgttgaa    3420
acagaaaagt ag                                                       3432

<210> SEQ ID NO 18
<211> LENGTH: 3432
<212> TYPE: DNA
<213> ORGANISM: Artificial
<220> FEATURE:
<223> OTHER INFORMATION: Synthetic nucleotide sequence designed for
      expression in a plant cell encoding TIC867_22.

<400> SEQUENCE: 18
atgaccagca accgaaagaa cgagaacgag atcatcaacg ccctgtccat accggccgtg      60
tcaaaccact ccgcccagat gaacctctcc accgacgcga ggatcgagga ctccctctgc     120
atcgccgagg gcaacaacat cgacccgttc gtgtctgcaa gcacggtcca gaccggcatc     180
aacatcgcgg gccgcatcct gggcgtgctc ggcgtgccct tcgcgggtca aatcgcctct     240
ttctactcat tcctcgtggg cgagctgtgg ccgcgcggac gtgacccgtg ggaaatcttc     300
ctggagcacg ttgagcagct catccggcag caagtgaccg agaacaccag ggacaccgca     360
ctggcacggc tccagggcct tgcaacagc ttccgcgcct accagcagtc gctgaggac      420 tggctggaga accgagacga cgccagaacc cgctcagttc tgtacacaca gtacatcgcc     480
```

-continued

```
ctagagctgg acttcctcaa cgctatgccg ctcttcgcca tccgtaacca ggaagtaccg      540
cttctgatgg tgtacgcaca agcagcgaac ctccatctgc tcctgctgcg agacgcatct      600
ctgttcggca gtgagttcgg gctgacgagc caggagatcc agcgctacta cgagcgccaa      660
gtggagaaga ctcgtgagta cagcgactac tgcgcgcgct ggtacaacac gggcttgaac      720
aaccttcgcg gacaaacgc cgaatcctgg cttcgctaca accagttccg ccgcgacctc       780
acgctgggtg tgctggacct ggtcgcgctc ttcccgtcct acgacacacg ggtgtaccca      840
atgaacacga gcgcacagct cacccgtgag atctacacag atcccatcgg ccgcaccaac      900
gctcccagtg gcttcgcaag cacgaattgg ttcaacaata cgctccttc tttctctgcc       960 atcgaggccg ctgtcatcag accgccgcac ttactcgatt tcccggagca gctcactatc     1020
ttctctgtgt tgtcccggtg gtcgaacacg cagtacatga actactgggt gggccacagg     1080
ctagagagcc ggaccatccg tggcagtctc tcaacctcga cccacggcaa cacgaacacg     1140
agcatcaacc ctgtcactct ccagtttaca tctaggacg tttacaggac agagtcgttc      1200
gctggcatta acattctgtt gaccactccg gtgaacggcg tcccttgggc ccgcttcaac     1260
tggaggaatc ctctgaactc actgcgcggc agccttctct acactatcgg ctacaccggc     1320
gttgggacgc aactcttcga ctcggagacc gagctgccgc ccgagaccac cgagcggcct     1380
aactacgaga gttattcaca caggctctcc aacatccgct tgatttctgg gaacaccttg     1440
cgggctccgg tgtactcctg gacgcaccgc agcgccgaca gaactaatac catcagctcc     1500
gactcgatca cccagatccc gctggtgaag gctcacacgc ttcagtcggg caccacagtc     1560
gtcaagggcc ctggcttcac cggcggcgac atcctgcgtc gcacatctgg cggacccttc     1620
gccttcagca acgtgaactt ggacttcaat ttgtcacagc ggtatcgtgc cagaatccgg     1680
tacgccagca ctacgaacct gcgaatctat gttactgtgg cgggcgagcg gatcttcgcc     1740
gggcaattcg acaagacgat ggacgcggga gcacctctga cattccagtc attctcttac     1800
gccacgatca acacggcatt cacgtttccg gagcgttcca gtagcctgac cgtgggcgct     1860
gataccttca gtagcgggaa cgaggtgtac gttgaccgtt tcgagctgat cccggtcacc     1920
gccaccaacc cgacgcggga agctgaggaa gacttggaag ccgccaagaa agcggtcgcc     1980
agcctgttta ctcggacgcg ggacgggctc caagtgaatg tgacggacta tcaagtggat     2040
caggccgcta acctcgtgtc atgcctgagc gacgagcagt acggtcacga caagaaaatg     2100
ctgctggagg ccgtccgggc cgccaagcgg ctgtccaggg agcgtaacct gctacaagat     2160 cccgactttta acacgatcaa cagcacagag gagaatggct ggaaggccag caacggagtt     2220
acgataagcg agggcggtcc gttctacaag ggtcgtgccc tccagctcgc ctctgcaagg     2280
gagaactatc caacctacat ctatcagaag gtgaacgcat ccgagcttaa gccctacaca     2340
cgctaccgcc tggacgggtt cgttaagtcc agtcaagacc tagagataga cctcatccac     2400
caccacaaag tgcatctggt caagaacgtt cccgataatc tcgtgagcga tacctactca     2460
gacggctcat gctctggcat gaacagatgt gaggagcaac agatggttaa tgctcaactc     2520
gaaaccgagc atcatcatcc tatggattgc tgcgaggccg cgcagaccca tgagttcagc     2580
tcttacatca acaccggaga cctcaacagt agcgtggatc agggaatttg ggtggtgctt     2640
aaagtgcgta caaccgacgg ctacgccacc ctcggcaacc ttgagcttgt cgaggtcgga     2700
ccacttagcg gcgagtccct ggaacgtgag cagcgggaca cgccaaatg gagcgcagag     2760 ctagggcgca aacgcgcgga gacggaccgg gtttatcagg acgcgaagca gtccatcaat     2820
cacctcttcg tggattatca ggaccagcag cttaatccag agatcggcat ggccgacatc     2880
```

-continued

```
atcgacgccc agaacctagt agcgtcgatt tccgatgtct attccgacgc cgtgcttcaa   2940 ataccctggca tcaactacga gatctacaca gagttgtcca acaggctcca gcaagcgtca   3000
tacctctaca ccagccgcaa cgccgtccag aatggcgact tcaattccgg actagactcc   3060
tggaacgcca cgggcggagc tacggtgcaa caagacggca caccccactt cctcgtactt   3120
agccactggg acgctcaagt gagtcagcaa ttccgggttc agccgaactg caagtacgtc   3180
ctgcgcgtaa cggccgagaa ggttggaggc ggagacggct acgttaccat ccgcgacggc   3240
gctcaccaca ccgagaaact gacgttcaac gcttgtgact acgacatcaa cggcacttac   3300
gtgacggaca cacctaccct gacgaaggag gtggtgttct attctcacac cgagcacatg   3360
tgggttgagg tcagcgagac cgagggagcc ttccacattg acagcatcga gttcgtggag   3420
actgagaagt ga                                                       3432
```

<210> SEQ ID NO 19
<211> LENGTH: 1143
<212> TYPE: PRT
<213> ORGANISM: Artificial
<220> FEATURE:
<223> OTHER INFORMATION: Amino acid sequence of the chimeric protein
      variant TIC867_22.

<400> SEQUENCE: 19

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255
```

```
Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
            275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
        370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
        450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
            515                 520                 525

Gly Asp Ile Leu Arg Arg Thr Ser Gly Gly Pro Phe Ala Phe Ser Asn
        530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
            595                 600                 605

Phe Pro Glu Arg Ser Ser Leu Thr Val Gly Ala Asp Thr Phe Ser
        610                 615                 620

Ser Gly Asn Glu Val Tyr Val Asp Arg Phe Glu Leu Ile Pro Val Thr
625                 630                 635                 640

Ala Thr Asn Pro Thr Arg Glu Ala Glu Glu Asp Leu Glu Ala Ala Lys
                645                 650                 655

Lys Ala Val Ala Ser Leu Phe Thr Arg Thr Arg Asp Gly Leu Gln Val
            660                 665                 670
```

-continued

Asn Val Thr Asp Tyr Gln Val Asp Gln Ala Ala Asn Leu Val Ser Cys
            675                 680                 685

Leu Ser Asp Glu Gln Tyr Gly His Asp Lys Lys Met Leu Leu Glu Ala
        690                 695                 700

Val Arg Ala Ala Lys Arg Leu Ser Arg Glu Arg Asn Leu Leu Gln Asp
705                 710                 715                 720

Pro Asp Phe Asn Thr Ile Asn Ser Thr Glu Glu Asn Gly Trp Lys Ala
                725                 730                 735

Ser Asn Gly Val Thr Ile Ser Glu Gly Pro Phe Tyr Lys Gly Arg
            740                 745                 750

Ala Leu Gln Leu Ala Ser Ala Arg Glu Asn Tyr Pro Thr Tyr Ile Tyr
        755                 760                 765

Gln Lys Val Asn Ala Ser Glu Leu Lys Pro Tyr Thr Arg Tyr Arg Leu
770                 775                 780

Asp Gly Phe Val Lys Ser Ser Gln Asp Leu Glu Ile Asp Leu Ile His
785                 790                 795                 800

His His Lys Val His Leu Val Lys Asn Val Pro Asp Asn Leu Val Ser
                805                 810                 815

Asp Thr Tyr Ser Asp Gly Ser Cys Ser Gly Met Asn Arg Cys Glu Glu
            820                 825                 830

Gln Gln Met Val Asn Ala Gln Leu Glu Thr Glu His His His Pro Met
        835                 840                 845

Asp Cys Cys Glu Ala Ala Gln Thr His Glu Phe Ser Ser Tyr Ile Asn
850                 855                 860

Thr Gly Asp Leu Asn Ser Ser Val Asp Gln Gly Ile Trp Val Val Leu
865                 870                 875                 880

Lys Val Arg Thr Thr Asp Gly Tyr Ala Thr Leu Gly Asn Leu Glu Leu
                885                 890                 895

Val Glu Val Gly Pro Leu Ser Gly Glu Ser Leu Glu Arg Glu Gln Arg
            900                 905                 910

Asp Asn Ala Lys Trp Ser Ala Glu Leu Gly Arg Lys Arg Ala Glu Thr
        915                 920                 925

Asp Arg Val Tyr Gln Asp Ala Lys Gln Ser Ile Asn His Leu Phe Val
930                 935                 940

Asp Tyr Gln Asp Gln Leu Asn Pro Glu Ile Gly Met Ala Asp Ile
945                 950                 955                 960

Ile Asp Ala Gln Asn Leu Val Ala Ser Ile Ser Asp Val Tyr Ser Asp
                965                 970                 975

Ala Val Leu Gln Ile Pro Gly Ile Asn Tyr Glu Ile Tyr Thr Glu Leu
            980                 985                 990

Ser Asn Arg Leu Gln Gln Ala Ser Tyr Leu Tyr Thr Ser Arg Asn Ala
        995                 1000                1005

Val Gln Asn Gly Asp Phe Asn Ser Gly Leu Asp Ser Trp Asn Ala
    1010                1015                1020

Thr Gly Gly Ala Thr Val Gln Gln Asp Gly Asn Thr His Phe Leu
    1025                1030                1035

Val Leu Ser His Trp Asp Ala Gln Val Ser Gln Gln Phe Arg Val
    1040                1045                1050

Gln Pro Asn Cys Lys Tyr Val Leu Arg Val Thr Ala Glu Lys Val
    1055                1060                1065

Gly Gly Gly Asp Gly Tyr Val Thr Ile Arg Asp Gly Ala His His
    1070                1075                1080

Thr Glu Lys Leu Thr Phe Asn Ala Cys Asp Tyr Asp Ile Asn Gly

```
                    1085            1090            1095
Thr Tyr Val Thr Asp Asn Thr Tyr Leu Thr Lys Glu Val Val Phe
    1100            1105            1110

Tyr Ser His Thr Glu His Met Trp Val Glu Val Ser Glu Thr Glu
    1115            1120            1125

Gly Ala Phe His Ile Asp Ser Ile Glu Phe Val Glu Thr Glu Lys
    1130            1135            1140

<210> SEQ ID NO 20
<211> LENGTH: 3696
<212> TYPE: DNA
<213> ORGANISM: Artificial
<220> FEATURE:
<223> OTHER INFORMATION: Synthetic nucleotide sequence designed for
      expression in a plant cell encoding TIC867_23.

<400> SEQUENCE: 20
```

| | | |
|---|---|---|
| atgaccagca accgaaagaa cgagaacgag atcatcaacg ccctgtccat accggccgtg | 60 |
| tcaaaccact ccgcccagat gaacctctcc accgacgcga ggatcgagga ctccctctgc | 120 |
| atcgccgagg gcaacaacat cgacccgttc gtgtctgcaa gcacggtcca gaccggcatc | 180 |
| aacatcgcgg gccgcatcct gggcgtgctc ggcgtgccct cgcgggtca aatcgcctct | 240 |
| ttctactcat tcctcgtggg cgagctgtgg ccgcgcggac gtgacccgtg ggaaatcttc | 300 |
| ctggagcacg ttgagcagct catccggcag caagtgaccg agaacaccag ggacaccgca | 360 |
| ctggcacggc tccagggcct tggcaacagc ttccgcgcct accagcagtc gctggaggac | 420 |
| tggctggaga accgagacga cgccagaacc cgctcagttc tgtacacaca gtacatcgcc | 480 |
| ctagagctgg acttcctcaa cgctatgccg ctcttcgcca tccgtaacca ggaagtaccg | 540 |
| cttctgatgt gtacgcaca gcagcgaac ctccatctgc tcctgctgcg agacgcatct | 600 |
| ctgttcggca gtgagttcgg gctgacgagc caggagatcc agcgctacta cgagcgccaa | 660 |
| gtggagaaga ctcgtgagta cagcgactac tgcgcgcgct ggtacaacac gggcttgaac | 720 |
| aaccttcgcg gacaaacgc cgaatcctgg cttcgctaca accagttccg ccgcgacctc | 780 |
| acgctgggtg tgctggacct ggtcgcgctc ttcccgtcct acgacacacg ggtgtaccca | 840 |
| atgaacacga gcgcacagct caccgtgag atctacacag atcccatcgg ccgcaccaac | 900 |
| gctcccagtg cttcgcaag cacgaattgg ttcaacaata cgctccttc tttctctgcc | 960 |
| atcgaggccg ctgtcatcag accgccgcac ttactcgatt tcccggagca gctcactatc | 1020 |
| ttctctgtgt tgtcccggtg gtcgaacacg cagtacatga actactgggt gggccacagg | 1080 |
| ctagagagcc ggaccatccg tggcagtctc tcaacctcga cccacggcaa cacgaacacg | 1140 |
| agcatcaacc ctgtcactct ccagtttaca tctagggacg tttacaggac agagtcgttc | 1200 |
| gctggcatta acattctgtt gaccactccg gtgaacggcg tcccttgggc ccgcttcaac | 1260 |
| tggaggaatc ctctgaactc actgcgcggc agccttctct acactatcgg ctacaccggc | 1320 |
| gttgggacgc aactcttcga ctcggagacc gagctgccgc cgagaccac cgagcggcct | 1380 |
| aactacgaga gttattcaca caggctctcc aacatccgct tgatttctgg gaacaccttg | 1440 |
| cgggctccgg tgtactcctg gacgcaccgc agcgccgaca gaactaatac catcagctcc | 1500 |
| gactcgatca cccagatccc gctggtgaag gctcacacgc ttcagtcggg caccacagtc | 1560 |
| gtcaagggcc ctggcttcac cggcggcgac atcctgcgtc gcacatctgg cggacccttc | 1620 |
| gccttcagca acgtgaactt ggacttcaat ttgtcacagc ggtatcgtgc cagaatccgg | 1680 |
| tacgccagca ctacgaacct gcgaatctat gttactgtgg cgggcgagcg gatcttcgcc | 1740 |

```
gggcaattcg acaagacgat ggacgcggga gcacctctga cattccagtc attctcttac   1800
gccacgatca acacggcatt cacgtttccg gagcgttcca gtagcctgac cgtgggcgct   1860
gataccttca gtagcgggaa cgaggtgtac gttgaccgtt tcgagctgat cccggtcacc   1920
gccaccacgg cgaccttcga ggcggagtat gacttggagc gggctcagga ggccgtcaac   1980
gcgctgttca caaacaccaa tcctcgccgc ctcaagacgg tgtgactga ttaccacatt   2040
gacgaggtct ccaacttggt cgcgtgtctg tccgatgagt tctgcctgga cgagaagcgg   2100
gaactgctgg agaaggtcaa gtacgccaag cgcctctccg acgaaaggaa cctcctccaa   2160
gatcccaact ttacttccat taacaagcag ccggacttca tctccaccaa cgagcagtcc   2220
aacttcacct caatccacga gcagtcggag cacgggtggt ggggcagcga aacatcacc   2280
atccaagagg gcaacgacgt cttcaaggag aactacgtga tcctgcccgg caccttcaac   2340
gagtgttacc cgacctatct ctaccagaag attggcgaag cggaactcaa ggcttacacc   2400
cgttaccaac tgagtggcta cattgaggac tcacaagacc tggaaatcta cctgatccgc   2460
tacaacgcca agcacgagac cctcgacgtg cctggcacgg agtccgtctg gcccttgagc   2520
gtggagtctc ctatcggtcg ttgcggcgag cccaatcgct cgctccgca ctttgagtgg   2580
aatcctgatt tggattgctc ctgccgagac ggtgagaaat gcgcccacca ctcgcaccac   2640
ttcagcctag acatcgacgt gggctgcatc gacctgcacg agaacttggg cgtctgggtc   2700
gtgttcaaga tcaagacaca ggagggccat gctcggcttg gaacctgga gttcatcgag   2760
gagaagccac tgctgggtga agccttgtca cgggtgaaac gcgccgagaa gaagtggcgg   2820
gacaaacggg agaagctcca gttggagaca aagcgtgtgt acacagaggc caaggaggcc   2880
gtggatgcct tgttcgtgga cagtcagtac gacaggctgc aagcggacac caacatcggg   2940
atgatccacg cggctgataa gcttgttcac agaatccgcg aggcgtacct gtcagagctt   3000
agcgtgatcc caggcgtcaa cgccgaaatc ttcgaggaac tggagggccg cattatcacg   3060
gcaatctcac tttatgacgc gaggaatgtg gtcaagaacg gtgacttcaa caacggcttg   3120
gcgtgttgga acgttaaagg gcacgtggat gtacaacagt cacaccacag aagtgtcttg   3180
gtcatcccgg agtgggaggc ggaagtgagc caggccgtcc gggtctgccc tgggcgcggt   3240
tacatcctcc gcgtgacagc gtacaaggag ggctacggtg agggctgcgt gacgatccac   3300
gagattgaga caacacggac gagcttaag ttcaagaact gcgaggagga ggaagtgtac   3360
ccgacagaca ccggcacctg caacgactac accgcccacc aagggaccgc cgcctgcaac   3420
agccgcaacg cgggctatga agatgcgtac gaggttgata ccaccgcctc agtgaactac   3480
aaaccgactt atgaggagga gacatacacg gacgtcaggc gcgacaacca ttgtgagtac   3540
gaccgtggct acgtgaacta tccgccggtg ccagcgggct acatgacgaa ggagctagaa   3600
tacttccctg agacggacaa ggtgtggatt gaaatcggcg agaccgaggg caagtttatc   3660
gtggattctg tcgagctgct gctaatggag gagtag                             3696
```

<210> SEQ ID NO 21
<211> LENGTH: 1231
<212> TYPE: PRT
<213> ORGANISM: Artificial
<220> FEATURE:
<223> OTHER INFORMATION: Amino acid sequence of the chimeric protein
      variant TIC867_23.

<400> SEQUENCE: 21

Met Thr Ser Asn Arg Lys Asn Glu Asn Glu Ile Ile Asn Ala Leu Ser

-continued

```
1               5                   10                  15
Ile Pro Ala Val Ser Asn His Ser Ala Gln Met Asn Leu Ser Thr Asp
                20                  25                  30
Ala Arg Ile Glu Asp Ser Leu Cys Ile Ala Glu Gly Asn Asn Ile Asp
                35                  40                  45
Pro Phe Val Ser Ala Ser Thr Val Gln Thr Gly Ile Asn Ile Ala Gly
 50                  55                  60
Arg Ile Leu Gly Val Leu Gly Val Pro Phe Ala Gly Gln Ile Ala Ser
 65                  70                  75                  80
Phe Tyr Ser Phe Leu Val Gly Glu Leu Trp Pro Arg Gly Arg Asp Pro
                85                  90                  95
Trp Glu Ile Phe Leu Glu His Val Glu Gln Leu Ile Arg Gln Gln Val
                100                 105                 110
Thr Glu Asn Thr Arg Asp Thr Ala Leu Ala Arg Leu Gln Gly Leu Gly
                115                 120                 125
Asn Ser Phe Arg Ala Tyr Gln Gln Ser Leu Glu Asp Trp Leu Glu Asn
                130                 135                 140
Arg Asp Asp Ala Arg Thr Arg Ser Val Leu Tyr Thr Gln Tyr Ile Ala
145                 150                 155                 160
Leu Glu Leu Asp Phe Leu Asn Ala Met Pro Leu Phe Ala Ile Arg Asn
                165                 170                 175
Gln Glu Val Pro Leu Leu Met Val Tyr Ala Gln Ala Ala Asn Leu His
                180                 185                 190
Leu Leu Leu Leu Arg Asp Ala Ser Leu Phe Gly Ser Glu Phe Gly Leu
                195                 200                 205
Thr Ser Gln Glu Ile Gln Arg Tyr Tyr Glu Arg Gln Val Glu Lys Thr
                210                 215                 220
Arg Glu Tyr Ser Asp Tyr Cys Ala Arg Trp Tyr Asn Thr Gly Leu Asn
225                 230                 235                 240
Asn Leu Arg Gly Thr Asn Ala Glu Ser Trp Leu Arg Tyr Asn Gln Phe
                245                 250                 255
Arg Arg Asp Leu Thr Leu Gly Val Leu Asp Leu Val Ala Leu Phe Pro
                260                 265                 270
Ser Tyr Asp Thr Arg Val Tyr Pro Met Asn Thr Ser Ala Gln Leu Thr
                275                 280                 285
Arg Glu Ile Tyr Thr Asp Pro Ile Gly Arg Thr Asn Ala Pro Ser Gly
                290                 295                 300
Phe Ala Ser Thr Asn Trp Phe Asn Asn Asn Ala Pro Ser Phe Ser Ala
305                 310                 315                 320
Ile Glu Ala Ala Val Ile Arg Pro Pro His Leu Leu Asp Phe Pro Glu
                325                 330                 335
Gln Leu Thr Ile Phe Ser Val Leu Ser Arg Trp Ser Asn Thr Gln Tyr
                340                 345                 350
Met Asn Tyr Trp Val Gly His Arg Leu Glu Ser Arg Thr Ile Arg Gly
                355                 360                 365
Ser Leu Ser Thr Ser Thr His Gly Asn Thr Asn Thr Ser Ile Asn Pro
                370                 375                 380
Val Thr Leu Gln Phe Thr Ser Arg Asp Val Tyr Arg Thr Glu Ser Phe
385                 390                 395                 400
Ala Gly Ile Asn Ile Leu Leu Thr Thr Pro Val Asn Gly Val Pro Trp
                405                 410                 415
Ala Arg Phe Asn Trp Arg Asn Pro Leu Asn Ser Leu Arg Gly Ser Leu
                420                 425                 430
```

```
Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
            500                 505                 510

Thr Leu Gln Ser Gly Thr Val Val Lys Gly Pro Gly Phe Thr Gly
            515                 520                 525

Gly Asp Ile Leu Arg Arg Thr Ser Gly Gly Pro Phe Ala Phe Ser Asn
    530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
                580                 585                 590

Leu Thr Phe Gln Ser Phe Ser Tyr Ala Thr Ile Asn Thr Ala Phe Thr
            595                 600                 605

Phe Pro Glu Arg Ser Ser Leu Thr Val Gly Ala Asp Thr Phe Ser
    610                 615                 620

Ser Gly Asn Glu Val Tyr Val Asp Arg Phe Glu Leu Ile Pro Val Thr
625                 630                 635                 640

Ala Thr Thr Ala Thr Phe Glu Ala Glu Tyr Asp Leu Glu Arg Ala Gln
                645                 650                 655

Glu Ala Val Asn Ala Leu Phe Thr Asn Thr Asn Pro Arg Arg Leu Lys
                660                 665                 670

Thr Gly Val Thr Asp Tyr His Ile Asp Glu Val Ser Asn Leu Val Ala
            675                 680                 685

Cys Leu Ser Asp Glu Phe Cys Leu Asp Glu Lys Arg Glu Leu Leu Glu
            690                 695                 700

Lys Val Lys Tyr Ala Lys Arg Leu Ser Asp Glu Arg Asn Leu Leu Gln
705                 710                 715                 720

Asp Pro Asn Phe Thr Ser Ile Asn Lys Gln Pro Asp Phe Ile Ser Thr
                725                 730                 735

Asn Glu Gln Ser Asn Phe Thr Ser Ile His Glu Gln Ser Glu His Gly
            740                 745                 750

Trp Trp Gly Ser Glu Asn Ile Thr Ile Gln Gly Asn Asp Val Phe
            755                 760                 765

Lys Glu Asn Tyr Val Ile Leu Pro Gly Thr Phe Asn Glu Cys Tyr Pro
    770                 775                 780

Thr Tyr Leu Tyr Gln Lys Ile Gly Glu Ala Glu Leu Lys Ala Tyr Thr
785                 790                 795                 800

Arg Tyr Gln Leu Ser Gly Tyr Ile Glu Asp Ser Gln Asp Leu Glu Ile
                805                 810                 815

Tyr Leu Ile Arg Tyr Asn Ala Lys His Glu Thr Leu Asp Val Pro Gly
            820                 825                 830

Thr Glu Ser Val Trp Pro Leu Ser Val Glu Ser Pro Ile Gly Arg Cys
            835                 840                 845
```

Gly Glu Pro Asn Arg Cys Ala Pro His Phe Glu Trp Asn Pro Asp Leu
850                 855                 860

Asp Cys Ser Cys Arg Asp Gly Glu Lys Cys Ala His His Ser His His
865                 870                 875                 880

Phe Ser Leu Asp Ile Asp Val Gly Cys Ile Asp Leu His Glu Asn Leu
            885                 890                 895

Gly Val Trp Val Val Phe Lys Ile Lys Thr Gln Glu Gly His Ala Arg
        900                 905                 910

Leu Gly Asn Leu Glu Phe Ile Glu Glu Lys Pro Leu Leu Gly Glu Ala
        915                 920                 925

Leu Ser Arg Val Lys Arg Ala Glu Lys Lys Trp Arg Asp Lys Arg Glu
930                 935                 940

Lys Leu Gln Leu Glu Thr Lys Arg Val Tyr Thr Glu Ala Lys Glu Ala
945                 950                 955                 960

Val Asp Ala Leu Phe Val Asp Ser Gln Tyr Asp Arg Leu Gln Ala Asp
                965                 970                 975

Thr Asn Ile Gly Met Ile His Ala Ala Asp Lys Leu Val His Arg Ile
            980                 985                 990

Arg Glu Ala Tyr Leu Ser Glu Leu Ser Val Ile Pro Gly Val Asn Ala
        995                 1000                1005

Glu Ile Phe Glu Glu Leu Glu Gly Arg Ile Ile Thr Ala Ile Ser
    1010                1015                1020

Leu Tyr Asp Ala Arg Asn Val Val Lys Asn Gly Asp Phe Asn Asn
    1025                1030                1035

Gly Leu Ala Cys Trp Asn Val Lys Gly His Val Asp Val Gln Gln
    1040                1045                1050

Ser His His Arg Ser Val Leu Val Ile Pro Glu Trp Glu Ala Glu
    1055                1060                1065

Val Ser Gln Ala Val Arg Val Cys Pro Gly Arg Gly Tyr Ile Leu
    1070                1075                1080

Arg Val Thr Ala Tyr Lys Glu Gly Tyr Gly Glu Gly Cys Val Thr
    1085                1090                1095

Ile His Glu Ile Glu Asn Asn Thr Asp Glu Leu Lys Phe Lys Asn
    1100                1105                1110

Cys Glu Glu Glu Val Tyr Pro Thr Asp Thr Gly Thr Cys Asn
    1115                1120                1125

Asp Tyr Thr Ala His Gln Gly Thr Ala Ala Cys Asn Ser Arg Asn
    1130                1135                1140

Ala Gly Tyr Glu Asp Ala Tyr Glu Val Asp Thr Thr Ala Ser Val
    1145                1150                1155

Asn Tyr Lys Pro Thr Tyr Glu Glu Thr Tyr Thr Asp Val Arg
    1160                1165                1170

Arg Asp Asn His Cys Glu Tyr Asp Arg Gly Tyr Val Asn Tyr Pro
    1175                1180                1185

Pro Val Pro Ala Gly Tyr Met Thr Lys Glu Leu Glu Tyr Phe Pro
    1190                1195                1200

Glu Thr Asp Lys Val Trp Ile Glu Ile Gly Glu Thr Glu Gly Lys
    1205                1210                1215

Phe Ile Val Asp Ser Val Glu Leu Leu Leu Met Glu Glu
    1220                1225                1230

<210> SEQ ID NO 22
<211> LENGTH: 3666
<212> TYPE: DNA

<213> ORGANISM: Artificial
<220> FEATURE:
<223> OTHER INFORMATION: Synthetic nucleotide sequence designed for
      expression in a plant cell encoding TIC867_24.

<400> SEQUENCE: 22

| | | | | | |
|---|---|---|---|---|---|
| atgaccagca | accgaaagaa | cgagaacgag | atcatcaacg | ccctgtccat | accggccgtg | 60 |
| tcaaaccact | ccgcccagat | gaacctctcc | accgacgcga | ggatcgagga | ctccctctgc | 120 |
| atcgccgagg | gcaacaacat | cgacccgttc | gtgtctgcaa | gcacggtcca | gaccggcatc | 180 |
| aacatcgcgg | gccgcatcct | gggcgtgctc | ggcgtgccct | cgcgggtca | aatcgcctct | 240 |
| ttctactcat | tcctcgtggg | cgagctgtgg | ccgcgcggac | gtgacccgtg | gaaatcttc | 300 |
| ctggagcacg | ttgagcagct | catccggcag | caagtgaccg | agaacaccag | ggacaccgca | 360 |
| ctggcacggc | tccagggcct | tggcaacagc | ttccgcgcct | accagcagtc | gctggaggac | 420 |
| tggctggaga | accgagacga | cgccagaacc | cgctcagttc | tgtacacaca | gtacatcgcc | 480 |
| ctagagctgg | acttcctcaa | cgctatgccg | ctcttcgcca | tccgtaacca | ggaagtaccg | 540 |
| cttctgatgg | tgtacgcaca | agcagcgaac | ctccatctgc | tcctgctgcg | agacgcatct | 600 |
| ctgttcggca | gtgagttcgg | gctgacgagc | caggagatcc | agcgctacta | cgagcgccaa | 660 |
| gtggagaaga | ctcgtgagta | cagcgactac | tgcgcgcgct | ggtacaacac | gggcttgaac | 720 |
| aaccttcgcg | gacaaacgc | cgaatcctgg | cttcgctaca | accagttccg | ccgcgaccct | 780 |
| acgctgggtg | tgctggacct | ggtcgcgctc | ttcccgtcct | acgacacacg | ggtgtaccca | 840 |
| atgaacacga | gcgcacagct | cacccgtgag | atctacacag | atcccatcgg | ccgcaccaac | 900 |
| gctcccagtg | gcttcgcaag | cacgaattgg | ttcaacaata | acgctccttc | tttctctgcc | 960 |
| atcgaggccg | ctgtcatcag | accgccgcac | ttactcgatt | cccggagca | gctcactatc | 1020 |
| ttctctgtgt | tgtcccggtg | gtcgaacacg | cagtacatga | actactgggt | gggccacagg | 1080 |
| ctagagagcc | ggaccatccg | tggcagtctc | tcaacctcga | cccacggcaa | cacgaacacg | 1140 |
| agcatcaacc | ctgtcactct | ccagtttaca | tctagggacg | tttacaggac | agagtcgttc | 1200 |
| gctggcatta | acattctgtt | gaccactccg | gtgaacggcg | tccctttgggc | ccgcttcaac | 1260 |
| tggaggaatc | ctctgaactc | actgcgcggc | agccttctct | acactatcgg | ctacaccggc | 1320 |
| gttgggacgc | aactcttcga | ctcggagacc | gagctgccgc | ccgagaccac | cgagcggcct | 1380 |
| aactacgaga | gttattcaca | caggctctcc | aacatccgct | tgatttctgg | gaacaccttg | 1440 |
| cgggctccgg | tgtactcctg | gacgcaccgc | agcgccgaca | gaactaatac | catcagctcc | 1500 |
| gactcgatca | cccagatccc | gctggtgaag | gctcacacgc | ttcagtcggg | caccacagtc | 1560 |
| gtcaagggcc | ctggcttcac | cggcggcgac | atcctgcgtc | gcacatctgg | cggacccttc | 1620 |
| gccttcagca | acgtgaactt | ggacttcaat | ttgtcacagc | ggtatcgtgc | cagaatccgg | 1680 |
| tacgccagca | ctacgaacct | gcgaatctat | gttactgtgg | cgggcgagcg | gatcttcgcc | 1740 |
| gggcaattcg | acaagacgat | ggacgcggga | gcacctctga | cattccagtc | attctcttac | 1800 |
| gccacgatca | acacggcatt | cacgtttccg | gagcgttcca | gtagcctgac | cgtgggcgct | 1860 |
| gataccttca | gtagcgggaa | cgaggtgtac | gttgaccgtt | tcgagctgat | cccggtcacc | 1920 |
| gccaccaccg | cgacgtttga | agctgaatcc | gacctcgagc | gtgcgcgcaa | ggcggtgaac | 1980 |
| gctctgttca | cgagcaccaa | ccctcgtggc | ttgaagacgg | atgtgacgga | ctaccacatc | 2040 |
| gaccaagtct | cgaacctcgt | ggagtgcctg | agcgacgagt | tctgtcttga | caagaagcgc | 2100 |
| gagctgctgg | aggaggtgaa | gtacgccaag | cgcctctccc | atgagcgcaa | cctgctccaa | 2160 |

```
gatcctacct tcacgtcgat ttccggccaa accgaccgtg gatggatcgg ctcgactggc   2220
atctccatcc agggcggcga cgacatcttc aaggagaact atgttcggct gccgggcacg   2280
gtggacgagt gttacccgac gtacctctac cagaagatag acgagagtca actcaagtcc   2340
tacacgcggt atcagttacg tggctacatt gaagactccc aggacttgga aatctatctc   2400
atacggtaca acgccaagca cgagacctta agcgtgccgg gaacggagtc gccctggcca   2460
agctctggcg tgtacccttc cggtaggtgc ggcgagccca accgctgtgc acctcgaatc   2520
gaatggaacc cggaccttga ctgctcttgc cggtacggcg agaagtgcgt ccatcattct   2580
caccacttca gcttggacat tgacgtcggc tgcaccgacc tcaatgaaga cctcggagtg   2640
tgggtcatct tcaagatcaa gacacaggac gggcacgcga aactaggaaa cctggagttc   2700
atcgaggaga agccactcct cggcaaggca ctttccaggg tcaagcgggc cgagaagaaa   2760
tggagggaca agtacgagaa actccagctc gaaacaaagc gggtgtacac ggaggcaaag   2820
gaatccgtgg acgccctgtt cgtggactct cagtacgaca agctccaggc gaacacaaac   2880
attggcatca tccacggtgc ggacaagcaa gtgcacagga tacgggagcc ttacctctcg   2940
gagctgccgg tgattccctc gatcaacgcg gcgatcttcg aggaactgga gggccacatc   3000
ttcaaggcgt attctctgta cgacgcgcgt aacgtcatca agaacggcga cttcaacaat   3060
gggctgtcct gctggaacgt taaaggccac gtcgatgtcc agcagaacca ccataggtca   3120
gtcctggtgc tgagcgagtg ggaggcggag gtgtcccaga aggtgcgcgt gtgcccggat   3180
cgcggctaca tcttgagggt gacagcctac aaggagggct acggcgaggg ctgtgtcacg   3240
atccatgagt tcgaggacaa cacgcgatgtc ctgaaattcc gtaacttcgt cgaggaggag   3300
gtctatccca caacaccgt gacctgcaac gactacacga ccaatcagtc ggctgagggc   3360
agtaccgatg cctgcaacag ctacaaccgt ggttacgaag atggatacga gaaccgctac   3420
gagcccaatc cttcggctcc cgtgaattac actcccacgt acgaggaggg catgtacact   3480
gacactcagg gctacaacca ttgcgtcagc gaccgtggct accgcaacca cacgccgctc   3540
ccagcgggct acgtgacgct ggagctggaa tactttcccg agacagaaca agtgtggata   3600
gagatcggcg agaccgaggg cacattcatc gtgggctctg tggaattgct cctcatggag   3660
gagtaa                                                              3666
```

<210> SEQ ID NO 23
<211> LENGTH: 1221
<212> TYPE: PRT
<213> ORGANISM: Artificial
<220> FEATURE:
<223> OTHER INFORMATION: Amino acid sequence of the chimeric protein
      variant TIC867_24.

<400> SEQUENCE: 23

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro

```
                  85                  90                  95
Trp Glu Ile Phe Leu Glu His Val Glu Gln Leu Ile Arg Gln Gln Val
                100                 105                 110
Thr Glu Asn Thr Arg Asp Thr Ala Leu Ala Arg Leu Gln Gly Leu Gly
                115                 120                 125
Asn Ser Phe Arg Ala Tyr Gln Gln Ser Leu Glu Asp Trp Leu Glu Asn
            130                 135                 140
Arg Asp Asp Ala Arg Thr Arg Ser Val Leu Tyr Thr Gln Tyr Ile Ala
145                 150                 155                 160
Leu Glu Leu Asp Phe Leu Asn Ala Met Pro Leu Phe Ala Ile Arg Asn
                165                 170                 175
Gln Glu Val Pro Leu Leu Met Val Tyr Ala Gln Ala Ala Asn Leu His
                180                 185                 190
Leu Leu Leu Leu Arg Asp Ala Ser Leu Phe Gly Ser Glu Phe Gly Leu
            195                 200                 205
Thr Ser Gln Glu Ile Gln Arg Tyr Tyr Glu Arg Gln Val Glu Lys Thr
        210                 215                 220
Arg Glu Tyr Ser Asp Tyr Cys Ala Arg Trp Tyr Asn Thr Gly Leu Asn
225                 230                 235                 240
Asn Leu Arg Gly Thr Asn Ala Glu Ser Trp Leu Arg Tyr Asn Gln Phe
                245                 250                 255
Arg Arg Asp Leu Thr Leu Gly Val Leu Asp Leu Val Ala Leu Phe Pro
            260                 265                 270
Ser Tyr Asp Thr Arg Val Tyr Pro Met Asn Thr Ser Ala Gln Leu Thr
        275                 280                 285
Arg Glu Ile Tyr Thr Asp Pro Ile Gly Arg Thr Asn Ala Pro Ser Gly
        290                 295                 300
Phe Ala Ser Thr Asn Trp Phe Asn Asn Asn Ala Pro Ser Phe Ser Ala
305                 310                 315                 320
Ile Glu Ala Ala Val Ile Arg Pro Pro His Leu Leu Asp Phe Pro Glu
                325                 330                 335
Gln Leu Thr Ile Phe Ser Val Leu Ser Arg Trp Ser Asn Thr Gln Tyr
            340                 345                 350
Met Asn Tyr Trp Val Gly His Arg Leu Glu Ser Arg Thr Ile Arg Gly
        355                 360                 365
Ser Leu Ser Thr Ser Thr His Gly Asn Thr Asn Thr Ser Ile Asn Pro
        370                 375                 380
Val Thr Leu Gln Phe Thr Ser Arg Asp Val Tyr Arg Thr Glu Ser Phe
385                 390                 395                 400
Ala Gly Ile Asn Ile Leu Leu Thr Thr Pro Val Asn Gly Val Pro Trp
                405                 410                 415
Ala Arg Phe Asn Trp Arg Asn Pro Leu Asn Ser Leu Arg Gly Ser Leu
            420                 425                 430
Leu Tyr Thr Ile Gly Tyr Thr Gly Val Gly Thr Gln Leu Phe Asp Ser
        435                 440                 445
Glu Thr Glu Leu Pro Pro Glu Thr Thr Glu Arg Pro Asn Tyr Glu Ser
        450                 455                 460
Tyr Ser His Arg Leu Ser Asn Ile Arg Leu Ile Ser Gly Asn Thr Leu
465                 470                 475                 480
Arg Ala Pro Val Tyr Ser Trp Thr His Arg Ser Ala Asp Arg Thr Asn
                485                 490                 495
Thr Ile Ser Ser Asp Ser Ile Thr Gln Ile Pro Leu Val Lys Ala His
            500                 505                 510
```

```
Thr Leu Gln Ser Gly Thr Thr Val Lys Gly Pro Gly Phe Thr Gly
            515                 520                 525
Gly Asp Ile Leu Arg Arg Thr Ser Gly Gly Pro Phe Ala Phe Ser Asn
530                 535                 540
Val Asn Leu Asp Phe Asn Leu Ser Gln Arg Tyr Arg Ala Arg Ile Arg
545                 550                 555                 560
Tyr Ala Ser Thr Thr Asn Leu Arg Ile Tyr Val Thr Val Ala Gly Glu
                565                 570                 575
Arg Ile Phe Ala Gly Gln Phe Asp Lys Thr Met Asp Ala Gly Ala Pro
            580                 585                 590
Leu Thr Phe Gln Ser Phe Ser Tyr Ala Thr Ile Asn Thr Ala Phe Thr
            595                 600                 605
Phe Pro Glu Arg Ser Ser Ser Leu Thr Val Gly Ala Asp Thr Phe Ser
        610                 615                 620
Ser Gly Asn Glu Val Tyr Val Asp Arg Phe Glu Leu Ile Pro Val Thr
625                 630                 635                 640
Ala Thr Thr Ala Thr Phe Glu Ala Glu Ser Asp Leu Glu Arg Ala Arg
                645                 650                 655
Lys Ala Val Asn Ala Leu Phe Thr Ser Thr Asn Pro Arg Gly Leu Lys
            660                 665                 670
Thr Asp Val Thr Asp Tyr His Ile Asp Gln Val Ser Asn Leu Val Glu
            675                 680                 685
Cys Leu Ser Asp Glu Phe Cys Leu Asp Lys Lys Arg Glu Leu Leu Glu
        690                 695                 700
Glu Val Lys Tyr Ala Lys Arg Leu Ser Asp Glu Arg Asn Leu Leu Gln
705                 710                 715                 720
Asp Pro Thr Phe Thr Ser Ile Ser Gly Gln Thr Asp Arg Gly Trp Ile
                725                 730                 735
Gly Ser Thr Gly Ile Ser Ile Gln Gly Gly Asp Asp Ile Phe Lys Glu
            740                 745                 750
Asn Tyr Val Arg Leu Pro Gly Thr Val Asp Glu Cys Tyr Pro Thr Tyr
            755                 760                 765
Leu Tyr Gln Lys Ile Asp Glu Ser Gln Leu Lys Ser Tyr Thr Arg Tyr
        770                 775                 780
Gln Leu Arg Gly Tyr Ile Glu Asp Ser Gln Asp Leu Glu Ile Tyr Leu
785                 790                 795                 800
Ile Arg Tyr Asn Ala Lys His Glu Thr Leu Ser Val Pro Gly Thr Glu
                805                 810                 815
Ser Pro Trp Pro Ser Ser Gly Val Tyr Pro Ser Gly Arg Cys Gly Glu
            820                 825                 830
Pro Asn Arg Cys Ala Pro Arg Ile Glu Trp Asn Pro Asp Leu Asp Cys
            835                 840                 845
Ser Cys Arg Tyr Gly Glu Lys Cys Val His Ser His His Phe Ser
        850                 855                 860
Leu Asp Ile Asp Val Gly Cys Thr Asp Leu Asn Glu Asp Leu Gly Val
865                 870                 875                 880
Trp Val Ile Phe Lys Ile Lys Thr Gln Asp Gly His Ala Lys Leu Gly
                885                 890                 895
Asn Leu Glu Phe Ile Glu Glu Lys Pro Leu Gly Lys Ala Leu Ser
            900                 905                 910
Arg Val Lys Arg Ala Glu Lys Lys Trp Arg Asp Lys Tyr Glu Lys Leu
            915                 920                 925
```

Gln Leu Glu Thr Lys Arg Val Tyr Thr Glu Ala Lys Glu Ser Val Asp
    930                 935                 940

Ala Leu Phe Val Asp Ser Gln Tyr Asp Lys Leu Gln Ala Asn Thr Asn
945                 950                 955                 960

Ile Gly Ile Ile His Gly Ala Asp Lys Gln Val His Arg Ile Arg Glu
                965                 970                 975

Pro Tyr Leu Ser Glu Leu Pro Val Ile Pro Ser Ile Asn Ala Ala Ile
                980                 985                 990

Phe Glu Glu Leu Glu Gly His Ile Phe Lys Ala Tyr Ser Leu Tyr Asp
            995                 1000                1005

Ala Arg Asn Val Ile Lys Asn Gly Asp Phe Asn Asn Gly Leu Ser
    1010                1015                1020

Cys Trp Asn Val Lys Gly His Val Asp Val Gln Gln Asn His His
    1025                1030                1035

Arg Ser Val Leu Val Leu Ser Glu Trp Glu Ala Glu Val Ser Gln
    1040                1045                1050

Lys Val Arg Val Cys Pro Asp Arg Gly Tyr Ile Leu Arg Val Thr
    1055                1060                1065

Ala Tyr Lys Glu Gly Tyr Gly Glu Gly Cys Val Thr Ile His Glu
    1070                1075                1080

Phe Glu Asp Asn Thr Asp Val Leu Lys Phe Arg Asn Phe Val Glu
    1085                1090                1095

Glu Glu Val Tyr Pro Asn Asn Thr Val Thr Cys Asn Asp Tyr Thr
    1100                1105                1110

Thr Asn Gln Ser Ala Glu Gly Ser Thr Asp Ala Cys Asn Ser Tyr
    1115                1120                1125

Asn Arg Gly Tyr Glu Asp Gly Tyr Glu Asn Arg Tyr Glu Pro Asn
    1130                1135                1140

Pro Ser Ala Pro Val Asn Tyr Thr Pro Thr Tyr Glu Glu Gly Met
    1145                1150                1155

Tyr Thr Asp Thr Gln Gly Tyr Asn His Cys Val Ser Asp Arg Gly
    1160                1165                1170

Tyr Arg Asn His Thr Pro Leu Pro Ala Gly Tyr Val Thr Leu Glu
    1175                1180                1185

Leu Glu Tyr Phe Pro Glu Thr Glu Gln Val Trp Ile Glu Ile Gly
    1190                1195                1200

Glu Thr Glu Gly Thr Phe Ile Val Gly Ser Val Glu Leu Leu Leu
    1205                1210                1215

Met Glu Glu
    1220

<210> SEQ ID NO 24
<211> LENGTH: 3651
<212> TYPE: DNA
<213> ORGANISM: Artificial
<220> FEATURE:
<223> OTHER INFORMATION: Synthetic nucleotide sequence designed for
      expression in a plant cell encoding TIC867_25.

<400> SEQUENCE: 24
atgaccagca accgaaagaa cgagaacgag atcatcaacg ccctgtccat accggccgtg      60
tcaaaccact ccgcccagat gaacctctcc accgacgcga ggatcgagga ctccctctgc     120
atcgccgagg caacaacat cgacccgttc gtgtctgcaa gcacggtcca gaccggcatc      180
aacatcgcgg gccgcatcct gggcgtgctc ggcgtgccct cgcgggtca aatcgcctct      240

```
ttctactcat tcctcgtggg cgagctgtgg ccgcgcggac gtgacccgtg ggaaatcttc      300
ctggagcacg ttgagcagct catccggcag caagtgaccg agaacaccag ggacaccgca      360
ctggcacggc tccagggcct tggcaacagc ttccgcgcct accagcagtc gctggaggac      420
tggctggaga accgagacga cgccagaacc cgctcagttc tgtacacaca gtacatcgcc      480
ctagagctgg acttcctcaa cgctatgccg ctcttcgcca tccgtaacca ggaagtaccg      540
cttctgatgg tgtacgcaca agcagcgaac ctccatctgc tcctgctgcg agacgcatct      600
ctgttcggca gtgagttcgg gctgacgagc caggagatcc agcgctacta cgagcgccaa      660
gtggagaaga ctcgtgagta cagcgactac tgcgcgcgct ggtacaacac gggcttgaac      720
aaccttcgcg ggacaaacgc cgaatcctgg cttcgctaca accagttccg ccgcgacctc      780
acgctgggtg tgctggacct ggtcgcgctc ttcccgtcct acgacacacg ggtgtaccca      840
atgaacacga gcgcacagct cacccgtgag atctacacag atcccatcgg ccgcaccaac      900
gctcccagtg gcttcgcaag cacgaattgg ttcaacaata acgctccttc tttctctgcc      960
atcgaggccg ctgtcatcag accgccgcac ttactcgatt tcccggagca gctcactatc     1020
ttctctgtgt tgtcccggtg gtcgaacacg cagtacatga actactgggt gggccacagg     1080
ctagagagcc ggaccatccg tggcagtctc tcaacctcga cccacggcaa cacgaacacg     1140
agcatcaacc ctgtcactct ccagtttaca tctagggacg tttacaggac agagtcgttc     1200
gctggcatta acattctgtt gaccactccg gtgaacggcg tcccttgggc ccgcttcaac     1260
tggaggaatc ctctgaactc actgcgcggc agccttctct acactatcgg ctacaccggc     1320
gttgggacgc aactcttcga ctcggagacc gagctgccgc ccgagaccac cgagcggcct     1380
aactacgaga gttattcaca caggctctcc aacatccgct tgatttctgg gaacaccttg     1440
cgggctccgg tgtactcctg gacgcaccgc agcgccgaca gaactaatac catcagctcc     1500
gactcgatca cccagatccc gctggtgaag gctcacacgc ttcagtcggg caccacagtc     1560
gtcaagggcc ctggcttcac cggcggcgac atcctgcgtc gcacatctgg cggacccttc     1620
gccttcagca acgtgaactt ggacttcaat ttgtcacagc ggtatcgtgc cagaatccgg     1680
tacgccagca ctacgaacct gcgaatctat gttactgtgg cgggcgagcg gatcttcgcc     1740
gggcaattcg acaagacgat ggacgcggga gcacctctga cattccagtc attctcttac     1800
gccacgatca cacggcatt cacgtttccg gagcgttcca gtagcctgac cgtgggcgct      1860
gataccttca gtagcgggaa cgaggtgtac gttgaccgtt tcgagctgat cccggtcacc     1920
gccaccgatg ctacctttga agcagagtcc gacttggaac gtgcacagaa ggcagtgaac     1980
gcactcttca cctcaagcaa ccagatcgga ttgaagacag atgtgacaga ttaccacatc     2040
gaccaagtga gcaacttggt ggattgcttg tcagatgagt tctgcttgga tgagaagcgt     2100
gaactctccg agaaggtgaa gcacgcaaag cgtctctcag atgaacgtaa tctccttcaa     2160
gaccctaact ttcgtggtat caatcgtcag ccagatcgtg gatggcgtgg atcaacagac     2220
atcaccatcc agggaggcga tgatgtgttc aaggagaact acgtgaccct cccaggaacc     2280
gtggatgaat gctacccaac ctacctctac cagaagatcg acgagtcaaa gctcaaggct     2340
tacacccgtt atgaactccg tggctacatc gaagatagcc aggatctcga aatctatctc     2400
atccgttaca atgctaagca cgaaatcgtg aatgtgccag gaaccggctc actctggcca     2460
ctctcagcac agtcaccaat cggcaagtgc ggcgaaccca atcgctgcgc tcctcatctc     2520
gaatggaatc ccgatctcga ctgctcctgc cgagacggcg agaagtgtgc acatcactca     2580
caccacttca ccctcgacat cgacgtgggc tgcaccgacc tcaatgaaga cctgggcgtg     2640
```

```
tgggtgatct tcaagatcaa gacccaggac ggccacgcac gactgggcaa tctggagttt    2700
ctggaggaga agccactgct tggcgaggca ctggcacgag tgaaacgagc cgagaagaaa    2760
tggcgagaca acgtgagaa gctgcaactg gagaccaaca tcgtgtacaa agaggccaaa     2820
gagtcagttg acgccctgtt tgtcaatagc cagtatgacc gactgcaagt tgacaccaac    2880
atcgccatga tccacgctgc ggacaagcgc gtccaccgca tccgcgaggc ttatctgccc    2940
gagctgagcg tcattcccgg cgtcaatgcc gcgatcttcg aggagttaga gggccgcatc    3000
ttcaccgcct acagcctcta tgacgcccgc aatgtcatta agaatggcga cttcaacaat    3060
ggcttactat gctggaatgt caaagggcac gttgacgtcg aggagcagaa caatcaccgc    3120
agcgtcttag tcatacccga gtgggaggcc gaagtcagcc aggaagtccg cgtctgtcca    3180
gggcgcgggt acatcctgcg ggtcaccgcc tacaaagagg gatacggcga gggttgtgtc    3240
accatacacg agatagagga caataccgac gaactcaagt tcagcaattg tgtcgaggag    3300
gaagtctatc ccaacaatac cgtaacctgc aacaactaca ccggaaccca ggaggagtat    3360
gaagggacgt acacctcgcg gaaccagggc tatgacgaag cctatgggaa caacccgtcg    3420
gtgcctgctg actatgcgtc ggtctatgag gagaaatcgt acacgacggg gcggcgggag    3480
aatccgtgtg agtcgaatcg cgggtatggt gactacacgc cgctaccggc gggctatgta    3540
acgaaagacc tggaatactt cccggagacg gacaaagtat ggatagagat aggcgagacg    3600
gagggaacgt tcatcgtgga ctcggtagag ctgctgctca tggaggagtg a             3651
```

<210> SEQ ID NO 25
<211> LENGTH: 1216
<212> TYPE: PRT
<213> ORGANISM: Artificial
<220> FEATURE:
<223> OTHER INFORMATION: Amino acid sequence of the chimeric protein variant TIC867_25.

<400> SEQUENCE: 25

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175
```

```
Gln Glu Val Pro Leu Leu Met Val Tyr Ala Gln Ala Ala Asn Leu His
                180                 185                 190
Leu Leu Leu Leu Arg Asp Ala Ser Leu Phe Gly Ser Glu Phe Gly Leu
            195                 200                 205
Thr Ser Gln Glu Ile Gln Arg Tyr Tyr Glu Arg Gln Val Glu Lys Thr
210                 215                 220
Arg Glu Tyr Ser Asp Tyr Cys Ala Arg Trp Tyr Asn Thr Gly Leu Asn
225                 230                 235                 240
Asn Leu Arg Gly Thr Asn Ala Glu Ser Trp Leu Arg Tyr Asn Gln Phe
                245                 250                 255
Arg Arg Asp Leu Thr Leu Gly Val Leu Asp Leu Val Ala Leu Phe Pro
                260                 265                 270
Ser Tyr Asp Thr Arg Val Tyr Pro Met Asn Thr Ser Ala Gln Leu Thr
            275                 280                 285
Arg Glu Ile Tyr Thr Asp Pro Ile Gly Arg Thr Asn Ala Pro Ser Gly
290                 295                 300
Phe Ala Ser Thr Asn Trp Phe Asn Asn Asn Ala Pro Ser Phe Ser Ala
305                 310                 315                 320
Ile Glu Ala Ala Val Ile Arg Pro Pro His Leu Leu Asp Phe Pro Glu
                325                 330                 335
Gln Leu Thr Ile Phe Ser Val Leu Ser Arg Trp Ser Asn Thr Gln Tyr
                340                 345                 350
Met Asn Tyr Trp Val Gly His Arg Leu Glu Ser Arg Thr Ile Arg Gly
            355                 360                 365
Ser Leu Ser Thr Ser Thr His Gly Asn Thr Asn Thr Ser Ile Asn Pro
370                 375                 380
Val Thr Leu Gln Phe Thr Ser Arg Asp Val Tyr Arg Thr Glu Ser Phe
385                 390                 395                 400
Ala Gly Ile Asn Ile Leu Leu Thr Thr Pro Val Asn Gly Val Pro Trp
                405                 410                 415
Ala Arg Phe Asn Trp Arg Asn Pro Leu Asn Ser Leu Arg Gly Ser Leu
                420                 425                 430
Leu Tyr Thr Ile Gly Tyr Thr Gly Val Gly Thr Gln Leu Phe Asp Ser
            435                 440                 445
Glu Thr Glu Leu Pro Pro Glu Thr Thr Glu Arg Pro Asn Tyr Glu Ser
450                 455                 460
Tyr Ser His Arg Leu Ser Asn Ile Arg Leu Ile Ser Gly Asn Thr Leu
465                 470                 475                 480
Arg Ala Pro Val Tyr Ser Trp Thr His Arg Ser Ala Asp Arg Thr Asn
                485                 490                 495
Thr Ile Ser Ser Asp Ser Ile Thr Gln Ile Pro Leu Val Lys Ala His
            500                 505                 510
Thr Leu Gln Ser Gly Thr Thr Val Val Lys Gly Pro Gly Phe Thr Gly
            515                 520                 525
Gly Asp Ile Leu Arg Arg Thr Ser Gly Gly Pro Phe Ala Phe Ser Asn
            530                 535                 540
Val Asn Leu Asp Phe Asn Leu Ser Gln Arg Tyr Arg Ala Arg Ile Arg
545                 550                 555                 560
Tyr Ala Ser Thr Thr Asn Leu Arg Ile Tyr Val Thr Val Ala Gly Glu
                565                 570                 575
Arg Ile Phe Ala Gly Gln Phe Asp Lys Thr Met Asp Ala Gly Ala Pro
                580                 585                 590
Leu Thr Phe Gln Ser Phe Ser Tyr Ala Thr Ile Asn Thr Ala Phe Thr
```

```
              595                 600                 605
Phe Pro Glu Arg Ser Ser Leu Thr Val Gly Ala Asp Thr Phe Ser
610                 615                 620

Ser Gly Asn Glu Val Tyr Val Asp Arg Phe Glu Leu Ile Pro Val Thr
625                 630                 635                 640

Ala Thr Asp Ala Thr Phe Glu Ala Glu Ser Asp Leu Glu Arg Ala Gln
                645                 650                 655

Lys Ala Val Asn Ala Leu Phe Thr Ser Ser Asn Gln Ile Gly Leu Lys
                660                 665                 670

Thr Asp Val Thr Asp Tyr His Ile Asp Gln Val Ser Asn Leu Val Asp
                675                 680                 685

Cys Leu Ser Asp Glu Phe Cys Leu Asp Glu Lys Arg Glu Leu Ser Glu
690                 695                 700

Lys Val Lys His Ala Lys Arg Leu Ser Asp Glu Arg Asn Leu Leu Gln
705                 710                 715                 720

Asp Pro Asn Phe Arg Gly Ile Asn Arg Gln Pro Asp Arg Gly Trp Arg
                725                 730                 735

Gly Ser Thr Asp Ile Thr Ile Gln Gly Gly Asp Asp Val Phe Lys Glu
                740                 745                 750

Asn Tyr Val Thr Leu Pro Gly Thr Val Asp Glu Cys Tyr Pro Thr Tyr
                755                 760                 765

Leu Tyr Gln Lys Ile Asp Glu Ser Lys Leu Lys Ala Tyr Thr Arg Tyr
770                 775                 780

Glu Leu Arg Gly Tyr Ile Glu Asp Ser Gln Asp Leu Glu Ile Tyr Leu
785                 790                 795                 800

Ile Arg Tyr Asn Ala Lys His Glu Ile Val Asn Val Pro Gly Thr Gly
                805                 810                 815

Ser Leu Trp Pro Leu Ser Ala Gln Ser Pro Ile Gly Lys Cys Gly Glu
                820                 825                 830

Pro Asn Arg Cys Ala Pro His Leu Glu Trp Asn Pro Asp Leu Asp Cys
                835                 840                 845

Ser Cys Arg Asp Gly Glu Lys Cys Ala His His Ser His His Phe Thr
850                 855                 860

Leu Asp Ile Asp Val Gly Cys Thr Asp Leu Asn Glu Asp Leu Gly Val
865                 870                 875                 880

Trp Val Ile Phe Lys Ile Lys Thr Gln Asp Gly His Ala Arg Leu Gly
                885                 890                 895

Asn Leu Glu Phe Leu Glu Glu Lys Pro Leu Leu Gly Glu Ala Leu Ala
                900                 905                 910

Arg Val Lys Arg Ala Glu Lys Lys Trp Arg Asp Lys Arg Glu Lys Leu
915                 920                 925

Gln Leu Glu Thr Asn Ile Val Tyr Lys Glu Ala Lys Glu Ser Val Asp
                930                 935                 940

Ala Leu Phe Val Asn Ser Gln Tyr Asp Arg Leu Gln Val Asp Thr Asn
945                 950                 955                 960

Ile Ala Met Ile His Ala Ala Asp Lys Arg Val His Arg Ile Arg Glu
                965                 970                 975

Ala Tyr Leu Pro Glu Leu Ser Val Ile Pro Gly Val Asn Ala Ala Ile
                980                 985                 990

Phe Glu Glu Leu Glu Gly Arg Ile  Phe Thr Ala Tyr Ser  Leu Tyr Asp
                995                  1000                 1005

Ala Arg  Asn Val Ile Lys Asn  Gly Asp Phe Asn Asn  Gly Leu Leu
    1010                 1015                 1020
```

Cys Trp Asn Val Lys Gly His Val Asp Val Glu Glu Gln Asn Asn
1025                1030                1035

His Arg Ser Val Leu Val Ile Pro Glu Trp Glu Ala Glu Val Ser
     1040                1045                1050

Gln Glu Val Arg Val Cys Pro Gly Arg Gly Tyr Ile Leu Arg Val
1055                1060                1065

Thr Ala Tyr Lys Glu Gly Tyr Gly Glu Gly Cys Val Thr Ile His
1070                1075                1080

Glu Ile Glu Asp Asn Thr Asp Glu Leu Lys Phe Ser Asn Cys Val
1085                1090                1095

Glu Glu Glu Val Tyr Pro Asn Asn Thr Val Thr Cys Asn Asn Tyr
1100                1105                1110

Thr Gly Thr Gln Glu Glu Tyr Glu Gly Thr Tyr Thr Ser Arg Asn
1115                1120                1125

Gln Gly Tyr Asp Glu Ala Tyr Gly Asn Asn Pro Ser Val Pro Ala
1130                1135                1140

Asp Tyr Ala Ser Val Tyr Glu Glu Lys Ser Tyr Thr Asp Gly Arg
1145                1150                1155

Arg Glu Asn Pro Cys Glu Ser Asn Arg Gly Tyr Gly Asp Tyr Thr
1160                1165                1170

Pro Leu Pro Ala Gly Tyr Val Thr Lys Asp Leu Glu Tyr Phe Pro
1175                1180                1185

Glu Thr Asp Lys Val Trp Ile Glu Ile Gly Glu Thr Glu Gly Thr
1190                1195                1200

Phe Ile Val Asp Ser Val Glu Leu Leu Leu Met Glu Glu
1205                1210                1215

<210> SEQ ID NO 26
<211> LENGTH: 3600
<212> TYPE: DNA
<213> ORGANISM: Artificial
<220> FEATURE:
<223> OTHER INFORMATION: Recombinant nucleotide sequence used for
      expression in a bacterial cell encoding TIC868.

<400> SEQUENCE: 26
atgacttcaa ataggaaaaa tgagaatgaa attataaatg ctttatcgat tccagctgta      60
tcgaatcatt ccgcacaaat gaatctatca accgatgctc gtattgagga tagcttgtgt     120
atagccgagg ggaacaatat cgatccattt gttagcgcat caacagtcca acgggtatt      180 aacatagctg gtagaatact aggtgtatta ggcgtaccgt tgctggaca aatagctagt      240 ttttatagtt ttcttgttgg tgaattatgg ccccgcggca gagatccttg ggaaattttc     300
ctagaacatg tcgaacaact tataagacaa caagtaacag aaaatactag ggatacggct     360
cttgctcgat acaaggtttt aggaaattcc tttagagcct atcaacagtc acttgaagat     420
tggctagaaa accgtgatga tgcaagaacg agaagtgttc tttataccca atatatagcc     480
ttagaacttg atttttctta tgcgatgccg cttttcgcaa ttagaaacca agaagttcca     540
ttattaatgg tatatgctca agctgcaaat ttacacctat tattattgag agatgcctct     600
cttttttggt gtgaatttgg gcttacatcc caagaaattc aacgttatta tgagcgccaa     660
gtggaaaaaa cgagagaata ttctgattat tgcgcaagat ggtataatac gggttaaaat    720
aatttgagag ggacaaatgc tgaaagttgg ttgcgatata atcaattccg tagagactta     780
acgctaggag tattagatct agtggcacta ttcccaagct atgacacgcg tgtttatcca     840

```
atgaataccca gtgctcaatt aacaagagaa atttatacag atccaattgg gagaacaaat      900
gcaccttcag gatttgcaag tacgaattgg tttaataata atgcaccatc gttttctgcc      960
atagaggctg ccgttattag gcctccgcat ctacttgatt ttccagaaca gcttacaatt     1020
ttcagcgtat taagtcgatg gagtaatact caatatatga attactgggt gggacataga     1080
cttgaatcgc gaacaataag ggggtcatta agtacctcga cacacggaaa taccaatact     1140
tctattaatc ctgtaacatt acagttcaca tctcgagacg tttatagaac agaatcattt     1200
gcagggataa atatacttct aactactcct gtgaatggag taccttgggc tagatttaat     1260
tggagaaatc ccctgaattc tcttagaggt agccttctct atactatagg gtatactgga     1320
gtggggacac aactatttga ttcagaaact gaattaccac cagaaacaac agaacgacca     1380
aattatgaat cttacagtca tagattatct aatataagac taatatcagg aaacactttg     1440
agagcaccag tatattcttg gacgcaccgt agtgcagatc gtacaaatac cattagttca     1500
gatagcatta atcaaatacc tttagtgaaa ggatttagag tttgggggggg cacctctgtc     1560
attacaggac caggatttac aggaggggat atccttcgaa gaaataccctt tggtgatttt     1620
gtatctctac aagtcaatat taattcacca attacccaaa gataccgttt aagatttcgt     1680
tacgcttcca gtagggatgc acgagttata gtattaacag gagcggcatc cacaggagtg     1740
ggaggccaag ttagtgtaaa tatgcctctt cagaaaacta tggaaatagg ggagaactta     1800
acatctagaa catttagata taccgatttt agtaatcctt tttcatttag agctaatcca     1860
gatataattg ggataagtga acaacctcta tttggtgcag gttctattag tagcggtgaa     1920
ctttatatag ataaaattga aattattcta gcagatgcaa catttgaagc agaatctgat     1980
ttagaaagag cacaaaaggc ggtgaatgag ctgtttactt cttccaatca aatcgggtta     2040
aaaacagatg tgacggatta tcatattgat caagtatcca atttagttga gtgtttatct     2100
gatgaatttt gtctggatga aaaaaagaa ttgtccgaga agtcaaaca tgcgaagcga      2160
cttagtgatg agcggaattt acttcaagat ccaaacttta gagggatcaa tagcaacta     2220
gaccgtggct ggagaggaag tacggatatt accatccaag gaggcgatga cgtattcaaa     2280
gagaattacg ttacgctatt gggtaccttt gatgagtgct atccaacgta tttatatcaa     2340
aaaatagatg agtcgaaatt aaaagcctat acccgttacc aattaagagg gtatatcgaa     2400
gatagtcaag acttagaaat ctatttaatt cgctacaatg ccaaacacga aacagtaaat     2460
gtgccaggta cgggttcctt atggccgctt tcagccccaa gtccaatcgg aaaatgtgcc     2520
catcattccc atcatttctc cttggacatt gatgttggat gtacagactt aaatgaggac     2580
ttaggtgtat gggtgatatt caagattaag acgcaagatg gccatgcaag actaggaaat     2640
ctagaatttc tcgaagagaa accattagta ggagaagcac tagctcgtgt gaaaagagcg     2700
gagaaaaaat ggagagacaa acgtgaaaaa ttggaatggg aaacaaatat tgtttataaa     2760
gaggcaaaag aatctgtaga tgctttattt gtaaactctc aatatgatag attacaagcg     2820
gataccaaca tcgcgatgat tcatgcggca gataaacgcg ttcatagcat tcgagaagct     2880
tatctgcctg agctgtctgt gattccgggt gtcaatgcgg ctattttga agaattagaa     2940
gggcgtattt tcactgcatt ctccctatat gatgcgagaa atgtcattaa aaatggtgat     3000
tttaataatg gcttatcctg ctggaacgtg aaagggcatg tagatgtaga agaacaaaac     3060
aaccaccgtt cggtccttgt tgttccggaa tgggaagcag aagtgtcaca agaagttcgt     3120
gtctgtccgg gtcgtggcta tatccttcgt gtcacagcgt acaaggaggg atatggaaa     3180
ggttgcgtaa ccattcatga gatcgagaac aatacagacg aactgaagtt tagcaactgt     3240
```

```
gtagaagagg aagtatatcc aaacaacacg gtaacgtgta atgattatac tgcgactcaa    3300
gaagaatatg agggtacgta cacttctcgt aatcgaggat atgacggagc ctatgaaagc    3360
aattcttctg taccagctga ttatgcatca gcctatgaag aaaaagcata tacagatgga    3420
cgaagagaca atccttgtga atctaacaga ggatatgggg attacacacc actaccagct    3480
ggctatgtga caaaagaatt agagtacttc ccagaaaccg ataaggtatg gattgagatc    3540
ggagaaacgg aaggaacatt catccgtgac agcgtggaat tacttcttat ggaggaatag    3600
```

<210> SEQ ID NO 27
<211> LENGTH: 3600
<212> TYPE: DNA
<213> ORGANISM: Artificial
<220> FEATURE:
<223> OTHER INFORMATION: Synthetic nucleotide sequence designed for
      expression in a plant cell encoding TIC868.

<400> SEQUENCE: 27

```
atgacgagca accggaagaa cgagaacgag atcatcaacg ccctctcgat ccctgctgtt      60
tcaaaccact ccgcgcagat gaacctgtcc accgacgcgc gcatcgagga ctccctctgc     120
atagccgagg caacaacat cgacccattc gtgtcggcca gcacggttca gaccggcatc      180
aacatcgcgg gccgtatcct cggcgtcctc ggtgtcccat cgccggtca gatcgcgtcc      240 ttctactcgt tccttgtggg cgagctgtgg cctcgcggtc gtgacccgtg ggagatcttc      300
ctggagcatg tggagcagtt gatccggcag caagtcacgg agaacacccg cgatactgct      360
ctggccaggc tacagggcct gggaaaactcc tttcgggcat accagcagtc actggaggac     420
tggttggaga cagggatga cgcgcgaaca cgctcggtac tctacaccca gtacatcgct      480
ctcgaactcg acttcctgaa cgctatgccg ctgttcgcca tcaggaacca ggaagttcca      540
ctccttatgg tgtacgccca ggccgccaac ttacatctgc tcctgctgcg ggacgccagc      600
ctgttcggct ccgagttcgg actcacatct caagaaatcc agcgttacta cgagcgccaa      660
gtggagaaga cccgtgagta cagtgactac tgcgctcgat ggtacaacac agggctcaac      720
aacctgcgcg gcaccaacgc tgagtcatgg ctccgttaca accagttccg ccgcgacttg      780
actttgggtg tcctagacct ggtggcgcta ttcccgtctt acgacacacg ggtgtaccca      840
atgaacacta gcgcgcaact cacgcgggag atctacacag acccaatcgg ccggacgaac      900
gcaccctccg gtttcgcatc cacgaattgg ttcaacaaca acgcaccctc cttctcggca      960
atcgaggccg ccgtcatccg ccctcctcac ctgctcgact ttcccgagca gctcacgatc     1020
ttctccgtgc tctcacgctg gtccaacaca cagtacatga actactgggt cgggcaccga    1080
ttggagagta ggacgatccg tggcagcttg agcaccagta cccacggcaa caccaacacc    1140
tccatcaacc cagttacgct acagttcacg agccgcgacg tttaccggac tgagtcgttc    1200
gcgggcatta acatccttct gacaacgccc gtcaacggcg tccgtgggc ccggttcaac    1260 tggcgtaacc cgttgaactc cctgcgcggg tcattgctct acaccatcgg gtacacgggc    1320
gtcggcaccc agctcttcga cagtgaaact gagctgccgc ccgagaccac ggaacgcccg    1380
aactacgagt cctacagcca ccgcctgtcc aacatccggc tcatctctgg caacacgctg    1440
cgtgcgccgg tgtactcctg gacacaccgc agcgccgacc ggaccaacac gatctcttcc    1500
gactccatta accagatccc gctcgtgaag ggcttccgtg tgtggggtgg cacgagcgtc    1560
atcaccggtc cgggcttcac cggtggagac atactgcggc gcaacacttt cggcgacttc    1620
gtttcgttgc aagtgaacat caactcgccg atcacccagc gttaccgtct gaggttccgc    1680
```

```
tacgcttcaa gccgcgacgc gagggtcatt gtcctgaccg gagccgcgtc cacaggcgtg    1740
ggaggccaag tctcagtcaa catgcctctc cagaagacga tggagatagg cgagaacttg    1800
actagccgaa ccttccggta cactgatttc tcgaaccctt tctcattcag agcgaaccct    1860
gacatcattg gatctccga gcaaccgctg ttcggtgctg gctccatcag ctctggcgaa    1920
ctgtacatcg acaagattga gatcatcctg gcggatgcga cgttcgaggc cgagtctgac    1980
ctggagcggg ctcagaaggc tgtcaacgaa ctgttcacca gcagcaacca gattgggctc    2040
aagaccgacg tcacggacta tcacattgac caagtgtcca accttgtgga gtgcctgtcc    2100
gacgagttct gcctcgacga agaaggag ctgtccgaga aggtcaaaca cgcgaagcgt    2160
ctgagtgacg agcggaattt gctccaggac ccgaacttcc gtggcatcaa ccgccagctc    2220
gaccgtggtt ggcgcgggag tacagacatc accatccagg gaggcgacga tgtgttcaag    2280
gagaactatg tgacgctgct cgggactttc gacgaatgct acccgacgta tctctaccag    2340
aagatagacg agagtaaatt gaaggcgtac acccgctacc agcttcgcgg gtacatcgag    2400
gatagtcagg acctggaaat ctacctgatc cgatacaacg ccaagcacga gacagtgaac    2460
gtgccaggca cgggctcact ttggccattg agcgctccct ctccaatcgg aaagtgcgct    2520
caccactcgc accacttctc tctggacatc gacgtgggct gcaccgacct caacgaggac    2580
ctgggtgtct gggttatctt caagattaag acccaggacg gacatgcccg cctcggcaac    2640
ctggagttcc ttgaggagaa gcctctcgtg ggcgaggccc tcgctcgtgt gaagcgcgcc    2700
gagaagaaat ggcgagacaa gcgggagaag ctggagtggg agaccaacat cgtgtacaag    2760
gaggccaagg agtcagtgga cgcactcttc gtcaacagcc agtacgaccg cctccaggct    2820
gacaccaaca tcgccatgat ccacgcggct gacaagcggg tccacagcat ccgtgaggcg    2880
tacctgcccg agctgtcagt gatccctggt gtgaacgcgg cgatcttcga ggaactggag    2940
ggccgcatct tcacagcatt cagcctgtac gatgccagga atgttattaa gaacggtgac    3000
ttcaacaacg gctgagttg ctggaacgtc aagggccatg tggacgtcga ggagcagaac    3060
aaccaccggt ccgtgctggt cgtgccgag tgggaggcag aggtgagcca ggaggtccgc    3120
gtctgccctg gtcgcggcta catcctccgt gtgactgcgt acaaggaagg ctacggtgaa    3180
ggctgcgtga ctatccacga gatcgagaac aacaccgacg agctcaagtt ctcgaactgt    3240
gtggaggagg aggtgtaccc gaacaacacc gttacttgca acgactacac tgccacgcaa    3300
gaggagtacg agggcactta cacttcccgg aatcgcggct atgatggcgc gtacgagtcc    3360
aacagcagcg tgcctgcgga ttatgcgtcc gcttacgagg agaaggcgta caccgacgga    3420
cggagggaca acccttgcga gtccaaccgt ggctacggtg actacactcc gctgcccgcc    3480
gggtacgtca ccaaggagct ggagtacttc ccggagaccc acaaagtctg gatcgagatc    3540
ggcgagacgg agggcacttt catcgtggac tcggtcgagc tgctactgat ggaggagtga    3600
```

<210> SEQ ID NO 28
<211> LENGTH: 1199
<212> TYPE: PRT
<213> ORGANISM: Artificial
<220> FEATURE:
<223> OTHER INFORMATION: Amino acid sequence of the chimeric protein TIC868.

<400> SEQUENCE: 28

```
Met Thr Ser Asn Arg Lys Asn Glu Asn Glu Ile Ile Asn Ala Leu Ser
1               5                   10                  15
```

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
            115                 120                 125

Asn Ser Phe Arg Ala Tyr Gln Gln Ser Leu Glu Asp Trp Leu Glu Asn
        130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser

-continued

```
            435                 440                 445
Glu Thr Glu Leu Pro Pro Glu Thr Thr Glu Arg Pro Asn Tyr Glu Ser
        450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
    610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Phe Glu
                645                 650                 655

Ala Glu Ser Asp Leu Glu Arg Ala Gln Lys Ala Val Asn Glu Leu Phe
            660                 665                 670

Thr Ser Ser Asn Gln Ile Gly Leu Lys Thr Asp Val Thr Asp Tyr His
        675                 680                 685

Ile Asp Gln Val Ser Asn Leu Val Glu Cys Leu Ser Asp Glu Phe Cys
    690                 695                 700

Leu Asp Glu Lys Lys Glu Leu Ser Glu Lys Val Lys His Ala Lys Arg
705                 710                 715                 720

Leu Ser Asp Glu Arg Asn Leu Leu Gln Asp Pro Asn Phe Arg Gly Ile
                725                 730                 735

Asn Arg Gln Leu Asp Arg Gly Trp Arg Gly Ser Thr Asp Ile Thr Ile
            740                 745                 750

Gln Gly Gly Asp Asp Val Phe Lys Glu Asn Tyr Val Thr Leu Leu Gly
        755                 760                 765

Thr Phe Asp Glu Cys Tyr Pro Thr Tyr Leu Tyr Gln Lys Ile Asp Glu
    770                 775                 780

Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
                805                 810                 815

Glu Thr Val Asn Val Pro Gly Thr Gly Ser Leu Trp Pro Leu Ser Ala
            820                 825                 830

Pro Ser Pro Ile Gly Lys Cys Ala His His Ser His His Phe Ser Leu
        835                 840                 845

Asp Ile Asp Val Gly Cys Thr Asp Leu Asn Glu Asp Leu Gly Val Trp
    850                 855                 860
```

Val Ile Phe Lys Ile Lys Thr Gln Asp Gly His Ala Arg Leu Gly Asn
865                 870                 875                 880

Leu Glu Phe Leu Glu Glu Lys Pro Leu Val Gly Glu Ala Leu Ala Arg
            885                 890                 895

Val Lys Arg Ala Glu Lys Lys Trp Arg Asp Lys Arg Glu Lys Leu Glu
            900                 905                 910

Trp Glu Thr Asn Ile Val Tyr Lys Glu Ala Lys Glu Ser Val Asp Ala
            915                 920                 925

Leu Phe Val Asn Ser Gln Tyr Asp Arg Leu Gln Ala Asp Thr Asn Ile
930                 935                 940

Ala Met Ile His Ala Ala Asp Lys Arg Val His Ser Ile Arg Glu Ala
945                 950                 955                 960

Tyr Leu Pro Glu Leu Ser Val Ile Pro Gly Val Asn Ala Ala Ile Phe
            965                 970                 975

Glu Glu Leu Glu Gly Arg Ile Phe Thr Ala Phe Ser Leu Tyr Asp Ala
            980                 985                 990

Arg Asn Val Ile Lys Asn Gly Asp Phe Asn Asn Gly Leu Ser Cys Trp
            995                 1000                1005

Asn Val Lys Gly His Val Asp Val Glu Glu Gln Asn Asn His Arg
    1010                1015                1020

Ser Val Leu Val Val Pro Glu Trp Glu Ala Glu Val Ser Gln Glu
    1025                1030                1035

Val Arg Val Cys Pro Gly Arg Gly Tyr Ile Leu Arg Val Thr Ala
    1040                1045                1050

Tyr Lys Glu Gly Tyr Gly Gly Cys Val Thr Ile His Glu Ile
    1055                1060                1065

Glu Asn Asn Thr Asp Glu Leu Lys Phe Ser Asn Cys Val Glu Glu
    1070                1075                1080

Glu Val Tyr Pro Asn Asn Thr Val Thr Cys Asn Asp Tyr Thr Ala
    1085                1090                1095

Thr Gln Glu Glu Tyr Glu Gly Thr Tyr Thr Ser Arg Asn Arg Gly
    1100                1105                1110

Tyr Asp Gly Ala Tyr Glu Ser Asn Ser Ser Val Pro Ala Asp Tyr
    1115                1120                1125

Ala Ser Ala Tyr Glu Glu Lys Ala Tyr Thr Asp Gly Arg Arg Asp
    1130                1135                1140

Asn Pro Cys Glu Ser Asn Arg Gly Tyr Gly Asp Tyr Thr Pro Leu
    1145                1150                1155

Pro Ala Gly Tyr Val Thr Lys Glu Leu Glu Tyr Phe Pro Glu Thr
    1160                1165                1170

Asp Lys Val Trp Ile Glu Ile Gly Glu Thr Glu Gly Thr Phe Ile
    1175                1180                1185

Val Asp Ser Val Glu Leu Leu Leu Met Glu Glu
    1190                1195

<210> SEQ ID NO 29
<211> LENGTH: 3600
<212> TYPE: DNA
<213> ORGANISM: Artificial
<220> FEATURE:
<223> OTHER INFORMATION: Synthetic nucleotide sequence designed for
      expression in a plant cell encoding TIC868_9.

<400> SEQUENCE: 29
atgacgagca accggaagaa cgagaacgag atcatcaacg ccctctcgat ccctgctgtt    60

-continued

| | |
|---|---|
| tcaaaccact ccgcgcagat gaacctgtcc accgacgcgc gcatcgagga ctccctctgc | 120 |
| atagccgagg gcaacaacat cgacccattc gtgtcggcca gcacggttca gaccggcatc | 180 |
| aacatcgcgg gccgtatcct cggcgtcctc ggtgtcccat tcgccggtca gatcgcgtcc | 240 |
| ttctactcgt tccttgtggg cgagctgtgg cctcgcggtc gtgaccgtg ggagatcttc | 300 |
| ctggagcatg tggagcagtt gatccggcag caagtcacgg agaacacccg cgatactgct | 360 |
| ctggccaggc tacagggcct gggaaactcc tttcgggcat accagcagtc actggaggac | 420 |
| tggttggaga cagggatga cgcgcgaaca cgctcggtac tctacaccca gtacatcgct | 480 |
| ctcgaactcg acttcctgaa cgctatgccg ctgttcgcca tcaggaacca ggaagttcca | 540 |
| ctccttatgg tgtacgccca ggccgccaac ttacatctgc tcctgctgcg ggacgccagc | 600 |
| ctgttcggct ccgagttcgg actcacatct caagaaatcc agcgttacta cgagcgccaa | 660 |
| gtggagaaga cccgtgagta cagtgactac tgcgctcgat ggtacaacac agggctcaac | 720 |
| agcctgcgcg gcaccaacgc tgagtcatgg ctccgttaca accagttccg ccgcgacttg | 780 |
| actttgggtg tcctagacct ggtggcgcta ttcccgtctt acgacacacg ggtgtaccca | 840 |
| atgaacacta gcgcgcaact cacgcgggag atctacacag cccaatcgg ccggacgaac | 900 |
| gcaccctccg gtttcgcatc cacgaattgg ttcaacaaca cgcaccctc cttctcggca | 960 |
| atcgaggccg ccgtcatccg ccctcctcac ctgctcgact ttcccgagca gctcacgatc | 1020 |
| ttctccgtgc tctcacgctg gtccaacaca cagtacatga actactgggt cgggcaccga | 1080 |
| ttggagagta ggacgatccg tggcagcttg agcaccagta cccacggcaa caccaacacc | 1140 |
| tccatcaacc cagttacgct acagttcacg agccgcgacg tttaccggac tgagtcgcag | 1200 |
| gcgggcatta acatccttat gacaacgccc gtcaacggcg tcccgtgggc ccggttcaac | 1260 |
| tggcgtaacc cgaagaactc cctgcgcggg tcattgctct acaccatcgg gtacacgggc | 1320 |
| gtcggcaccc agctcttcga cagtgaaact gagctgccgc ccgagaccac ggaacgcccg | 1380 |
| aactacgagt cctacagcca ccgcctgtcc aacatccggc tcatctctgg caacacgctg | 1440 |
| cgtgcgccgg tgtactcctg gacacaccgc agcgccgacc ggaccaacac gatctcttcc | 1500 |
| gactccatta accagatccc gctcgtgaag ggcttccgtg tgtggggtgg cacgagcgtc | 1560 |
| atcaccggtc cgggcttcac cggtggagac atactgcggc gcaacacttt cggcgacttc | 1620 |
| gtttcgttgc aagtgaacat caactcgccg atcacccagc gttaccgtct gaggttccgc | 1680 |
| tacgcttcaa gccgcgacgc gagggtcatt gtcctgaccg gagccgcgtc cacaggcgtg | 1740 |
| ggaggccaag tctcagtcaa catgcctctc cagaagacga tggagatagg cgagaacttg | 1800 |
| actagccgaa ccttccggta cactgatttc tcgaacccct tctcattcag agcgaaccct | 1860 |
| gacatcattg gatctccga gcaaccgctg ttcggtgctg gctccatcag ctctggcgaa | 1920 |
| ctgtacatcg acaagattga gatcatcctg gcggatgcga cgttcgaggc cgagtctgac | 1980 |
| ctggagcggg ctcagaaggc tgtcaacgaa ctgttcacca gcagcaacca gattgggctc | 2040 |
| aagaccgacg tcacggacta tcacattgac caagtgtcca accttgtgga gtgcctgtcc | 2100 |
| gacgagttct gcctcgacga agaaggag ctgtccgaga ggtcaaaaca cgcgaagcgt | 2160 |
| ctgagtgacg agcggaattt gctccaggac ccgaacttcc gtggcatcaa ccgccagctc | 2220 |
| gaccgtggtt ggcgcgggag tacagacatc accatccagg gaggcgacga tgtgttcaag | 2280 |
| gagaactatg tgacgctgct cgggactttc gacgaatgct acccgacgta tctctaccag | 2340 |
| aagatagacg agagtaaatt gaaggcgtac acccgctacc agcttcgcgg gtacatcgag | 2400 |

-continued

```
gatagtcagg acctggaaat ctacctgatc cgatacaacg ccaagcacga gacagtgaac    2460
gtgccaggca cgggctcact ttggccattg agcgctccct ctccaatcgg aaagtgcgct    2520
caccactcgc accacttctc tctggacatc gacgtgggct gcaccgacct caacgaggac    2580
ctgggtgtct gggttatctt caagattaag acccaggacg acatgcccg cctcggcaac     2640 ctggagttcc ttgaggagaa gcctctcgtg ggcgaggccc tcgctcgtgt gaagcgcgcc    2700
gagaagaaat ggcgagacaa gcgggagaag ctggagtggg agaccaacat cgtgtacaag    2760
gaggccaagg agtcagtgga cgcactcttc gtcaacagcc agtacgaccg cctccaggct    2820
gacaccaaca tcgccatgat ccacgcggct gacaagcggg tccacagcat ccgtgaggcg    2880
tacctgcccg agctgtcagt gatccctggt gtgaacgcgg cgatcttcga ggaactggag    2940
ggccgcatct tcacagcatt cagcctgtac gatgccagga atgttattaa gaacggtgac    3000
ttcaacaacg ggctgagttg ctggaacgtc aagggccatg tggacgtcga ggagcagaac    3060
aaccaccggt ccgtgctggt cgtgccggag tgggaggcag aggtgagcca ggaggtccgc    3120
gtctgccctg gtcgcggcta catcctccgt gtgactgcgt acaaggaagg ctacggtgaa    3180
ggctgcgtga ctatccacga gatcgagaac aacaccgacg agctcaagtt ctcgaactgt    3240
gtggaggagg aggtgtaccc gaacaacacc gttacttgca acgactacac tgccacgcaa    3300
gaggagtacg agggcactta cacttcccgg aatcgcggct atgatggcgc gtacgagtcc    3360
aacagcagcg tgcctgcgga ttatgcgtcc gcttacgagg agaaggcgta caccgacgga    3420
cggagggaca accettgcga gtccaaccgt ggctacggtg actacactcc gctgcccgcc    3480
gggtacgtca ccaaggagct ggagtacttc ccggagaccg acaaagtctg gatcgagatc    3540
ggcgagacgg agggcacttt catcgtggac tcggtcgagc tgctactgat ggaggagtga    3600
```

<210> SEQ ID NO 30  
<211> LENGTH: 1199  
<212> TYPE: PRT  
<213> ORGANISM: Artificial  
<220> FEATURE:  
<223> OTHER INFORMATION: Amino acid sequence of the chimeric protein variant TIC868_9.

<400> SEQUENCE: 30

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
                20                  25                  30

Ala Arg Ile Glu Asp Ser Leu Cys Ile Ala Glu Gly Asn Asn Ile Asp
            35                  40                  45

Pro Phe Val Ser Ala Ser Thr Val Gln Thr Gly Ile Asn Ile Ala Gly
        50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
                100                 105                 110

Thr Glu Asn Thr Arg Asp Thr Ala Leu Ala Arg Leu Gln Gly Leu Gly
            115                 120                 125

Asn Ser Phe Arg Ala Tyr Gln Gln Ser Leu Glu Asp Trp Leu Glu Asn
        130                 135                 140

Arg Asp Asp Ala Arg Thr Arg Ser Val Leu Tyr Thr Gln Tyr Ile Ala
```

```
               145                 150                 155                 160
      Leu Glu Leu Asp Phe Leu Asn Ala Met Pro Leu Phe Ala Ile Arg Asn
                          165                 170                 175

Gln Glu Val Pro Leu Met Val Tyr Ala Gln Ala Ala Asn Leu His
                      180                 185                 190

Leu Leu Leu Leu Arg Asp Ala Ser Leu Phe Gly Ser Glu Phe Gly Leu
                  195                 200                 205

Thr Ser Gln Glu Ile Gln Arg Tyr Tyr Glu Arg Gln Val Glu Lys Thr
              210                 215                 220

Arg Glu Tyr Ser Asp Tyr Cys Ala Arg Trp Tyr Asn Thr Gly Leu Asn
      225                 230                 235                 240

Ser Leu Arg Gly Thr Asn Ala Glu Ser Trp Leu Arg Tyr Asn Gln Phe
                      245                 250                 255

Arg Arg Asp Leu Thr Leu Gly Val Leu Asp Leu Val Ala Leu Phe Pro
                  260                 265                 270

Ser Tyr Asp Thr Arg Val Tyr Pro Met Asn Thr Ser Ala Gln Leu Thr
              275                 280                 285

Arg Glu Ile Tyr Thr Asp Pro Ile Gly Arg Thr Asn Ala Pro Ser Gly
      290                 295                 300

Phe Ala Ser Thr Asn Trp Phe Asn Asn Asn Ala Pro Ser Phe Ser Ala
      305                 310                 315                 320

Ile Glu Ala Ala Val Ile Arg Pro Pro His Leu Leu Asp Phe Pro Glu
                      325                 330                 335

Gln Leu Thr Ile Phe Ser Val Leu Ser Arg Trp Ser Asn Thr Gln Tyr
                  340                 345                 350

Met Asn Tyr Trp Val Gly His Arg Leu Glu Ser Arg Thr Ile Arg Gly
              355                 360                 365

Ser Leu Ser Thr Ser Thr His Gly Asn Thr Asn Thr Ser Ile Asn Pro
              370                 375                 380

Val Thr Leu Gln Phe Thr Ser Arg Asp Val Tyr Arg Thr Glu Ser Gln
      385                 390                 395                 400

Ala Gly Ile Asn Ile Leu Met Thr Thr Pro Val Asn Gly Val Pro Trp
                      405                 410                 415

Ala Arg Phe Asn Trp Arg Asn Pro Lys Asn Ser Leu Arg Gly Ser Leu
                  420                 425                 430

Leu Tyr Thr Ile Gly Tyr Thr Gly Val Gly Thr Gln Leu Phe Asp Ser
              435                 440                 445

Glu Thr Glu Leu Pro Pro Glu Thr Thr Glu Arg Pro Asn Tyr Glu Ser
      450                 455                 460

Tyr Ser His Arg Leu Ser Asn Ile Arg Leu Ile Ser Gly Asn Thr Leu
      465                 470                 475                 480

Arg Ala Pro Val Tyr Ser Trp Thr His Arg Ser Ala Asp Arg Thr Asn
                      485                 490                 495

Thr Ile Ser Ser Asp Ser Ile Asn Gln Ile Pro Leu Val Lys Gly Phe
                  500                 505                 510

Arg Val Trp Gly Gly Thr Ser Val Ile Thr Gly Pro Gly Phe Thr Gly
              515                 520                 525

Gly Asp Ile Leu Arg Arg Asn Thr Phe Gly Asp Phe Val Ser Leu Gln
              530                 535                 540

Val Asn Ile Asn Ser Pro Ile Thr Gln Arg Tyr Arg Leu Arg Phe Arg
      545                 550                 555                 560

Tyr Ala Ser Ser Arg Asp Ala Arg Val Ile Val Leu Thr Gly Ala Ala
                      565                 570                 575
```

```
Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
            595                 600                 605

Asp Phe Ser Asn Pro Phe Ser Phe Arg Ala Asn Pro Asp Ile Ile Gly
            610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Phe Glu
                645                 650                 655

Ala Glu Ser Asp Leu Glu Arg Ala Gln Lys Ala Val Asn Glu Leu Phe
            660                 665                 670

Thr Ser Ser Asn Gln Ile Gly Leu Lys Thr Asp Val Thr Asp Tyr His
            675                 680                 685

Ile Asp Gln Val Ser Asn Leu Val Glu Cys Leu Ser Asp Glu Phe Cys
690                 695                 700

Leu Asp Glu Lys Lys Glu Leu Ser Glu Lys Val Lys His Ala Lys Arg
705                 710                 715                 720

Leu Ser Asp Glu Arg Asn Leu Leu Gln Asp Pro Asn Phe Arg Gly Ile
                725                 730                 735

Asn Arg Gln Leu Asp Arg Gly Trp Arg Gly Ser Thr Asp Ile Thr Ile
                740                 745                 750

Gln Gly Gly Asp Asp Val Phe Lys Glu Asn Tyr Val Thr Leu Leu Gly
            755                 760                 765

Thr Phe Asp Glu Cys Tyr Pro Thr Tyr Leu Tyr Gln Lys Ile Asp Glu
            770                 775                 780

Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
                805                 810                 815

Glu Thr Val Asn Val Pro Gly Thr Gly Ser Leu Trp Pro Leu Ser Ala
            820                 825                 830

Pro Ser Pro Ile Gly Lys Cys Ala His His Ser His His Phe Ser Leu
            835                 840                 845

Asp Ile Asp Val Gly Cys Thr Asp Leu Asn Glu Asp Leu Gly Val Trp
850                 855                 860

Val Ile Phe Lys Ile Lys Thr Gln Asp Gly His Ala Arg Leu Gly Asn
865                 870                 875                 880

Leu Glu Phe Leu Glu Glu Lys Pro Leu Val Gly Glu Ala Leu Ala Arg
                885                 890                 895

Val Lys Arg Ala Glu Lys Lys Trp Arg Asp Lys Arg Glu Lys Leu Glu
            900                 905                 910

Trp Glu Thr Asn Ile Val Tyr Lys Glu Ala Lys Glu Ser Val Asp Ala
            915                 920                 925

Leu Phe Val Asn Ser Gln Tyr Asp Arg Leu Gln Ala Asp Thr Asn Ile
            930                 935                 940

Ala Met Ile His Ala Ala Asp Lys Arg Val His Ser Ile Arg Glu Ala
945                 950                 955                 960

Tyr Leu Pro Glu Leu Ser Val Ile Pro Gly Val Asn Ala Ala Ile Phe
                965                 970                 975

Glu Glu Leu Glu Gly Arg Ile Phe Thr Ala Phe Ser Leu Tyr Asp Ala
            980                 985                 990
```

| | | | | | | | | | | | | |
|---|---|---|---|---|---|---|---|---|---|---|---|---|
|Arg|Asn|Val|Ile|Lys|Asn|Gly|Asp|Phe|Asn|Asn|Gly|Leu|Ser|Cys|Trp|
| | |995| | | |1000| | | |1005| | |

Asn Val Lys Gly His Val Asp Val Glu Glu Gln Asn Asn His Arg
    1010            1015            1020

Ser Val Leu Val Val Pro Glu Trp Glu Ala Glu Val Ser Gln Glu
    1025            1030            1035

Val Arg Val Cys Pro Gly Arg Gly Tyr Ile Leu Arg Val Thr Ala
    1040            1045            1050

Tyr Lys Glu Gly Tyr Gly Glu Gly Cys Val Thr Ile His Glu Ile
    1055            1060            1065

Glu Asn Asn Thr Asp Glu Leu Lys Phe Ser Asn Cys Val Glu Glu
    1070            1075            1080

Glu Val Tyr Pro Asn Asn Thr Val Thr Cys Asn Asp Tyr Thr Ala
    1085            1090            1095

Thr Gln Glu Glu Tyr Glu Gly Thr Tyr Thr Ser Arg Asn Arg Gly
    1100            1105            1110

Tyr Asp Gly Ala Tyr Glu Ser Asn Ser Ser Val Pro Ala Asp Tyr
    1115            1120            1125

Ala Ser Ala Tyr Glu Glu Lys Ala Tyr Thr Asp Gly Arg Arg Asp
    1130            1135            1140

Asn Pro Cys Glu Ser Asn Arg Gly Tyr Gly Asp Tyr Thr Pro Leu
    1145            1150            1155

Pro Ala Gly Tyr Val Thr Lys Glu Leu Glu Tyr Phe Pro Glu Thr
    1160            1165            1170

Asp Lys Val Trp Ile Glu Ile Gly Glu Thr Glu Gly Thr Phe Ile
    1175            1180            1185

Val Asp Ser Val Glu Leu Leu Leu Met Glu Glu
    1190            1195

<210> SEQ ID NO 31
<211> LENGTH: 3678
<212> TYPE: DNA
<213> ORGANISM: Artificial
<220> FEATURE:
<223> OTHER INFORMATION: Recombinant nucleotide sequence used for
      expression in a bacterial cell encoding TIC868_10.

<400> SEQUENCE: 31

| | |
|---|---|
|atgacttcaa ataggaaaaa tgagaatgaa attataaatg ctttatcgat tccagctgta|60|
|tcgaatcatt ccgcacaaat gaatctatca accgatgctc gtattgagga tagcttgtgt|120|
|atagccgagg ggaacaatat cgatccattt gttagcgcat caacagtcca aacgggtatt|180|
|aacatagctg gtagaatact aggtgtatta ggcgtaccgt ttgctggaca aatagctagt|240|
|ttttatagtt ttcttgttgg tgaattatgg ccccgcggca gagatccttg ggaattttc|300|
|ctagaacatg tcgaacaact tataagacaa caagtaacag aaaatactag ggatacggct|360|
|cttgctcgat acaaggtttt aggaaattcc tttagagcct atcaacagtc acttgaagat|420|
|tggctagaaa accgtgatga tgcaagaacg agaagtgttc tttataccca atatatagcc|480|
|ttagaacttg atttctttaa tcgatgccg cttttcgcaa ttagaaacca agaagttcca|540|
|ttattaatgg tatatgctca agctgcaaat ttacacctat tattattgag agatgcctct|600|
|ctttttggta gtgaatttgg cttacatcc caagaaattc aacgttatta tgagcgccaa|660|
|gtggaaaaaa cgagagaata ttctgattat tgcgcaagat ggtataatac gggtttaaat|720|
|aatttgagag ggacaaatgc tgaaagttgg ttgcgatata tcaattccg tagagactta|780|

```
acgctaggag tattagatct agtggcacta ttcccaagct atgacacgcg tgtttatcca    840
atgaatacca gtgctcaatt aacaagagaa atttatacag atccaattgg gagaacaaat    900
gcaccttcag gatttgcaag tacgaattgg tttaataata atgcaccatc gtttttctgcc   960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacggaaa taccaatact   1140
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta atcaaatacc tttagtgaaa ggatttagag ttttggggggg cacctctgtc   1560
attacaggac caggatttac aggaggggat atccttcgaa gaaataccct tggtgatttt   1620
gtatctctac aagtcaatat taattcacca attacccaaa gataccgttt aagatttcgt   1680
tacgcttcca gtagggatgc acgagttata gtattaacag gagcggcatc cacaggagtg   1740
ggaggccaag ttagtgtaaa tatgcctctt cagaaaacta tggaaatagg ggagaactta   1800
acatctagaa catttagata taccgatttt agtaatcctt tttcatttag agctaatcca   1860
gatataattg ggataagtga acaacctcta tttggtgcag gttctattag tagcggtgaa   1920
ctttatatag ataaaattga aattattcta gcagatgcaa catttgaggc agaatatgat   1980
ttagaaaagag cgcaaaaggt ggtgaatgcc ctgtttacgt ctacaaacca actagggcta   2040
aaaacagatg tgacggatta tcatattgat caggtatcca atctagttgc gtgtttatcg   2100
gatgaatttt gtctggatga aaagagagaa ttgtccgaga agttaaaaca tgcaaagcga   2160
ctcagtgatg agcggaattt acttcaagat ccaaacttca gagggatcaa taggcaacca   2220
gaccgtggct ggagaggaag tacgatatt actatccaag gaggagatga cgtattcaaa   2280
gagaattacg ttacgctacc gggtacccttt gatgagtgct atccaacgta tttatatcaa   2340
aaaatagatg agtcgaaatt aaaagccat acccgttatc aattaagagg gtatatcgaa   2400
gatagtcaag acttagaaat ctatttaatt cgttacaatg caaaacacga aatagtaaat   2460
gtaccaggta caggaagttt atggcctctt tctgtagaaa atcaaattgg accttgtgga   2520
gaaccgaatc gatgcgcgcc acaccttgaa tggaatcctg atttacactg ttcctgcaga   2580
gacggggaaa aatgtgcaca tcattctcat cattctctt tggacattga tgttggatgt   2640
acagacttaa atgaggactt aggtgtatgg gtgatattca agattaagac gcaagatggc   2700
cacgcacgac tagggaatct agagtttctc gaagagaaac cattattagg aagcacta     2760
gctcgtgtga aaagagcgga gaaaaaatgg agagacaaac gcgaaacatt acaattggaa   2820
acaactatcg tttataaaga ggcaaaagaa tctgtagatg ctttatttgt aaactctcaa   2880
tatgatagat acaagcgga tacgaacatc gcgatgattc atgcggcaga taaacgcgtt   2940
catagaattc gagaagcgta tctgccggag ctgtctgtga ttccgggtgt caatgcggct   3000
attttgaag aattagaaga gcgtattttc actgcatttt ccctatatga tgcgagaaat   3060
attattaaaa atgcgatttt caataatggc ttattatgct ggaacgtgaa agggcatgta   3120
gaggtagaag aacaaaacaa tcaccgttca gtcctggtta tcccagaatg ggaggcagaa   3180
```

```
gtgtcacaag aggttcgtgt ctgtccaggt cgtggctata tccttcgtgt tacagcgtac   3240
aaagagggat atggagaagg ttgcgtaacg atccatgaga tcgagaacaa tacagacgaa   3300
ctgaaattca acaactgtgt agaagaggaa gtatatccaa acaacacggt aacgtgtatt   3360
aattatactg cgactcaaga agaatatgag ggtacgtaca cttctcgtaa tcgaggatat   3420
gacgaagcct atggtaataa cccttccgta ccagctgatt atgcgtcagt ctatgaagaa   3480
aaatcgtata cagatagacg aagagagaat ccttgtgaat ctaacagagg atatggagat   3540
tacacaccac taccagctgg ttatgtaaca aaggaattag agtacttccc agagaccgat   3600
aaggtatgga ttgagattgg agaaacagaa ggaacattca tcgtggacag cgtggaatta   3660
ctccttatgg aggaatag                                                 3678

<210> SEQ ID NO 32
<211> LENGTH: 3678
<212> TYPE: DNA
<213> ORGANISM: Artificial
<220> FEATURE:
<223> OTHER INFORMATION: Synthetic nucleotide sequence designed for
      expression in a plant cell encoding TIC868_10.

<400> SEQUENCE: 32
atgacgagca accggaagaa cgagaacgag atcatcaacg ccctctcgat ccctgctgtt     60
tcaaaccact ccgcgcagat gaacctgtcc accgacgcgc gcatcgagga ctccctctgc    120
atagccgagg gcaacaacat cgacccattc gtgtcggcca gcacggttca gaccggcatc    180
aacatcgcgg gccgtatcct cggcgtcctc ggtgtcccat cgccggtca gatcgcgtcc    240 ttctactcgt tccttgtggg cgagctgtgg cctcgcggtc gtgacccgtg ggagatcttc    300
ctggagcatg tggagcagtt gatccggcag caagtcacgg agaacacccg cgatactgct    360
ctggccaggc tacagggcct gggaaactcc tttcgggcat accagcagtc actggaggac    420
tggttggaga cagggatga cgcgcgaaca cgctcggtac tctacaccca gtacatcgct    480
ctcgaactcg acttcctgaa cgctatgccg ctgttcgcca tcaggaacca ggaagttcca    540
ctccttatgt gtacgcccca ggccgccaac ttacatctgc tcctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag acccaatcgg ccggacgaac    900
gcaccctccg gtttcgcatc cacgaattgg ttcaacaaca acgcaccctc cttctcggca    960
atcgaggccg ccgtcatccg ccctcctcac ctgctcgact ttcccgagca gctcacgatc   1020
ttctccgtgc tctcacgctg gtccaacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200 gcggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
```

```
gactccatta accagatccc gctcgtgaag ggcttccgtg tgtggggtgg cacgagcgtc    1560
atcaccggtc cgggcttcac cggtggagac atactgcggc gcaacacttt cggcgacttc    1620
gtttcgttgc aagtgaacat caactcgccg atcacccagc gttaccgtct gaggttccgc    1680
tacgcttcaa gccgcgacgc gagggtcatt gtcctgaccg gagccgcgtc cacaggcgtg    1740
ggaggccaag tctcagtcaa catgcctctc cagaagacga tggagatagg cgagaacttg    1800
actagccgaa ccttccggta cactgatttc tcgaacccct tctcattcag agcgaaccct    1860
gacatcattg ggatctccga gcaaccgctg ttcggtgctg gctccatcag ctctggcgaa    1920
ctgtacatcg acaagattga gatcatcctg gcggatgcga cgttcgaggc cgagtacgac    1980
cttgagcgcg cccagaaggt ggtgaacgcc ctcttcacta gcactaacca gctaggcctg    2040
aagactgacg tgaccgacta ccacatcgac caagtgagca acctagtggc ctgcctctcc    2100
gacgagttct gcctcgacga gaagcgcgag ctgtccgaga aggtgaagca cgccaagcgc    2160
ctctccgacg agcgcaacct gctccaggac cccaacttca ggggcatcaa caggcagccc    2220
gaccgcggct ggcgcggctc caccgacatc accatccagg gcggtgacga cgtattcaag    2280
gagaactacg ttaccctccc cggcaccttc gacgagtgtt accccaccta cctctaccag    2340
aagatcgacg agtccaagct gaaggcctac acccgctacc agctccgcgg ctacatcgag    2400
gactcccagg acctggaaat ctacctcatc cgctacaacg ccaagcacga gatcgtgaac    2460
gtgcctggca ccggcagcct ctggcctctc agcgtggaga accagatcgg cccttgcggc    2520
gagcctaacc gctgcgcccc tcacctcgag tggaaccctg acctccactg ctcgtgcagg    2580
gacggcgaga agtgcgccca ccatagccac cacttctctc tggacatcga cgtgggctgc    2640
accgacctga cgaggacct gggcgtgtgg gttatcttca agatcaagac ccaggacggt    2700
cacgccaggc tgggtaacct ggagttcctt gaggaaaagc ctctgctggg tgaggccctg    2760
gccagggtca agagggctga gaagaaatgg agggataaga gggagaccct gcagctggag    2820
accactatcg tctacaagga ggctaaggag tctgtcgatg ctctgttcgt caactctcag    2880
tacgatagac tgcaagctga taccaacatc gctatgatcc acgctgcgga taagcgggtc    2940
caccggatcc gggaggctta ccttccggag ctttctgtca tcccgggtgt caacgctgcg    3000
atcttcgagg aacttgagga acggatcttc actgcgttta gtctttacga tgcgcggaac    3060
atcatcaaga acgggacttt caacaatggt ctgctgtgct ggaacgtcaa gggtcatgtc    3120
gaggtcgagg aacaaaacaa tcatcgtagt gtccttgtca ttcctgagtg ggaggcggag    3180
gtctctcaag aggtccgtgt ttgcccgggg cgtgggtaca ttcttcgtgt tactgcgtac    3240
aaggagggt acgggagg gtgcgttact attcatgaga ttgagaacaa tactgatgag    3300
cttaagttca caattgtgt tgaggaggag gtttacccga acaatactgt tacgtgcatc    3360
aactacacgg caacgcaaga ggaatacgag gggacgtaca cctcgcgtaa tagagggtat    3420
gatgaggcgt acgaaacaa cccgtcggtt ccagcagatt atgcctcggt ttatgaggag    3480
aagtcgtaca cggatagacg acgcgagaat ccatgtgagt caaatcgagg atacggagat    3540
tacacaccat taccagcagg atacgttaca aaggagttgg aatacttccc ggaaacagat    3600
aaagtttgga ttgaaatcgg agaaacagaa ggaacattca tcgtcgactc agtagaattg    3660
ttgttgatgg aagaatga                                                    3678
```

<210> SEQ ID NO 33
<211> LENGTH: 1225
<212> TYPE: PRT

<213> ORGANISM: Artificial
<220> FEATURE:
<223> OTHER INFORMATION: Amino acid sequence of the chimeric protein variant TIC868_10.

<400> SEQUENCE: 33

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380
```

```
Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
            405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
            450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
            485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
            515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
            565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
            595                 600                 605

Asp Phe Ser Asn Pro Phe Ser Phe Arg Ala Asn Pro Asp Ile Ile Gly
            610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Phe Glu
            645                 650                 655

Ala Glu Tyr Asp Leu Glu Arg Ala Gln Lys Val Val Asn Ala Leu Phe
            660                 665                 670

Thr Ser Thr Asn Gln Leu Gly Leu Lys Thr Asp Val Thr Asp Tyr His
            675                 680                 685

Ile Asp Gln Val Ser Asn Leu Val Ala Cys Leu Ser Asp Glu Phe Cys
            690                 695                 700

Leu Asp Glu Lys Arg Glu Leu Ser Glu Lys Val Lys His Ala Lys Arg
705                 710                 715                 720

Leu Ser Asp Glu Arg Asn Leu Leu Gln Asp Pro Asn Phe Arg Gly Ile
            725                 730                 735

Asn Arg Gln Pro Asp Arg Gly Trp Arg Gly Ser Thr Asp Ile Thr Ile
            740                 745                 750

Gln Gly Gly Asp Asp Val Phe Lys Glu Asn Tyr Val Thr Leu Pro Gly
            755                 760                 765

Thr Phe Asp Glu Cys Tyr Pro Thr Tyr Leu Tyr Gln Lys Ile Asp Glu
            770                 775                 780

Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
```

-continued

```
                805                 810                 815
Glu Ile Val Asn Val Pro Gly Thr Gly Ser Leu Trp Pro Leu Ser Val
                820                 825                 830
Glu Asn Gln Ile Gly Pro Cys Gly Glu Pro Asn Arg Cys Ala Pro His
                835                 840                 845
Leu Glu Trp Asn Pro Asp Leu His Cys Ser Cys Arg Asp Gly Glu Lys
850                 855                 860
Cys Ala His His Ser His His Phe Ser Leu Asp Ile Asp Val Gly Cys
865                 870                 875                 880
Thr Asp Leu Asn Glu Asp Leu Gly Val Trp Val Ile Phe Lys Ile Lys
                885                 890                 895
Thr Gln Asp Gly His Ala Arg Leu Gly Asn Leu Glu Phe Leu Glu Glu
                900                 905                 910
Lys Pro Leu Leu Gly Glu Ala Leu Ala Arg Val Lys Arg Ala Glu Lys
                915                 920                 925
Lys Trp Arg Asp Lys Arg Glu Thr Leu Gln Leu Glu Thr Thr Ile Val
            930                 935                 940
Tyr Lys Glu Ala Lys Glu Ser Val Asp Ala Leu Phe Val Asn Ser Gln
945                 950                 955                 960
Tyr Asp Arg Leu Gln Ala Asp Thr Asn Ile Ala Met Ile His Ala Ala
                965                 970                 975
Asp Lys Arg Val His Arg Ile Arg Glu Ala Tyr Leu Pro Glu Leu Ser
            980                 985                 990
Val Ile Pro Gly Val Asn Ala Ala Ile Phe Glu Glu Leu Glu Glu Arg
            995                 1000                1005
Ile Phe Thr Ala Phe Ser Leu Tyr Asp Ala Arg Asn Ile Ile Lys
1010                1015                1020
Asn Gly Asp Phe Asn Asn Gly Leu Leu Cys Trp Asn Val Lys Gly
    1025                1030                1035
His Val Glu Val Glu Glu Gln Asn Asn His Arg Ser Val Leu Val
    1040                1045                1050
Ile Pro Glu Trp Glu Ala Glu Val Ser Gln Glu Val Arg Val Cys
    1055                1060                1065
Pro Gly Arg Gly Tyr Ile Leu Arg Val Thr Ala Tyr Lys Glu Gly
    1070                1075                1080
Tyr Gly Glu Gly Cys Val Thr Ile His Glu Ile Glu Asn Asn Thr
    1085                1090                1095
Asp Glu Leu Lys Phe Asn Asn Cys Val Glu Glu Glu Val Tyr Pro
    1100                1105                1110
Asn Asn Thr Val Thr Cys Ile Asn Tyr Thr Ala Thr Gln Glu Glu
    1115                1120                1125
Tyr Glu Gly Thr Tyr Thr Ser Arg Asn Arg Gly Tyr Asp Glu Ala
    1130                1135                1140
Tyr Gly Asn Asn Pro Ser Val Pro Ala Asp Tyr Ala Ser Val Tyr
    1145                1150                1155
Glu Glu Lys Ser Tyr Thr Asp Arg Arg Arg Glu Asn Pro Cys Glu
    1160                1165                1170
Ser Asn Arg Gly Tyr Gly Asp Tyr Thr Pro Leu Pro Ala Gly Tyr
    1175                1180                1185
Val Thr Lys Glu Leu Glu Tyr Phe Pro Glu Thr Asp Lys Val Trp
    1190                1195                1200
Ile Glu Ile Gly Glu Thr Glu Gly Thr Phe Ile Val Asp Ser Val
    1205                1210                1215
```

Glu Leu Leu Leu Met Glu Glu
    1220           1225

<210> SEQ ID NO 34
<211> LENGTH: 3726
<212> TYPE: DNA
<213> ORGANISM: Artificial
<220> FEATURE:
<223> OTHER INFORMATION: Recombinant nucleotide sequence used for
      expression in a bacterial cell encoding TIC868_11.

<400> SEQUENCE: 34

| | | | | |
|---|---|---|---|---|
| atgacttcaa | ataggaaaaa | tgagaatgaa | attataaatg ctttatcgat tccagctgta | 60 |
| tcgaatcatt | ccgcacaaat | gaatctatca | accgatgctc gtattgagga tagcttgtgt | 120 |
| atagccgagg | ggaacaatat | cgatccattt | gttagcgcat caacagtcca aacgggtatt | 180 |
| aacatagctg | gtagaatact | aggtgtatta | ggcgtaccgt tgctggaca aatagctagt | 240 |
| ttttatagtt | tcttgttgg | tgaattatgg | ccccgcggca gagatccttg ggaattttc | 300 |
| ctagaacatg | tcgaacaact | tataagacaa | caagtaacag aaaatactag ggatacggct | 360 |
| cttgctcgat | tacaaggttt | aggaaattcc | tttagagcct atcaacagtc acttgaagat | 420 |
| tggctagaaa | accgtgatga | tgcaagaacg | agaagtgttc tttataccca atatatagcc | 480 |
| ttagaacttg | attttcttaa | tgcgatgccg | cttttcgcaa ttagaaacca agaagttcca | 540 |
| ttattaatgg | tatatgctca | agctgcaaat | ttacacctat tattattgag agatgcctct | 600 |
| cttttggta | gtgaatttgg | gcttacatcc | caagaaattc aacgttatta tgagcgccaa | 660 |
| gtggaaaaaa | cgagagaata | ttctgattat | tgcgcaagat ggtataatac gggtttaaat | 720 |
| aatttgagag | ggacaaatgc | tgaaagttgg | ttgcgatata atcaattccg tagagactta | 780 |
| acgctaggag | tattagatct | agtggcacta | ttcccaagct atgacacgcg tgtttatcca | 840 |
| atgaatacca | gtgctcaatt | aacaagagaa | atttatacag atccaattgg gagaacaaat | 900 |
| gcaccttcag | gatttgcaag | tacgaattgg | tttaataata atgcaccatc gttttctgcc | 960 |
| atagaggctg | ccgttattag | gcctccgcat | ctacttgatt ttccagaaca gcttacaatt | 1020 |
| ttcagcgtat | taagtcgatg | gagtaatact | caatatatga attactgggt gggacataga | 1080 |
| cttgaatcgc | gaacaataag | ggggtcatta | agtacctcga cacacggaaa taccaatact | 1140 |
| tctattaatc | ctgtaacatt | acagttcaca | tctcgagacg tttatagaac agaatcattt | 1200 |
| gcagggataa | atatacttct | aactactcct | gtgaatggag taccttgggc tagatttaat | 1260 |
| tggagaaatc | ccctgaattc | tcttagaggt | agccttctct atactatagg gtatactgga | 1320 |
| gtggggacac | aactatttga | ttcagaaact | gaattaccac cagaaacaac agaacgacca | 1380 |
| aattatgaat | cttacagtca | tagattatct | aatataagac taatatcagg aaacactttg | 1440 |
| agagcaccag | tatattcttg | gacgcaccgt | agtgcagatc gtacaaatac cattagttca | 1500 |
| gatagcatta | atcaaatacc | tttagtgaaa | ggatttagag tttgggggggg cacctctgtc | 1560 |
| attacaggac | caggatttac | aggaggggat | atccttcgaa gaaataccctt tggtgatttt | 1620 |
| gtatctctac | aagtcaatat | taattcacca | attacccaaa gataccgttt aagatttcgt | 1680 |
| tacgcttcca | gtagggatgc | acgagttata | gtattaacag gagcggcatc cacaggagtg | 1740 |
| ggaggccaag | ttagtgtaaa | tatgcctctt | cagaaaacta tggaaatagg ggagaactta | 1800 |
| acatctagaa | catttagata | taccgatttt | agtaatcctt tttcatttag agctaatcca | 1860 |
| gatataattg | ggataagtga | acaacctcta | tttggtgcag gttctattag tagcggtgaa | 1920 |

| | |
|---|---|
| ctttatatag ataaaattga aattattcta gcagatgcaa caggaacgac aacctatgag | 1980 |
| tatgaagaga agcagaatct agaaaaagcg cagaaagcgt tgaacgcttt gtttacggat | 2040 |
| ggcacgaatg gctatctaca aatggatgcc actgattatg atatcaatca aactgcaaac | 2100 |
| ttaatagaat gtgtatcaga tgaattgtat gcaaaagaaa agatagtttt attagatgaa | 2160 |
| gtcaaatatg cgaagcggct tagcatatca cgtaacctac ttttgaacga tgatttagaa | 2220 |
| ttttcagatg gatttggaga aaacggatgg acgacaagtg ataatatttc aatccaggcg | 2280 |
| gataatcccc tttttaaggg gaattattta aaaatgtttg gggcaagaga tattgatgga | 2340 |
| accctatttc caacttatct ctatcaaaaa atagatgagt ccaggttaaa accatataca | 2400 |
| cgttatcgag taagagggtt tgtgggaagt agtaaaaatc taaaattagt ggtaacacgc | 2460 |
| tatgagaaag aaattgatgc cattatgaat gttccaaatg atttggcaca tatgcagctt | 2520 |
| aacccttcat gtggagatta tcgctgtgaa tcatcgtccc agttttggt gaaccaagtg | 2580 |
| catcctacac aacagctgg atatgctctt gatatgtatg catgcccgtc aagttcagat | 2640 |
| aaaaaacata ttatgtgtca cgatcgtcat ccatttgatt ttcatattga caccggagaa | 2700 |
| ttaaatccaa acacaaacct gggtattgat gtcttgttta aaatttctaa tccaaatgga | 2760 |
| tacgctacat tagggaatct agaagtcatt gaagaaggac cactaacaga tgaagcattg | 2820 |
| gtacatgtaa aacaaaagga aaagaaatgg cgtcagcaca tggagaaaaa acgaatggaa | 2880 |
| acacaacaag cctatgatcc agcaaaacaa gctgtagatg cattatttac aaatgaacaa | 2940 |
| gagttagact atcatactac tttagatcat attcagaacg ccgatcagct ggtacaggcg | 3000 |
| attccctatg tacaccatgc ttggttaccg gatgctccag gtatgaacta tgatgtatat | 3060 |
| caagggttaa acgcacgtat catgcaggcg tacaatttat atgatgcacg aaatgtcata | 3120 |
| ataaatggtg actttacaca aggactacaa ggatggcacg caacaggaaa agcagcggta | 3180 |
| caacaaatag atggagcttc agtattagtt ctatcaaact ggagtgccga ggtatctcag | 3240 |
| aatctgcatg cccaagatca tcatggatat atgttacgtg tgattgccaa aaaagaaggt | 3300 |
| cctggaaaag ggtatgtaat gatgatggat tttaatggaa agcaggaaac acttacgttc | 3360 |
| acttcttgtg aagaaggata tataacaaaa acaatagagg tattcccgga agtgatcga | 3420 |
| atacgaattg aaatgggaga aacagagggt acgttttatg tagatagcat cgagttgctt | 3480 |
| tgtatgcaag gatatgctag cgataataac ccgcacacgg gtaatatgta tgagcaaagt | 3540 |
| tataatggaa attataatca aaatactagc gatgtgtatc accaaggata tataaacaac | 3600 |
| tataaccaaa attctagtag tatgtataat caaaattata ttaacaatga tgacctgcat | 3660 |
| tccggttgca catgtaacca agggcataac tctggctgta catgtaatca aggatataac | 3720 |
| cgttag | 3726 |

<210> SEQ ID NO 35
<211> LENGTH: 3726
<212> TYPE: DNA
<213> ORGANISM: Artificial
<220> FEATURE:
<223> OTHER INFORMATION: Synthetic nucleotide sequence designed for expression in a plant cell encoding TIC868_11.

<400> SEQUENCE: 35

| | |
|---|---|
| atgacgagca accggaagaa cgagaacgag atcatcaacg ccctctcgat ccctgctgtt | 60 |
| tcaaaccact ccgcgcagat gaacctgtcc accgacgcgc gcatcgagga ctccctctgc | 120 |
| atagccgagg gcaacaacat cgacccattc gtgtcggcca gcacggttca gaccggcatc | 180 |

```
aacatcgcgg gccgtatcct cggcgtcctc ggtgtcccat tcgccggtca gatcgcgtcc    240
ttctactcgt tccttgtggg cgagctgtgg cctcgcggtc gtgacccgtg ggagatcttc    300
ctggagcatg tggagcagtt gatccggcag caagtcacgg agaacacccg cgatactgct    360
ctggccaggc tacagggcct gggaaactcc tttcgggcat accagcagtc actggaggac    420
tggttggaga cagggatga cgcgcgaaca cgctcggtac tctacaccca gtacatcgct    480
ctcgaactcg acttcctgaa cgctatgccg ctgttcgcca tcaggaacca ggaagttcca    540
ctccttatgg tgtacgccca ggccgccaac ttacatctgc tcctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag acccaatcgg ccggacgaac    900
gcaccctccg gtttcgcatc cacgaattgg ttcaacaaca acgcaccctc cttctcggca    960
atcgaggccg ccgtcatccg ccctcctcac ctgctcgact ttcccgagca gctcacgatc   1020
ttctccgtgc tctcacgctg gtccaacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
actagccgaa ccttccggta cactgatttc tcgaacccct tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cggggactac cacctacgag   1980
tacgaggaga agcagaatct cgagaaggct cagaaggctc tgaacgctct gttcactgac   2040
gggaccaacg gctacctcca gatggacgcc actgactacg acatcaacca gacagctaac   2100
ctgattgagt gtgtgagtga cgaactgtac gctaaggaga agatcgtact cctggacgag   2160
gtgaagtacg ctaagcgcct gagcattagc cgtaacctgc tgctgaacga cgatctggag   2220
ttcagcgacg gctttggcga gaacggctgg accaccagcg acaacatctc catccaggcc   2280
gacaatccac tcttcaaagg caactacctc aagatgttcg gagccaggga catcgacggc   2340
accctctttc cgacctacct ctaccagaag atcgacgagt cccgcctcaa accctacacc   2400
cgctacaggg tgcgcggctt cgtgggcagc agcaagaacc tcaagctcgt ggtcacacgg   2460
tatgagaagg agatcgacgc catcatgaac gtgcccaacg atctcgccca catgcagctc   2520
aatccatcct gcggcgacta ccggtgcgag tccagctccc agttcctcgt gaaccaggtg   2580
```

```
caccctactc cgaccgctgg ctatgccctg gacatgtacg cctgccctag ttcctccgac    2640
aagaagcaca tcatgtgcca cgaccgtcat ccgttcgact tccacatcga caccggcgaa    2700
ctgaacccga acaccaacct gggcatcgac gtactgttca agatttccaa cccgaacggg    2760
tacgccacct tgggcaacct ggaggtcatc gaagaaggcc cgctgaccga cgaggccctg    2820
gtccacgtca acagaagga gaagaagtgg cggcagcaca tggagaagaa gcggatggag    2880
actcaacaag cctacgaccc ggccaagcaa gctgtggacg ctctgttcac caacgagcaa    2940
gagcttgact accacactac tcttgaccac atccagaatg ctgaccagct tgtccaggct    3000
attccgtacg tccaccacgc ttggctaccg gacgctccag ggatgaacta cgatgtgtac    3060
cagggtctga acgcgcggat catgcaagcg tacaacctgt acgacgcgcg taacgtcatc    3120
atcaacggtg acttcactca gggtcttcaa ggttggcacg cgactggcaa agcggcagtc    3180
cagcagattg atggtgcgtc tgttcttgtg ttgagcaact ggtctgcgga ggtttctcag    3240
aacctgcacg cacaggatca ccacggctac atgctgaggg tgattgctaa gaaggagggc    3300
cctggcaaag gctacgtcat gatgatggac ttcaacggaa agcaagaaac cctgaccttc    3360
actagctgtg aggagggcta catcactaag accattgagg tctttccgga gtctgaccgc    3420
atccggatcg agatgggcga gaccgaaggc acgttctacg tggactccat cgaactcctc    3480
tgcatgcaag gctacgcctc cgacaacaac ccacacacgg caacatgta cgagcagtcc    3540
tacaacggga actacaacca gaacacctcc gatgtgtacc atcagggcta catcaacaac    3600
tacaaccaga acagcagcag catgtacaac cagaactaca tcaacaacga tgacttgcac    3660
tcgggttgca cctgcaacca gggtcacaac agtgggtgca cgtgcaacca gggatacaac    3720
cgttga                                                               3726
```

```
<210> SEQ ID NO 36
<211> LENGTH: 1241
<212> TYPE: PRT
<213> ORGANISM: Artificial
<220> FEATURE:
<223> OTHER INFORMATION: Amino acid sequence of the chimeric protein
      variant TIC868_11.

<400> SEQUENCE: 36

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140
```

```
Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
```

```
                565                 570                 575
Ser Thr Gly Val Gly Gly Gln Val Ser Val Asn Met Pro Leu Gln Lys
                580                 585                 590
Thr Met Glu Ile Gly Glu Asn Leu Thr Ser Arg Thr Phe Arg Tyr Thr
                595                 600                 605
Asp Phe Ser Asn Pro Phe Ser Phe Arg Ala Asn Pro Asp Ile Ile Gly
                610                 615                 620
Ile Ser Glu Gln Pro Leu Phe Gly Ala Gly Ser Ile Ser Ser Gly Glu
625                 630                 635                 640
Leu Tyr Ile Asp Lys Ile Glu Ile Ile Leu Ala Asp Ala Thr Gly Thr
                645                 650                 655
Thr Thr Tyr Glu Tyr Glu Lys Gln Asn Leu Glu Lys Ala Gln Lys
                660                 665                 670
Ala Leu Asn Ala Leu Phe Thr Asp Gly Thr Asn Gly Tyr Leu Gln Met
                675                 680                 685
Asp Ala Thr Asp Tyr Asp Ile Asn Gln Thr Ala Asn Leu Ile Glu Cys
                690                 695                 700
Val Ser Asp Glu Leu Tyr Ala Lys Glu Lys Ile Val Leu Leu Asp Glu
705                 710                 715                 720
Val Lys Tyr Ala Lys Arg Leu Ser Ile Ser Arg Asn Leu Leu Leu Asn
                725                 730                 735
Asp Asp Leu Glu Phe Ser Asp Gly Phe Gly Glu Asn Gly Trp Thr Thr
                740                 745                 750
Ser Asp Asn Ile Ser Ile Gln Ala Asp Asn Pro Leu Phe Lys Gly Asn
                755                 760                 765
Tyr Leu Lys Met Phe Gly Ala Arg Asp Ile Asp Gly Thr Leu Phe Pro
                770                 775                 780
Thr Tyr Leu Tyr Gln Lys Ile Asp Glu Ser Arg Leu Lys Pro Tyr Thr
785                 790                 795                 800
Arg Tyr Arg Val Arg Gly Phe Val Gly Ser Ser Lys Asn Leu Lys Leu
                805                 810                 815
Val Val Thr Arg Tyr Glu Lys Glu Ile Asp Ala Ile Met Asn Val Pro
                820                 825                 830
Asn Asp Leu Ala His Met Gln Leu Asn Pro Ser Cys Gly Asp Tyr Arg
                835                 840                 845
Cys Glu Ser Ser Ser Gln Phe Leu Val Asn Gln Val His Pro Thr Pro
                850                 855                 860
Thr Ala Gly Tyr Ala Leu Asp Met Tyr Ala Cys Pro Ser Ser Ser Asp
865                 870                 875                 880
Lys Lys His Ile Met Cys His Asp Arg His Pro Phe Asp Phe His Ile
                885                 890                 895
Asp Thr Gly Glu Leu Asn Pro Asn Thr Asn Leu Gly Ile Asp Val Leu
                900                 905                 910
Phe Lys Ile Ser Asn Pro Asn Gly Tyr Ala Thr Leu Gly Asn Leu Glu
                915                 920                 925
Val Ile Glu Glu Gly Pro Leu Thr Asp Glu Ala Leu Val His Val Lys
930                 935                 940
Gln Lys Glu Lys Lys Trp Arg Gln His Met Glu Lys Lys Arg Met Glu
945                 950                 955                 960
Thr Gln Gln Ala Tyr Asp Pro Ala Lys Gln Ala Val Asp Ala Leu Phe
                965                 970                 975
Thr Asn Glu Gln Glu Leu Asp Tyr His Thr Thr Leu Asp His Ile Gln
                980                 985                 990
```

Asn Ala Asp Gln Leu Val Gln Ala Ile Pro Tyr Val His His Ala Trp
       995                1000                1005

Leu Pro Asp Ala Pro Gly Met Asn Tyr Asp Val Tyr Gln Gly Leu
   1010                1015                1020

Asn Ala Arg Ile Met Gln Ala Tyr Asn Leu Tyr Asp Ala Arg Asn
   1025                1030                1035

Val Ile Ile Asn Gly Asp Phe Thr Gln Gly Leu Gln Gly Trp His
   1040                1045                1050

Ala Thr Gly Lys Ala Ala Val Gln Gln Ile Asp Gly Ala Ser Val
   1055                1060                1065

Leu Val Leu Ser Asn Trp Ser Ala Glu Val Ser Gln Asn Leu His
   1070                1075                1080

Ala Gln Asp His His Gly Tyr Met Leu Arg Val Ile Ala Lys Lys
   1085                1090                1095

Glu Gly Pro Gly Lys Gly Tyr Val Met Met Met Asp Phe Asn Gly
   1100                1105                1110

Lys Gln Glu Thr Leu Thr Phe Thr Ser Cys Glu Glu Gly Tyr Ile
   1115                1120                1125

Thr Lys Thr Ile Glu Val Phe Pro Glu Ser Asp Arg Ile Arg Ile
   1130                1135                1140

Glu Met Gly Glu Thr Glu Gly Thr Phe Tyr Val Asp Ser Ile Glu
   1145                1150                1155

Leu Leu Cys Met Gln Gly Tyr Ala Ser Asp Asn Asn Pro His Thr
   1160                1165                1170

Gly Asn Met Tyr Glu Gln Ser Tyr Asn Gly Asn Tyr Asn Gln Asn
   1175                1180                1185

Thr Ser Asp Val Tyr His Gln Gly Tyr Ile Asn Asn Tyr Asn Gln
   1190                1195                1200

Asn Ser Ser Ser Met Tyr Asn Gln Asn Tyr Ile Asn Asn Asp Asp
   1205                1210                1215

Leu His Ser Gly Cys Thr Cys Asn Gln Gly His Asn Ser Gly Cys
   1220                1225                1230

Thr Cys Asn Gln Gly Tyr Asn Arg
   1235                1240

<210> SEQ ID NO 37
<211> LENGTH: 3468
<212> TYPE: DNA
<213> ORGANISM: Artificial
<220> FEATURE:
<223> OTHER INFORMATION: Recombinant nucleotide sequence used for
      expression in a bacterial cell encoding TIC868_12.

<400> SEQUENCE: 37
atgacttcaa ataggaaaaa tgagaatgaa attataaatg ctttatcgat tccagctgta      60
tcgaatcatt ccgcacaaat gaatctatca accgatgctc gtattgagga tagcttgtgt     120
atagccgagg ggaacaatat cgatccattt gttagcgcat caacagtcca aacgggtatt     180
aacatagctg gtagaatact aggtgtatta ggcgtaccgt tgctggaca aatagctagt     240 ttttatagtt ttcttgttgg tgaattatgg ccccgcggca gagatccttg ggaaattttc     300
ctagaacatg tcgaacaact tataagacaa caagtaacag aaaatactag ggatacggct     360
cttgctcgat tacaaggttt aggaaattcc tttagagcct atcaacagtc acttgaagat     420
tggctagaaa accgtgatga tgcaagaacg agaagtgttc tttataccca atatatagcc     480

```
ttagaacttg attttcttaa tgcgatgccg cttttcgcaa ttagaaacca agaagttcca    540
ttattaatgg tatatgctca agctgcaaat ttacacctat tattattgag agatgcctct    600 cttttttggta gtgaatttgg gcttacatcc caagaaattc aacgttatta tgagcgccaa    660
gtggaaaaaa cgagagaata ttctgattat tgcgcaagat ggtataatac gggtttaaat    720
aatttgagag ggacaaatgc tgaaagttgg ttgcgatata atcaattccg tagagactta    780
acgctaggag tattagatct agtggcacta ttcccaagct atgacacgcg tgttatccca    840
atgaatacca gtgctcaatt aacaagagaa atttatacag atccaattgg gagaacaaat    900
gcaccttcag gatttgcaag tacgaattgg tttaataata atgcaccatc gttttctgcc    960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag ggggtcatta agtacctcga cacacggaaa taccaatact   1140
tctattaatc ctgtaacatt acagttcaca tctcgagacg tttatagaac agaatcattt   1200
gcagggataa atatacttct aactactcct gtgaatggaa taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta atcaaatacc tttagtgaaa ggatttagag tttgggggg cacctctgtc    1560 attacaggac caggatttac aggagggat atccttcgaa gaaataccctt tggtgatttt    1620 gtatctctac aagtcaatat taattcacca attacccaaa gataccgttt aagatttcgt    1680
tacgcttcca gtagggatgc acgagttata gtattaacag gagcggcatc cacaggagtg   1740
ggaggccaag ttagtgtaaa tatgcctctt cagaaaacta tggaaatagg ggagaactta    1800
acatctagaa catttagata taccgatttt agtaatcctt tttcatttag agctaatcca    1860
gatataattg ggataagtga acaaccctct atttggtgcag gttctattag tagcggtgaa   1920
ctttatatag ataaaattga aattattcta gcagatgcaa caaatccgac gcgagaggcg   1980
gaagaggatc tagaagcagc gaagaaagcg gtggcgagct tgtttacacg tacaagggac   2040
ggattacaag taaatgtgac agattatcaa gtcgatcaag cggcaaattt agtgtcatgc    2100
ttatcagatg aacaatatgg gcatgacaaa aagatgttat tggaagcggt aagagcggca   2160
aaacgcctca gccgagaacg caacttactt caggatccag attttaatac aatcaatagt   2220
acagaagaaa atggatggaa agcaagtaac ggcgttacta ttagcgaggg cggtccattc   2280
tataaaggcc gtgcgcttca gctagcaagc gcaagagaaa attacccaac atacattttat   2340 caaaaagtaa atgcatcaga gttaaagccg tatacacgtt atagactgga tgggttcgtg    2400
aagagtagtc aagatttaga aattgatctc attcaccatc ataaagtcca tctcgtgaaa   2460
aatgtaccag ataatttagt atccgatact tactcggatg gttcttgcag tggaatgaat   2520
cgatgtgagg aacaacagat ggtaaatgcg caactggaaa cagaacatca tcatccgatg   2580
gattgctgtg aagcggctca aacacatgag ttttcttcct atattaatac aggcgatcta   2640
aattcaagtg tagatcaagg catttgggtt gtattgaaag ttcgaacaac cgatggttat   2700
gcgacgctag gaaatcttga attggtagag gtcggaccgt tatcgggtga atctctagaa   2760
cgtgaacaaa gggataatgc gaaatggagt gcagagctag gaagaaagcg tgcagaaaca   2820
gatcgcgtgt atcaagatgc caaacaatcc atcaatcatt tatttgtgga ttatcaagat   2880
```

-continued

```
caacaattaa atccagaaat agggatggca gatattattg acgctcaaaa tcttgtcgca    2940
tcaatttcag atgtgtatag cgatgcagta ctgcaaatcc ctggaattaa ctatgagatt    3000
tacacagagc tatccaatcg cttacaacaa gcatcgtatc tgtatacgtc tcgaaatgcg    3060
gtgcaaaatg gggactttaa cagcggtcta gatagttgga atgcaacagg ggggctacg     3120 gtacaacagg atggcaatac gcatttctta gttctttctc attgggatgc acaagtttct    3180
caacaattta gagtgcagcc gaattgtaaa tatgtattac gtgtaacagc agagaaagta    3240
ggcggcggag acggatacgt gacaatccgg gatggtgctc atcatacaga aaagcttaca    3300
tttaatgcat gtgattatga tataaatggc acgtacgtga ctgataatac gtatctaaca    3360
aaagaagtgg tattctattc acatacagaa cacatgtggg tagaggtaag tgaaacagaa    3420
ggtgcatttc atatagatag tattgaattc gttgaaacag aaaagtag                 3468
```

<210> SEQ ID NO 38
<211> LENGTH: 3468
<212> TYPE: DNA
<213> ORGANISM: Artificial
<220> FEATURE:
<223> OTHER INFORMATION: Synthetic nucleotide sequence designed for expression in a plant cell encoding TIC868_12.

<400> SEQUENCE: 38

```
atgacgagca accggaagaa cgagaacgag atcatcaacg ccctctcgat ccctgctgtt      60
tcaaaccact ccgcgcagat gaacctgtcc accgacgcgc gcatcgagga ctccctctgc     120
atagccgagg gcaacaacat cgacccattc gtgtcggcca gcacggttca gaccggcatc     180
aacatcgcgg gccgtatcct cggcgtcctc ggtgtcccat cgccggtca gatcgcgtcc      240 ttctactcgt tccttgtggg cgagctgtgg cctcgcggtc gtgaccgtg ggagatcttc       300 ctggagcatg tggagcagtt gatccggcag caagtcacgg agaacacccg cgatactgct     360
ctggccaggc tacagggcct gggaaactcc tttcgggcat accagcagtc actggaggac     420
tggttggaga caggggatga cgcgcgaaca cgctcggtac tctacaccca gtacatcgct     480
ctcgaactcg acttcctgaa cgctatgccg ctgttcgcca tcaggaacca ggaagttcca     540
ctccttatgg tgtacgccca ggccgccaac ttacatctgc tcctgctgcg ggacgccagc     600
ctgttcggct ccgagttcgg actcacatct caagaaatcc agcgttacta cgagcgccaa     660
gtggagaaga cccgtgagta cagtgactac tgcgctcgat ggtacaacac agggctcaac     720
aacctgcgcg gcaccaacgc tgagtcatgg ctccgttaca accagttccg ccgcgacttg     780
actttgggtg tcctagacct ggtggcgcta ttcccgtctt acgacacacg ggtgtaccca     840
atgaacacta gcgcgcaact cacgcgggag atctacacag acccaatcgg ccggacgaac     900
gcaccctccg gtttcgcatc cacgaattgg ttcaacaaca acgcacccct cttctcggca     960
atcgaggccg ccgtcatccg ccctcctcac ctgctcgact ttcccgagca gctcacgatc    1020
ttctccgtgc tctcacgctg gtccaacaca cagtacatga actactgggt cgggcaccga    1080
ttggagagta ggacgatccg tggcagcttg agcaccagta cccacggcaa caccaacacc    1140
tccatcaacc cagttacgct acagttcacg agccgcgacg tttaccggac tgagtcgttc    1200
gcgggcatta acatccttct gacaacgccc gtcaacggcg tcccgtgggc ccggttcaac    1260
tggcgtaacc cgttgaactc cctgcgcggg tcattgctct acaccatcgg gtacacgggc    1320
gtcggcaccg agctcttcga cagtgaaact gagctgccgc ccgagaccac ggaacgcccg    1380
aactacgagt cctacagcca ccgcctgtcc aacatccggc tcatctctgg caacacgctg    1440
```

```
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg agccgcgtc cacaggcgtg    1740 ggaggccaag tctcagtcaa catgcctctc cagaagacga tggagatagg cgagaacttg   1800
actagccgaa ccttccggta cactgatttc tcgaacccct tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cgaacccgac gcgggaagct   1980
gaggaagact tggaagccgc caagaaagcg gtcgccagcc tgtttactcg gacgcgggac   2040
gggctccaag tgaatgtgac ggactatcaa gtggatcagg ccgctaacct cgtgtcatgc   2100
ctgagcgacg agcagtacgg tcacgacaag aaaatgctgc tggaggccgt ccgggccgcc   2160
aagcggctgt ccagggagcg taacctgcta caagatcccg actttaacac gatcaacagc   2220
acagaggaga atggctggaa ggccagcaac ggagttacga taagcgaggg cggtccgttc   2280
tacaagggtc gtgccctcca gctcgcctct gcaagggaga actatccaac ctacatctat   2340
cagaaggtga acgcatccga gcttaagccc tacacacgct accgcctgga cgggttcgtt   2400
aagtccagtc aagacctaga gatagacctc atccaccacc acaaagtgca tctggtcaag   2460
aacgttcccg ataatctcgt gagcgatacc tactcagacg gctcatgctc tggcatgaac   2520
agatgtgagg agcaacagat ggttaatgct caactcgaaa ccgagcatca tcatcctatg   2580
gattgctgcg aggccgcgca gacccatgag ttcagctctt acatcaacac cggagacctc   2640
aacagtagcg tggatcaggg aatttgggtg gtgcttaaag tgcgtacaac cgacggctac   2700 gccacccctcg gcaaccttga gcttgtcgag gtcggaccac ttagcggcga gtccctggaa   2760
cgtgagcagc gggacaacgc caaatggagc gcagagctag ggcgcaaacg cgcggagacg   2820
gaccgggttt atcaggacgc gaagcagtcc atcaatcacc tcttcgtgga ttatcaggac   2880
cagcagctta atccagagat cggcatggcc gacatcatcg acgcccagaa cctagtagcg   2940
tcgatttccg atgtctattc cgacgccgtg cttcaaatac ctggcatcaa ctacgagatc   3000
tacacagagt tgtccaacag gctccagcaa gcgtcatacc tctacaccag ccgcaacgcc   3060
gtccagaatg gcgacttcaa ttccggacta gactcctgga acgccacggg cggagctacg   3120
gtgcaacaag acggcaacac ccacttcctc gtacttagcc actgggacgc tcaagtgagt   3180
cagcaattcc gggttcagcc gaactgcaag tacgtcctgc gcgtaacggc cgagaaggtt   3240
ggaggcggag acggctacgt taccatccgc gacggcgctc accaccga gaaactgacg    3300 ttcaacgctt gtgactacga catcaacggc acttacgtga cggacaacac ctacctgacg   3360
aaggaggtgg tgttctattc tcacaccgag cacatgtggg ttgaggtcag cgagaccgag   3420
ggagccttcc acattgacag catcgagttc gtggagactg agaagtga                3468
```

<210> SEQ ID NO 39
<211> LENGTH: 1155
<212> TYPE: PRT
<213> ORGANISM: Artificial
<220> FEATURE:
<223> OTHER INFORMATION: Amino acid sequence of the chimeric protein
      variant TIC868_12.

<400> SEQUENCE: 39

-continued

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
                100                 105                 110

Thr Glu Asn Thr Arg Asp Thr Ala Leu Ala Arg Leu Gln Gly Leu Gly
                115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Val Glu Lys Thr
210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
            245                 250                 255

Arg Arg Asp Leu Thr Leu Gly Val Leu Asp Leu Val Ala Leu Phe Pro
        260                 265                 270

Ser Tyr Asp Thr Arg Val Tyr Pro Met Asn Thr Ser Ala Gln Leu Thr
    275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
                340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415
```

```
Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
        530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
        610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Asn Pro
                645                 650                 655

Thr Arg Glu Ala Glu Asp Leu Glu Ala Ala Lys Lys Ala Val Ala
            660                 665                 670

Ser Leu Phe Thr Arg Thr Arg Asp Gly Leu Gln Val Asn Val Thr Asp
        675                 680                 685

Tyr Gln Val Asp Gln Ala Ala Asn Leu Val Ser Cys Leu Ser Asp Glu
    690                 695                 700

Gln Tyr Gly His Asp Lys Lys Met Leu Leu Glu Ala Val Arg Ala Ala
705                 710                 715                 720

Lys Arg Leu Ser Arg Glu Arg Asn Leu Leu Gln Asp Pro Asp Phe Asn
                725                 730                 735

Thr Ile Asn Ser Thr Glu Glu Asn Gly Trp Lys Ala Ser Asn Gly Val
            740                 745                 750

Thr Ile Ser Glu Gly Gly Pro Phe Tyr Lys Gly Arg Ala Leu Gln Leu
        755                 760                 765

Ala Ser Ala Arg Glu Asn Tyr Pro Thr Tyr Ile Tyr Gln Lys Val Asn
    770                 775                 780

Ala Ser Glu Leu Lys Pro Tyr Thr Arg Tyr Arg Leu Asp Gly Phe Val
785                 790                 795                 800

Lys Ser Ser Gln Asp Leu Glu Ile Asp Leu Ile His His Lys Val
                805                 810                 815

His Leu Val Lys Asn Val Pro Asp Asn Leu Val Ser Asp Thr Tyr Ser
            820                 825                 830

Asp Gly Ser Cys Ser Gly Met Asn Arg Cys Glu Glu Gln Gln Met Val
```

Asn Ala Gln Leu Glu Thr Glu His His His Pro Met Asp Cys Cys Glu
            835                 840                 845
Ala Ala Gln Thr His Glu Phe Ser Ser Tyr Ile Asn Thr Gly Asp Leu
865                 870                 875                 880
Asn Ser Ser Val Asp Gln Gly Ile Trp Val Leu Lys Val Arg Thr
                885                 890                 895
Thr Asp Gly Tyr Ala Thr Leu Gly Asn Leu Glu Leu Val Glu Val Gly
            900                 905                 910
Pro Leu Ser Gly Glu Ser Leu Glu Arg Glu Gln Arg Asp Asn Ala Lys
            915                 920                 925
Trp Ser Ala Glu Leu Gly Arg Lys Arg Ala Glu Thr Asp Arg Val Tyr
            930                 935                 940
Gln Asp Ala Lys Gln Ser Ile Asn His Leu Phe Val Asp Tyr Gln Asp
945                 950                 955                 960
Gln Gln Leu Asn Pro Glu Ile Gly Met Ala Asp Ile Ile Asp Ala Gln
            965                 970                 975
Asn Leu Val Ala Ser Ile Ser Asp Val Tyr Ser Asp Ala Val Leu Gln
            980                 985                 990
Ile Pro Gly Ile Asn Tyr Glu Ile Tyr Thr Glu Leu Ser Asn Arg Leu
            995                 1000                1005
Gln Gln Ala Ser Tyr Leu Tyr Thr Ser Arg Asn Ala Val Gln Asn
    1010                1015                1020
Gly Asp Phe Asn Ser Gly Leu Asp Ser Trp Asn Ala Thr Gly Gly
    1025                1030                1035
Ala Thr Val Gln Gln Asp Gly Asn Thr His Phe Leu Val Leu Ser
    1040                1045                1050
His Trp Asp Ala Gln Val Ser Gln Gln Phe Arg Val Gln Pro Asn
    1055                1060                1065
Cys Lys Tyr Val Leu Arg Val Thr Ala Glu Lys Val Gly Gly Gly
    1070                1075                1080
Asp Gly Tyr Val Thr Ile Arg Asp Gly Ala His His Thr Glu Lys
    1085                1090                1095
Leu Thr Phe Asn Ala Cys Asp Tyr Asp Ile Asn Gly Thr Tyr Val
    1100                1105                1110
Thr Asp Asn Thr Tyr Leu Thr Lys Glu Val Val Phe Tyr Ser His
    1115                1120                1125
Thr Glu His Met Trp Val Glu Val Ser Glu Thr Glu Gly Ala Phe
    1130                1135                1140
His Ile Asp Ser Ile Glu Phe Val Glu Thr Glu Lys
    1145                1150                1155

<210> SEQ ID NO 40
<211> LENGTH: 3732
<212> TYPE: DNA
<213> ORGANISM: Artificial
<220> FEATURE:
<223> OTHER INFORMATION: Synthetic nucleotide sequence designed for
    expression in a plant cell encoding TIC868_13.

<400> SEQUENCE: 40
atgacgagca accggaagaa cgagaacgag atcatcaacg ccctctcgat ccctgctgtt     60
tcaaaccact ccgcgcagat gaacctgtcc accgacgcgc gcatcgagga ctccctctgc    120
atagccgagg caacaacat cgacccattc gtgtcggcca gcacggttca gaccggcatc    180

```
aacatcgcgg gccgtatcct cggcgtcctc ggtgtcccat tcgccggtca gatcgcgtcc    240
ttctactcgt tccttgtggg cgagctgtgg cctcgcggtc gtgacccgtg ggagatcttc    300
ctggagcatg tggagcagtt gatccggcag caagtcacgg agaacacccg cgatactgct    360
ctggccaggc tacagggcct gggaaactcc tttcgggcat accagcagtc actggaggac    420
tggttggaga cagggatga cgcgcgaaca cgctcggtac tctacaccca gtacatcgct    480
ctcgaactcg acttcctgaa cgctatgccg ctgttcgcca tcaggaacca ggaagttcca    540
ctccttatgg tgtacgccca ggccgccaac ttacatctgc tcctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag cccaatcgg ccggacgaac    900 gcaccctccg gtttcgcatc cacgaattgg ttcaacaaca cgcaccctc cttctcggca    960 atcgaggccg ccgtcatccg ccctcctcac ctgctcgact ttcccgagca gctcacgatc    1020
ttctccgtgc tctcacgctg gtccaacaca cagtacatga actactgggt cgggcaccga    1080
ttggagagta ggacgatccg tggcagcttg agcaccagta cccacggcaa caccaacacc    1140
tccatcaacc cagttacgct acagttcacg agccgcgacg tttaccggac tgagtcgttc    1200
gcgggcatta acatccttct gacaacgccc gtcaacggcg tcccgtgggc ccggttcaac    1260
tggcgtaacc cgttgaactc cctgcgcggg tcattgctct acaccatcgg gtacacgggc    1320
gtcggcaccc agctcttcga cagtgaaact gagctgccgc ccgagaccac ggaacgcccg    1380
aactacgagt cctacagcca ccgcctgtcc aacatccggc tcatctctgg caacacgctg    1440
cgtgcgccgg tgtactcctg gacacaccgc agcgccgacc ggaccaacac gatctcttcc    1500
gactccatta accagatccc gctcgtgaag ggcttccgtg tgtggggtgg cacgagcgtc    1560
atcaccggtc cgggcttcac cggtggagac atactgcggc gcaacacttt cggcgacttc    1620
gtttcgttgc aagtgaacat caactcgccg atcacccagc gttaccgtct gaggttccgc    1680
tacgcttcaa gccgcgacgc gagggtcatt gtcctgaccg gagccgcgtc cacaggcgtg    1740
ggaggccaag tctcagtcaa catgcctctc cagaagacga tggagatagg cgagaacttg    1800
actagccgaa ccttccggta cactgatttc tcgaacccct tctcattcag agcgaaccct    1860
gacatcattg ggatctccga gcaaccgctg ttcggtgctg gctccatcag ctctggcgaa    1920
ctgtacatcg acaagattga gatcatcctg gcggatgcga cgacggcgac cttcgaggcg    1980
gagtatgact tggagcgggc tcaggaggcc gtcaacgcgc tgttcacaaa caccaatcct    2040
cgccgcctca agacgggtgt gactgattac cacattgacg aggtctccaa cttggtcgcg    2100
tgtctgtccg atgagttctg cctggacgag aagcgggaac tgctggagaa ggtcaagtac    2160
gccaagcgcc tctccgacga aaggaacctc ctccaagatc ccaactttac ttccattaac    2220
aagcagccgg acttcatctc caccaacgag cagtccaact tcacctcaat ccacgagcag    2280
tcggagcacg gtggtgggg cagcgagaac atcaccatcc aagagggcaa cgacgtcttc    2340
aaggagaact acgtgatcct gcccggcacc ttcaacgagt gttacccgac ctatctctac    2400
cagaagattg gcgaagcgga actcaaggct tacacccgtt accaactgag tggctacatt    2460
gaggactcac aagacctgga aatctacctg atccgctaca acgccaagca cgagaccctc    2520
gacgtgcctg gcacggagtc cgtctggccc ttgagcgtgg agtctcctat cggtcgttgc    2580
```

```
ggcgagccca atcgctgcgc tccgcactt  gagtggaatc ctgatttgga ttgctcctgc    2640
cgagacggtg agaaatgcgc ccaccactcg caccacttca gcctagacat cgacgtgggc    2700
tgcatcgacc tgcacgagaa cttgggcgtc tgggtcgtgt tcaagatcaa gacacaggag    2760
ggccatgctc ggcttgggaa cctggagttc atcgaggaga agccactgct gggtgaagcc    2820
ttgtcacggg tgaaacgcgc cgagaagaag tggcgggaca acgggagaa gctccagttg    2880 gagacaaagc gtgtgtacac agaggccaag gaggccgtgg atgccttgtt cgtggacagt    2940
cagtacgaca ggctgcaagc ggacaccaac atcgggatga tccacgcggc tgataagctt    3000
gttcacagaa tccgcgaggc gtacctgtca gagcttagcg tgatcccagg cgtcaacgcc    3060
gaaatcttcg aggaactgga gggccgcatt atcacggcaa tctcactta tgacgcgagg    3120 aatgtggtca agaacggtga cttcaacaac ggcttggcgt gttggaacgt taaagggcac    3180
gtggatgtac aacagtcaca ccacagaagt gtcttggtca tcccggagtg ggaggcggaa    3240
gtgagccagg ccgtccgggt ctgccctggg cgcggttaca tcctccgcgt gacagcgtac    3300
aaggagggct acggtgaggg ctgcgtgacg atccacgaga ttgagaacaa cacggacgag    3360
cttaagttca agaactgcga ggaggaggaa gtgtacccga cagacaccgg cacctgcaac    3420
gactacaccg cccaccaagg gaccgccgcc tgcaacagcc gcaacgcggg ctatgaagat    3480
gcgtacgagt tgataccac cgcctcagtg aactacaaac cgacttatga ggaggagaca    3540
tacacggacg tcaggcgcga caaccattgt gagtacgacc gtggctacgt gaactatccg    3600
ccggtgccag cgggctacat gacgaaggag ctagaatact tccctgagac ggacaaggtg    3660
tggattgaaa tcggcgagac cgagggcaag tttatcgtgg attctgtcga gctgctgcta    3720
atggaggagt ag                                                        3732
```

<210> SEQ ID NO 41
<211> LENGTH: 1243
<212> TYPE: PRT
<213> ORGANISM: Artificial
<220> FEATURE:
<223> OTHER INFORMATION: Amino acid sequence of the chimeric protein variant TIC868_13.

<400> SEQUENCE: 41

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140
```

```
Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Asn Leu His
            180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Val Glu Lys Thr
        210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
        370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
        530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
```

```
                565                 570                 575
Ser Thr Gly Val Gly Gly Gln Val Ser Val Asn Met Pro Leu Gln Lys
            580                 585                 590
Thr Met Glu Ile Gly Glu Asn Leu Thr Ser Arg Thr Phe Arg Tyr Thr
            595                 600                 605
Asp Phe Ser Asn Pro Phe Ser Phe Arg Ala Asn Pro Asp Ile Ile Gly
            610                 615                 620
Ile Ser Glu Gln Pro Leu Phe Gly Ala Gly Ser Ile Ser Ser Gly Glu
625                 630                 635                 640
Leu Tyr Ile Asp Lys Ile Glu Ile Ile Leu Ala Asp Ala Thr Thr Ala
                645                 650                 655
Thr Phe Glu Ala Glu Tyr Asp Leu Glu Arg Ala Gln Glu Ala Val Asn
            660                 665                 670
Ala Leu Phe Thr Asn Thr Asn Pro Arg Arg Leu Lys Thr Gly Val Thr
            675                 680                 685
Asp Tyr His Ile Asp Glu Val Ser Asn Leu Val Ala Cys Leu Ser Asp
            690                 695                 700
Glu Phe Cys Leu Asp Glu Lys Arg Glu Leu Leu Glu Lys Val Lys Tyr
705                 710                 715                 720
Ala Lys Arg Leu Ser Asp Glu Arg Asn Leu Leu Gln Asp Pro Asn Phe
                725                 730                 735
Thr Ser Ile Asn Lys Gln Pro Asp Phe Ile Ser Thr Asn Glu Gln Ser
            740                 745                 750
Asn Phe Thr Ser Ile His Glu Gln Ser Glu His Gly Trp Trp Gly Ser
            755                 760                 765
Glu Asn Ile Thr Ile Gln Glu Gly Asn Asp Val Phe Lys Glu Asn Tyr
770                 775                 780
Val Ile Leu Pro Gly Thr Phe Asn Glu Cys Tyr Pro Thr Tyr Leu Tyr
785                 790                 795                 800
Gln Lys Ile Gly Glu Ala Glu Leu Lys Ala Tyr Thr Arg Tyr Gln Leu
                805                 810                 815
Ser Gly Tyr Ile Glu Asp Ser Gln Asp Leu Glu Ile Tyr Leu Ile Arg
            820                 825                 830
Tyr Asn Ala Lys His Glu Thr Leu Asp Val Pro Gly Thr Glu Ser Val
            835                 840                 845
Trp Pro Leu Ser Val Glu Ser Pro Ile Gly Arg Cys Gly Glu Pro Asn
            850                 855                 860
Arg Cys Ala Pro His Phe Glu Trp Asn Pro Asp Leu Asp Cys Ser Cys
865                 870                 875                 880
Arg Asp Gly Glu Lys Cys Ala His His Ser His His Phe Ser Leu Asp
                885                 890                 895
Ile Asp Val Gly Cys Ile Asp Leu His Glu Asn Leu Gly Val Trp Val
            900                 905                 910
Val Phe Lys Ile Lys Thr Gln Glu Gly His Ala Arg Leu Gly Asn Leu
            915                 920                 925
Glu Phe Ile Glu Glu Lys Pro Leu Leu Gly Glu Ala Leu Ser Arg Val
            930                 935                 940
Lys Arg Ala Glu Lys Lys Trp Arg Asp Lys Arg Glu Lys Leu Gln Leu
945                 950                 955                 960
Glu Thr Lys Arg Val Tyr Thr Glu Ala Lys Glu Ala Val Asp Ala Leu
                965                 970                 975
Phe Val Asp Ser Gln Tyr Asp Arg Leu Gln Ala Asp Thr Asn Ile Gly
            980                 985                 990
```

```
Met Ile His Ala Ala Asp Lys Leu Val His Arg Ile Arg Glu Ala Tyr
        995                 1000                1005

Leu Ser Glu Leu Ser Val Ile Pro Gly Val Asn Ala Glu Ile Phe
    1010                1015                1020

Glu Glu Leu Glu Gly Arg Ile Ile Thr Ala Ile Ser Leu Tyr Asp
    1025                1030                1035

Ala Arg Asn Val Val Lys Asn Gly Asp Phe Asn Asn Gly Leu Ala
    1040                1045                1050

Cys Trp Asn Val Lys Gly His Val Asp Val Gln Gln Ser His His
    1055                1060                1065

Arg Ser Val Leu Val Ile Pro Glu Trp Glu Ala Glu Val Ser Gln
    1070                1075                1080

Ala Val Arg Val Cys Pro Gly Arg Gly Tyr Ile Leu Arg Val Thr
    1085                1090                1095

Ala Tyr Lys Glu Gly Tyr Gly Glu Gly Cys Val Thr Ile His Glu
    1100                1105                1110

Ile Glu Asn Asn Thr Asp Glu Leu Lys Phe Lys Asn Cys Glu Glu
    1115                1120                1125

Glu Glu Val Tyr Pro Thr Asp Thr Gly Thr Cys Asn Asp Tyr Thr
    1130                1135                1140

Ala His Gln Gly Thr Ala Ala Cys Asn Ser Arg Asn Ala Gly Tyr
    1145                1150                1155

Glu Asp Ala Tyr Glu Val Asp Thr Thr Ala Ser Val Asn Tyr Lys
    1160                1165                1170

Pro Thr Tyr Glu Glu Glu Thr Tyr Thr Asp Val Arg Arg Asp Asn
    1175                1180                1185

His Cys Glu Tyr Asp Arg Gly Tyr Val Asn Tyr Pro Pro Val Pro
    1190                1195                1200

Ala Gly Tyr Met Thr Lys Glu Leu Glu Tyr Phe Pro Glu Thr Asp
    1205                1210                1215

Lys Val Trp Ile Glu Ile Gly Glu Thr Glu Gly Lys Phe Ile Val
    1220                1225                1230

Asp Ser Val Glu Leu Leu Leu Met Glu Glu
    1235                1240

<210> SEQ ID NO 42
<211> LENGTH: 3702
<212> TYPE: DNA
<213> ORGANISM: Artificial
<220> FEATURE:
<223> OTHER INFORMATION: Synthetic nucleotide sequence designed for
      expression in a plant cell encoding TIC868_14.

<400> SEQUENCE: 42
atgacgagca accggaagaa cgagaacgag atcatcaacg ccctctcgat ccctgctgtt    60
tcaaaccact ccgcgcagat gaacctgtcc accgacgcgc gcatcgagga ctccctctgc   120
atagccgagg gcaacaacat cgacccattc gtgtcggcca gcacggttca gaccggcatc   180
aacatcgcgg gccgtatcct cggcgtcctc ggtgtcccat cgccggtca gatcgcgtcc   240 ttctactcgt tccttgtggg cgagctgtgg cctcgcggtc gtgacccgtg ggagatcttc   300
ctggagcatg tggagcagtt gatccggcag caagtcacgg agaacacccg cgatactgct   360
ctggccaggc tacagggcct gggaaactcc tttcgggcat accagcagtc actgaggac    420 tggttggaga acaggatga cgcgcgaaca cgctcggtac tctacaccca gtacatcgct   480
```

```
ctcgaactcg acttcctgaa cgctatgccg ctgttcgcca tcaggaacca ggaagttcca    540
ctccttatgg tgtacgccca ggccgccaac ttacatctgc tcctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag acccaatcgg ccggacgaac    900
gcaccctccg gtttcgcatc cacgaattgg ttcaacaaca acgcaccctc cttctcggca    960
atcgaggccg ccgtcatccg ccctcctcac ctgctcgact ttcccgagca gctcacgatc   1020
ttctccgtgc tctcacgctg gtccaacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta ccagatcccg ctcgtgaagg gcttccgtg tgtgggtgg cacgagcgtc   1560 atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
actagccgaa ccttccggta cactgatttc tcgaaccctt tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cgaccgcgac gtttgaagct   1980
gaatccgacc tcgagcgtgc gcgcaaggcg gtgaacgctc tgttcacgag caccaaccct   2040
cgtggcttga agacggatgt gacggactac cacatcgacc aagtctcgaa cctcgtggag   2100
tgcctgagcg acgagttctg tcttgacaag aagcgcgagc tgctggagga ggtgaagtac   2160
gccaagcgcc tctccgatga gcgcaacctg ctccaagatc ctaccttcac gtcgatttcc   2220
ggccaaaccg accgtggatg gatcggctcg actggcatct ccatccaggg cggcgacgac   2280
atcttcaagg agaactatgt tcggctgccg ggcacggtgg acgagtgtta cccgacgtac   2340
ctctaccaga agatagacga gagtcaactc aagtcctaca cgcggtatca gttacgtggc   2400
tacattgaag actcccagga cttggaaatc tatctcatac ggtacaacgc caagcacgag   2460
accttaagcg tgccgggaac ggagtcgccc tggccaagct ctggcgtgta cccttccggt   2520
aggtgcggcg agcccaaccg ctgtgcacct cgaatcgaat ggaacccgga ccttgactgc   2580
tcttgccggt acgcgagaa gtgcgtccat cattctcacc acttcagctt ggacattgac   2640
gtcggctgca ccgacctcaa tgaagacctc ggagtgtggg tcatcttcaa gatcaagaca   2700
caggacgggc acgcgaaact aggaaacctg gagttcatcg aggagaagcc actcctcggc   2760
aaggcacttt ccagggtcaa gcgggccgag aagaaatgga gggacaagta cgagaaactc   2820
cagctcgaaa caaagcgggt gtacacggag gcaaaggaat ccgtggacgc cctgttcgtg   2880
```

```
gactctcagt acgacaagct ccaggcgaac acaaacattg gcatcatcca cggtgcggac    2940
aagcaagtgc acaggatacg ggagccttac ctctcggagc tgccggtgat ccctcgatc    3000 aacgcggcga tcttcgagga actggagggc cacatcttca aggcgtattc tctgtacgac    3060
gcgcgtaacg tcatcaagaa cggcgacttc aacaatgggc tgtcctgctg gaacgttaaa    3120
ggccacgtcg atgtccagca gaaccaccat aggtcagtcc tggtgctgag cgagtgggag    3180
gcggaggtgt cccagaaggt gcgcgtgtgc ccggatcgcg gctacatctt gagggtgaca    3240
gcctacaagg agggctacgg cgagggctgt gtcacgatcc atgagttcga ggacaacacg    3300
gatgtcctga aattccgtaa cttcgtcgag gaggaggtct atcccaacaa caccgtgacc    3360
tgcaacgact acacgaccaa tcagtcggct gagggcagta ccgatgcctg caacagctac    3420
aaccgtggtt acgaagatgg atacgagaac cgctacgagc ccaatccttc ggctcccgtg    3480
aattacactc ccacgtacga ggagggcatg tacactgaca ctcagggcta caaccattgc    3540
gtcagcgacc gtggctaccg caaccacacg ccgctcccag cgggctacgt gacgctggag    3600
ctggaatact ttcccgagac agaacaagtg tggatagaga tcggcgagac cgagggcaca    3660
ttcatcgtgg gctctgtgga attgctcctc atggaggagt aa                     3702

<210> SEQ ID NO 43
<211> LENGTH: 1200
<212> TYPE: PRT
<213> ORGANISM: Artificial
<220> FEATURE:
<223> OTHER INFORMATION: Amino acid sequence of the chimeric protein
      variant TIC868_14.

<400> SEQUENCE: 43

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
                20                  25                  30

Ala Arg Ile Glu Asp Ser Leu Cys Ile Ala Glu Gly Asn Asn Ile Asp
            35                  40                  45

Pro Phe Val Ser Ala Ser Thr Val Gln Thr Gly Ile Asn Ile Ala Gly
        50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
                100                 105                 110

Thr Glu Asn Thr Arg Asp Thr Ala Leu Ala Arg Leu Gln Gly Leu Gly
            115                 120                 125

Asn Ser Phe Arg Ala Tyr Gln Gln Ser Leu Glu Asp Trp Leu Glu Asn
        130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205
```

-continued

| | | | | | | | | | | | | |
|---|---|---|---|---|---|---|---|---|---|---|---|---|
|Thr|Ser|Gln|Glu|Ile|Gln|Arg|Tyr|Tyr|Glu|Arg|Gln|Val|Glu|Lys|Thr|
|210| | | | |215| | | | |220| | | | |

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
            245                 250                 255

Arg Arg Asp Leu Thr Leu Gly Val Leu Asp Leu Val Ala Leu Phe Pro
        260                 265                 270

Ser Tyr Asp Thr Arg Val Tyr Pro Met Asn Thr Ser Ala Gln Leu Thr
    275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
            325                 330                 335

Gln Leu Thr Ile Phe Ser Val Leu Ser Arg Trp Ser Asn Thr Gln Tyr
        340                 345                 350

Met Asn Tyr Trp Val Gly His Arg Leu Glu Ser Arg Thr Ile Arg Gly
    355                 360                 365

Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
            405                 410                 415

Ala Arg Phe Asn Trp Arg Asn Pro Leu Asn Ser Leu Arg Gly Ser Leu
        420                 425                 430

Leu Tyr Thr Ile Gly Tyr Thr Gly Val Gly Thr Gln Leu Phe Asp Ser
    435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
            485                 490                 495

Thr Ile Ser Ser Asp Ser Ile Asn Gln Ile Pro Leu Val Lys Gly Phe
        500                 505                 510

Arg Val Trp Gly Gly Thr Ser Val Ile Thr Gly Pro Gly Phe Thr Gly
    515                 520                 525

Gly Asp Ile Leu Arg Arg Asn Thr Phe Gly Asp Phe Val Ser Leu Gln
530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
            565                 570                 575

Ser Thr Gly Val Gly Gly Gln Val Ser Val Asn Met Pro Leu Gln Lys
        580                 585                 590

Thr Met Glu Ile Gly Glu Asn Leu Thr Ser Arg Thr Phe Arg Tyr Thr
    595                 600                 605

Asp Phe Ser Asn Pro Phe Ser Phe Arg Ala Asn Pro Asp Ile Ile Gly
610                 615                 620

Ile Ser Glu Gln Pro Leu Phe Gly Ala Gly Ser Ile Ser Ser Gly Glu

```
              625                 630                 635                 640
Leu Tyr Ile Asp Lys Ile Glu Ile Ile Leu Ala Asp Ala Thr Thr Ala
                645                 650                 655

Thr Phe Glu Ala Glu Ser Asp Leu Glu Arg Ala Arg Lys Ala Val Asn
                660                 665                 670

Ala Leu Phe Thr Ser Thr Asn Pro Arg Gly Leu Lys Thr Asp Val Thr
                675                 680                 685

Asp Tyr His Ile Asp Gln Val Ser Asn Leu Val Glu Cys Leu Ser Asp
                690                 695                 700

Glu Phe Cys Leu Asp Lys Lys Arg Glu Leu Leu Glu Glu Val Lys Tyr
705                 710                 715                 720

Ala Lys Arg Leu Ser Asp Glu Arg Asn Leu Leu Gln Asp Pro Thr Phe
                725                 730                 735

Thr Ser Ile Ser Gly Gln Thr Asp Arg Gly Trp Ile Gly Ser Thr Gly
                740                 745                 750

Ile Ser Ile Gln Gly Gly Asp Asp Ile Phe Lys Glu Asn Tyr Val Arg
                755                 760                 765

Leu Pro Gly Thr Val Asp Glu Cys Tyr Pro Thr Tyr Leu Tyr Gln Lys
                770                 775                 780

Ile Asp Glu Ser Gln Leu Lys Ser Tyr Thr Arg Tyr Gln Leu Arg Gly
785                 790                 795                 800

Tyr Ile Glu Asp Ser Gln Asp Leu Glu Ile Tyr Leu Ile Arg Tyr Asn
                805                 810                 815

Ala Lys His Glu Thr Leu Ser Val Pro Gly Thr Glu Ser Pro Trp Pro
                820                 825                 830

Ser Ser Gly Val Tyr Pro Ser Gly Arg Cys Gly Glu Pro Asn Arg Cys
                835                 840                 845

Ala Pro Arg Ile Glu Trp Asn Pro Asp Leu Asp Cys Ser Cys Arg Tyr
                850                 855                 860

Gly Glu Lys Cys Val His His Ser His His Phe Ser Leu Asp Ile Asp
865                 870                 875                 880

Val Gly Cys Thr Asp Leu Asn Glu Asp Leu Gly Val Trp Val Ile Phe
                885                 890                 895

Lys Ile Lys Thr Gln Asp Gly His Ala Lys Leu Gly Asn Leu Glu Phe
                900                 905                 910

Ile Glu Glu Lys Pro Leu Leu Gly Lys Ala Leu Ser Arg Val Lys Arg
                915                 920                 925

Ala Glu Lys Lys Trp Arg Asp Lys Tyr Glu Lys Leu Gln Leu Glu Thr
                930                 935                 940

Lys Arg Val Tyr Thr Glu Ala Lys Glu Ser Val Asp Ala Leu Phe Val
945                 950                 955                 960

Asp Ser Gln Tyr Asp Lys Leu Gln Ala Asn Thr Asn Ile Gly Ile Ile
                965                 970                 975

His Gly Ala Asp Lys Gln Val His Arg Ile Arg Glu Pro Tyr Leu Ser
                980                 985                 990

Glu Leu Pro Val Ile Pro Ser Ile Asn Ala Ala Ile Phe Glu Glu Leu
                995                 1000                1005

Glu Gly His Ile Phe Lys Ala Tyr Ser Leu Tyr Asp Ala Arg Asn
            1010                1015                1020

Val Ile Lys Asn Gly Asp Phe Asn Asn Gly Leu Ser Cys Trp Asn
            1025                1030                1035

Val Lys Gly His Val Asp Val Gln Gln Asn His His Arg Ser Val
            1040                1045                1050
```

```
Leu Val Leu Ser Glu Trp Glu Ala Glu Val Ser Gln Lys Val Arg
    1055                1060                1065

Val Cys Pro Asp Arg Gly Tyr Ile Leu Arg Val Thr Ala Tyr Lys
    1070                1075                1080

Glu Gly Tyr Gly Glu Gly Cys Val Thr Ile His Glu Phe Glu Asp
    1085                1090                1095

Asn Thr Asp Val Leu Lys Phe Arg Asn Phe Val Glu Glu Glu Val
    1100                1105                1110

Tyr Pro Asn Asn Thr Val Thr Cys Asn Asp Tyr Thr Thr Asn Gln
    1115                1120                1125

Ser Ala Glu Gly Ser Thr Asp Ala Cys Asn Ser Tyr Asn Arg Gly
    1130                1135                1140

Tyr Glu Asp Gly Tyr Glu Asn Arg Tyr Glu Pro Asn Pro Ser Ala
    1145                1150                1155

Pro Val Asn Tyr Thr Pro Thr Tyr Glu Glu Gly Met Tyr Thr Asp
    1160                1165                1170

Thr Gln Gly Tyr Asn His Cys Val Ser Asp Arg Gly Tyr Arg Asn
    1175                1180                1185

His Thr Pro Leu Pro Ala Gly Tyr Val Thr Leu Glu
    1190                1195                1200

<210> SEQ ID NO 44
<211> LENGTH: 3687
<212> TYPE: DNA
<213> ORGANISM: Artificial
<220> FEATURE:
<223> OTHER INFORMATION: Synthetic nucleotide sequence designed for
      expression in a plant cell encoding TIC868_15.

<400> SEQUENCE: 44
atgacgagca accggaagaa cgagaacgag atcatcaacg ccctctcgat ccctgctgtt      60
tcaaaccact ccgcgcagat gaacctgtcc accgacgcgc gcatcgagga ctccctctgc     120
atagccgagg gcaacaacat cgacccattc gtgtcggcca gcacggttca gaccggcatc     180
aacatcgcgg gccgtatcct cggcgtcctc ggtgtcccat cgccggtca gatcgcgtcc     240 ttctactcgt tccttgtggg cgagctgtgg cctcgcggtc gtgacccgtg ggagatcttc     300
ctggagcatg tggagcagtt gatccggcag caagtcacgg agaacacccg cgatactgct     360
ctggccaggc tacagggcct gggaaactcc tttcgggcat accagcagtc actggaggac     420
tggttggaga caggggatga cgcgcgaaca cgctcggtac tctacaccca gtacatcgct     480
ctcgaactcg acttcctgaa cgctatgccg ctgttcgcca tcaggaacca ggaagttcca     540
ctccttatgg tgtacgccca ggccgccaac ttacatctgc cctgctgcg ggacgccagc     600 ctgttcggct ccgagttcgg actcacatct caagaaatcc agcgttacta cgagcgccaa     660
gtggagaaga cccgtgagta cagtgactac tgcgctcgat ggtacaacac agggctcaac     720
aacctgcgcg gcaccaacgc tgagtcatgg ctccgttaca accagttccg ccgcgacttg     780
actttgggtg tcctagacct ggtggcgcta ttcccgtctt acgacacacg ggtgtaccca     840
atgaacacta gcgcgcaact cacgcgggag atctacacag acccaatcgg ccggacgaac     900
gcaccctccg gtttcgcatc cacgaattgg ttcaacaaca acgcaccctc cttctcggca     960
atcgaggccg ccgtcatccg ccctcctcac ctgctcgact ttcccgagca gctcacgatc    1020
ttctccgtgc tctcacgctg gtccaacaca cagtacatga actactgggt cgggcaccga    1080
ttggagagta ggacgatccg tggcagcttg agcaccagta cccacggcaa caccaacacc    1140
```

```
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
actagccgaa ccttccggta cactgatttc tcgaaccctt tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cggatgctac ctttgaagca   1980
gagtccgact tggaacgtgc acagaaggca gtgaacgcac tcttcacctc aagcaaccag   2040
atcggattga agacagatgt gacagattac cacatcgacc aagtgagcaa cttggtggat   2100
tgcttgtcag atgagttctg cttggatgag aagcgtgaac tctccgagaa ggtgaagcac   2160
gcaaagcgtc tctcagatga acgtaatctc cttcaagacc ctaactttcg tggtatcaat   2220
cgtcagccag atcgtggatg gcgtggatca acagacatca ccatccaggg aggcgatgat   2280
gtgttcaagg agaactacgt gaccctccca ggaaccgtgg atgaatgcta cccaacccta c   2340 ctctaccaga agatcgacga gtcaaagctc aaggcttaca cccgttatga actccgtggc   2400
tacatcgaag atagccagga tctcgaaatc tatctcatcc gttacaatgc taagcacgaa   2460
atcgtgaatg tgccaggaac cggctcactc tggccactct cagcacagtc accaatcggc   2520
aagtgcggcg aacccaatcg ctgcgctcct catctcgaat ggaatcccga tctcgactgc   2580
tcctgccgag acggcgagaa gtgtgcacat cactcacacc acttcaccct cgacatcgac   2640
gtgggctgca ccgacctcaa tgaagacctg ggcgtgtggg tgatcttcaa gatcaagacc   2700
caggacggcc acgcacgact gggcaatctg gagtttctgg aggagaagcc actgcttggc   2760
gaggcactgg cacgagtgaa acgagccgag aagaaatggc gagacaaacg tgagaagctg   2820
caactggaga ccaacatcgt gtacaaagag gccaaagagt cagttgacgc cctgtttgtc   2880
aatagccagt atgaccgact gcaagttgac accaacatcg ccatgatcca cgctgcggac   2940
aagcgcgtcc accgcatccg cgaggcttat ctgcccgagc tgagcgtcat tcccggcgtc   3000
aatgccgcga tcttcgagga gttagagggc cgcatcttca ccgcctacag cctctatgac   3060
gcccgcaatg tcattaagaa tggcgacttc aacaatggct actatgctg gaatgtcaaa   3120 gggcacgttg acgtcgagga gcagaacaat caccgcagcg tcttagtcat acccgagtgg   3180
gaggccgaag tcagccagga agtccgcgtc tgtccagggc gcgggtacat cctgcgggtc   3240
accgcctaca agagggata cggcgagggt tgtgtcacca tacacgagat agaggacaat   3300
accgacgaac tcaagttcag caattgtgtc gaggaggaag tctatcccaa caataccgta   3360
acctgcaaca actacaccgg aacccaggag gagtatgaag gacgtacac ctcgcggaac   3420 cagggctatg acgaagccta tgggaacaac ccgtcggtgc ctgctgacta tgcgtcggtc   3480
```

```
tatgaggaga aatcgtacac ggacgggcgg cgggagaatc cgtgtgagtc gaatcgcggg    3540
tatggtgact acacgccgct accggcgggc tatgtaacga aagacctgga atacttcccg    3600
gagacggaca aagtatggat agagataggc gagacggagg gaacgttcat cgtggactcg    3660
gtagagctgc tgctcatgga ggagtga                                        3687
```

```
<210> SEQ ID NO 45
<211> LENGTH: 1228
<212> TYPE: PRT
<213> ORGANISM: Artificial
<220> FEATURE:
<223> OTHER INFORMATION: Amino acid sequence of the chimeric protein
      variant TIC868_15.

<400> SEQUENCE: 45
```

| | | | | | | | | | | | | | | |
|---|---|---|---|---|---|---|---|---|---|---|---|---|---|---|
| Met | Thr | Ser | Asn | Arg | Lys | Asn | Glu | Asn | Glu | Ile | Ile | Asn | Ala | Leu | Ser |
| 1 | | | | 5 | | | | | 10 | | | | | 15 | |
| Ile | Pro | Ala | Val | Ser | Asn | His | Ser | Ala | Gln | Met | Asn | Leu | Ser | Thr | Asp |
| | | | 20 | | | | | 25 | | | | | 30 | | |
| Ala | Arg | Ile | Glu | Asp | Ser | Leu | Cys | Ile | Ala | Glu | Gly | Asn | Asn | Ile | Asp |
| | | 35 | | | | | 40 | | | | | 45 | | | |
| Pro | Phe | Val | Ser | Ala | Ser | Thr | Val | Gln | Thr | Gly | Ile | Asn | Ile | Ala | Gly |
| | 50 | | | | | 55 | | | | | 60 | | | | |
| Arg | Ile | Leu | Gly | Val | Leu | Gly | Val | Pro | Phe | Ala | Gly | Gln | Ile | Ala | Ser |
| 65 | | | | | 70 | | | | | 75 | | | | | 80 |
| Phe | Tyr | Ser | Phe | Leu | Val | Gly | Glu | Leu | Trp | Pro | Arg | Gly | Arg | Asp | Pro |
| | | | 85 | | | | | 90 | | | | | 95 | | |
| Trp | Glu | Ile | Phe | Leu | Glu | His | Val | Glu | Gln | Leu | Ile | Arg | Gln | Gln | Val |
| | | 100 | | | | | 105 | | | | | 110 | | | |
| Thr | Glu | Asn | Thr | Arg | Asp | Thr | Ala | Leu | Ala | Arg | Leu | Gln | Gly | Leu | Gly |
| | 115 | | | | | 120 | | | | | 125 | | | | |
| Asn | Ser | Phe | Arg | Ala | Tyr | Gln | Gln | Ser | Leu | Glu | Asp | Trp | Leu | Glu | Asn |
| 130 | | | | | 135 | | | | | 140 | | | | | |
| Arg | Asp | Asp | Ala | Arg | Thr | Arg | Ser | Val | Leu | Tyr | Thr | Gln | Tyr | Ile | Ala |
| 145 | | | | | 150 | | | | | 155 | | | | | 160 |
| Leu | Glu | Leu | Asp | Phe | Leu | Asn | Ala | Met | Pro | Leu | Phe | Ala | Ile | Arg | Asn |
| | | | | 165 | | | | | 170 | | | | | 175 | |
| Gln | Glu | Val | Pro | Leu | Leu | Met | Val | Tyr | Ala | Gln | Ala | Ala | Asn | Leu | His |
| | | | 180 | | | | | 185 | | | | | 190 | | |
| Leu | Leu | Leu | Leu | Arg | Asp | Ala | Ser | Leu | Phe | Gly | Ser | Glu | Phe | Gly | Leu |
| | | | 195 | | | | | 200 | | | | | 205 | | |
| Thr | Ser | Gln | Glu | Ile | Gln | Arg | Tyr | Tyr | Glu | Arg | Gln | Val | Glu | Lys | Thr |
| | 210 | | | | | 215 | | | | | 220 | | | | |
| Arg | Glu | Tyr | Ser | Asp | Tyr | Cys | Ala | Arg | Trp | Tyr | Asn | Thr | Gly | Leu | Asn |
| 225 | | | | | 230 | | | | | 235 | | | | | 240 |
| Asn | Leu | Arg | Gly | Thr | Asn | Ala | Glu | Ser | Trp | Leu | Arg | Tyr | Asn | Gln | Phe |
| | | | | 245 | | | | | 250 | | | | | 255 | |
| Arg | Arg | Asp | Leu | Thr | Leu | Gly | Val | Leu | Asp | Leu | Val | Ala | Leu | Phe | Pro |
| | | | 260 | | | | | 265 | | | | | 270 | | |
| Ser | Tyr | Asp | Thr | Arg | Val | Tyr | Pro | Met | Asn | Thr | Ser | Ala | Gln | Leu | Thr |
| | | 275 | | | | | 280 | | | | | 285 | | | |
| Arg | Glu | Ile | Tyr | Thr | Asp | Pro | Ile | Gly | Arg | Thr | Asn | Ala | Pro | Ser | Gly |
| | 290 | | | | | 295 | | | | | 300 | | | | |
| Phe | Ala | Ser | Thr | Asn | Trp | Phe | Asn | Asn | Asn | Ala | Pro | Ser | Phe | Ser | Ala |
| 305 | | | | | 310 | | | | | 315 | | | | | 320 |

-continued

```
Ile Glu Ala Ala Val Ile Arg Pro Pro His Leu Leu Asp Phe Pro Glu
            325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
            370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
            405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
            450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
            485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
            515                 520                 525

Gly Asp Ile Leu Arg Arg Asn Thr Phe Gly Asp Phe Val Ser Leu Gln
            530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
            565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
            595                 600                 605

Asp Phe Ser Asn Pro Phe Ser Phe Arg Ala Asn Pro Asp Ile Ile Gly
            610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Asp Ala
            645                 650                 655

Thr Phe Glu Ala Glu Ser Asp Leu Glu Arg Ala Gln Lys Ala Val Asn
            660                 665                 670

Ala Leu Phe Thr Ser Ser Asn Gln Ile Gly Leu Lys Thr Asp Val Thr
            675                 680                 685

Asp Tyr His Ile Asp Gln Val Ser Asn Leu Val Asp Cys Leu Ser Asp
            690                 695                 700

Glu Phe Cys Leu Asp Glu Lys Arg Glu Leu Ser Glu Lys Val Lys His
705                 710                 715                 720

Ala Lys Arg Leu Ser Asp Glu Arg Asn Leu Leu Gln Asp Pro Asn Phe
            725                 730                 735

Arg Gly Ile Asn Arg Gln Pro Asp Arg Gly Trp Arg Gly Ser Thr Asp
```

```
                    740                 745                 750
Ile Thr Ile Gln Gly Gly Asp Asp Val Phe Lys Glu Asn Tyr Val Thr
                755                 760                 765
Leu Pro Gly Thr Val Asp Glu Cys Tyr Pro Thr Tyr Leu Tyr Gln Lys
            770                 775                 780
Ile Asp Glu Ser Lys Leu Lys Ala Tyr Thr Arg Tyr Glu Leu Arg Gly
785                 790                 795                 800
Tyr Ile Glu Asp Ser Gln Asp Leu Glu Ile Tyr Leu Ile Arg Tyr Asn
                805                 810                 815
Ala Lys His Glu Ile Val Asn Val Pro Gly Thr Gly Ser Leu Trp Pro
                820                 825                 830
Leu Ser Ala Gln Ser Pro Ile Gly Lys Cys Gly Glu Pro Asn Arg Cys
            835                 840                 845
Ala Pro His Leu Glu Trp Asn Pro Asp Leu Asp Cys Ser Cys Arg Asp
            850                 855                 860
Gly Glu Lys Cys Ala His His Ser His His Phe Thr Leu Asp Ile Asp
865                 870                 875                 880
Val Gly Cys Thr Asp Leu Asn Glu Asp Leu Gly Val Trp Val Ile Phe
                885                 890                 895
Lys Ile Lys Thr Gln Asp Gly His Ala Arg Leu Gly Asn Leu Glu Phe
                900                 905                 910
Leu Glu Glu Lys Pro Leu Leu Gly Glu Ala Leu Ala Arg Val Lys Arg
            915                 920                 925
Ala Glu Lys Lys Trp Arg Asp Lys Arg Glu Lys Leu Gln Leu Glu Thr
            930                 935                 940
Asn Ile Val Tyr Lys Glu Ala Lys Glu Ser Val Asp Ala Leu Phe Val
945                 950                 955                 960
Asn Ser Gln Tyr Asp Arg Leu Gln Val Asp Thr Asn Ile Ala Met Ile
                965                 970                 975
His Ala Ala Asp Lys Arg Val His Arg Ile Arg Glu Ala Tyr Leu Pro
                980                 985                 990
Glu Leu Ser Val Ile Pro Gly Val Asn Ala Ala Ile Phe Glu Glu Leu
            995                 1000                1005
Glu Gly Arg Ile Phe Thr Ala Tyr Ser Leu Tyr Asp Ala Arg Asn
    1010                1015                1020
Val Ile Lys Asn Gly Asp Phe Asn Asn Gly Leu Leu Cys Trp Asn
    1025                1030                1035
Val Lys Gly His Val Asp Val Glu Glu Gln Asn Asn His Arg Ser
    1040                1045                1050
Val Leu Val Ile Pro Glu Trp Glu Ala Glu Val Ser Gln Glu Val
    1055                1060                1065
Arg Val Cys Pro Gly Arg Gly Tyr Ile Leu Arg Val Thr Ala Tyr
    1070                1075                1080
Lys Glu Gly Tyr Gly Glu Gly Cys Val Thr Ile His Glu Ile Glu
    1085                1090                1095
Asp Asn Thr Asp Glu Leu Lys Phe Ser Asn Cys Val Glu Glu Glu
    1100                1105                1110
Val Tyr Pro Asn Asn Thr Val Thr Cys Asn Asn Tyr Thr Gly Thr
    1115                1120                1125
Gln Glu Glu Tyr Glu Gly Thr Tyr Thr Ser Arg Asn Gln Gly Tyr
    1130                1135                1140
Asp Glu Ala Tyr Gly Asn Asn Pro Ser Val Pro Ala Asp Tyr Ala
    1145                1150                1155
```

| | | | | | | | | | |
|---|---|---|---|---|---|---|---|---|---|
|Ser|Val|Tyr|Glu|Glu|Lys|Ser|Tyr|Thr|Asp|Gly|Arg|Arg|Glu|Asn|
|1160| | | | |1165| | | | |1170| | | | |

Pro Cys Glu Ser Asn Arg Gly Tyr Gly Asp Tyr Thr Pro Leu Pro
1175 1180 1185

Ala Gly Tyr Val Thr Lys Asp Leu Glu Tyr Phe Pro Glu Thr Asp
1190 1195 1200

Lys Val Trp Ile Glu Ile Gly Glu Thr Glu Gly Thr Phe Ile Val
1205 1210 1215

Asp Ser Val Glu Leu Leu Leu Met Glu Glu
1220 1225

<210> SEQ ID NO 46
<211> LENGTH: 3600
<212> TYPE: DNA
<213> ORGANISM: Artificial
<220> FEATURE:
<223> OTHER INFORMATION: Synthetic nucleotide sequence designed for
      expression in a plant cell encoding TIC868_29.

<400> SEQUENCE: 46

```
atgacgagca accggaagaa cgagaacgag atcatcaacg ccctctcgat ccctgctgtt     60
tcaaaccact ccgcgcagat gaacctgtcc accgacgcgc gcatcgagga ctccctctgc    120
atagccgagg caacaacat cgacccattc gtgtcggcca gcacggttca gaccggcatc    180
aacatcgcgg gccgtatcct cggcgtcctc ggtgtcccat cgccggtca gatcgcgtcc    240
ttctactcgt tccttgtggg cgagctgtgg cctcgcggtc gtgacccgtg ggagatcttc    300
ctggagcatg tggagcagtt gatccggcag caagtcacgg agaacacccg cgatactgct    360
ctggccaggc tacagggcct gggaaactcc tttcgggcat accagtactc actggaggac    420
tggttggaga cagggatga cgcgcgaaca cgctcggtac tctacaccca gtacatcgct    480
ctcgaactcg acttcctgaa cgctatgccg ctgttcgcca tcaggaacca ggaagttcca    540
ctccttatgg tgtacgccca ggccgccaac ttacatctgc cctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag acccaatcgg ccggacgaac    900
gcaccctccg gtttcgcatc cacgaattgg ttcaacaaca acgcaccctc cttctcggca    960
atcgaggccg ccgtcatccg ccctcctcac ctgctcgact ttcccgagca gctcacgatc   1020
ttctcccagc tctcacgctg gtcccacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta ccagatcccc gctcgtgaag ggcttccgtg tgtgggggtgg cacgagcgtc   1560
```

| | |
|---|---|
| atcaccggtc cgggcttcac cggtggagac atactgcggc gcaacacttt cggcgacttc | 1620 |
| gtttcgttgc aagtgaacat caactcgccg atcacccagc gttaccgtct gaggttccgc | 1680 |
| tacgcttcaa gccgcgacgc gagggtcatt gtcctgaccg gagccgcgtc cacaggcgtg | 1740 |
| ggaggccaag tctcagtcaa catgcctctc cagaagacga tggagatagg cgagaacttg | 1800 |
| actagccgaa ccttccggta cactgatttc tcgaacccgt tctcattcag agcgaaccct | 1860 |
| gacatcattg ggatctccga gcaaccgctg ttcggtgctg gctccatcag ctctggcgaa | 1920 |
| ctgtacatcg acaagattga gatcatcctg gcggatgcga cgttcgaggc cgagtctgac | 1980 |
| ctggagcggg ctcagaaggc tgtcaacgaa ctgttcacca gcagcaacca gattgggctc | 2040 |
| aagaccgacg tcacggacta tcacattgac caagtgtcca accttgtgga gtgcctgtcc | 2100 |
| gacgagttct gcctcgacga gaagaaggag ctgtccgaga aggtcaaaca cgcgaagcgt | 2160 |
| ctgagtgacg agcggaattt gctccaggac ccgaacttcc gtggcatcaa ccgccagctc | 2220 |
| gaccgtggtt ggcgcgggag tacagacatc accatccagg gaggcgacga tgtgttcaag | 2280 |
| gagaactatg tgacgctgct cgggactttc gacgaatgct acccgacgta tctctaccag | 2340 |
| aagatagacg agagtaaatt gaaggcgtac acccgctacc agcttcgcgg gtacatcgag | 2400 |
| gatagtcagg acctggaaat ctacctgatc cgatacaacg ccaagcacga gacagtgaac | 2460 |
| gtgccaggca cgggctcact ttggccattg agcgctccct ctccaatcgg aaagtgcgct | 2520 |
| caccactcgc accacttctc tctggacatc gacgtgggct gcaccgacct caacgaggac | 2580 |
| ctgggtgtct gggttatctt caagattaag acccaggacg gacatgcccg cctcggcaac | 2640 |
| ctggagttcc ttgaggagaa gcctctcgtg ggcgaggccc tcgctcgtgt gaagcgcgcc | 2700 |
| gagaagaaat ggcgagacaa gcgggagaag ctggagtggg agaccaacat cgtgtacaag | 2760 |
| gaggccaagg agtcagtgga cgcactcttc gtcaacagcc agtacgaccg cctccaggct | 2820 |
| gacaccaaca tcgccatgat ccacgcggct gacaagcggg tccacagcat ccgtgaggcg | 2880 |
| tacctgcccg agctgtcagt gatccctggt gtgaacgcgg cgatcttcga ggaactggag | 2940 |
| ggccgcatct tcacagcatt cagcctgtac gatgccagga atgttattaa gaacggtgac | 3000 |
| ttcaacaacg ggctgagttg ctggaacgtc aagggccatg tggacgtcga ggagcagaac | 3060 |
| aaccaccggt ccgtgctggt cgtgccggag tgggaggcag aggtgagcca ggaggtccgc | 3120 |
| gtctgccctg gtcgcggcta catcctccgt gtgactgcgt acaaggaagg ctacggtgaa | 3180 |
| ggctgcgtga ctatccacga gatcgagaac aacaccgacg agctcaagtt ctcgaactgt | 3240 |
| gtggaggagg aggtgtaccc gaacaacacc gttacttgca acgactacac tgccacgcaa | 3300 |
| gaggagtacg agggcactta cacttcccgg aatcgcggct atgatggcgc gtacgagtcc | 3360 |
| aacagcagcg tgcctgcgga ttatgcgtcc gcttacgagg agaaggcgta caccgacgga | 3420 |
| cggagggaca acccttgcga gtccaaccgt ggctacggtg actacactcc gctgcccgcc | 3480 |
| gggtacgtca ccaaggagct ggagtacttc ccggagaccg acaaagtctg gatcgagatc | 3540 |
| ggcgagacgg agggcacttt catcgtggac tcggtcgagc tgctactgat ggaggagtga | 3600 |

<210> SEQ ID NO 47
<211> LENGTH: 1199
<212> TYPE: PRT
<213> ORGANISM: Artificial
<220> FEATURE:
<223> OTHER INFORMATION: Amino acid sequence of the chimeric protein
      variant TIC868_29.

<400> SEQUENCE: 47

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
            85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
            115                 120                 125

Asn Ser Phe Arg Ala Tyr Gln Tyr Ser Leu Glu Asp Trp Leu Glu Asn
        130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
            165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
        210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
            245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
            290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
            325                 330                 335

Gln Leu Thr Ile Phe Ser Gln Leu Ser Arg Trp Ser His Thr Gln Tyr
            340                 345                 350

Met Asn Tyr Trp Val Gly His Arg Leu Glu Ser Arg Thr Ile Arg Gly
            355                 360                 365

Ser Leu Ser Thr Ser Thr His Gly Asn Thr Asn Thr Ser Ile Asn Pro
        370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
            405                 410                 415

Ala Arg Phe Asn Trp Arg Asn Pro Leu Asn Ser Leu Arg Gly Ser Leu
```

-continued

```
            420                 425                 430
Leu Tyr Thr Ile Gly Tyr Thr Gly Val Gly Thr Gln Leu Phe Asp Ser
                435                 440                 445
Glu Thr Glu Leu Pro Pro Glu Thr Thr Glu Arg Pro Asn Tyr Glu Ser
    450                 455                 460
Tyr Ser His Arg Leu Ser Asn Ile Arg Leu Ile Ser Gly Asn Thr Leu
465                 470                 475                 480
Arg Ala Pro Val Tyr Ser Trp Thr His Arg Ser Ala Asp Arg Thr Asn
                485                 490                 495
Thr Ile Ser Ser Asp Ser Ile Asn Gln Ile Pro Leu Val Lys Gly Phe
            500                 505                 510
Arg Val Trp Gly Gly Thr Ser Val Ile Thr Gly Pro Gly Phe Thr Gly
            515                 520                 525
Gly Asp Ile Leu Arg Arg Asn Thr Phe Gly Asp Phe Val Ser Leu Gln
            530                 535                 540
Val Asn Ile Asn Ser Pro Ile Thr Gln Arg Tyr Arg Leu Arg Phe Arg
545                 550                 555                 560
Tyr Ala Ser Ser Arg Asp Ala Arg Val Ile Val Leu Thr Gly Ala Ala
                565                 570                 575
Ser Thr Gly Val Gly Gly Gln Val Ser Val Asn Met Pro Leu Gln Lys
            580                 585                 590
Thr Met Glu Ile Gly Glu Asn Leu Thr Ser Arg Thr Phe Arg Tyr Thr
            595                 600                 605
Asp Phe Ser Asn Pro Phe Ser Phe Arg Ala Asn Pro Asp Ile Ile Gly
            610                 615                 620
Ile Ser Glu Gln Pro Leu Phe Gly Ala Gly Ser Ile Ser Ser Gly Glu
625                 630                 635                 640
Leu Tyr Ile Asp Lys Ile Glu Ile Ile Leu Ala Asp Ala Thr Phe Glu
                645                 650                 655
Ala Glu Ser Asp Leu Glu Arg Ala Gln Lys Ala Val Asn Glu Leu Phe
            660                 665                 670
Thr Ser Ser Asn Gln Ile Gly Leu Lys Thr Asp Val Thr Asp Tyr His
            675                 680                 685
Ile Asp Gln Val Ser Asn Leu Val Glu Cys Leu Ser Asp Glu Phe Cys
            690                 695                 700
Leu Asp Glu Lys Lys Glu Leu Ser Glu Lys Val Lys His Ala Lys Arg
705                 710                 715                 720
Leu Ser Asp Glu Arg Asn Leu Leu Gln Asp Pro Asn Phe Arg Gly Ile
                725                 730                 735
Asn Arg Gln Leu Asp Arg Gly Trp Arg Gly Ser Thr Asp Ile Thr Ile
                740                 745                 750
Gln Gly Gly Asp Asp Val Phe Lys Glu Asn Tyr Val Thr Leu Leu Gly
            755                 760                 765
Thr Phe Asp Glu Cys Tyr Pro Thr Tyr Leu Tyr Gln Lys Ile Asp Glu
            770                 775                 780
Ser Lys Leu Lys Ala Tyr Thr Arg Tyr Gln Leu Arg Gly Tyr Ile Glu
785                 790                 795                 800
Asp Ser Gln Asp Leu Glu Ile Tyr Leu Ile Arg Tyr Asn Ala Lys His
                805                 810                 815
Glu Thr Val Asn Val Pro Gly Thr Gly Ser Leu Trp Pro Leu Ser Ala
            820                 825                 830
Pro Ser Pro Ile Gly Lys Cys Ala His His Ser His His Phe Ser Leu
            835                 840                 845
```

Asp Ile Asp Val Gly Cys Thr Asp Leu Asn Glu Asp Leu Gly Val Trp
850                 855                 860

Val Ile Phe Lys Ile Lys Thr Gln Asp Gly His Ala Arg Leu Gly Asn
865                 870                 875                 880

Leu Glu Phe Leu Glu Glu Lys Pro Leu Val Gly Glu Ala Leu Ala Arg
            885                 890                 895

Val Lys Arg Ala Glu Lys Lys Trp Arg Asp Lys Arg Glu Lys Leu Glu
            900                 905                 910

Trp Glu Thr Asn Ile Val Tyr Lys Glu Ala Lys Glu Ser Val Asp Ala
            915                 920                 925

Leu Phe Val Asn Ser Gln Tyr Asp Arg Leu Gln Ala Asp Thr Asn Ile
930                 935                 940

Ala Met Ile His Ala Ala Asp Lys Arg Val His Ser Ile Arg Glu Ala
945                 950                 955                 960

Tyr Leu Pro Glu Leu Ser Val Ile Pro Gly Val Asn Ala Ala Ile Phe
            965                 970                 975

Glu Glu Leu Glu Gly Arg Ile Phe Thr Ala Phe Ser Leu Tyr Asp Ala
            980                 985                 990

Arg Asn Val Ile Lys Asn Gly Asp Phe Asn Asn Gly Leu Ser Cys Trp
            995                 1000                1005

Asn Val Lys Gly His Val Asp Val Glu Glu Gln Asn Asn His Arg
    1010                1015                1020

Ser Val Leu Val Val Pro Glu Trp Glu Ala Glu Val Ser Gln Glu
    1025                1030                1035

Val Arg Val Cys Pro Gly Arg Gly Tyr Ile Leu Arg Val Thr Ala
    1040                1045                1050

Tyr Lys Glu Gly Tyr Gly Glu Gly Cys Val Thr Ile His Glu Ile
    1055                1060                1065

Glu Asn Asn Thr Asp Glu Leu Lys Phe Ser Asn Cys Val Glu Glu
    1070                1075                1080

Glu Val Tyr Pro Asn Asn Thr Val Thr Cys Asn Asp Tyr Thr Ala
    1085                1090                1095

Thr Gln Glu Glu Tyr Glu Gly Thr Tyr Thr Ser Arg Asn Arg Gly
    1100                1105                1110

Tyr Asp Gly Ala Tyr Glu Ser Asn Ser Ser Val Pro Ala Asp Tyr
    1115                1120                1125

Ala Ser Ala Tyr Glu Glu Lys Ala Tyr Thr Asp Gly Arg Arg Asp
    1130                1135                1140

Asn Pro Cys Glu Ser Asn Arg Gly Tyr Gly Asp Tyr Thr Pro Leu
    1145                1150                1155

Pro Ala Gly Tyr Val Thr Lys Glu Leu Glu Tyr Phe Pro Glu Thr
    1160                1165                1170

Asp Lys Val Trp Ile Glu Ile Gly Glu Thr Glu Gly Thr Phe Ile
    1175                1180                1185

Val Asp Ser Val Glu Leu Leu Leu Met Glu Glu
    1190                1195

<210> SEQ ID NO 48
<211> LENGTH: 3432
<212> TYPE: DNA
<213> ORGANISM: Artificial
<220> FEATURE:
<223> OTHER INFORMATION: Recombinant nucleotide sequence used for
      expression in a bacterial cell encoding TIC869.

```
<400> SEQUENCE: 48
atggagataa ataatcagaa gcaatgcata ccatataatt gcttaagtaa tcctgaggaa      60
gtacttttgg atggggagag atattaccct gatatcgatc cactcgaagt ttctttgtcg     120
cttttgcaat ttcttttgaa taactttgtt ccaggggag gctttatttc aggattagtt     180
gataaaatat gggggctt gagaccatct gaatgggact tatttcttgc acagattgaa     240
cggttgattg atcaaagaat agaagcaaca gtaagagcaa aagcaatcac tgaattagaa     300
ggattaggga gaaattatca aatatacgct gaagcattta aagaatggga atcagatcct     360
gataacgaag cggctaaaag tagagtaatt gatcgctttc gtatacttga tggtctaatt     420
gaagcaaata tcccttcatt tcggataatt ggatttgaag tgccactttt atcggtttat     480
gttcaagcag ctaatctaca tctcgctcta ttgagagatt ctgttatttt tggagagaga     540
tggggattga cgacaaaaaa tgtcaatgat atctataata gacaaattag agaaattcat     600
gaatatagca atcattgcgt agatacgtat aacacagaac tagaacgtct agggtttaga     660
tctatagcgc agtggagaat atataatcag tttagaagag aactaacact aactgtatta     720
gatattgtcg ctctttttccc gaactatgac agtagactgt atccgatcca aacttttttct     780
caattgacaa gagaaattgt tacatcccca gtaagcgaat tttattatgg tgttattaat     840
agtggtaata taattggtac tcttactgaa cagcagataa ggcgaccaca tcttatggac     900
ttctttaact ccatgatcat gtatacatca gataatagac gggaacatta ttggtcagga     960
cttgaaatga cggcttattt tacaggattt gcaggagctc aagtgtcatt ccctttagtc    1020
gggactagag gggagtcagc tccaccatta actgttagaa gtgttaatga tggaattat    1080
agaatattat cggcaccgtt ttattcagcg ccttttctag gcaccattgt attgggaagt    1140
cgtggagaaa aatttgattt tgcgcttaat aatatttcac ctccgccatc tacaatatac    1200
agacatcctg gaacagtaga ttcactagtc agtataccgc cacaggataa tagcgtacca    1260
ccgcacaggg gatctagtca tcgattaagt catgttacaa tgcgcgcaag ttcccctata    1320
ttccattgga cgcatcgcag cgcaaccact acaaatacaa ttaatccaaa tgctattatc    1380
caaataccac tagtaaaagc atttaacctt cattcaggtg ccactgttgt tagaggacca    1440
gggtttacag gtggagatct cttacgaaga acgaatactg gtacatttgc agacataaga    1500
gtcaatgttc cttcatcact atttttcccaa agatatcgcg taaggattcg ttatgcttct    1560
actaccgatt tacaattttt cacgagaatt aatggaactt ctgttaatca aggtaatttc    1620
tcaaaaacga tggatagagg ggataaactg aaatctgaaa actttagaac tgccggattt    1680
agtactcctt ttagatttc aaatttcaa agtacattca cgttgggtac tcaggctttt    1740
tcaaatcagg aagtttatat agatagaatt gaatttgtcc cggcagaagt aacattcgag    1800
gcagaatctg atttagaaag agcacaaaag gcggtgaatg agctgtttac ttcttccaat    1860
caaatcgggt taaaaacaga tgtgacggat tatcatattg atcaagtatc caatttagtt    1920
gagtgtttat ctgatgaatt ttgtctggat gaaaaaaaag aattgtccga gaaagtcaaa    1980
catgcgaagc gacttagtga tgagcggaat ttacttcaag atccaaactt tagagggatc    2040
aatagacaac tagaccgtgg ctggagagga agtacgagata ttaccatcca aggaggcgat    2100
gacgtattca agagaattta cgttacgcta ttgggtacct ttgatgagtg ctatccaacg    2160
tatttatatc aaaaaatata tgagtcgaaa ttaaaagcct atacccgttta ccaattaaga    2220
gggtatatcg aagatagtca agacttagaa atctatttaa ttcgctacaa tgccaaacac    2280
gaaacagtaa atgtgccagg tacgggttcc ttatggccgc tttcagcccc aagtccaatc    2340
```

```
ggaaaatgtg cccatcattc ccatcatttc tccttggaca ttgatgttgg atgtacagac    2400
ttaaatgagg acttaggtgt atgggtgata ttcaagatta agacgcaaga tggccatgca    2460
agactaggaa atctagaatt tctcgaagag aaaccattag taggagaagc actagctcgt    2520
gtgaaaagag cggagaaaaa atggagagac aaacgtgaaa aattggaatg ggaaacaaat    2580
attgtttata aagaggcaaa agaatctgta gatgctttat ttgtaaactc tcaatatgat    2640
agattacaag cggataccaa catcgcgatg attcatgcgg cagataaacg cgttcatagc    2700
attcgagaag cttatctgcc tgagctgtct gtgattccgg gtgtcaatgc ggctattttt    2760
gaagaattag aagggcgtat tttcactgca ttctccctat atgatgcgag aaatgtcatt    2820
aaaaatggtg attttaataa tggcttatcc tgctggaacg tgaaagggca tgtagatgta    2880
gaagaacaaa acaaccaccg ttcggtcctt gttgttccgg aatgggaagc agaagtgtca    2940
caagaagttc gtgtctgtcc gggtcgtggc tatatccttc gtgtcacagc gtacaaggag    3000
ggatatggag aaggttgcgt aaccattcat gagatcgaga acaatacaga cgaactgaag    3060
tttagcaact gtgtagaaga ggaagtatat ccaaacaaca cggtaacgtg taatgattat    3120
actgcgactc aagaagaata tgagggtacg tacacttctc gtaatcgagg atatgacgga    3180
gcctatgaaa gcaattcttc tgtaccagct gattatgcat cagcctatga agaaaaagca    3240
tatacagatg gacgaagaga caatccttgt gaatctaaca gaggatatgg ggattacaca    3300
ccactaccag ctggctatgt gacaaaagaa ttagagtact tcccagaaac cgataaggta    3360
tggattgaga tcggagaaac ggaaggaaca ttcatcgtgg acagcgtgga attacttctt    3420
atggaggaat ag                                                       3432

<210> SEQ ID NO 49
<211> LENGTH: 3432
<212> TYPE: DNA
<213> ORGANISM: Artificial
<220> FEATURE:
<223> OTHER INFORMATION: Synthetic nucleotide sequence designed for
      expression in a plant cell encoding TIC869.

<400> SEQUENCE: 49
atggagataa acaaccagaa gcagtgcatt ccgtacaact gcctcagcaa cccggaggag      60
gtgctgctgg acggcgagcg tatcctccca gacatcgacc cactggaggt cagcctgagc     120
ctcctccagt tcctcctcaa taacttcgtg ccaggcggcg gcttcatctc cggcctggtg     180
gacaagatct ggggcgcact ccggccaagt gagtgggatc tgttcctggc ccaaatcgag     240
cgcctgatcg accagaggat cgaggcgacg gtccgcgcca aggcgataac cgagctggag     300
ggcctcggtc gcaactacca gatctacgca gaggcgttca aggagtggga gagcgacccg     360
gacaacgagg cggccaagtc tcgggtgatt gaccgcttcc gcatcctcga cggcctcatc     420
gaagccaaca tcccttcctt ccggatcata ggcttcgaag tcccgctcct cagcgtgtac     480
gtgcaagcgg ccaatctcca cctcgcgttg ctccgtgaca cgtcatcttt ggcgagaga     540 tggggcctga cgacgaagaa cgtgaacgac atctacaaca ggcagatccg agagattcac     600
gagtacagca accactgcgt ggacacatac aacacggagc tggagcggct cggcttccgc     660
tcaatcgctc agtggcggat ctacaaccag ttccgccgcg agctgaccct caccgtgctc     720
gacatcgtcg cattgtttcc caattacgac tcacgcctct acccaatcca gactttcagc     780
cagctcacac gcgagattgt gaccagcccg gtgtcagagt tctactacgg cgtcatcaac     840
tcaggcaaca tcatcgggac actgactgaa cagcagatca gacgtccgca cttgatggac     900
```

```
ttcttcaact ccatgattat gtacacatca gacaacagga gagagcacta ctggtccggg    960
ttggagatga ctgcttactt caccggcttc gccggtgccc aagtgagctt cccactggtc   1020
ggaactcgtg gcgagtcagc tcctccgcta actgtgcgat ctgtcaacga cgggatctac   1080
agaatactgt cggctccctt ctacagtgcg ccgttcctcg gcaccatcgt cctcggctca   1140
cgtggtgaga agttcgactt cgcactgaac aacattagcc cgccgcctag tacaatctac   1200
aggcaccctg gcaccgtgga ctcactggtt tcgatcccgc cacaagacaa cagtgtgccg   1260
ccacatcgtg gttctagcca caggctctcc catgtgacca tgcgcgcctc ttcaccgatc   1320
tttcactgga cccatcggtc cgctacaacc acaaacacca tcaaccctaa cgccatcatc   1380
caaatcccgc tggtgaaggc gtttaacctc cacagcggcg caactgtcgt gcgcggccct   1440
ggattcaccg tggtgacct gctccgtcgg accaatactg gcacgttcgc agacatccga   1500
gtgaacgtcc cgtcctcgct gttcagtcag cgctaccgtg tccgcattcg gtacgcttcc   1560
accacggatc tccagttctt tactcgcatc aatgggacga gcgtcaacca gggcaacttc   1620
agcaagacga tggaccgtgg agataagctc aagtccgaga cttccgcac ggctggcttc   1680
tcgacaccgt tcagattcag caacttccag agcactttca cgctgggcac acaggcgttc   1740
tccaaccagg aggtgtacat cgaccgcatc gagttcgtgc ctgctgaggt taccttcgag   1800
gcggaaagcg acctcgaaag gcccagaag gccgtcaacg agctgttcac ctccagcaac   1860
cagatcggtc tcaagaccga cgtcactgac tatcacattg accaagtcag caacctggtg   1920
gagtgcctca gtgatgagtt ctgcctggat gagaagaagg agcttagcga gaaggtcaag   1980
cacgcaaagc gcttgagcga cgagcgcaac cttctccagg acccgaattt ccgtggtatc   2040
aatagacagc ttgaccgtgg gtggcgcggt agtaccgaca taaccatcca gggtggcgac   2100
gatgtgttca aggagaatta tgttacgctg ctcggtacgt tcgacgagtg ctatcccacg   2160
tacttgtacc agaagattga cgagagcaag ctcaaggcgt acacccgtta ccagctccgt   2220
ggctacatcg aggacagcca ggatctggaa atctaccta tccgatacaa tgctaagcac   2280
gagacagtca acgtgcccgg aacagggtcg ctctggccgc tcagtgctcc gtcgcccatt   2340
ggcaagtgcg cgcaccattc gcatcacttc tcacttgaca ttgacgtggg ctgcaccgac   2400
ctgaacgagg atctgggtgt ctgggtcatc ttcaagatca agacccaaga cggccacgcg   2460
cgcctcggga acctggagtt cctggaggag aagccttttgg taggtgaagc cctggcccgc   2520
gtcaagcgcg cggagaagaa gtggcgcgac aagagggaga agctggaatg ggagaccaac   2580
atcgtgtaca aggaggcgaa ggagtcggtg gacgcactat tcgtgaactc ccagtacgac   2640
cgtctccagg ccgacaccaa catcgccatg atccacgccg ctgacaaacg agttcattcc   2700
attcgtgaag cctatcttcc cgagctgtct gtcataccgg gcgtcaacgc ggccatcttc   2760
gaggagttag agggtcggat ctttacagct ttctcactgt acgatgcccg caacgtcatc   2820
aagaacggcg acttcaacaa cggtctctcc tgttggaacg tgaagggcca cgtggatgtc   2880
gaggagcaga caaccaccg ctctgtgctt gtggtgcccg agtgggaggc cgaggtgagc   2940
caggaggtcc gcgtctgtcc gggtcgcggc tacatcctgc gggtcaccgc ctacaaggag   3000
ggctacggcg aaggctgcgt tactattcac gagattgaga caataccga cgaactcaag   3060
ttctccaact gtgtcgagga ggaggtgtac ccgaacaaca ccgtgacgtg caacgactac   3120
accgcgacac aggaggaata cgagggcacc tacaccagcc gcaaccgagg ctacgacgga   3180
gcgtacgaga gcaactcgtc cgtgcccgct gattacgcga gtgcgtacga ggagaaggct   3240
```

```
tacaccgacg dacggcgcga caatccctgc gagagtaacc gtggatacgg agattacacg    3300
ccgctacccg ctggctacgt cactaaggaa ctggagtact tcccagagac ggacaaggtg    3360
tggatcgaaa tcggcgagac agagggcacg ttcatcgtgg actccgtgga gctgctgctg    3420
atggaggagt ga                                                        3432
```

<210> SEQ ID NO 50
<211> LENGTH: 1143
<212> TYPE: PRT
<213> ORGANISM: Artificial
<220> FEATURE:
<223> OTHER INFORMATION: Amino acid sequence of the chimeric protein TIC869.

<400> SEQUENCE: 50

```
Met Glu Ile Asn Asn Gln Lys Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Leu Ser Leu Gln Phe Leu Leu Asn Asn
        35                  40                  45

Phe Val Pro Gly Gly Gly Phe Ile Ser Gly Leu Val Asp Lys Ile Trp
    50                  55                  60

Gly Ala Leu Arg Pro Ser Glu Trp Asp Leu Phe Leu Ala Gln Ile Glu
65                  70                  75                  80

Arg Leu Ile Asp Gln Arg Ile Glu Ala Thr Val Arg Ala Lys Ala Ile
                85                  90                  95

Thr Glu Leu Glu Gly Leu Gly Arg Asn Tyr Gln Ile Tyr Ala Glu Ala
            100                 105                 110

Phe Lys Glu Trp Glu Ser Asp Pro Asp Asn Glu Ala Ala Lys Ser Arg
        115                 120                 125

Val Ile Asp Arg Phe Arg Ile Leu Asp Gly Leu Ile Glu Ala Asn Ile
    130                 135                 140

Pro Ser Phe Arg Ile Ile Gly Phe Glu Val Pro Leu Leu Ser Val Tyr
145                 150                 155                 160

Val Gln Ala Ala Asn Leu His Leu Ala Leu Leu Arg Asp Ser Val Ile
                165                 170                 175

Phe Gly Glu Arg Trp Gly Leu Thr Thr Lys Asn Val Asn Asp Ile Tyr
            180                 185                 190

Asn Arg Gln Ile Arg Glu Ile His Glu Tyr Ser Asn His Cys Val Asp
        195                 200                 205

Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
            260                 265                 270

Glu Phe Tyr Tyr Gly Val Ile Asn Ser Gly Asn Ile Ile Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320
```

-continued

Leu Glu Met Thr Ala Tyr Phe Thr Gly Phe Ala Gly Ala Gln Val Ser
                    325                 330                 335

Phe Pro Leu Val Gly Thr Arg Gly Glu Ser Ala Pro Pro Leu Thr Val
            340                 345                 350

Arg Ser Val Asn Asp Gly Ile Tyr Arg Ile Leu Ser Ala Pro Phe Tyr
        355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Ser Thr Ile Tyr
385                 390                 395                 400

Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
            420                 425                 430

Thr Met Arg Ala Ser Ser Pro Ile Phe His Trp Thr His Arg Ser Ala
        435                 440                 445

Thr Thr Thr Asn Thr Ile Asn Pro Asn Ala Ile Ile Gln Ile Pro Leu
    450                 455                 460

Val Lys Ala Phe Asn Leu His Ser Gly Ala Thr Val Val Arg Gly Pro
465                 470                 475                 480

Gly Phe Thr Gly Gly Asp Leu Leu Arg Arg Thr Asn Thr Gly Thr Phe
                485                 490                 495

Ala Asp Ile Arg Val Asn Val Pro Ser Ser Leu Phe Ser Gln Arg Tyr
            500                 505                 510

Arg Val Arg Ile Arg Tyr Ala Ser Thr Thr Asp Leu Gln Phe Phe Thr
        515                 520                 525

Arg Ile Asn Gly Thr Ser Val Asn Gln Gly Asn Phe Ser Lys Thr Met
    530                 535                 540

Asp Arg Gly Asp Lys Leu Lys Ser Glu Asn Phe Arg Thr Ala Gly Phe
545                 550                 555                 560

Ser Thr Pro Phe Arg Phe Ser Asn Phe Gln Ser Thr Phe Thr Leu Gly
                565                 570                 575

Thr Gln Ala Phe Ser Asn Gln Glu Val Tyr Ile Asp Arg Ile Glu Phe
            580                 585                 590

Val Pro Ala Glu Val Thr Phe Glu Ala Glu Ser Asp Leu Glu Arg Ala
        595                 600                 605

Gln Lys Ala Val Asn Glu Leu Phe Thr Ser Ser Asn Gln Ile Gly Leu
    610                 615                 620

Lys Thr Asp Val Thr Asp Tyr His Ile Asp Gln Val Ser Asn Leu Val
625                 630                 635                 640

Glu Cys Leu Ser Asp Glu Phe Cys Leu Asp Glu Lys Lys Glu Leu Ser
                645                 650                 655

Glu Lys Val Lys His Ala Lys Arg Leu Ser Asp Glu Arg Asn Leu Leu
            660                 665                 670

Gln Asp Pro Asn Phe Arg Gly Ile Asn Arg Gln Leu Asp Arg Gly Trp
        675                 680                 685

Arg Gly Ser Thr Asp Ile Thr Ile Gln Gly Gly Asp Asp Val Phe Lys
    690                 695                 700

Glu Asn Tyr Val Thr Leu Leu Gly Thr Phe Asp Glu Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Gln Leu Arg Gly Tyr Ile Glu Asp Ser Gln Asp Leu Glu Ile Tyr

```
                  740                 745                 750
Leu Ile Arg Tyr Asn Ala Lys His Glu Thr Val Asn Val Pro Gly Thr
            755                 760                 765
Gly Ser Leu Trp Pro Leu Ser Ala Pro Ser Pro Ile Gly Lys Cys Ala
            770                 775                 780
His His Ser His His Phe Ser Leu Asp Ile Asp Val Gly Cys Thr Asp
785                 790                 795                 800
Leu Asn Glu Asp Leu Gly Val Trp Val Ile Phe Lys Ile Lys Thr Gln
            805                 810                 815
Asp Gly His Ala Arg Leu Gly Asn Leu Glu Phe Leu Glu Glu Lys Pro
            820                 825                 830
Leu Val Gly Glu Ala Leu Ala Arg Val Lys Arg Ala Glu Lys Lys Trp
            835                 840                 845
Arg Asp Lys Arg Glu Lys Leu Glu Trp Glu Thr Asn Ile Val Tyr Lys
            850                 855                 860
Glu Ala Lys Glu Ser Val Asp Ala Leu Phe Val Asn Ser Gln Tyr Asp
865                 870                 875                 880
Arg Leu Gln Ala Asp Thr Asn Ile Ala Met Ile His Ala Ala Asp Lys
            885                 890                 895
Arg Val His Ser Ile Arg Glu Ala Tyr Leu Pro Glu Leu Ser Val Ile
            900                 905                 910
Pro Gly Val Asn Ala Ala Ile Phe Glu Glu Leu Glu Gly Arg Ile Phe
            915                 920                 925
Thr Ala Phe Ser Leu Tyr Asp Ala Arg Asn Val Ile Lys Asn Gly Asp
            930                 935                 940
Phe Asn Asn Gly Leu Ser Cys Trp Asn Val Lys Gly His Val Asp Val
945                 950                 955                 960
Glu Glu Gln Asn Asn His Arg Ser Val Leu Val Val Pro Glu Trp Glu
            965                 970                 975
Ala Glu Val Ser Gln Glu Val Arg Val Cys Pro Gly Arg Gly Tyr Ile
            980                 985                 990
Leu Arg Val Thr Ala Tyr Lys Glu Gly Tyr Gly Glu Gly Cys Val Thr
            995                1000                1005
Ile His Glu Ile Glu Asn Asn Thr Asp Glu Leu Lys Phe Ser Asn
            1010                1015                1020
Cys Val Glu Glu Glu Val Tyr Pro Asn Asn Thr Val Thr Cys Asn
            1025                1030                1035
Asp Tyr Thr Ala Thr Gln Glu Glu Tyr Glu Gly Thr Tyr Thr Ser
            1040                1045                1050
Arg Asn Arg Gly Tyr Asp Gly Ala Tyr Glu Ser Asn Ser Ser Val
            1055                1060                1065
Pro Ala Asp Tyr Ala Ser Ala Tyr Glu Glu Lys Ala Tyr Thr Asp
            1070                1075                1080
Gly Arg Arg Asp Asn Pro Cys Glu Ser Asn Arg Gly Tyr Gly Asp
            1085                1090                1095
Tyr Thr Pro Leu Pro Ala Gly Tyr Val Thr Lys Glu Leu Glu Tyr
            1100                1105                1110
Phe Pro Glu Thr Asp Lys Val Trp Ile Glu Ile Gly Glu Thr Glu
            1115                1120                1125
Gly Thr Phe Ile Val Asp Ser Val Glu Leu Leu Leu Met Glu Glu
            1130                1135                1140

<210> SEQ ID NO 51
```

<211> LENGTH: 3513
<212> TYPE: DNA
<213> ORGANISM: Artificial
<220> FEATURE:
<223> OTHER INFORMATION: Recombinant nucleotide sequence used for
      expression in a bacterial cell encoding TIC836.

<400> SEQUENCE: 51

```
atggagaata atattcaaaa tcaatgcgta ccttacaatt gtttaaataa tcctgaagta      60
gaaatattaa atgaagaaag aagtactggc agattaccgt tagatatatc cttatcgctt     120
acacgtttcc ttttgagtga atttgttcca ggtgtgggag ttgcgtttgg attatttgat     180
ttaatatggg gttttataac tccttctgat tggagcttat ttcttttaca gattgaacaa     240
ttgattgagc aaagaataga acattggaa ggaaccggg caattactac attacgaggg      300
ttagcagata gctatgaaat ttatattgaa gcactaagag agtgggaagc aaatcctaat     360
aatgcacaat aagggaaga tgtgcgtatt cgatttgcta atacagacga cgctttaata     420
acagcaataa ataattttac acttacaagt tttgaaatcc ctcttttatc ggtctatgtt     480
caagcggcga atttacattt atcactatta agagacgctg tatcgtttgg gcagggttgg     540
ggactggata tagctactgt taataatcat tataatagat aataaatct tattcataga     600
tatcgaaac attgtttgga cacatacaat caaggattag aaaacttaag aggtactaat     660
actcgacaat gggcaagatt caatcagttt aggagagatt taacacttac tgtattagat     720
atcgttgctc ttttccgaa ctcgatgtt agaacatatc caattcaaac gtcatcccaa      780
ttaacaaggg aaatttatac aagttcagta attgaggatt ctccagtttc tgctaatata     840
cctaatggtt ttaataggc ggaatttgga gttagaccgc cccatcttat ggactttatg      900
aattctttgt tgtaactgc agagactgtt agaagtcaaa ctgtgtgggg aggacactta     960
gttagttcac gaaatacggc tggtaaccgt ataaatttcc ctagttacgg ggtcttcaat    1020
cctggtggcg ccatttggat tgcagatgag gatccacgtc cttttttatcg gacattatca    1080
gatcctgttt ttgtccgagg aggatttggg aatcctcatt atgtactggg gcttagggga    1140
gtagcatttc aacaaactgg tacgaaccac acccgaacat ttagaaatag tgggaccata    1200
gattctctag atgaaatccc acctcaggat aatagtgggg caccttggaa tgattatagt    1260
catgtattaa atcatgttac atttgtacga tggccaggtg agatttcagg aagtgattca    1320
tggagagctc caatgttttc ttggacgcac cgtagtgcaa cccctacaaa tacaattgat    1380
ccggagagga ttacacaaat accctttaaca aaatctacta atcttggctc tggaacttct    1440
gtcgttaaag gaccaggatt tacaggagga gatattcttc gaagaacttc acctggccag    1500
atttcaacct taagagtaaa tattactgca ccattatcac aaagatatcg ggtaagaatt    1560
cgctacgctt ctaccacaaa tttacaattc catacatcaa ttgacggaag acctattaat    1620
caggggaatt tttcagcaac tatgagtagt gggagtaatt acagtccgg aagctttagg    1680
actgtaggtt ttactactcc gtttaacttt tcaaatggat caagtgtatt tacgttaagt    1740
gctcatgtct tcaattcagg caatgaagtt tatatagatc gaattgaatt tgttccggca    1800
gaagtaacct tgaggcaga atatgattta gaaagagcgc agaaggcggt gaatgcgctg    1860
tttacgtcta caaaccaact agggctaaaa acaaatgtaa cggattatca tattgatcaa    1920
gtgtccaatt tagttacgta tttatcggat gaattttgtc tggatgaaaa gcgagaattg    1980
tccgagaaag tcaaacatgc gaagcgactc agtgatgaac gcaatttact ccaagattca    2040
aatttcaaag acattaatag gcaaccagaa cgtgggtggg gcggaagtac agggattacc    2100
```

```
atccaaggag gggatgacgt atttaaagaa aattacgtca cactatcagg tacctttgat   2160
gagtgctatc caacatattt gtatcaaaaa atcgatgaat caaaattaaa agcctttacc   2220
cgttatcaat taagagggta tatcgaagat agtcaagact tagaaatcta tttaattcgc   2280
tacaatgcaa aacatgaaac agtaaatgtg ccaggtacgg gttccttatg ccgctttca    2340 gcccaaagtc caatcggaaa gtgtggagag ccgaatcgat gcgcgccaca ccttgaatgg   2400
aatcctgact tagattgttc gtgtagggat ggagaaaagt gtgcccatca ttcgcatcat   2460
ttctccttag acattgatgt aggatgtaca gacttaaatg aggacctagg tgtatgggtg   2520
atctttaaga ttaagacgca agatgggcac gcaagactag gaatctaga gtttctcgaa   2580 gaaaaaccat tagtaggaga agcgctagct cgtgtgaaaa gagcggagaa aaaatggaga   2640
gacaaacgtg aaaaattgga atgggaaaca aatatcgttt ataaagaggc aaaagaatct   2700
gtagatgctt tatttgtaaa ctctcaatat gatcaattac aagcggatac gaatattgcc   2760
atgattcatg cggcagataa acgtgttcat agcattcgag aagcttatct gcctgagctg   2820
tctgtgattc cgggtgtcaa tgcggctatt tttgaagaat tagaagggcg tattttcact   2880
gcattctccc tatatgatgc gagaaatgtc attaaaaatg gtgattttaa taatggctta   2940
tcctgctgga acgtgaaagg gcatgtagat gtagaagaac aaaacaacca acgttcggtc   3000
cttgttgttc cggaatggga agcagaagtg tcacaagaag ttcgtgtctg tccgggtcgt   3060
ggctatatcc ttcgtgtcac agcgtacaag gagggatatg gagaaggttg cgtaaccatt   3120
catgagatcg agaacaatac agacgaactg aagtttagca actgcgtaga ggaggaaatc   3180
tatccaaata acacggtaac gtgtaatgat tatactgtaa atcaagaaga atacggaggt   3240
gcgtacactt ctcgtaatcg aggatataac gaagctcctt ccgtaccagc tgattatgcg   3300
tcagtctatg aagaaaaatc gtatacagat ggacgtagag agaatccttg tgaatttaac   3360
agagggtata gggattacac gccactacca gttggttatg tgacaaaaga attagaatac   3420
ttcccagaaa ccgataaggt atggattgag attggagaaa cggaaggaac atttatcgtg   3480
gacagcgtgg aattactcct tatggaggaa taa                                3513
```

<210> SEQ ID NO 52
<211> LENGTH: 3513
<212> TYPE: DNA
<213> ORGANISM: Artificial
<220> FEATURE:
<223> OTHER INFORMATION: Synthetic nucleotide sequence designed for
      expression in a plant cell encoding TIC836.

<400> SEQUENCE: 52

```
atggagaaca acatccagaa ccagtgcgtg ccctacaact gcctgaacaa ccctgaggtt    60
gagatcctga cgaggagcg tagcaccggt aggctcccgc tagacatctc cctgagcctg   120
acccgcttcc tccttagtga gttcgtgccc ggcgtgggcg tggccttcgg cctcttcgac   180
ctcatctggg gcttcatcac tccttccgac tggtccctct tcctccttca gattgagcaa   240
ctgatcgagc agcgcatcga gacccttgag cgcaaccgcg ccatcaccac tctcagaggt   300
ctcgccgact cctacgaaat ctacatcgag gcactccgtg agtgggaggc caacccgaac   360
aatgcccagc tccgcgagga cgtgaggatc agattcgcca acaccgacga tgccctcatc   420
accgccatca acaatttcac cctcacctcc ttcgagatcc ctcttctgtc tgtgtacgtt   480
caagctgcta accttcacct ttccctcctg cgcgacgccg tgagcttcgg ccagggctgg   540
ggcctcgaca tcgccaccgt gaacaatcac tacaaccgcc tcatcaacct catccaccgc   600
```

```
tacaccaagc actgccttga cacctacaac cagggccttg agaacctccg tggcaccaac      660
acccgccagt gggcccgctt caaccagttc cgcagagacc tcaccctcac cgtgctcgac      720
atcgtggcac tcttcccaaa ctacgacgtg cgtacctacc ctatccagac ctccagccag      780
ctcaccaggg aaatctacac ctccagcgtg atcgaggact ctcctgtgtc cgccaacatc      840
cctaacggct caaccgcgc cgagttcggc gtgcgccctc ctcacctcat ggacttcatg       900
aactccctct cgtcactgc cgagaccgtg cgctcccaga ccgtgtgggg cggtcacctc       960
gtgtccagcc gtaacaccgc tggcaacagg atcaacttcc cgtcctacgg cgtgttcaac     1020
ccaggcggtg ccatctggat cgccgatgaa gaccctcgtc ctttctaccg tacccctgtcc    1080 gaccctgtgt tcgtgcgtgg cggtttcggc aaccctcact acgtgctggg cctgcgtggc    1140
gtggccttcc agcaaaccgg caccaaccac accaggacgt tccgtaactc cggcaccatc    1200
gacagtcttg acgagatccc tccgcaagac aactccggtg caccttggaa cgactactcc    1260
cacgtgctga accacgtgac cttcgtgagg tggcctggcg aaatctccgg ctccgactcc    1320
tggagggctc ctatgttcag ttggacccac aggagcgcta cgcctaccaa caccatcgac    1380
cctgagcgta tcactcagat ccctctgact aagagcacta acctgggcag cggcactagc    1440
gtggtcaagg gccctggctt cactggcggt gacatcctga ggcggactag ccctggccag    1500
atcagcactc tgagggtgaa catcactgct ccgctgagcc agcgttacag ggtcagaatc    1560
cgttacgctt ctactactaa ccttcagttc cacactagca tcgacggccg tccgatcaac    1620
cagggcaact tctctgctac tatgagttct ggcagtaacc tccagtctgg tagtttccgg    1680
actgtcggtt tcactacgcc gttcaacttc tccaacggta gttctgtctt cactctgtct    1740
gctcacgtgt tcaactctgg caacgaggtg tacatcgacc ggatcgagtt cgtccctgct    1800
gaggtgacgt tcgaggccga gtacgacctg gagcgggctc agaaggctgt caacgctctg    1860
ttcacttcta ctaaccagct tggtttgaag actaacgtga ccgactacca cattgatcaa    1920
gtcagtaacc tggtcacgta cctgtctgac gagttctgtc ttgacgagaa gcgggagctg    1980
tctgagaagg tcaagcacgc taagcggctg tctgacgagc ggaacctgct tcaagacagt    2040
aacttcaagg acattaaccg ccagcctgag cgtggttggg gagggtccac gggtattacg    2100
attcaaggag gtgacgatgt cttttaagga gaactatgtga cgctttcggg tacgtttgat    2160
gagtgctatc caacgtacct ttaccagaag attgacgagt cgaagctgaa ggctttcact    2220
cgttaccagc ttcgtggtta cattgaggac tcgcaagacc tcgaaatcta cctcattcgt    2280
tacaacgcta agcacgagac tgtcaacgtc cctggtacgg gtagtctttg ccgctttct    2340 gctcagtcgc cgattggcaa gtgtggcgag ccgaaccgtt gcgctcctca cttggagtgg    2400
aacccggatc tcgattgctc gtgccgtgac ggtgagaagt gcgcgcacca tagtcatcac    2460
tttagccttg acattgatgt cggttgcacg gatcttaacg aggatcttgg agtctgggtg    2520 atttcaaga tcaaaactca ggatgggcac gcgcgtcttg gaatcttga gttcctggag     2580 gagaagccac ttgtcggtga ggcgcttgcg cgtgtcaagc gtgcggagaa gaaatggcgt    2640
gataagcgtg agaagttgga gtgggagacg aacatcgtgt acaaggaggc gaaggagtcg    2700
gtcgatgcgt tgtttgtcaa tagtcaatac gatcaattgc aagcggatac gaacatcgca    2760
atgattcatg cggcagataa gcgtgtccat tcgattcgtg aggcgtactt gccagagttg    2820
tcggtcatcc caggagttaa tgcggcaatc tttgaggaat tggagggcag aatcttcacg    2880
gcgttctcgt tgtacgatgc aagaaatgtt attaagaatg agatttcaa caatgggttc    2940 tcatgctgga atgttaaggg tcacgttgat gttgaagaac agaacaacca gagatcagtg    3000
```

```
ttggttgtac cagagtggga ggcagaggtt tcacaagagg tgagagtttg cccaggcaga  3060
ggctacatct tgagagttac agcatacaaa gagggatacg gcgagggatg tgttacaatc  3120
cacgaaatcg agaacaatac cgatgagcta aagttctcaa attgtgttga ggaggagatc  3180
tacccgaaca cacggttac ttgtaatgat tacacagtga accaggagga gtatggtggt  3240
gcatacacat caagaaatag aggctacaat gaagcaccat cagttccagc agattatgcc  3300
tcagtttatg aggagaagtc atacacagat ggacgacgtg agaatccatg tgagttcaat  3360
cgaggatacc gagattacac accactacca gttggatacg ttacaaagga actagaatac  3420
ttcccagaaa cagataaagt atggatagag atcggagaaa cagaaggaac attcatcgtt  3480
gattcagtag aactactact tatggaagaa tga                              3513
```

<210> SEQ ID NO 53
<211> LENGTH: 1170
<212> TYPE: PRT
<213> ORGANISM: Artificial
<220> FEATURE:
<223> OTHER INFORMATION: Amino acid sequence of the chimeric protein
      TIC836.

<400> SEQUENCE: 53

```
Met Glu Asn Asn Ile Gln Asn Gln Cys Val Pro Tyr Asn Cys Leu Asn
1               5                   10                  15

Asn Pro Glu Val Glu Ile Leu Asn Glu Arg Ser Thr Gly Arg Leu
                20                  25                  30

Pro Leu Asp Ile Ser Leu Ser Leu Thr Arg Phe Leu Leu Ser Glu Phe
            35                  40                  45

Val Pro Gly Val Gly Val Ala Phe Gly Leu Phe Asp Leu Ile Trp Gly
        50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
```

```
                260                 265                 270
Asp Ser Pro Val Ser Asn Ile Pro Asn Gly Phe Asn Arg Ala Glu
        275                 280                 285
Phe Gly Val Arg Pro His Leu Met Asp Phe Met Asn Ser Leu Phe
        290                 295                 300
Val Thr Ala Glu Thr Val Arg Ser Gln Thr Val Trp Gly Gly His Leu
305                 310                 315                 320
Val Ser Ser Arg Asn Thr Ala Gly Asn Arg Ile Asn Phe Pro Ser Tyr
                325                 330                 335
Gly Val Phe Asn Pro Gly Gly Ala Ile Trp Ile Ala Asp Glu Asp Pro
                340                 345                 350
Arg Pro Phe Tyr Arg Thr Leu Ser Asp Pro Val Phe Val Arg Gly Gly
                355                 360                 365
Phe Gly Asn Pro His Tyr Val Leu Gly Leu Arg Gly Val Ala Phe Gln
                370                 375                 380
Gln Thr Gly Thr Asn His Thr Arg Thr Phe Arg Asn Ser Gly Thr Ile
385                 390                 395                 400
Asp Ser Leu Asp Glu Ile Pro Pro Gln Asp Asn Ser Gly Ala Pro Trp
                405                 410                 415
Asn Asp Tyr Ser His Val Leu Asn His Val Thr Phe Val Arg Trp Pro
                420                 425                 430
Gly Glu Ile Ser Gly Ser Asp Ser Trp Arg Ala Pro Met Phe Ser Trp
                435                 440                 445
Thr His Arg Ser Ala Thr Pro Thr Asn Thr Ile Asp Pro Glu Arg Ile
                450                 455                 460
Thr Gln Ile Pro Leu Thr Lys Ser Thr Asn Leu Gly Ser Gly Thr Ser
465                 470                 475                 480
Val Val Lys Gly Pro Gly Phe Thr Gly Gly Asp Ile Leu Arg Arg Thr
                485                 490                 495
Ser Pro Gly Gln Ile Ser Thr Leu Arg Val Asn Ile Thr Ala Pro Leu
                500                 505                 510
Ser Gln Arg Tyr Arg Val Arg Ile Arg Tyr Ala Ser Thr Thr Asn Leu
                515                 520                 525
Gln Phe His Thr Ser Ile Asp Gly Arg Pro Ile Asn Gln Gly Asn Phe
                530                 535                 540
Ser Ala Thr Met Ser Ser Gly Ser Asn Leu Gln Ser Gly Ser Phe Arg
545                 550                 555                 560
Thr Val Gly Phe Thr Thr Pro Phe Asn Phe Ser Asn Gly Ser Ser Val
                565                 570                 575
Phe Thr Leu Ser Ala His Val Phe Asn Ser Gly Asn Glu Val Tyr Ile
                580                 585                 590
Asp Arg Ile Glu Phe Val Pro Ala Glu Val Thr Phe Glu Ala Glu Tyr
                595                 600                 605
Asp Leu Glu Arg Ala Gln Lys Ala Val Asn Ala Leu Phe Thr Ser Thr
                610                 615                 620
Asn Gln Leu Gly Leu Lys Thr Asn Val Thr Asp Tyr His Ile Asp Gln
625                 630                 635                 640
Val Ser Asn Leu Val Thr Tyr Leu Ser Asp Glu Phe Cys Leu Asp Glu
                645                 650                 655
Lys Arg Glu Leu Ser Glu Lys Val Lys His Ala Lys Arg Leu Ser Asp
                660                 665                 670
Glu Arg Asn Leu Leu Gln Asp Ser Asn Phe Lys Asp Ile Asn Arg Gln
                675                 680                 685
```

-continued

Pro Glu Arg Gly Trp Gly Gly Ser Thr Gly Ile Thr Ile Gln Gly Gly
690                 695                 700

Asp Asp Val Phe Lys Glu Asn Tyr Val Thr Leu Ser Gly Thr Phe Asp
705                 710                 715                 720

Glu Cys Tyr Pro Thr Tyr Leu Tyr Gln Lys Ile Asp Glu Ser Lys Leu
                725                 730                 735

Lys Ala Phe Thr Arg Tyr Gln Leu Arg Gly Tyr Ile Glu Asp Ser Gln
            740                 745                 750

Asp Leu Glu Ile Tyr Leu Ile Arg Tyr Asn Ala Lys His Glu Thr Val
        755                 760                 765

Asn Val Pro Gly Thr Gly Ser Leu Trp Pro Leu Ser Ala Gln Ser Pro
    770                 775                 780

Ile Gly Lys Cys Gly Glu Pro Asn Arg Cys Ala Pro His Leu Glu Trp
785                 790                 795                 800

Asn Pro Asp Leu Asp Cys Ser Cys Arg Asp Gly Glu Lys Cys Ala His
                805                 810                 815

His Ser His His Phe Ser Leu Asp Ile Asp Val Gly Cys Thr Asp Leu
            820                 825                 830

Asn Glu Asp Leu Gly Val Trp Val Ile Phe Lys Ile Lys Thr Gln Asp
        835                 840                 845

Gly His Ala Arg Leu Gly Asn Leu Glu Phe Leu Glu Glu Lys Pro Leu
    850                 855                 860

Val Gly Glu Ala Leu Ala Arg Val Lys Arg Ala Glu Lys Lys Trp Arg
865                 870                 875                 880

Asp Lys Arg Glu Lys Leu Glu Trp Glu Thr Asn Ile Val Tyr Lys Glu
                885                 890                 895

Ala Lys Glu Ser Val Asp Ala Leu Phe Val Asn Ser Gln Tyr Asp Gln
            900                 905                 910

Leu Gln Ala Asp Thr Asn Ile Ala Met Ile His Ala Ala Asp Lys Arg
        915                 920                 925

Val His Ser Ile Arg Glu Ala Tyr Leu Pro Glu Leu Ser Val Ile Pro
    930                 935                 940

Gly Val Asn Ala Ala Ile Phe Glu Glu Leu Glu Gly Arg Ile Phe Thr
945                 950                 955                 960

Ala Phe Ser Leu Tyr Asp Ala Arg Asn Val Ile Lys Asn Gly Asp Phe
                965                 970                 975

Asn Asn Gly Leu Ser Cys Trp Asn Val Lys Gly His Val Asp Val Glu
            980                 985                 990

Glu Gln Asn Asn Gln Arg Ser Val Leu Val Val Pro Glu Trp Glu Ala
        995                 1000                1005

Glu Val Ser Gln Glu Val Arg Val Cys Pro Gly Arg Gly Tyr Ile
    1010                1015                1020

Leu Arg Val Thr Ala Tyr Lys Glu Gly Tyr Gly Glu Gly Cys Val
    1025                1030                1035

Thr Ile His Glu Ile Glu Asn Asn Thr Asp Glu Leu Lys Phe Ser
    1040                1045                1050

Asn Cys Val Glu Glu Glu Ile Tyr Pro Asn Asn Thr Val Thr Cys
    1055                1060                1065

Asn Asp Tyr Thr Val Asn Gln Glu Glu Tyr Gly Gly Ala Tyr Thr
    1070                1075                1080

Ser Arg Asn Arg Gly Tyr Asn Glu Ala Pro Ser Val Pro Ala Asp
    1085                1090                1095

-continued

| Tyr | Ala | Ser | Val | Tyr | Glu | Glu | Lys | Ser | Tyr | Thr | Asp | Gly | Arg | Arg |
| | 1100 | | | | | 1105 | | | | | 1110 | | | |
| Glu | Asn | Pro | Cys | Glu | Phe | Asn | Arg | Gly | Tyr | Arg | Asp | Tyr | Thr | Pro |
| | 1115 | | | | | 1120 | | | | | 1125 | | | |
| Leu | Pro | Val | Gly | Tyr | Val | Thr | Lys | Glu | Leu | Glu | Tyr | Phe | Pro | Glu |
| | 1130 | | | | | 1135 | | | | | 1140 | | | |
| Thr | Asp | Lys | Val | Trp | Ile | Glu | Ile | Gly | Glu | Thr | Glu | Gly | Thr | Phe |
| | 1145 | | | | | 1150 | | | | | 1155 | | | |
| Ile | Val | Asp | Ser | Val | Glu | Leu | Leu | Leu | Met | Glu | Glu | | | |
| | 1160 | | | | | 1165 | | | | | 1170 | | | |

CHIMERIC INSECTICIDAL PROTEINS TOXIC OR INHIBITORY TO LEPIDOPTERAN PESTS

REFERENCE TO RELATED APPLICATION

This application is a continuation of U.S. patent application Ser. No. 14/884,469, filed Oct. 15, 2015, which claims the benefit of U.S. provisional application No. 62/064,989, filed Oct. 16, 2014, each of which are herein incorporated by reference in their entireties.

INCORPORATION OF SEQUENCE LISTING

A computer readable form of the Sequence Listing is filed with this application by electronic submission and is incorporated into this application by reference in its entirety. The Sequence Listing is contained in the file created on Dec. 11, 2017, having the file name P34230US05_SEQ.txt, and which is 371,792 bytes in size (as measured in the MS-Windows® operating system).

FIELD OF THE INVENTION

The invention generally relates to the field of insect inhibitory proteins. A novel class of chimeric insecticidal proteins exhibiting insect inhibitory activity against agriculturally-relevant pests of crop plants and seeds is disclosed in this application. In particular, the disclosed class of proteins exhibits insecticidal activity against the Lepidopteran order of insect pests. Plants, plant parts, and seeds containing a recombinant nucleic acid molecule encoding one or more of the disclosed toxin proteins are provided.

BACKGROUND OF THE INVENTION

Improving crop yield from agriculturally-significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts with respect to food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera, are considered a major cause of damage to field crops, thereby decreasing crop yields in infested areas. Lepidopteran pest species which negatively impact agriculture include, but are not limited to, fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Chrysodeixis includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*), European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*), codling moth (*Cydia pomonella*), grape berry moth (*Endopiza viteana*), oriental fruit moth (*Grapholita molesta*), sunflower bud moth (*Suleima helianthana*), diamondback moth (*Plutella xylostella*), pink bollworm (*Pectinophora gossypiella*), pink stem borer (*Sesamia inferens*), gypsy moth (*Lymantria dispar*), cotton leaf worm (*Alabama argillacea*), fruit tree leaf roller (*Archips argyrospila*), European leafroller (*Archips rosana*), Asiatic rice borer, or rice stem borer (*Chilo suppressalis*), rice leaf roller (*Cnaphalocrocis medinalis*), corn root webworm (*Crambus caliginosellus*), bluegrass webworm (*Crambus teterrellus*), southwestern corn borer (*Diatraea grandiosella*)), sugarcane borer (*Diatraea saccharalis*), spiny bollworm (*Earias insulana*), spotted bollworm (*Earias vittella*), Old World cotton bollworm (*Helicoverpa armigera*), corn earworm, soy podworm or cotton bollworm (*Helicoverpa zea*), sod webworm (*Herpetogramma licarsisalis*), European grape vine moth (*Lobesia botrana*), citrus leafminer (*Phyllocnistis citrella*), large white butterfly (*Pieris brassicae*), imported cabbageworm, or small white butterfly (*Pieris rapae*), tobacco cutworm, or cluster caterpillar (*Spodoptera litura*), and tomato leafminer (*Tuta absoluta*).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for insecticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of other bacterial species, such as *Brevibacillus laterosporus*, *Lysinibacillus sphaericus* ("Ls" formerly known as *Bacillus sphaericus*) and *Paenibacillus popilliae*.

Crystalline and secreted soluble insecticidal protein toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal proteins has been globally adopted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal proteins used in these crops has created a selection pressure for existing insect alleles that impart resistance to the currently-utilized insecticidal proteins.

The development of resistance in target pests to insecticidal proteins creates the continuing need for discovery and development of new forms of insecticidal proteins that are useful for managing the increase in insect resistance to transgenic crops expressing insecticidal proteins. New insecticidal proteins with improved efficacy and which exhibit control over a broader spectrum of susceptible insect species will reduce the number of surviving insects which can develop resistance alleles. In addition, the use in one plant of two or more transgenic insecticidal proteins toxic to the same insect pest and displaying different modes of action reduces the probability of resistance in any single target insect species.

Consequently, there is a critical need to identify additional insecticidal proteins with improved insecticidal properties such as increased efficacy against a broader spectrum of target insect pests species and different modes of action compared to the toxins currently used in agricultural practices. To meet this need, the present invention discloses novel Cry1 chimeric insecticidal proteins that exhibit activity against significant target Lepidopteran pest species.

Members of the family of Cry1 crystal proteins are known in the art to exhibit bioactivity against Lepidopteran pests. The precursor form of Cry 1 crystal proteins consists of two approximately equal-sized segments. The carboxy-terminal portion of the precursor protein, known as the protoxin segment, stabilizes crystal formation and exhibits no insecticidal activity. The amino-terminal half of the precursor protein comprises the toxin segment of the Cry1 protein and, based on alignment of conserved or substantially conserved sequences within Cry1 family members, can be further sub-divided into three structural domains, domain I, domain II, and domain III. Domain I comprises about the first third of the active toxin segment and has been shown to be essential for channel formation. Domains II and III have both been implicated in receptor binding and insect species specificity, depending on the insect and insecticidal protein being examined.

The likelihood of arbitrarily creating a chimeric protein with enhanced properties from the assortment of the domain structures of the numerous native insecticidal proteins known in the art is remote. This is a result of the complex nature of protein structure, oligomerization, and activation (including correct proteolytic processing of the chimeric precursor, if expressed in such a form) required to release an insecticidal protein segment. Only by careful selection of protoxins and specific targets within each parental protein for the creation of a chimeric structure can functional chimeric insecticidal toxins be constructed that exhibit improved insecticidal activity in comparison to the parental proteins from which the chimeras are derived. It is known in the art that reassembly of the protoxin and toxin domains I, II and III of any two or more toxins that are different from each other often results in the construction of proteins that exhibit faulty crystal formation or the complete lack of any detectable insecticidal activity directed to a preferred target insect pest species. Only by trial and error are effective insecticidal chimeras designed, and even then, the skilled artisan is not certain to end up with a chimera that exhibits insecticidal activity that is equivalent to or improved in comparison to any single parental toxin protein from which the constituent protoxin or toxin domains of the chimera may have been derived. For example, the literature reports numerous examples of the construction or assembly of chimeric proteins from two or more crystal protein precursors. See, e.g. Jacqueline S. Knight, et al. "A Strategy for Shuffling Numerous *Bacillus thuringiensis* Crystal Protein Domains." *J. Economic Entomology,* 97 (6) (2004): 1805-1813; Bosch, et al. (U.S. Pat. No. 6,204,246); Malvar and Gilmer (U.S. Pat. No. 6,017,534). In each of these examples, many of the resultant chimeras failed to exhibit insecticidal or crystal forming properties that were equivalent to or improved in comparison to the precursor proteins from which the components of the chimeras were derived.

SUMMARY OF THE INVENTION

Recombinant nucleic acid molecules are provided that encode chimeric insecticidal proteins toxic to Lepidopteran species of plant pests. Each of the chimeric insecticidal proteins can be used alone or in combination with each other and with other insecticidal proteins and insect inhibitory agents in formulations and in planta; thus providing alternatives to insecticidal proteins and insecticidal chemistries currently in use in agricultural systems.

In certain embodiments disclosed herein is a chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50 or 53. This chimeric insecticidal protein exhibits inhibitory activity against an insect species of the order Lepidoptera such as, but not limited to, *Anticarsia gemmatalis, Diatraea saccharalis, Elasmopalpus lignosellus, Helicoverpa zea, Heliothis virescens, Chrysodeixis includens, Spodoptera cosmioides, Spodoptera eridania, Spodoptera frugiperda, Spodoptera exigua, Helicoverpa armigera, Spodoptera litura, Pectinophora gossypiella, Diatraea grandiosella, Earias vitella, Helicoverpa gelotopeon,* and *Rachiplusia nu.*

In another embodiment, a polynucleotide encoding a chimeric insecticidal protein, wherein the polynucleotide is operably linked to a heterologous promoter and the chimeric insecticidal protein comprises the amino acid sequence as set forth in any of SEQ ID NOs: 21, 10, 28, 7, 4, 13, 16, 19, 23, 25, 30, 33, 36, 39, 41, 43, 45, 47, 50 or 53 is disclosed. A polynucleotide encoding a chimeric insecticidal protein, wherein the polynucleotide comprises a nucleotide sequence that optionally: hybridizes under stringent conditions to the reverse complement of the polynucleotide sequence as set forth in any of SEQ ID NOs:1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52; or encodes the chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50 or 53 is also contemplated.

In other embodiments disclosed herein is a host cell comprising the polynucleotide set forth in any of SEQ ID NO: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52, wherein the host cell is selected from the group consisting of a bacterial host cell or a plant host cell. Contemplated bacterial host include *Agrobacterium, Rhizobium, Bacillus, Brevibacillus, Escherichia, Pseudomonas, Klebsiella,* and *Erwinia;* and wherein the *Bacillus* species is a *Bacillus*

*cereus* or a *Bacillus thuringiensis*, said *Brevibacillus* is a *Brevibacillus laterosperous*, and said *Escherichia* is an *Escherichia coli*. Contemplated plant cells include monocots and dicots.

Other embodiments disclosed herein include insect inhibitory compositions comprising a chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50 or 53. In certain embodiments, the insect inhibitory composition further comprises at least one insect inhibitory agent different from the chimeric insecticidal protein. Contemplated insect inhibitory agents different from the chimeric insecticidal protein include an insect inhibitory protein, an insect inhibitory dsRNA molecule, and an insect inhibitory chemistry. These insect inhibitory agents different from the chimeric insecticidal protein can exhibit activity against one or more pest species of the orders Lepidoptera, Coleoptera, Hemiptera, Homoptera, or Thysanoptera.

In yet another embodiment, disclosed herein is a seed comprising an insect inhibitory effective amount of: a chimeric insecticidal protein comprising the amino acid sequence as set forth in any of SEQ ID NOs: 21, 10, 28, 7, 4, 13, 16, 19, 23, 25, 30, 33, 36, 39, 41, 43, 45, 47, 50 or 53; or a polynucleotide set forth in any of SEQ ID NOs:1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52.

Methods of controlling a Lepidopteran pest comprising contacting the Lepidopteran pest with an inhibitory amount of a chimeric insecticidal protein of the invention are also contemplated.

In another embodiment, disclosed herein is a transgenic plant cell, plant or plant part comprising a chimeric insecticidal protein, wherein: the chimeric insecticidal protein comprises any amino acid sequence set forth in any of SEQ ID NO: 21, 10, 28, 7, 4, 13, 16, 19, 23, 25, 30, 33, 36, 39, 41, 43, 45, 47, 50 or 53; or the chimeric insecticidal protein comprises a protein having: at least 94% identical to SEQ ID NOs:21, 10; at least 93% identical to SEQ ID NO:28 at least 87% identical to SEQ ID NO:7; at least 90% identity to SEQ ID NO:4; at least 91% identical to SEQ ID NO:13; at least 64% identical to SEQ ID NO:16; at least 66% identical to SEQ ID NO:19; at least 86% identical to SEQ ID NO:23; at least 91% identical to SEQ ID NO:25; at least 94% identical to SEQ ID NO:30; at least 91% identical to SEQ ID NO:33; at least 64% identical to SEQ ID NO:36; at least 66% identical to SEQ ID NO:39; at least 94% identical to SEQ ID NO:41; at least 84% identical to SEQ ID NO:43; at least 93% identical to SEQ ID NO:45; at least 94% identical to SEQ ID NO: 47; at least 91% identical to SEQ ID NO:50; or at least 93% identical to SEQ ID NO:53. Methods of controlling a Lepidopteran pest which comprise exposing the pest to this transgenic plant cell, plant or plant part, wherein said plant cell, plant or plant part expresses a Lepidopteran inhibitory amount of the chimeric insecticidal protein are also contemplated.

In other embodiments herein, commodity products derived from the plant cell, plant, or plant part wherein the product comprises a detectable amount of the chimeric insecticidal protein are provided. Contemplated commodity products include plant biomass, oil, meal, animal feed, flour, flakes, bran, lint, hulls, and processed seed.

Yet another method disclosed herein is a method of producing a seed comprising a chimeric insecticidal protein, the method comprising: planting at least one seed comprising a chimeric insecticidal protein; growing plants from said seed; and harvesting seed from said plants, wherein said harvested seed comprises the chimeric insecticidal protein.

Recombinant polynucleotide molecules encoding a chimeric insecticidal protein, comprising a nucleotide sequence selected from the group consisting of 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52; and optionally a polynucleotide sequence encoding an insect inhibitory agent different from the chimeric insecticidal protein are also contemplated herein.

Another recombinant nucleic acid molecule contemplated herein comprises a heterologous promoter operably linked to a polynucleotide segment encoding a chimeric insecticidal proteins, wherein: the chimeric insecticidal protein comprises any amino acid sequence set forth in any of SEQ ID NO: 21, 10, 28, 7, 4, 13, 16, 19, 23, 25, 30, 33, 36, 39, 41, 43, 45, 47, 50 or 53; or the chimeric insecticidal protein comprises a protein having: at least 94% identical to SEQ ID NOs:21, 10; at least 93% identical to SEQ ID NO:28; at least 87% identical to SEQ ID NO:7; at least 90% identity to SEQ ID NO:4; at least 91% identical to SEQ ID NO:13; at least 64% identical to SEQ ID NO:16; at least 66% identical to SEQ ID NO:19; at least 86% identical to SEQ ID NO:23; at least 91% identical to SEQ ID NO:25; at least 94% identical to SEQ ID NO:30; at least 91% identical to SEQ ID NO:33; at least 64% identical to SEQ ID NO:36; at least 66% identical to SEQ ID NO:39; at least 94% identical to SEQ ID NO:41; at least 84% identical to SEQ ID NO:43; at least 93% identical to SEQ ID NO:45; at least 94% identical to SEQ ID NO: 47; at least 91% identical to SEQ ID NO:50; or at least 93% identical to SEQ ID NO:53; or the polynucleotide segment hybridizes to a polynucleotide having a nucleotide sequence as set forth in any of SEQ ID NO: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52.

Other embodiments, features, and advantages of the invention will be apparent from the following detailed description, examples, and claims.

BRIEF DESCRIPTION OF THE SEQUENCES

SEQ ID SEQ ID NO: 1 is a recombinant DNA sequence encoding TIC1100 used for expression in a bacterial cell.

SEQ ID NO: 2 is a synthetic DNA sequence encoding TIC1100 for expression in a plant cell.

SEQ ID NO: 3 is a synthetic DNA sequence encoding TIC1100 for expression in a plant cell.

SEQ ID NO: 4 is the amino acid sequence of TIC1100.

SEQ ID NO: 5 is a recombinant DNA sequence encoding TIC860 used for expression in a bacterial cell.

SEQ ID NO: 6 is a synthetic DNA sequence encoding TIC860 for expression in a plant cell.

SEQ ID NO: 7 is the amino acid sequence of TIC860.

SEQ ID NO: 8 is a recombinant DNA sequence encoding TIC867 used for expression in a bacterial cell.

SEQ ID NO: 9 is a synthetic DNA sequence encoding TIC867 for expression in a plant cell.

SEQ ID NO: 10 is the amino acid sequence of TIC867.

SEQ ID NO: 11 is a recombinant DNA sequence encoding TIC867_20 used for expression in a bacterial cell.

SEQ ID NO: 12 is a synthetic DNA sequence encoding TIC867_20 for expression in a plant cell.

SEQ ID NO: 13 is the amino acid sequence of TIC867_20.

SEQ ID NO: 14 is a recombinant DNA sequence encoding TIC867_21 used for expression in a bacterial cell.

SEQ ID NO: 15 is a synthetic DNA sequence encoding TIC867_21 for expression in a plant cell.

SEQ ID NO: 16 is the amino acid sequence of TIC867_21.

SEQ ID NO: 17 is a recombinant DNA sequence encoding TIC867_22 used for expression in a bacterial cell.

SEQ ID NO: 18 is a synthetic DNA sequence encoding TIC867_22 for expression in a plant cell.

SEQ ID NO: 19 is the amino acid sequence of TIC867_22.

SEQ ID NO: 20 is a synthetic DNA sequence encoding TIC867_23 for expression in the plant cell.

SEQ ID NO: 21 is the amino acid sequence of TIC867_23.

SEQ ID NO: 22 is a synthetic DNA sequence encoding TIC867_24 for expression in a plant cell.

SEQ ID NO: 23 is the amino acid sequence of TIC867_24.

SEQ ID NO: 24 is a synthetic DNA sequence encoding TIC867_24 for expression in a plant cell.

SEQ ID NO: 25 is the amino acid sequence of TIC867_25.

SEQ ID NO: 26 is a recombinant DNA sequence encoding TIC868 used for expression in a bacterial cell.

SEQ ID NO: 27 is a synthetic DNA sequence encoding TIC868 for expression in a plant cell.

SEQ ID NO: 28 is the amino acid sequence of TIC868.

SEQ ID NO: 29 is a synthetic DNA sequence encoding TIC868_9 for expression in a plant cell.

SEQ ID NO: 30 is the amino acid sequence of TIC868_9.

SEQ ID NO: 31 is a recombinant DNA sequence encoding TIC868_10 used for expression in a bacterial cell.

SEQ ID NO: 32 is a synthetic DNA sequence for expression in the plant cell encoding the TIC868 variant, TIC868_10.

SEQ ID NO: 33 is the amino acid sequence of TIC868_10.

SEQ ID NO: 34 is a recombinant DNA sequence encoding TIC868_11 used for expression in a bacterial cell.

SEQ ID NO: 35 is a synthetic DNA sequence encoding TIC868_11 for expression in a plant cell.

SEQ ID NO: 36 is the amino acid sequence of TIC868_11.

SEQ ID NO: 37 is a recombinant DNA sequence encoding TIC868_12 used for expression in a bacterial cell.

SEQ ID NO: 38 is a synthetic DNA sequence encoding TIC868_12 for expression in the plant cell.

SEQ ID NO: 39 is the amino acid sequence of TIC868_12.

SEQ ID NO: 40 is a synthetic DNA sequence encoding TIC868_13 for expression in the plant cell.

SEQ ID NO: 41 is the amino acid sequence of TIC868_13.

SEQ ID NO: 42 is a synthetic DNA sequence encoding TIC868_14 for expression in a plant cell.

SEQ ID NO: 43 is the amino acid sequence of TIC868_14.

SEQ ID NO: 44 is a synthetic DNA sequence encoding TIC868_15 for expression in a plant cell.

SEQ ID NO: 45 is the amino acid sequence of TIC868_15.

SEQ ID NO: 46 is a synthetic DNA sequence encoding TIC868_29 for expression in a plant cell.

SEQ ID NO: 47 is the amino acid sequence of TIC868_29.

SEQ ID NO: 48 is a recombinant DNA sequence encoding TIC869 used for expression in a bacterial cell.

SEQ ID NO: 49 is a synthetic DNA sequence encoding TIC869 for expression in a plant cell.

SEQ ID NO: 50 is the amino acid sequence of TIC869.

SEQ ID NO: 51 is a recombinant DNA sequence encoding TIC836 used for expression in a bacterial cell.

SEQ ID NO: 52 is a synthetic DNA sequence encoding TIC836 for expression in a plant cell.

SEQ ID NO: 53 is the amino acid sequence of TIC836.

DETAILED DESCRIPTION OF THE INVENTION

The problem in the art of agricultural pest control can be characterized as a need for new insecticidal proteins that are efficacious against target pests, exhibit broad spectrum toxicity against target pest species, are capable of being expressed in plants without causing undesirable agronomic issues, and provide an alternative mode of action compared to current toxins that are used commercially in plants. Novel chimeric insecticidal proteins are disclosed herein, and address each of these needs, particularly against a broad spectrum of Lepidopteran insect pests.

In order to avoid the development of, or circumvent insect resistance against currently used insecticidal proteins, new insecticidal proteins with different modes-of-action (MOA), as well as a broad spectrum and efficacy, are needed for Lepidoptera control. One way to address this need is to discover new insecticidal proteins from different biological sources, preferably from bacteria, fungi or plants. Another approach is to interchange segments between various Bt proteins that exhibit structural similarities to create new chimeric Bt proteins having insect inhibitory properties. The likelihood of creating a chimeric protein with enhanced properties from the re-assortment of the domain structures of numerous native insecticidal crystal proteins known in the art is known in the art to be remote. See, e.g. Jacqueline S. Knight, et al. "A Strategy for Shuffling Numerous *Bacillus thuringiensis* Crystal Protein Domains." *J. Economic Entomology,* 97 (6) (2004): 1805-1813.

Disclosed herein are recombinant nucleic acid molecule sequences that encode novel chimeric insecticidal proteins. These insecticidal proteins address the ongoing need in the art to engineer additional toxic insecticidal proteins with improved insecticidal properties such as increased efficacy against a broader spectrum of target insect pests species and different modes of action. Members of this group of proteins, including the exemplary proteins disclosed herein, exhibit insecticidal activity against Lepidopteran insect pest species.

The term "segment" or "fragment" is used in this application to describe consecutive amino acid or nucleic acid sequences that are shorter than the complete amino acid or nucleic acid sequence describing a disclosed chimeric insecticidal protein. A segment or fragment exhibiting insect inhibitory activity is also disclosed in this application if alignment of such segment or fragment, with the corresponding section of the chimeric insecticidal protein, results in amino acid sequence identity of any fraction percentage from about 65 to about 100 percent between the segment or fragment and the corresponding section of the chimeric insecticidal protein.

Reference in this application to the terms "active" or "activity", "pesticidal activity" or "pesticidal", or "insecticidal activity", "insect inhibitory" or "insecticidal" refer to efficacy of a toxic agent, such as an insecticidal protein, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the insecticidal protein) or killing (causing the morbidity, mortality, or reduced fecundity of) a pest. These terms are intended to include the result of providing a pesticidally effective amount of an insecticidal protein to a pest where the exposure of the pest to the insecticidal protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the insecticidal protein in or on the plant. In general, pesticidal activity refers to the ability of an insecticidal protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera. The insecticidal protein can be produced by the plant or can be applied to the plant or to the environment within the location where the plant is located. The terms "bioactivity", "effective", "efficacious" or variations thereof are also terms interchangeably utilized in this application to describe the effects of the chimeric insecticidal proteins of the present invention on target insect pests.

A pesticidally effective amount of a toxic agent, when provided in the diet of a target pest, exhibits pesticidal activity when the toxic agent contacts the pest. A toxic agent can be an insecticidal protein or one or more chemical agents known in the art. Insecticidal chemical agents and insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Insecticidal protein agents include the chimeric insecticidal proteins set forth in this application, as well as other proteinaceous toxic agents including those that target Lepidopteran pest species, as well as protein toxins that are used to control other plant pests such as Cry proteins available in the art for use in controlling Coleopteran, Thysanopteranm, Hemipteran and Homopteran species.

It is intended that reference to a pest, particularly a pest of a crop plant, means insect pests of crop plants, particularly those Lepidopteran insect pests that are controlled by the disclosed chimeric insecticidal proteins. However, reference to a pest can also include Coleopteran, Hemipteran and Homopteran insect pests of plants, as well as nematodes and fungi when toxic agents targeting these pests are co-localized or present together with the chimeric insecticidal protein, or a protein that is 65 to about 100 percent identical to the chimeric insecticidal protein.

The chimeric insecticidal proteins disclosed herein exhibit insecticidal activity towards insect pests from the Lepidopteran insect species, including adults, pupae, larvae, and neonates, as well as Hemipteran insect species, including adults and nymphs. The insects of the order Lepidoptera include, but are not limited to, armyworms, cutworms, loopers, and heliothines in the Family Noctuidae, e.g., fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*) and gypsy moth (*Lymantria dispar*). Other insect pests of order Lepidoptera include, e.g., *Alabama argillacea* (cotton leaf worm), *Archips argyrospila* (fruit tree leaf roller), *Archips rosana* (European leafroller) and other *Archips* species, *Chilo suppressalis* (Asiatic rice borer, or rice stem borer), *Cnaphalocrocis medinalis* (rice leaf roller), *Crambus caliginosellus* (corn root webworm), *Crambus teterrellus* (bluegrass webworm), *Diatraea grandiosella* (southwestern corn borer), *Diatraea saccharalis* (surgarcane borer), *Earias insulana* (spiny bollworm), *Earias vittella* (spotted bollworm), *Helicoverpa armigera* (American bollworm), *Helicoverpa zea* (corn earworm or cotton bollworm), *Heliothis virescens* (tobacco budworm), *Herpetogramma licarsisalis* (sod webworm), *Lobesia botrana* (European grape vine moth), *Phyllocnistis citrella* (citrus leafminer), *Pieris brassicae* (large white butterfly), *Pieris rapae* (imported cabbageworm, or small white butterfly), *Plutella xylostella* (diamondback moth), *Spodoptera exigua* (beet armyworm), *Spodoptera litura* (tobacco cutworm, cluster caterpillar), and *Tuta absoluta* (tomato leafminer).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further in the Examples, through a chimeragenesis effort about eight hundred and forty four (844) nucleotide sequences that encode chimeric insecticidal proteins were constructed from the protoxin and toxin domains of known insecticidal toxins (referred to herein as the "parent proteins"), and expressed and tested in bioassay for Lepidopteran activity. A small number of the constructed chimeric insecticidal proteins exhibited improved Lepidopteran activity or an enhanced Lepidopteran spectrum compared to the parent proteins from which its toxin components were derived.

These novel chimeric insecticidal proteins with improved Lepidopteran activity or an enhanced Lepidopteran spectrum were constructed from the following insecticidal parent protein protoxin and toxin domains: Cry1Ah (Domain I), Cry1Bb1 (Domains I and II), Cry1Be2 (Domains I and II), Cry1Ja1 (Domains I and II), Cry1Fa1 (Domains I and II), Cry1Ac (Domain II and protoxin), Cry1Ca (Domain III and protoxin), Cry1Ka (Domain III and protoxin), Cry1Jx (Domain III), Cry1Ab (Domain III), Cry1Ab3 (protoxin), Cry1Da1 (protoxin), Cry4 (protoxin), Cry9 (protoxin), Cry1Be (protoxin), and Cry1Ka (protoxin).

Specifically, the novel chimeric insecticidal proteins of this invention with improved Lepidopteran activity or an enhanced Lepidopteran spectrum comprise the following protoxin and domain combinations: TIC1100/SEQ ID NO:4 (Domain I— Cry1Ah, Domain II— Cry1Ac, Domain III— Cry1Ca, Protoxin-Cry1Ac), TIC860/SEQ ID NO:7 (Domain I— Cry1Bb1, Domain II— Cry1BB1, Domain III— Cry1Ca, Protoxin-Cry1Ac), TIC867/SEQ ID NO:10 (Domain I-Cry1Be2, Domain II— Cry1Be2, Domain III-Cry1Ka, Protoxin-Cry1Ab3), TIC868/SEQ ID NO:28 (Domain I— Cry1Be2, Domain II-Cry1Be2, and Domain III— Cry1Ca, Protoxin-Cry1Ab3), TIC869/SEQ ID NO:50 (Domain I-Cry1Ja1, Domain II— Cry1Ja1, Domain III-Cry1Jx, Protoxin-Cry1Ab3) and TIC836/SEQ ID NO:53 (Domain I-Cry1Fa1, Domain II-Cry1Fa1, Domain III— Cry1Ab, Protoxin-Cry1Ac).

Variants in which amino acid substitutions or alternate protoxin domains were introduced were also constructed for the chimeric insecticidal proteins TIC867 and TIC868. Specifically, these variants of TIC867 and TIC868 comprise the following amino acid substitutions or alternate protoxin domains: TIC867_20/SEQ ID NO:13 (alternate protoxin domain Cry1Da1), TIC867_21/SEQ ID NO:16 (alternate protoxin domain Cry4), TIC867_22/SEQ ID NO:19 (alternate protoxin domain Cry9), TIC867_23/SEQ ID NO:21 (alternate protoxin domain Cry1Be), TIC867_24/SEQ ID NO:23 (alternate protoxin domain Cry1Ka), TIC867_25/ SEQ ID NO: 25 (alternate protoxin domain Cry1Ka), TIC868_9/SEQ ID NO:30 (amino acid modification N240S_Y343Q_N349T), TIC868_10/SEQ ID NO:33 (alternate protoxin domain Cry1Da1), TIC868_11/SEQ ID NO:36 (alternate protoxin domain Cry4), TIC868_12/SEQ ID NO:39 (alternate protoxin domain Cry 9), TIC868_13/SEQ ID NO:41 (alternate protoxin domain Cry1Be), TIC868_14/ SEQ ID NO:43 (alternate protoxin domain Cry1Ka), TIC868_15/SEQ ID NO:45 (alternate protoxin domain Cry1Ca), and TIC868_29/SEQ ID NO:47 (amino acid modification Q136Y_Y343Q_N349T).

As demonstrated in the Examples, each of these TIC867 and TIC868 variants altered the Lepidopteran activity and/or reduced the Lepidopteran activity spectrum of the parent chimeric insecticidal protein, thus indicating that the alternate protoxin domain and the amino acid substitutions had a direct consequence on the insecticidal activity and spectrum of the chimeric insecticidal proteins TIC867 and TIC868.

Many of the chimeric insecticidal proteins demonstrate insecticidal activity against multiple Lepidopteran insect pest species. Specifically, the novel chimeric insecticidal proteins disclosed in this application exhibited activity against one or more of the following Lepidopteran insect pests, Velvet bean caterpillar (VBC, *Anticarsia gemmatalis*), Sugarcane borer (SCB, *Diatraea saccharalis*), Lesser cornstalk borer (LSCB, *Elasmopalpus lignosellus*), Corn earworm (CEW, *Helicoverpa zea*), Soybean pod worm (SPW, *Helicoverpa zea*), Cotton bollworm (CBW, *Helicoverpa zea*), Tobacco budworm (TBW, *Heliothis virescens*), Soybean looper (SBL, *Chrysodeixis includens*), Black armyworm (BLAW, *Spodoptera cosmioides*), Southern armyworm (SAW, *Spodoptera eridania*), Fall armyworm (FAW, *Spodoptera frugiperda*), Beet armyworm (BAW, *Spodoptera exigua*), Old World bollworm (OBW, *Helicoverpa armigera*), Oriental leafworm (OLW, *Spodoptera litura*), Pink bollworm (PBW, *Pectinophora gossypiella*), Southwestern Corn Borer (SWCB, *Diatraea grandiosella*), Spotted bollworm (SBW, *Earias vitella*), American bollworm (SABW, *Helicoverpa gelotopeon*), and Sunflower looper (SFL, *Rachiplusia nu*). Thus, the exemplary proteins described in this application are related by common function and exhibit insecticidal activity towards insect pests from the Lepidoptera insect species including adults, larvae and pupae.

Proteins that resemble the chimeric insecticidal proteins can be identified by comparison to each other using various computer based algorithms known in the art. For example, amino acid sequence identities of proteins related to the chimeric insecticidal proteins can be analyzed using a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of the subject protein). Other alignment algorithms are also available in the art, provide results similar to those obtained using Clustal W alignment and are contemplated in this application.

It is intended that a query protein exhibiting insect inhibitory activity is disclosed in this application if alignment of such query protein with the subject chimeric insecticidal proteins set forth in SEQ ID NOs: 4, 7, 10, 13, 16, 19, 21, 23, 25, 28, 30, 33, 36, 39, 41, 43, 45, 47, 50 and 53 and results in at least about 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% amino acid sequence identity (or any fraction percentage in this range) between the query and subject protein.

As described further in the Examples of this application, synthetic or artificial sequences encoding the chimeric insecticidal proteins were designed for use in plants. Exemplary synthetic nucleotide sequences that were designed for use in plants are set forth in SEQ ID NOs: 2 and 3 (TIC1100), SEQ ID NO:6 (TIC860), SEQ ID NO:9 (TIC867), SEQ ID NO:12 (TIC867_20), SEQ ID NO:15 (TIC867_21), SEQ ID NO:18 (TIC867_22), SEQ ID NO:20 (TIC867_23), SEQ ID NO:22 (TIC867_24), SEQ ID NO: 24 (TIC867_25), SEQ ID NO:27

(TIC868), SEQ ID NO:29 (TIC868_9), SEQ ID NO:32 (TIC868_10), SEQ ID NO:35 (TIC868_11), SEQ ID NO:38 (TIC868_12), SEQ ID NO:40 (TIC868_13), SEQ ID NO:42 (TIC868_14), SEQ ID NO:44 (TIC868_15), SEQ ID NO:46 (TIC868_29), SEQ ID NO:49 (TIC869) and SEQ ID NO:52 (TIC836).

For expression in plant cells, the chimeric insecticidal proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the chimeric insecticidal proteins to the chloroplast, a sequence encoding a chloroplast transit peptide is placed 5' in operable linkage and in frame to a synthetic coding sequence encoding the chimeric insecticidal protein that has been designed for optimal expression in plant cells.

Expression cassettes and vectors containing these synthetic or artificial nucleotide sequences were constructed and introduced into corn, cotton, and soybean plant cells in accordance with transformation methods and techniques which are known in the art. Transformed cells were regenerated into transformed plants that were observed to be expressing the chimeric insecticidal protein. To test pesticidal activity, bioassays were performed in the presence of Lepidopteran pest larvae using plant leaf disks obtained from the transformed plants. Recombinant nucleic acid molecule compositions that encode the chimeric insecticidal proteins are contemplated. For example, the chimeric insecticidal proteins can be expressed with recombinant DNA constructs in which a polynucleotide molecule with an ORF encoding a chimeric insecticidal protein is operably linked to genetic expression elements such as a promoter and any other regulatory element necessary for expression in the system for which the construct is intended. Non-limiting examples include a plant-functional promoter operably linked to the synthetic chimeric insecticidal protein encoding sequences for expression of the chimeric insecticidal protein in plants or a Bt-functional promoter operably linked to a chimeric insecticidal protein encoding sequence for expression of the protein in a Bt bacterium or other *Bacillus* species. Other elements can be operably linked to the chimeric insecticidal proteins encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites.

Exemplary recombinant polynucleotide molecules provided herein include, but are not limited to, a heterologous promoter operably linked to a polynucleotide such as SEQ ID NOs: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51, and 52, that encodes the polypeptide or protein having the amino acid sequence as set forth in SEQ ID NOs: 4 (TIC1100), 7 (TIC860), 10 (TIC867), 13 (TIC867_20), 16 (TIC867_21), 19 (TIC867_22), 21 (TIC867_23), 23 (TIC867_24), 25 (TIC867_25), 28 (TIC868), 30 (TIC868_9), 33 (TIC868_10), 36 (TIC868_11), 39 (TIC867_12), 41 (TIC867_13), 43 (TIC867_14), 45 (TIC867_15), 47 (TIC867_29), 50 (TIC869) and 53 (TIC836). A heterologous promoter can also be operably linked to synthetic DNA coding sequences encoding a plastid targeted chimeric insecticidal protein and untargeted chimeric insecticidal protein. It is contemplated that the codons of a recombinant nucleic acid molecule encoding for a chimeric insecticidal protein disclosed herein can be substituted by synonymous codons (known in the art as a silent substitution).

A recombinant DNA molecule or construct comprising a chimeric insecticidal protein encoding sequence can further comprise a region of DNA that encodes for one or more toxic agents which can be configured to concomitantly express or co-express with a DNA sequence encoding a chimeric insecticidal protein, a protein different from a chimeric insecticidal protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA molecule or construct can be assembled so that all proteins or dsRNA molecules are expressed from one promoter or each protein or dsRNA molecule is under separate promoter control or some combination thereof. The proteins of this invention can be expressed from a multi-gene expression system in which a chimeric insecticidal protein is expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes, each expressing a different protein or other toxic agent such as one or more dsRNA molecules.

Recombinant nucleic acid molecules or recombinant DNA constructs comprising chimeric insecticidal protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a chimeric insecticidal protein encoding sequence in a host cell, or subsequent expression of the encoded polypeptide. An exogenous recombinant polynucleotide or recombinant DNA construct that comprises chimeric insecticidal protein sequence encoding sequence and that is introduced into a host cell is referred herein as a "transgene".

Transgenic bacteria, transgenic plant cells, transgenic plants, and transgenic plant parts that contain a polynucleotide that encodes any one or more of the chimeric insecticidal proteins are provided herein. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a dicotyledonous cell or a monocotyledonous cell. Contemplated plants and plant cells include, but are not limited to, alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise Lepidoptera-inhibitory amounts of a chimeric insecticidal proteins are provided. Such plants can be made by introducing a polynucleotide that encodes the chimeric insecticidal proteins provided in this application into a plant cell, and selecting a plant derived from said plant cell that expresses an insect or Lepidoptera-inhibitory amount of the chimeric insecticidal protein. Plants can be derived from the plant cells by regeneration, seed, pollen, or meristem transformation techniques. Methods for transforming plants are known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), and 2008/0256667 (cotton).

Plants expressing the chimeric insecticidal proteins can be crossed by breeding with transgenic events expressing other insecticidal proteins and/or expressing other transgenic traits such as other insect control traits, herbicide tolerance genes, genes conferring yield or stress tolerance traits, and the like, or such traits can be combined in a single vector so that the traits are all linked.

Processed plant products, wherein the processed product comprises a detectable amount of a chimeric insecticidal protein, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a chimeric insecticidal protein.

Methods of controlling insects, in particular Lepidoptera infestations of crop plants, with the chimeric insecticidal proteins are also disclosed in this application. Such methods can comprise growing a plant comprising an insect- or Lepidoptera-inhibitory amount of the chimeric insecticidal protein. In certain embodiments, such methods can further comprise any one or more of: (i) applying any composition comprising or encoding a chimeric insecticidal protein to a plant or a seed that gives rise to a plant; and (ii) transforming a plant or a plant cell that gives rise to a plant with a polynucleotide encoding a chimeric insecticidal protein. In general, it is contemplated that chimeric insecticidal protein can be provided in a composition, provided in a microorganism, or provided in a transgenic plant to confer insect inhibitory activity against Lepidopteran insects.

In certain embodiments, the chimeric insecticidal protein is the insecticidally active ingredient of an insect inhibitory composition prepared by culturing recombinant *Bacillus* or any other recombinant bacterial cell transformed to express a chimeric insecticidal protein under conditions suitable for expression. Such a composition can be prepared by desiccation, lyophilization, homogenization, extraction, filtration, centrifugation, sedimentation, or concentration of a culture of such recombinant cells expressing/producing the chimeric insecticidal protein. Such a process can result in a *Bacillus* or other entomopathogenic bacterial cell extract, cell suspension, cell homogenate, cell lysate, cell supernatant, cell filtrate, or cell pellet. By obtaining the chimeric insecticidal protein so produced, a composition that includes the chimeric insecticidal protein can include bacterial cells, bacterial spores, and parasporal inclusion bodies and can be formulated for various uses, including as agricultural insect inhibitory spray products or as insect inhibitory formulations in diet bioassays.

The aforementioned compound or formulation can further comprise an agriculturally-acceptable carrier, such as a bait, a powder, dust, pellet, granule, spray, emulsion, a colloidal suspension, an aqueous solution, a *Bacillus* spore or crystal preparation or a seed treatment. The compound or formulation can also further comprise a recombinant plant cell, plant tissue, seed or plant transformed to express one or more of the proteins; or bacterium transformed to express one or more of the proteins. Depending on the level of insect inhibitory or insecticidal inhibition inherent in the recombinant polypeptide and the level of compound or formulation to be applied to a plant or diet assay, the compound or formulation can include various by weight amounts of the recombinant polypeptide, e.g. from 0.0001% to 0.001% to 0.01% to 1% to 99% by weight of the recombinant polypeptide.

In an embodiment, in order to reduce the likelihood of resistance development, an insect inhibitory composition or transgenic plant comprising a chimeric insecticidal protein can further comprise at least one additional toxic agent that exhibits insect inhibitory activity against the same Lepidopteran insect species, but which is different from the chimeric insecticidal protein. Possible additional toxic agents for such a composition include an insect inhibitory protein and an insect inhibitory dsRNA molecule. One example for the use of such ribonucleotide sequences to control insect pests is described in Baum, et al. (*U.S. Patent Publication 2006/0021087 A1*). Such additional polypeptide (s) for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. Patent Publication Ser. No. 10/525,318), Cry1C (U.S. Pat. No. 6,033,874), Cry1D, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and the like.

In other embodiments, an insect inhibitory composition or transgenic plant can further comprise at least one additional toxic agent that exhibits insect inhibitory activity to an insect pest that is not inhibited by the chimeric insecticidal proteins of the present invention (such as Coleopteran, Hemipteran and Homopteran pests), in order to expand the spectrum of insect inhibition obtained.

Such additional toxic agent for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), axmi207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1), and $\overline{\omega}$-Hexatoxin-Hv1a (U.S. Patent Application Publication US2014-0366227 A1).

Such additional toxic agent for the control of Hemipteran pests may be selected from the group consisting of Hemipteran-active proteins such as, but not limited to, TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Additional polypeptides for the control of Coleopteran, Lepidopteran, and Hemipteran insect pests can be found on the *Bacillus thuringiensis* toxin nomenclature web site maintained by Neil Crickmore (on the world wide web at btnomenclature.info).

Chimeric insecticidal protein-encoding sequences and sequences having a substantial percentage identity to the chimeric insecticidal proteins can be identified using methods known to those of ordinary skill in the art such as polymerase chain reaction (PCR), thermal amplification and hybridization. For example, the chimeric insecticidal proteins can be used to produce antibodies that bind specifically to related proteins, and can be used to screen for and to find other proteins that are closely related.

Furthermore, nucleotide sequences encoding the chimeric insecticidal proteins can be used as probes and primers for screening to identify other members of the class using thermal-cycle or isothermal amplification and hybridization methods. For example, oligonucleotides derived from sequences as set forth in SEQ ID NO:2 can be used to determine the presence or absence of a chimeric insecticidal transgene in a deoxyribonucleic acid sample derived from a commodity product. Given the sensitivity of certain nucleic acid detection methods that employ oligonucleotides, it is anticipated that oligonucleotides derived from sequences as set forth in any of SEQ ID NO:2 can be used to detect the respective chimeric insecticidal protein in commodity products derived from pooled sources where only a fraction of the commodity product is derived from a transgenic plant containing any of SEQ ID NO:2.

EXAMPLES

In view of the foregoing, those of skill in the art will appreciate that the following disclosed embodiments are merely representative of the invention, which may be embodied in various forms. Thus, specific structural and functional details disclosed herein are not to be interpreted as limiting.

Example 1

Creation and Cloning of Lepidopteran-active Novel Chimeric Insecticidal Protein Coding Sequences This Example illustrates the creation of the novel chimeric insecticidal proteins and the cloning and expressing of the chimeric insecticidal proteins.

Recombinant nucleic acid sequences were constructed from known Cry protein genes to produce polynucleotide sequences encoding novel chimeric insecticidal proteins. The resulting polynucleotide sequences were cloned into a *Bacillus thuringiensis* (Bt) expression plasmid vector. After confirmation of the polynucleotide sequence, the expression plasmid was transformed into Bt and expressed. Preparations of the expressed novel chimeric proteins were assayed for activity against various Lepidopteran pests.

Many polynucleotide sequences encoding chimeric insecticidal proteins were produced and tested in bioassay. Not all of the chimeric insecticidal proteins demonstrated activity. Only a few of the chimeric insecticidal proteins were selected based upon their activity to specific Lepidoptera demonstrated in bioassay. Amino acid variants in which amino acid substitutions, or alternate protoxin domains, were introduced were also produced based upon the original chimeric insecticidal proteins TIC867 and TIC868. The components of the chimeric insecticidal proteins (domains I, II and III and the protoxin) of the present invention are presented in Table 1. The amino acid substitutions in the TIC868 variants relative to the original TIC868 protein sequence are also presented.

TABLE 1

Novel chimeric pesticidal proteins and their components.

| Toxin | PRT SEQ ID NO: | Dom1 | Dom2 | Dom3 | Protox | Amino Acid Modifications* |
|---|---|---|---|---|---|---|
| TIC1100 | 4 | Cry1Ah | Cry1Ac | Cry1Ca | Cry1Ac | |
| TIC860 | 7 | Cry1Bb1 | Cry1Bb1 | Cry1Ca | Cry1Ac | |
| TIC867 | 10 | Cry1Be2 | Cry1Be2 | Cry1Ka | Cry1Ab3 | |
| TIC867_20 | 13 | Cry1Be2 | Cry1Be2 | Cry1Ka | Cry1Da1 | |
| TIC867_21 | 16 | Cry1Be2 | Cry1Be2 | Cry1Ka | Cry4 | |
| TIC867_22 | 19 | Cry1Be2 | Cry1Be2 | Cry1Ka | Cry9 | |
| TIC867_23 | 21 | Cry1Be2 | Cry1Be2 | Cry1Ka | Cry1Be | |
| TIC867_24 | 23 | Cry1Be2 | Cry1Be2 | Cry1Ka | Cry1Ka | |
| TIC867_25 | 25 | Cry1Be2 | Cry1Be2 | Cry1Ka | Cry1Ca | |
| TIC868 | 28 | Cry1Be2 | Cry1Be2 | Cry1Ca | Cry1Ab3 | |
| TIC868_9 | 30 | Cry1Be2 | Cry1Be2 | Cry1Ca | Cry1Ab3 | N240S_Y343Q_N349T |
| TIC868_10 | 33 | Cry1Be2 | Cry1Be2 | Cry1Ca | Cry1Da1 | |
| TIC868_11 | 36 | Cry1Be2 | Cry1Be2 | Cry1Ca | Cry4 | |
| TIC868_12 | 39 | Cry1Be2 | Cry1Be2 | Cry1Ca | Cry9 | |
| TIC868_13 | 41 | Cry1Be2 | Cry1Be2 | Cry1Ca | Cry1Be | |
| TIC868_14 | 43 | Cry1Be2 | Cry1Be2 | Cry1Ca | Cry1Ka | |
| TIC868_15 | 45 | Cry1Be2 | Cry1Be2 | Cry1Ca | Cry1Ca | |
| TIC868_29 | 47 | Cry1Be2 | Cry1Be2 | Cry1Ca | Cry1Ab3 | Q136Y_Y343Q_N349T |
| TIC869 | 50 | Cry1Ja1 | Cry1Ja1 | Cry1Jx | Cry1Ab3 | |
| TIC836 | 53 | Cry1Fa1 | Cry1Fa1 | Cry1Ab | Cry1Ac | |

*The amino acid mutations are identified using the standard IUPAC amino acid code. See IUPAC-IUB Joint Commission on Biochemical Nomenclature. Nomenclature and Symbolism for Amino Acids and Peptides. Eur. J. Biochem. 138: 9-37 (1984). The first amino acid sequence abbreviation indicates the original amino acid in the given scaffold protein, the number represents the position of the amino acid, and the second amino acid sequence abbreviation indicates the amino acid placed in that position in the improved variant protein.

Example 2

The Novel Chimeric Insecticidal Proteins Demonstrate Activity Against Lepidopteran Pests This Example illustrates the testing of the chimeric insecticidal proteins described in Example 1 and the Lepidopteran activity observed for the chimeric insecticidal proteins.

Polynucleotide sequences encoding chimeric insecticidal proteins were expressed in Bt. The expressed chimeric insecticidal proteins were then assayed against a variety of Lepidoptera known to be pests of corn, sugarcane, soybean and cotton, as well as other crop plants. Specifically, the insecticidal proteins were assayed for activity against Velvetbean caterpillar (VBC, *Anticarsia gemmatalis*), Sugarcane borer (SCB, *Diatraea saccharalis*), Lesser cornstalk borer (LSCB, *Elasmopalpus lignosellus*), Corn earworm (CEW, *Helicoverpa zea*), Tobacco budworm (TBW, *Heliothis virescens*), Soybean looper (SBL, *Chrysodeixis includens*), Black armyworm (BLAW, *Spodoptera cosmioides*), Southern armyworm (SAW, *Spodoptera eridania*), Fall armyworm (FAW, *Spodoptera frupperda*), Beet armyworm (BAW, *Spodoptera exigua*), Old World bollworm (OBW, *Helicoverpa armigera*), Oriental leafworm (OLW, *Spodoptera litura*), Pink bollworm (PBW, *Pectinophora gossypiella*), Black cutworm (BCW, *Agrotis ipsilon*), Southwestern Corn Borer (SWCB, *Diatraea grandiosella*), Spotted bollworm (SBW, *Earias vitella*), and European corn borer (ECB, *Ostrinia nubilalis*). Corn earworm (CEW, *Helicoverpa zea*) is also referred to as Soybean pod worm (SPW) and Cotton bollworm (CBW). Activity was determined through a combination of mortality and stunting scores as well as MIC50 scores. MIC50 refers to a molt inhibition concentration wherein both the dead larvae and L1 larvae (larvae that failed to molt to second instars) are factored into the score. Table 2 shows the activity of each chimeric insecticidal protein. A '+' sign indicates activity observed to the specific insect pest.

TABLE 2

Bioassay activity against selected Lepidoptera.

| Toxin | PRT SEQ ID NO: | VBC | SCB | LSCB | CEW SPW CBW | BLAW | TBW | SBL | SAW | FAW | BAW | OBW | OLW | PBW | BCW | SWCB | ECB | SBW |
|---|---|---|---|---|---|---|---|---|---|---|---|---|---|---|---|---|---|---|
| TIC1100 | 4 | + | + |  |  | + |  | + |  | + |  | + | + |  |  |  |  |  |
| TIC860 | 7 | + | + | + |  | + | + | + | + | + | + | + | + |  |  | + |  | + |
| TIC867 | 10 | + | + |  |  | + |  | + |  | + | + | + | + |  |  | + |  |  |
| TIC867_20 | 13 |  |  |  |  |  |  |  |  |  |  |  |  |  |  |  |  |  |
| TIC867_21 | 16 |  |  |  | + |  |  |  |  |  |  |  |  |  |  |  |  |  |
| TIC867_22 | 19 |  |  |  | + |  |  |  |  | + |  |  |  |  |  |  |  |  |
| TIC868 | 28 | + | + |  |  | + |  | + |  | + | + |  | + | + |  | + |  | + |
| TIC868_10 | 33 |  |  |  |  |  |  |  |  | + |  |  |  |  |  |  |  |  |
| TIC868_11 | 36 |  |  |  |  |  |  |  |  | + |  |  |  |  |  |  |  |  |
| TIC868_12 | 39 |  |  |  |  |  |  |  |  | + |  |  |  |  |  |  |  |  |
| TIC869 | 50 | + | + |  |  |  |  | + |  | + |  |  |  |  |  | + |  |  |
| TIC836 | 53 | + |  |  |  | + |  | + | + | + |  |  |  |  |  |  |  |  |

As can be seen in Table 2 above, most of the chimeric insecticidal proteins exhibited activity against one or more Lepidopteran pest species.

Example 3

Synthesis of Genes Encoding Chimeric Insecticidal Proteins and for Expression in Plants This Example illustrates the synthesis of polynucleotides encoding the chimeric insecticidal proteins for expression in plants.

Synthetic coding sequences were constructed for use in expression of the chimeric insecticidal proteins in plants. The synthetic sequences were designed and synthesized according to methods generally described in U.S. Pat. No. 5,500,365, avoiding certain inimical problem sequences such as ATTTA and A/T rich plant polyadenylation sequences while preserving the amino acid sequence of the chimeric insecticidal protein. The nucleotide sequences for these genes encoding the chimeric insecticidal proteins for expression in plants are listed in Table 3.

TABLE 3

Polynucleotide Sequences Encoding Chimeric Insecticidal Proteins Designed for Use in Plants.

| Insecticidal Protein | DNA SEQ ID NO: | PRT SEQ ID NO: |
| --- | --- | --- |
| TIC1100 | 2 | 4 |
| TIC1100 | 3 | 4 |
| TIC860 | 6 | 7 |
| TIC867 | 9 | 10 |
| TIC867_20 | 12 | 13 |
| TIC867_21 | 15 | 16 |
| TIC867_22 | 18 | 19 |
| TIC867_23 | 20 | 21 |
| TIC867_24 | 22 | 23 |
| TIC867_25 | 24 | 25 |
| TIC868 | 27 | 28 |
| TIC868_9 | 29 | 30 |
| TIC868_10 | 32 | 33 |
| TIC868_11 | 35 | 36 |
| TIC868_12 | 38 | 39 |
| TIC868_13 | 40 | 41 |
| TIC868_14 | 42 | 43 |
| TIC868_15 | 44 | 45 |
| TIC868_29 | 46 | 47 |
| TIC869 | 49 | 50 |
| TIC836 | 52 | 53 |

Example 4

Expression Cassettes for the Expression of Chimeric Insecticidal Proteins in Plants This Example illustrates the construction of expression cassettes comprising polynucleotide sequences designed for use in plants which encode chimeric insecticidal proteins.

A variety of plant expression cassettes were constructed with the polynucleotide sequences encoding the chimeric insecticidal proteins designed for plant expression provided in Table 3. Such expression cassettes are useful for transient expression in plant protoplasts or transformation of plant cells. Typical expression cassettes were designed with respect to the eventual placement of the protein within the cell. One set of expression cassettes was designed in a manner to allow the protein to be translated and remain in the cytosol. Another set of expression cassettes was designed to have a transit peptide contiguous with the toxin protein to allow targeting to an organelle of the cell such as the chloroplast or plastid. All expression cassettes were designed to begin at the 5' end with a promoter, which can be comprised of multiple promoter elements, enhancer elements, or other expression elements known to those of ordinary skill in the art operably linked to boost the expression of the transgene. The promoter sequence was usually followed contiguously with one or more leader sequences 3' to the promoter. An intron sequence was usually provided 3' to the leader sequence to improve expression of the transgene. A coding sequence for the toxin or transit peptide and coding sequence for the toxin was usually located 3' to the operably linked promoter, leader and intron configuration. A 3'UTR sequence was usually provided 3' of the coding sequence to facilitate termination of transcription and to provide sequences important for the polyadenylation of the resulting transcript. All of the elements described above were operably linked and arranged sequentially, often with additional sequences provided for the construction of the expression cassette.

Example 5

Lepidopteran Activity of the Chimeric Insecticidal Proteins in Stably Transformed Corn This Example illustrates the inhibitory activity exhibited by the chimeric insecticidal proteins against Lepidopteran pests when expressed in corn plants and provided as a diet to the respective corn insect pest.

Corn variety LH244 was transformed with the binary transformation vectors described in Example 4 using an *Agrobacterium*-mediated transformation method. The transformed cells were induced to form plants by methods known in the art. Bioassays using plant leaf disks were performed analogous to those described in U.S. Pat. No. 8,344,207. A non-transformed LH244 plant was used to obtain tissue to be used as a negative control. Multiple transformation events from each binary vector were assessed against Corn earworm (CEW, *Helicoverpa zea*), Fall armyworm (FAW, *Spodoptera frupperda*), Black cutworm (BCW, *Agrotis ipsilon*) and Southwestern Corn Borer (SWCB, *Diatraea grandiosella*).

Leaf disc bioassay was performed on $R_0$ and $F_1$ generation transgenic plants. In addition, leaf damage ratings were assessed for whole transgenic $F_1$ plants expressing certain chimeric insecticidal proteins infested with the Lepidopteran insect pests. $F_1$ transgenic events expressing TIC860 and TIC868 were also assessed for activity in the field against FAW, CEW, and SWCB. The assay results are shown in Table 4. A '+' sign indicates activity observed to the specific insect pest. As can be seen in Table 4, most of the chimeric insecticidal proteins and many of the chimeric insecticidal protein variants demonstrated activity against one or more Lepidopteran pest species.

TABLE 4

Bioassay activity of chimeric insecticidal proteins from stably transformed corn leaf tissue.

| Toxin | PRT SEQ ID NO: | VBC | SCB | LSCB | CEW SPW CBW | BLAW | TBW | SBL | SAW | FAW | BAW | OBW | OLW | PBW | BCW | SWCB | ECB | SBW |
|---|---|---|---|---|---|---|---|---|---|---|---|---|---|---|---|---|---|---|
| TIC1100 | 4 | + | + | | | + | | | + | | + | | + | + | | | | |
| TIC860 | 7 | + | + | + | | + | + | + | + | + | + | | + | + | | + | | + |
| TIC867 | 10 | + | + | | | + | | + | | + | + | + | | | | + | | |
| TIC867_20 | 13 | NT | NT | NT | | NT | NT | NT | NT | | NT | NT | NT | NT | NT | NT | NT | NT |
| TIC867_21 | 16 | NT | NT | NT | + | NT | NT | NT | NT | | NT | NT | NT | NT | NT | NT | NT | NT |
| TIC867_22 | 19 | NT | NT | NT | + | NT | NT | NT | NT | + | NT | NT | NT | NT | NT | NT | NT | NT |
| TIC868 | 28 | + | + | | | + | | + | + | + | | + | + | | + | | | + |
| TIC868_10 | 33 | NT | NT | NT | + | NT | NT | NT | NT | + | NT | NT | NT | NT | NT | NT | NT | NT |
| TIC868_11 | 36 | NT | NT | NT | + | NT | NT | NT | NT | + | NT | NT | NT | NT | NT | NT | NT | NT |
| TIC868_12 | 39 | NT | NT | NT | + | NT | NT | NT | NT | + | NT | NT | NT | NT | NT | NT | NT | NT |
| TIC869 | 50 | + | + | | | | | + | + | + | | | | | + | | | |
| TIC836 | 53 | + | | | | + | | + | + | + | | | | | | | | |

Example 6

Lepidopteran Activity of the Chimeric Insecticidal Proteins in Stably Transformed Soybean This Example illustrates the inhibitory activity exhibited by the chimeric insecticidal proteins against Lepidopteran pests when expressed in soybean plants and provided as a diet to the respective insect pest.

The coding sequences for selected chimeric insecticidal proteins were redesigned for plant expression, cloned into a binary plant transformation vector, and used to transform soybean plant cells. The plant transformation vectors comprised a first transgene cassette for expression of the chimeric insecticidal protein as described in Example 4 and a second transgene cassette for the selection of transformed plant cells using spectinomycin selection. In some instances, such as in the case of TIC1100, TIC860 and TIC836, a chloroplast transit peptide coding sequence was operably linked to the chimeric insecticidal coding sequence. Assays were performed with plastid targeted and untargeted TIC1100, TIC860 and TIC836. Table 5 below shows the chimeric insecticidal and TIC867 variant chimeric insecticidal protein and associated coding sequences used for expression in stably transformed soybean.

Soybean plant cells were transformed using the binary transformation vectors described above by *Agrobacterium*-mediated transformation. The resulting transformed plant cells were induced to form whole soybean plants. Leaf tissue was harvested and used in bioassay as described in Example 5 or alternatively, lyophilized tissue was used in the insect diet for bioassay. Bioassay was performed against FAW, Southern armyworm (SAW, *Spodoptera eridania*), Soybean looper (SBL, *Chrysodeixis includens*), Soybean Pod Worm (SPW, *Helicoverpa zea*), Velvetbean caterpillar (VBC, *Anticarsia gemmatalis*), Tobacco budworm (TBW, *Heliothis virescens*), Black armyworm (BLAW, *Spodoptera cosmioides*), Lesser cornstalk borer (LSCB, *Elasmopalpus lignosellus*) and Old World bollworm (OBW, *Hehcoverpa armigera*).

Table 5 shows the activity against selected species of Lepidoptera for each insecticidal protein in $R_0$ generation plants, wherein '+' indicates activity. As can be seen in Table 5, each of the chimeric insecticidal proteins expressed in stably transformed soybean demonstrated activity against multiple Lepidopteran species. Of particular note is that the TIC867 variant, TIC867_23 demonstrated activity against SPW.

TABLE 5

Bioassay activity of chimeric insecticidal proteins from stably transformed $R_0$ soybean leaf tissue.

| Insecticidal Protein | FAW | SAW | SBL | SPW | VBC | TBW | BLAW | LSCB | OBW |
|---|---|---|---|---|---|---|---|---|---|
| TIC1100 | + | + | + | | + | | + | + | + |
| TIC860 | + | + | + | | + | | | + | |
| TIC867 | + | + | + | | + | + | | + | |
| TIC867_20 | | + | + | | | | | | |
| TIC867_21 | | + | + | | | | | | |
| TIC867_22 | | + | + | | | | | | |
| TIC867_23 | + | + | + | + | | | | | |
| TIC867_24 | | + | + | | | | | | |
| TIC867_25 | | + | + | | | | | | |
| TIC868 | + | | + | | + | | + | + | |
| TIC869 | | | + | | + | + | | + | |
| TIC836 | + | + | + | | + | + | + | | + |

Selected transformed events were allowed to self-pollinate and the resulting seed was grown. Leaf tissue was harvested from the $R_1$ generation plants and used in a feeding bioassay. $R_1$ plants expressing TIC1100, TIC860, TIC867, TIC868, TIC869 and TIC836 were assayed for activity against SAW, SBL, SPW and VBC. Table 6 shows the activity observed in these tests. A '+' sign indicates activity observed to the specific insect pest. As demonstrated in Table 6, most of the expressed chimeric insecticidal proteins from $R_1$ generation plants demonstrated activity to one or more Lepidopteran species.

TABLE 6

Bioassay activity of chimeric insecticidal proteins from stably transformed $R_1$ soybean leaf tissue.

| Toxin | SAW | SBL | SPW | VBC |
|---|---|---|---|---|
| TIC1100 | + | + |  | + |
| TIC860 | + | + |  | + |
| TIC867 | + |  |  |  |
| TIC868 | + | + |  | + |
| TIC869 | + | + |  | + |
| TIC836 | + | + |  | + |

Table 7 demonstrates the results of field tests conducted in screen houses with stably transformed $R_1$ generation soybean plants expressing TIC1100, TIC860, and TIC836. Species used to infest plants in the screen houses include SAW, SBL and SPW. Resistance was defined as being less than or equal to fifteen percent defoliation in the soybean plants. The resistance observed in these cage trials is consistent with the resistance observed in the $R_1$ generation soybean leaf tissue assay presented in Table 6. A '+' sign indicates activity observed to the specific insect pest.

TABLE 7

Activity Profile of TIC1100, TIC860 and TIC836 Expressed in $R_1$ Generation Soybean Tested in Screen House Field Tests.

| Toxin | SAW | SBL | SPW |
|---|---|---|---|
| TIC1100 | + | + |  |
| TIC860 | + | + |  |
| TIC836 | + | + |  |

Field tests in screen houses with stably transformed $R_1$ generation soybean plants expressing TIC867 and TIC869 were also conducted at two different locations in Argentina, Acevedo and Fontezuela. Species used to infest plants in the screen houses include South American bollworm (SABW, *Helicoverpa gelotopeon*), VBC, BLAW, and Sunflower looper (SFL, *Rachiplusia nu*). Resistance was defined as being less than or equal to fifteen percent defoliation in the soybean plants. Table 8 below shows the resistance observed. A '+' sign indicates activity observed to the specific insect pest. As demonstrated in Table 8, transgenic soybean plants expressing TIC867 demonstrated resistance to BLAW and VBC. Transgenic soybean plants expressing TIC869 demonstrated resistance to SABW, SFL, BLAW, and VBC.

TABLE 8

Activity Profile of TIC867 and TIC869 Expressed in $R_1$ Generation Soybean Tested in Screen House Field Tests.

| | Acevedo | | | Fontezuela | | |
|---|---|---|---|---|---|---|
| Toxin | SABW | SFL | VBC | SABW | BLAW | VBC |
| TIC867 |  | + |  |  | + | + |
| TIC869 |  | + | + | + | + | + |

Example 7

Lepidopteran Activity of the Chimeric Insecticidal Proteins in Stably Transformed Cotton This Example illustrates the inhibitory activity exhibited by the chimeric insecticidal proteins against Lepidopteran pests when expressed in cotton plants and provided as a diet to the respective insect pest.

The coding sequences for selected chimeric insecticidal proteins were redesigned for plant expression, cloned into a binary plant transformation vector, and used to transform cotton plant cells. The resulting binary vectors were similar to those described in Example 4 and were used to express plastid targeted and untargeted TIC860 (coding sequence: SEQ ID NO: 6; protein sequence: SEQ ID NO: 7), TIC867 (coding sequence: SEQ ID NO: 9; protein sequence: SEQ ID NO: 10), TIC868 (coding sequence: SEQ ID NO: 27; protein sequence: SEQ ID NO: 28) and TIC867_23 (coding sequence: SEQ ID NO: 20; protein sequence: SEQ ID NO: 23).

Cotton plant cells were transformed by an *Agrobacterium*-mediated transformation method. Transformed cotton cells were induced to form whole plants. Cotton leaf tissue was used in bioassay as described in Example 5 against Cotton Boll Worm (CBW, *Helicoverpa zea*), FAW, TBW and SBL. Table 9 shows the activity observed against these Lepidopteran species for TIC860, TIC867, and TIC868 in stably transformed $R_0$ generation cotton, wherein '+' indicate activity. As can be seen in Table 9, TIC860, TIC867, and TIC868 demonstrated activity against two or more Lepidopteran pest species in stably transformed $R_0$ generation cotton.

TABLE 9

Bioassay activity of TIC860, TIC867 and TIC868 from stably transformed $R_0$ cotton leaf tissue.

| Toxin | CBW | FAW | TBW | SBL |
|---|---|---|---|---|
| TIC860 |  | + |  | + |
| TIC867 | + | + | + | NT |
| TIC868 |  | + |  | + |

Selected transformation events were used to produce $R_1$ seed. $R_1$ Plants expressing TIC860, TIC867, and TIC868 were assayed for resistance to CBW, FAW, TBW, and SBL. Leaf, square and boll tissues were used in assay. Table 10 shows the activity observed in these tests. A '+' sign indicates activity observed to the specific insect pest. As demonstrated in Table 10, TIC860 demonstrated activity against FAW in the leaf tissue. Further, the chimeric insecticidal protein TIC867 demonstrated activity against CBW and FAW in the leaf, square and boll tissues, as well as TBW and SBL in the leaf. The chimeric insecticidal protein TIC868 demonstrated activity against FAW in the leaf, square and boll tissues, as well as TBW and SBL in the leaf.

TABLE 10

Bioassay activity of chimeric insecticidal proteins from stably transformed R₁ cotton leaf tissue.

| Toxin | CBW | | | FAW | | | TBW | SBL |
|---|---|---|---|---|---|---|---|---|
| | Leaf | Square | Boll | Leaf | Square | Boll | Leaf | Leaf |
| TIC860 | | | | + | | | | |
| TIC867 | + | + | + | + | + | + | + | + |
| TIC868 | | | | + | + | + | + | + |

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A chimeric insecticidal protein comprising SEQ ID NO:21, wherein the chimeric insecticidal protein exhibits inhibitory activity against an insect species of the order Lepidoptera.

2. A polynucleotide encoding the chimeric insecticidal protein of claim 1, wherein the polynucleotide is operably linked to a heterologous promoter.

3. A polynucleotide encoding a chimeric insecticidal protein, wherein the polynucleotide:
   (a) comprises SEQ ID NO: 20; or
   (b) encodes the chimeric insecticidal protein of claim 1.

4. A host cell comprising the polynucleotide of claim 3, wherein said polynucleotide comprises SEQ ID NO:20, wherein the host cell is selected from the group consisting of a bacterial host cell and a plant host cell.

5. The host cell of claim 4, wherein the bacterial host cell is selected from the group consisting of *Agrobacterium, Rhizobium, Bacillus, Brevibacillus, Escherichia, Pseudomonas, Klebsiella*, and *Erwinia*.

6. The host cell of claim 4, wherein said plant host cell is selected from the group of plants consisting of monocots and dicots.

7. An insect inhibitory composition comprising the chimeric insecticidal protein of claim 1.

8. The insect inhibitory composition of claim 7, further comprising at least one insect inhibitory agent different from the chimeric insecticidal protein.

9. The insect inhibitory composition of claim 8, wherein said at least one insect inhibitory agent is selected from the group consisting of an insect inhibitory protein and an insect inhibitory dsRNA molecule.

10. The insect inhibitory composition of claim 8, wherein said at least one other pesticidal agent exhibits activity against one or more pest species of the orders Lepidoptera, Coleoptera, Hemiptera, Homoptera, or Thysanoptera.

11. A seed comprising an insect inhibitory effective amount of:
   (a) the chimeric insecticidal protein of claim 1; or
   (b) the polynucleotide set forth in SEQ ID NO:20.

12. A method of controlling a Lepidopteran pest, the method comprising contacting the Lepidopteran pest with an inhibitory amount of the chimeric insecticidal protein of claim 1.

13. A transgenic plant cell, plant or plant part comprising a chimeric insecticidal protein, wherein
   the chimeric insecticidal protein comprises SEQ ID NO:21.

14. A method of controlling a Lepidopteran pest, comprising exposing the pest to said transgenic plant cell, plant or plant part of claim 13, wherein said plant or plant part expresses a Lepidopteran inhibitory amount of the chimeric insecticidal protein.

15. A commodity product derived from said plant or plant part of claim 13, wherein the product comprises a detectable amount of the chimeric insecticidal protein.

16. The commodity product of claim 15, wherein the product is selected from the group consisting of plant biomass, oil, meal, animal feed, flour, flakes, bran, lint, hulls, and processed seed.

17. A method of producing a seed comprising the chimeric insecticidal protein of claim 1, the method comprising:
   (a) planting at least one seed comprising the chimeric insecticidal protein of claim 1;
   (b) growing plants from said seed; and
   (c) harvesting seeds from said at least one plant, wherein the harvested seeds comprises the chimeric insecticidal protein of claim 1.

18. A recombinant polynucleotide molecule encoding the chimeric insecticidal protein of claim 1, said molecule comprising SEQ ID NO:20 and a polynucleotide sequence encoding an insect inhibitory agent different from the chimeric insecticidal protein.

19. A recombinant nucleic acid molecule comprising a heterologous promoter operably linked to a polynucleotide segment encoding a chimeric insecticidal protein, wherein:
   (a) the chimeric insecticidal protein comprises SEQ ID NO:21; or
   (b) the polynucleotide segment comprises SEQ ID NO:20; wherein said chimeric insecticidal protein exhibits inhibitory activity against an insect species of the order Lepidoptera.

* * * * *